(12) United States Patent
Lee et al.

(10) Patent No.: US 10,644,245 B2
(45) Date of Patent: May 5, 2020

(54) COMPOSITION FOR ORGANIC PHOTOELECTRONIC ELEMENT, ORGANIC PHOTOELECTRONIC ELEMENT, AND DISPLAY APPARATUS

(71) Applicant: SAMSUNG SDI CO., LTD., Yongin-si, Gyeonggi-do (KR)

(72) Inventors: Sangshin Lee, Suwon-si (KR); Giwook Kang, Suwon-si (KR); Dong Min Kang, Suwon-si (KR); Youngkwon Kim, Suwon-si (KR); Eun Sun Yu, Suwon-si (KR); Byoungkwan Lee, Suwon-si (KR); Kipo Jang, Suwon-si (KR); Youngsung Park, Suwon-si (KR)

(73) Assignee: Samsung SDI Co., Ltd., Yongin-si, Gyeonggi-do (KR)

( * ) Notice: Subject to any disclaimer, the term of this patent is extended or adjusted under 35 U.S.C. 154(b) by 223 days.

(21) Appl. No.: 15/540,090

(22) PCT Filed: May 11, 2016

(86) PCT No.: PCT/KR2016/004929
§ 371 (c)(1),
(2) Date: Jun. 27, 2017

(87) PCT Pub. No.: WO2016/204406
PCT Pub. Date: Dec. 22, 2016

(65) Prior Publication Data
US 2018/0006238 A1 Jan. 4, 2018

(30) Foreign Application Priority Data

Jun. 19, 2015 (KR) .......................... 10-2015-0087776
May 10, 2016 (KR) .......................... 10-2016-0057082

(51) Int. Cl.
*H01L 51/50* (2006.01)
*H01L 51/00* (2006.01)
(Continued)

(52) U.S. Cl.
CPC ........ *H01L 51/0067* (2013.01); *C07D 209/86* (2013.01); *C07D 251/24* (2013.01);
(Continued)

(58) Field of Classification Search
None
See application file for complete search history.

(56) References Cited

U.S. PATENT DOCUMENTS

2012/0104941 A1 5/2012 Jung et al.
2013/0105787 A1* 5/2013 Tanaka ................ C07D 209/86
257/40
2014/0319492 A1 10/2014 Seo et al.

FOREIGN PATENT DOCUMENTS

CN 101654430 A 2/2010
CN 103985822 A 8/2014
(Continued)

OTHER PUBLICATIONS

International Search Report dated Jan. 19, 2017 for PCT/KR2016/011323 filed on Oct. 10, 2016.
(Continued)

*Primary Examiner* — Gregory D Clark
(74) *Attorney, Agent, or Firm* — Lee IP Law, PC

(57) ABSTRACT

The present invention relates to: a composition for an organic photoelectronic element comprising at least one type of a first chemical compound represented by chemical formula 1 and at least one type of a second chemical compound represented by chemical formula 2; an organic photoelectronic element comprising the same; and a display apparatus comprising said organic photoelectronic element.

(Continued)

Chemical formulas 1 and 2 are described in the specification of the present invention.

16 Claims, 1 Drawing Sheet

(51) Int. Cl.
| | |
|---|---|
| *C09K 11/06* | (2006.01) |
| *C07D 209/86* | (2006.01) |
| *C07D 251/24* | (2006.01) |
| *C07D 401/14* | (2006.01) |
| *C07D 403/10* | (2006.01) |
| *C09K 11/02* | (2006.01) |

(52) U.S. Cl.
CPC ......... *C07D 401/14* (2013.01); *C07D 403/10* (2013.01); *C09K 11/02* (2013.01); *C09K 11/06* (2013.01); *H01L 51/0054* (2013.01); *H01L 51/0072* (2013.01); *H01L 51/0085* (2013.01); *C09K 2211/1059* (2013.01); *C09K 2211/185* (2013.01); *H01L 51/5016* (2013.01); *H01L 2251/5384* (2013.01)

(56) References Cited

FOREIGN PATENT DOCUMENTS

| | | |
|---|---|---|
| DE | 102008036982 A1 | 2/2010 |
| EP | 2452997 A2 | 5/2012 |
| EP | 2776443 | 9/2014 |
| JP | 2007-314503 A | 12/2007 |
| JP | 2008-280330 A | 11/2008 |
| JP | 2011-530802 A | 12/2011 |
| JP | 2013525346 A | 6/2013 |
| JP | 5376063 B2 | 12/2013 |
| JP | 2014500612 A | 1/2014 |
| JP | 2015-504422 | 2/2015 |
| JP | 5821635 B2 | 11/2015 |
| JP | 2016-185914 A | 10/2016 |
| JP | 6299223 B2 | 3/2018 |
| KR | 10-2007-0091291 A | 9/2007 |
| KR | 10-2009-0007734 | 1/2009 |
| KR | 10-2009-0008737 A | 1/2009 |
| KR | 10-2010-0131745 A | 12/2010 |
| KR | 10-2011-0088513 A | 8/2011 |
| KR | 10-2012-0132423 | 12/2012 |
| KR | 10-2013-0084952 A | 7/2013 |
| KR | 10-1288566 B2 | 7/2013 |
| KR | 10-2013-0098226 | 9/2013 |
| KR | 10-2014-0014959 A | 2/2014 |
| KR | 10-2014-0087804 A | 7/2014 |
| KR | 10-2014-0094408 | 7/2014 |
| KR | 10-1502316 | 3/2015 |
| KR | 10-2015-0037318 | 4/2015 |
| KR | 10-2015-0042603 | 4/2015 |
| KR | 10-2015-0064410 | 6/2015 |
| KR | 10-2015-0083787 A | 7/2015 |
| KR | 10-2015-0104260 | 9/2015 |
| KR | 10-2017-0045558 A | 4/2017 |
| TW | 201509915 A | 3/2015 |
| TW | 201533038 A | 9/2015 |
| TW | 201638082 A | 11/2016 |
| WO | WO 2005/085387 A1 | 9/2005 |
| WO | WO 2010/038854 A1 | 4/2010 |
| WO | WO 2010/067894 A1 | 6/2010 |
| WO | WO 2012/163465 A1 | 12/2012 |
| WO | WO 2013-122082 A1 | 8/2013 |
| WO | WO 2013-187896 A1 | 12/2013 |
| WO | WO 2014-024750 A1 | 2/2014 |

OTHER PUBLICATIONS

Search Report dated May 2, 2017 of the corresponding Taiwanese Patent Application No. 105118875.
European Search Report dated Oct. 12, 2018, of the corresponding European Patent Application No. 16811819.8.
Chan Seok Oh, "High Efficiency Exciplex Emitters Using Donor—Acceptor Type Acceptor Material", J. Phys. Chem., Sep. 21, 2005, 119, 22618-22624.
European Search Report dated May 24, 2019.

* cited by examiner

【Figure 1】
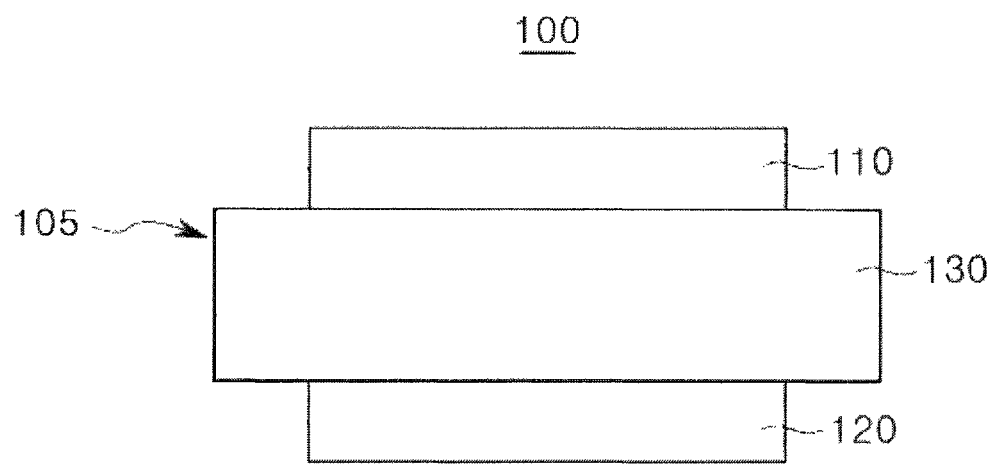
【Figure 2】
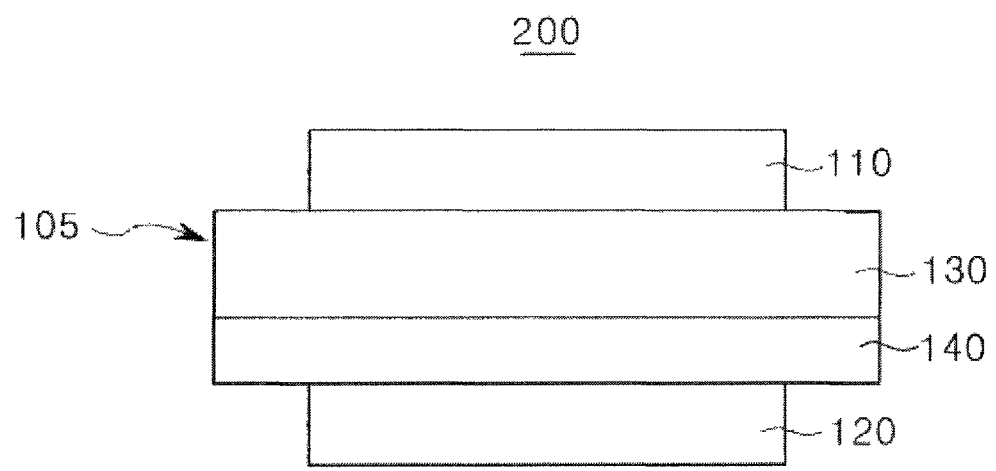

COMPOSITION FOR ORGANIC PHOTOELECTRONIC ELEMENT, ORGANIC PHOTOELECTRONIC ELEMENT, AND DISPLAY APPARATUS

TECHNICAL FIELD

An organic optoelectronic device and a display device are disclosed.

BACKGROUND ART

An organic optoelectronic device is a device that converts electrical energy into photoenergy, and vice versa.

An organic optoelectronic device may be classified as follows in accordance with its driving principles. One is an optoelectronic diode where excitons are generated by photoenergy, separated into electrons and holes, and are transferred to different electrodes to generate electrical energy, and the other is a light emitting device where a voltage or a current is supplied to an electrode to generate photoenergy from electrical energy.

Examples of the organic optoelectronic diode may be an organic photoelectric device, an organic light emitting diode, an organic solar cell, and an organic photo conductor drum.

Of these, an organic light emitting diode (OLED) has recently drawn attention due to an increase in demand for flat panel displays. The organic light emitting diode converts electrical energy into light by applying current to an organic light emitting material and has a structure in which an organic layer is interposed between an anode and a cathode.

A blue organic light emitting diode having a long life-span is considered to be one of the critical factors for realizing a long life-span full color display. Accordingly, development of a long life-span blue organic light emitting diode is being actively researched. In order to solve this problem, a long life-span blue organic light emitting diode is provided in this invention.

DISCLOSURE

Technical Problem

One embodiment provides a composition for an organic optoelectronic device capable of realizing having high efficiency and long life-span characteristics.

Another embodiment provides an organic optoelectronic device including the composition for an organic optoelectronic device.

Yet another embodiment provides a display device including the organic optoelectronic device.

Technical Solution

According to one embodiment, a composition for an organic optoelectronic device includes at least one first compound represented by Chemical Formula 1 and at least one second compound represented by Chemical Formula 2.

[Chemical Formula 1]

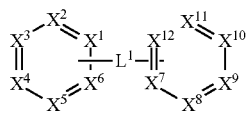

In Chemical Formula 1,
$X^1$ to $X^{12}$ are independently N, C, or $CR^a$,
at least one of $X^1$ to $X^6$ is N,
at least one of $X^7$ to $X^{12}$ is N,
$R^a$ is independently, hydrogen, deuterium, a substituted or unsubstituted C1 to C30 alkyl group, a substituted or unsubstituted C1 to C30 alkenyl group, a substituted or unsubstituted C1 to C30 alkynyl group, a substituted or unsubstituted C6 to C30 aryl group, a substituted or unsubstituted C6 to C30 aryloxy group, a substituted or unsubstituted C6 to C30 arylthio group, a substituted or unsubstituted C2 to C30 heteroaryl group, a hydroxy group, a thiol group, or a combination thereof,
$R^a$ is independently present or adjacent $R^a$s are linked to each other to provide a ring, and
$L^1$ is deuterium, a C1 to C40 silyl group, a C1 to C30 alkyl group, a C3 to C30 cycloalkyl group, a C2 to C30 heterocycloalkyl group, or a C6 to C30 arylene group substituted or unsubstituted with a C6 to C30 aryl group;

[Chemical Formula 2]

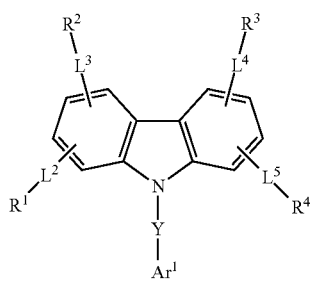

wherein, in Chemical Formula 2,
$L^2$ to $L^5$ and $Y^1$ are independently a single bond, or a substituted or unsubstituted C6 to C30 arylene group,
$Ar^1$ is a substituted or unsubstituted C6 to C30 aryl group, a substituted or unsubstituted C2 to C30 heterocyclic group, a substituted or unsubstituted C6 to C30 arylamine group, or a combination thereof,
$R^1$ to $R^4$ are independently hydrogen, deuterium, a substituted or unsubstituted C1 to C20 alkyl group, a substituted or unsubstituted C6 to C30 aryl group, a substituted or unsubstituted C2 to C30 heterocyclic group, a substituted or unsubstituted nitrile group, a substituted or unsubstituted isonitrile group, a hydroxy group, a thiol group, or a combination thereof,
$R^1$ to $R^4$ is independently present or adjacent groups are linked to each other to provide a ring,
at least one of $R^1$ to $R^4$ and $Ar^1$ is a substituted or unsubstituted triphenylene group, or a substituted or unsubstituted carbazolyl group,
one of $R^1$ and $R^2$ and one of $R^3$ and $R^4$ are not simultaneously a substituted or unsubstituted carbazolyl group, and
when one of $R^1$ to $R^4$ is a substituted carbazolyl group, the carbazolyl group is not substituted with a carbazolyl group,
wherein when a definition is not otherwise provided, "substituted" of Chemical Formulae 1 and 2 refers to that at least one hydrogen is replaced by deuterium, a halogen, a hydroxy group, an amino group, a C1 to C30 amine group, a C6 to C30 arylamine group, a nitro group, a C1 to C40 silyl group, a C1 to C30 alkyl group, a C3 to C30 cycloalkyl group, a C2 to C30 heterocycloalkyl group, a C6 to C30 aryl group, a C2 to C30 heterocyclic group, a C1 to C20 alkoxy group, a C1 to C10 trifluoroalkyl group, or a cyano group.

According to another embodiment, an organic optoelectronic device including the composition for an organic optoelectronic device is provided.

According to another embodiment, a display device including the organic optoelectronic device is provided.

Advantageous Effects

An organic optoelectronic device having high efficiency and long life-span may be realized.

DESCRIPTION OF THE DRAWINGS

FIGS. 1 and 2 are cross-sectional views showing organic optoelectronic devices according to one embodiment.

DESCRIPTION OF SYMBOLS

100, 200: organic light emitting diode
105: organic layer
110: cathode
120: anode
130: emission layer
140: auxiliary layer

MODE FOR INVENTION

Hereinafter, embodiments of the present invention are described in detail. However, these embodiments are exemplary, the present invention is not limited thereto and the present invention is defined by the scope of claims.

In the present specification, when a definition is not otherwise provided, "substituted" refers to one substituted with a substituent selected from deuterium, a halogen, a hydroxy group, an amino group, a C1 to C30 amine group, a C6 to C30 arylamine group, a nitro group, a C1 to C40 silyl group, a C1 to C30 alkyl group, a C3 to C30 cycloalkyl group, a C2 to C30 heterocycloalkyl group, a C6 to C30 aryl group, a C2 to C30 heterocyclic group, a C1 to C20 alkoxy group, a C1 to C10 trifluoroalkyl group, a cyano group, or a combination thereof, instead of at least one hydrogen of a substituent or a compound.

As one example of the present invention, "substituted" refers to one substituted with a substituent selected from deuterium, a C1 to C10 alkyl group, a C6 to C30 aryl group, a C2 to C30 heterocyclic group, or a combination thereof, instead of at least one hydrogen of a substituent or a compound.

In addition, two adjacent substituents of the substituted C1 to C30 amine group, C1 to C40 silyl group, C1 to C30 alkyl group, C1 to C10 alkylsilyl group, C3 to C30 cycloalkyl group, C2 to C30 heterocycloalkyl group, C6 to C30 aryl group, C2 to C30 heterocyclic group, or C1 to C20 alkoxy group may be fused with each other to form a ring. For example, the substituted C6 to C30 aryl group may be linked with another adjacent substituted C6 to C30 aryl group to form a substituted or unsubstituted fluorene ring, and the substituted C6 to C30 aryl group may be linked with an adjacent C1 to C30 alkenyl group to form a triphenylene ring, a naphthalene ring, a pyrazine ring, a quinazoline ring, a quinoxaline ring, a phenanthroline ring, and the like.

In the present specification, when specific definition is not otherwise provided, the term "hetero" refers to one including 1 to 3 hetero atoms selected from N, O, S, P, and Si, and remaining carbons in one functional group.

In the present specification, when a definition is not otherwise provided, "alkyl group" refers to an aliphatic hydrocarbon group. The alkyl group may be "a saturated alkyl group" without any double bond or triple bond.

The alkyl group may be a C1 to C30 alkyl group. More specifically, the alkyl group may be a C1 to C20 alkyl group or a C1 to C10 alkyl group. For example, a C1 to C4 alkyl group may have 1 to 4 carbon atoms in an alkyl chain which may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

In the present specification, an "aryl group" refers to a group including at least one hydrocarbon aromatic moiety, and all the elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like, and two or more hydrocarbon aromatic moieties are fused directly or indirectly to provide a non-aromatic fused ring. For example, it may be a fluorenyl group.

The aryl group may include a monocyclic, polycyclic or fused ring polycyclic (i.e., rings sharing adjacent pairs of carbon atoms) functional group.

In the present specification, "heterocyclic group" is a generic concept of a heteroaryl group, and may include at least one hetero atom selected from N, O, S, P, and Si instead of carbon (C) in a cyclic compound such as aryl group, a cycloalkyl group, a fused ring thereof, or a combination thereof. When the heterocyclic group is a fused ring, the entire ring or each ring of the heterocyclic group may include one or more heteroatoms.

For example, a "heteroaryl group" may refer to aryl group including at least one hetero atom selected from N, O, S, P, and Si instead of carbon (C). Two or more heteroaryl groups are linked by a sigma bond directly, or when the C2 to C60 heteroaryl group includes two or more rings, the two or more rings may be fused. When the heteroaryl group is a fused ring, each ring may include 1 to 3 hetero atoms.

Specific examples of the heteroaryl group may be a pyridinyl group, a pyrimidinyl group, a pyrazinyl group, a pyridazinyl group, a triazinyl group, a quinolinyl group, an isoquinolinyl group, and the like.

More specifically, the substituted or unsubstituted C6 to C30 aryl group and/or the substituted or unsubstituted C2 to C30 heterocyclic group may be a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted fluorenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridinyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted carbazolyl group, a substituted or unsubstituted dibenzofuranyl group, or a substituted or unsubstituted dibenzothiophenyl group, or a combination thereof, but are not limited thereto.

In the present specification, the single bond refers to a direct bond not by carbon or a hetero atom except carbon, and specifically the meaning that L is a single bond means that a substituent linked to L directly bonds with a central core. That is, in the present specification, the single bond does not refer to methylene that is bonded via carbon.

In the specification, hole characteristics refer to an ability to donate an electron to form a hole when an electric field is applied and that a hole formed in the anode may be easily injected into the emission layer and transported in the emission layer due to conductive characteristics according to a highest occupied molecular orbital (HOMO) level.

In addition, electron characteristics refer to an ability to accept an electron when an electric field is applied and that electron formed in the cathode may be easily injected into the emission layer and transported in the emission layer due to conductive characteristics according to a lowest unoccupied molecular orbital (LUMO) level.

Hereinafter, a composition for an organic optoelectronic device according to an embodiment is described.

A composition for an organic optoelectronic device according to an embodiment includes at least one first compound represented by Chemical Formula 1 and at least one second compound represented by Chemical Formula 2.

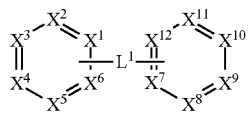

[Chemical Formula 1]

In Chemical Formula 1, $X^1$ to $X^{12}$ are independently N, C, or $CR^a$, at least one of $X^1$ to $X^6$ is N, at least one of $X^1$ to $X^{12}$ is N, $R^a$ is independently, hydrogen, deuterium, a substituted or unsubstituted C1 to C30 alkyl group, a substituted or unsubstituted C1 to C30 alkenyl group, a substituted or unsubstituted C1 to C30 alkynyl group, a substituted or unsubstituted C6 to C30 aryl group, a substituted or unsubstituted C6 to C30 aryloxy group, a substituted or unsubstituted C6 to C30 arylthio group, a substituted or unsubstituted C2 to C30 heteroaryl group, a hydroxy group, a thiol group, or a combination thereof, $R^a$ is independently present or adjacent $R^a$s are linked to each other to provide a ring, and $L^1$ is deuterium, a C1 to C40 silyl group, a C1 to C30 alkyl group, a C3 to C30 cycloalkyl group, a C2 to C30 heterocycloalkyl group, or a C6 to C30 arylene group substituted or unsubstituted with a C6 to C30 aryl group;

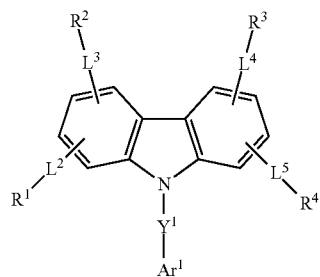

[Chemical Formula 2]

wherein, in Chemical Formula 2,
$L^2$ to $L^5$ and $Y^1$ are independently a single bond, or a substituted or unsubstituted C6 to C30 arylene group, AO is a substituted or unsubstituted C6 to C30 aryl group, a substituted or unsubstituted C2 to C30 heterocyclic group, a substituted or unsubstituted C6 to C30 arylamine group, or a combination thereof, $R^1$ to $R^4$ are independently hydrogen, deuterium, a substituted or unsubstituted C1 to C20 alkyl group, a substituted or unsubstituted C6 to C30 aryl group, a substituted or unsubstituted C2 to C30 heterocyclic group, a substituted or unsubstituted nitrile group, a substituted or unsubstituted isonitrile group, a hydroxy group, a thiol group, or a combination thereof, $R^1$ to $R^4$ is independently present or adjacent groups are linked to each other to provide a ring, at least one of $R^1$ to $R^4$ and $Ar^1$ is a substituted or unsubstituted triphenylene group, or a substituted or unsubstituted carbazolyl group, one of $R^1$ and $R^2$ and one of $R^3$ and $R^4$ are not simultaneously a substituted or unsubstituted carbazolyl group, and when one of $R^1$ to $R^4$ is a substituted carbazolyl group, the carbazolyl group is not substituted with a carbazolyl group, wherein when a definition is not otherwise provided, "substituted" of Chemical Formulae 1 and 2 refers to that at least one hydrogen is replaced by deuterium, a halogen, a hydroxy group, an amino group, a C1 to C30 amine group, a C6 to C30 arylamine group, a nitro group, a C1 to C40 silyl group, a C1 to C30 alkyl group, a C3 to C30 cycloalkyl group, a C2 to C30 heterocycloalkyl group, a C6 to C30 aryl group, a C2 to C30 heterocyclic group, a C1 to C20 alkoxy group, a C1 to C10 trifluoroalkyl group, or a cyano group.

In one example of the present invention, "substituted" of Chemical Formulae 1 and 2 refers to that at least one hydrogen is replaced by deuterium, C1 to C10 alkyl group, C6 to C18 aryl group, C2 to C18 heterocyclic group, or a combination thereof.

A composition for an organic optoelectronic device according to one embodiment of the present invention uses a first compound including a compound in which nitrogen-containing heterorings are linked through an arylene linker and thus having excellent electron injection and transport characteristics and a second compound including at least one carbazolyl group and thus having excellent hole injection and transport characteristics to form an emission layer and resultantly, may lower a driving voltage and simultaneously realize an organic light emitting diode having a long lifespan and high efficiency.

The first compound respectively includes at least one nitrogen-containing ring in substituents positioned at both ends of the linking group, L¹ and thus has a structure of easily accepting an electron when an electric field is applied and thus may increase the injection amount of electrons and have relatively strong electron transport characteristics.

In particular, various characteristics such as charge injection characteristics, a deposition temperature, a glass transition temperature, and the like may be adjusted depending on the number of N included in the substituents at both ends, a linking direction of the linking group, L¹, the number of an arylene group linked thereby, and the like.

Accordingly, the first compound may lower a driving voltage of an organic optoelectronic device and also, improve its efficiency.

Chemical Formula 1 according to an example embodiment of the present invention may be, for example represented by one of Chemical Formula 1-I to Chemical Formula 1-III in accordance with that adjacent $R^a$s are linked to each other to form a ring.

[Chemical Formula 1-I]

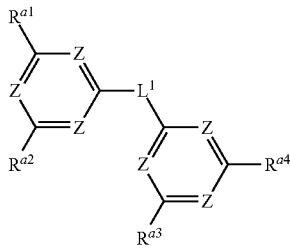

[Chemical Formula 1-II]

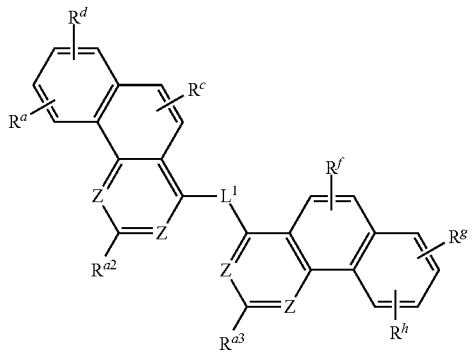

[Chemical Formula 1-III]

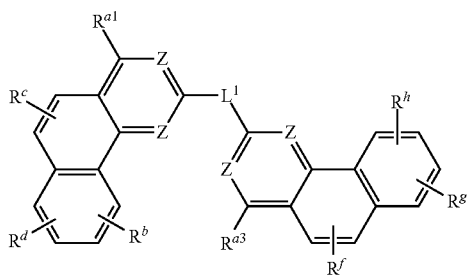

In Chemical Formulae 1-I to 1-III, L¹ is the same described above, Z is independently N, or CR$^a$, R$^a$ is the same described above, and at least one of Z may be N.

Various characteristics such as charge injection characteristics, a deposition temperature, a glass transition temperature, and the like may be adjusted depending on the number of N included in a substituent at both ends. Specifically, when the entire number of the N is greater than or equal to 4, electron injection characteristics may be stronger. For example, the number of the N may be respectively (1 and 3), (2 and 2), (2 and 3), or (3 and 3) and in particular, when the number of the N is (3 and 3), stability and mobility of injected electrons may be particularly improved.

$R^a$, $R^{a1}$ to $R^{a4}$, $R^c$, $R^d$, $R^e$, $R^f$, $R^g$, and $R^h$ are independently hydrogen, deuterium, a substituted or unsubstituted C1 to C30 alkyl group, a substituted or unsubstituted C6 to C30 aryl group, a substituted or unsubstituted C2 to C30 heteroaryl group, or a combination thereof, specifically, hydrogen or a substituted or unsubstituted C6 to C30 aryl group, and more specifically, hydrogen, a substituted or unsubstituted phenyl group, a substituted or unsubstituted biphenyl group, a substituted or unsubstituted terphenyl group, a substituted or unsubstituted quarterphenyl group, a substituted or unsubstituted naphthyl group, a substituted or unsubstituted anthracenyl group, a substituted or unsubstituted triphenylene group, a substituted or unsubstituted phenanthrenyl group, or a substituted or unsubstituted pyrenyl group.

For example, they may be substituted with deuterium, a C1 to C10 alkyl group, a C6 to C12 aryl group or they may be selected from the following unsubstituted groups of Group 1, but are not limited thereto.

[Group 1]

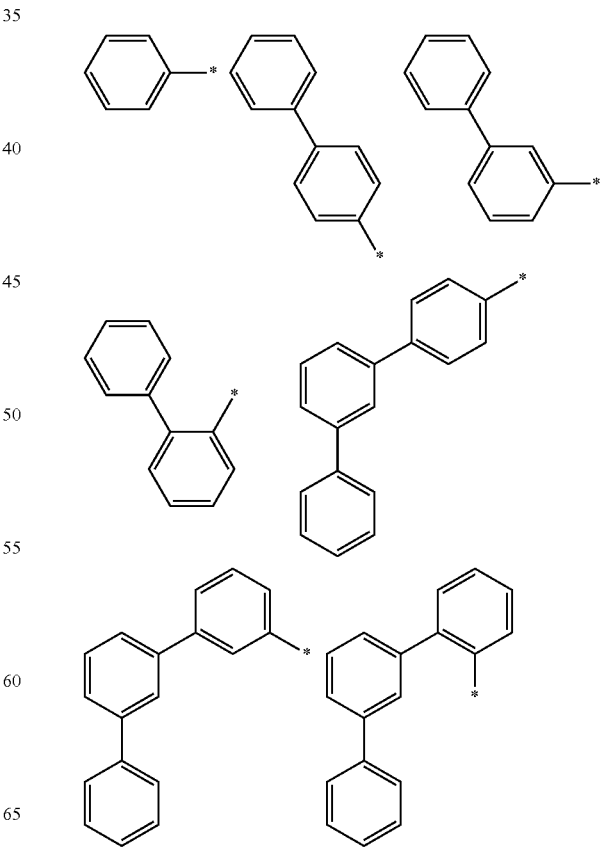

-continued

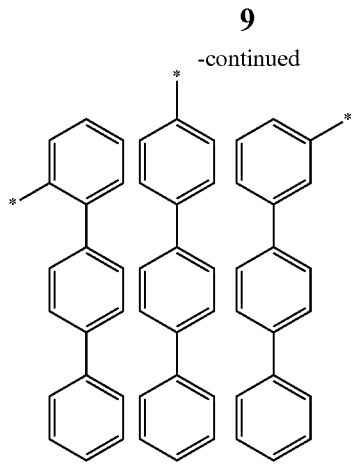

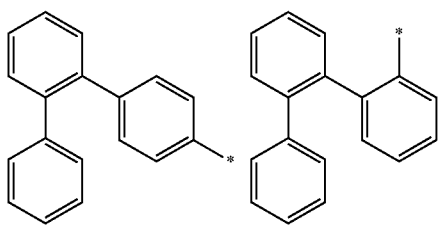

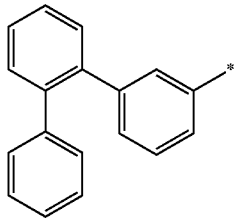

[Group 2]

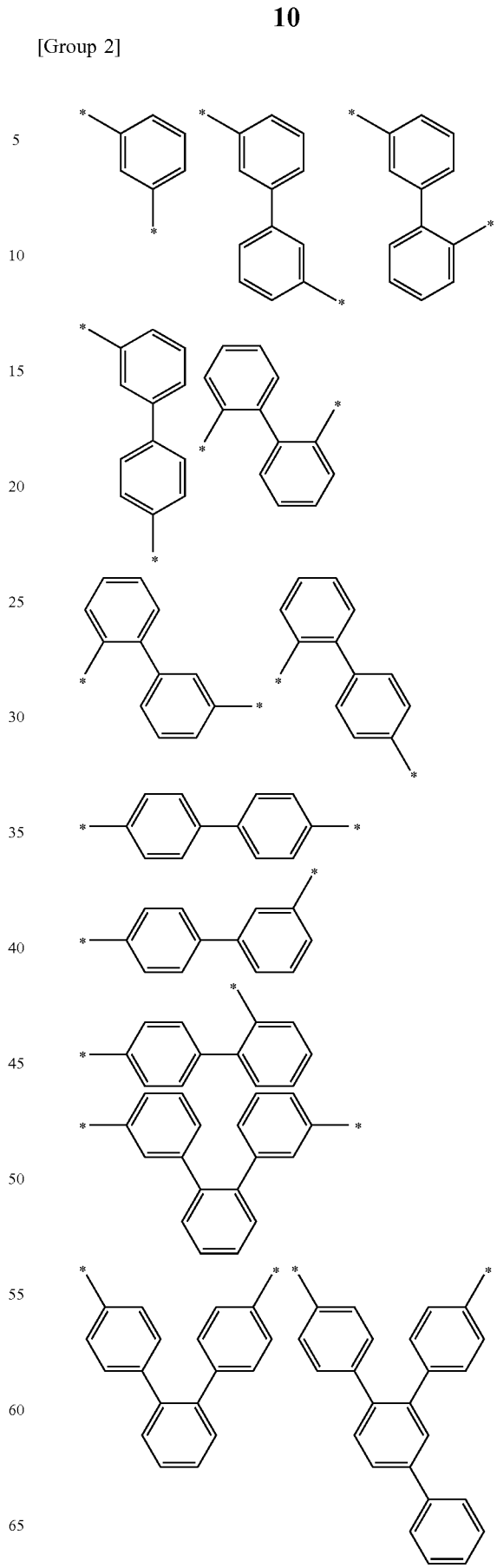

In Group 1, * is a linking point.

$L^1$ of Chemical Formula 1 according to an example embodiment of the present invention may be specifically a phenylene group that is unsubstituted or substituted with deuterium, a C1 to C40 silyl group, a C1 to C30 alkyl group, or a C6 to C30 aryl group; a biphenylene group that is unsubstituted or substituted with deuterium, a C1 to C40 silyl group, a C1 to C30 alkyl group, or a C6 to C30 aryl group; a terphenylene group that is unsubstituted or substituted with deuterium, a C1 to C40 silyl group, a C1 to C30 alkyl group, or a C6 to C30 aryl group; or a quarterphenylene group that is unsubstituted or substituted with deuterium, a C1 to C40 silyl group, a C1 to C30 alkyl group, or a C6 to C30 aryl group.

Particularly, various characteristics such as charge injection characteristics, a deposition temperature, a glass transition temperature, and the like may be adjusted depending on a linking direction of a linking group, $L^1$ and the number of an arylene group linked thereby, and herein, the linking group, $L^1$ may be for example, selected from substituted or unsubstituted linking groups provided in Group 2 but is not limited thereto.

-continued

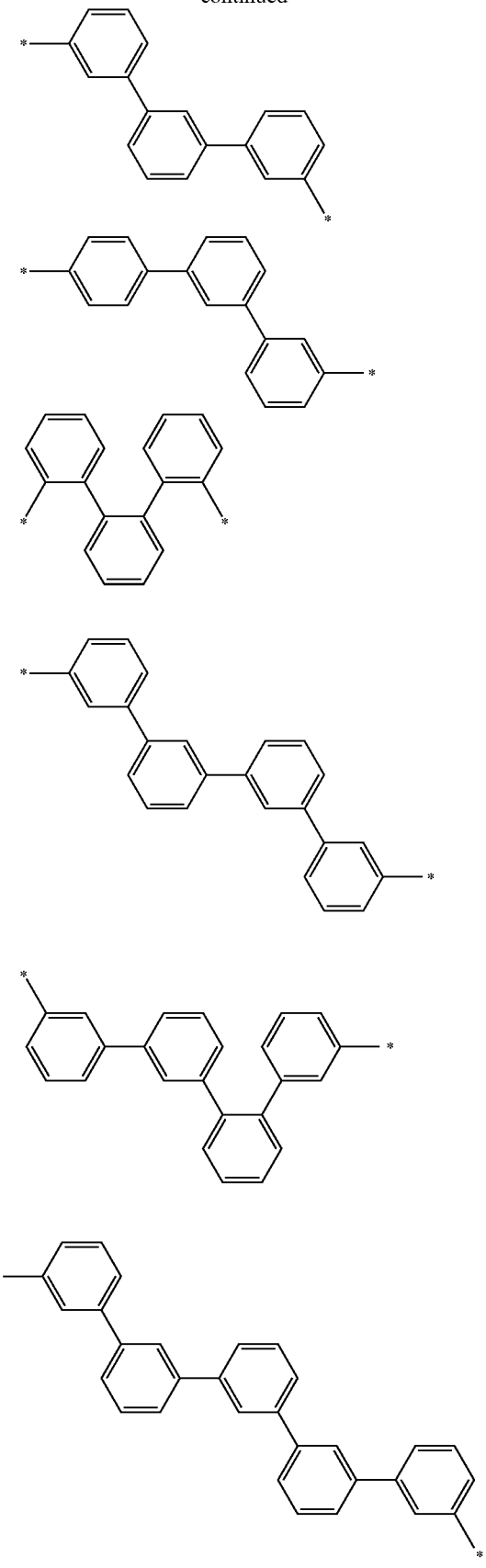

In Group 2, * is a linking point to an adjacent atom.

In one example of the present invention, linking groups of Group 2 may be further substituted with one selected from deuterium, a C1 to C5 alkyl group, a C6 to C18 aryl group, a C3 to C12 heteroaryl group, and a combination thereof.

Specifically, the linking groups of Group 2 may be further substituted with one selected from deuterium, a C1 to C5 alkyl group, a C6 to C18 aryl group, and a combination thereof.

When the $L^1$ is the same as above, Chemical Formula 1 may be a dimer including two N-containing heterorings, this dimer may easily adjust hole mobility and electron mobility characteristics depending on characteristics of a substituent and thus suppress formation of a crystalline phase compared with a timer including three N-containing heterorings.

In particular, as a ratio of a moiety linked at a para position in the $L^1$ increases, a molecule itself becomes firm and thus may increase charge mobility.

In addition, a deposition temperature and a glass transition temperature may be adjusted by controlling ratios of moieties linked as a meta or ortho position in the $L^1$. Particularly, a LUMO energy level and thus charge injection characteristics may be adjusted by controlling the number of aryl group included in the $L^1$ and a kind of and a direction of substituents included in the heterorings.

In an example embodiment of the present invention, $X^1$ to $X^{12}$ of Chemical Formula 1 are independently N, C, or $CR^a$, three of $X^1$ to $X^6$ are N, one to three of $X^7$ to $X^{12}$ are N, $R^a$ is independently, hydrogen, deuterium, a substituted or unsubstituted C1 to C30 alkyl group, a substituted or unsubstituted C6 to C30 aryl group, a substituted or unsubstituted C2 to C30 heteroaryl group, or a combination thereof, and $L^1$ is a C6 to C30 arylene group that is substituted or unsubstituted with deuterium, a C1 to C30 alkyl group, or a C6 to C30 aryl group, wherein when a definition is not otherwise provided, "substituted" refers to that at least one hydrogen is replaced by deuterium, a halogen, a hydroxy group, a C1 to C40 silyl group, a C1 to C30 alkyl group, a C3 to C30 cycloalkyl group, a C2 to C30 heterocycloalkyl group, a C6 to C30 aryl group, or a C2 to C30 heterocyclic group.

Specifically, the $R^a$ may be a substituted or unsubstituted C6 to C30 aryl group, and the C6 to C30 aryl group may be a substituted or unsubstituted phenyl group, a substituted or unsubstituted biphenyl group, a substituted or unsubstituted terphenyl group, a substituted or unsubstituted quarterphenyl group, a substituted or unsubstituted naphthyl group, a substituted or unsubstituted anthracenyl group, a substituted or unsubstituted fluorenyl group, a substituted or unsubstituted triphenylene group, or a substituted or unsubstituted phenanthrenyl group.

The first compound represented by Chemical Formula 1 may be, for example compounds of Group 3, but is not limited thereto.

[Group 3]
(all hetero atoms of 6-membered ring are "N")
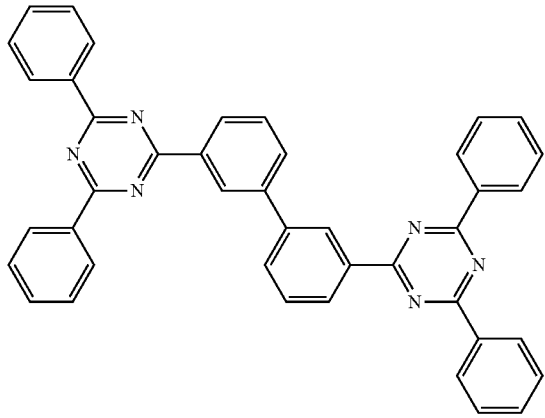
1
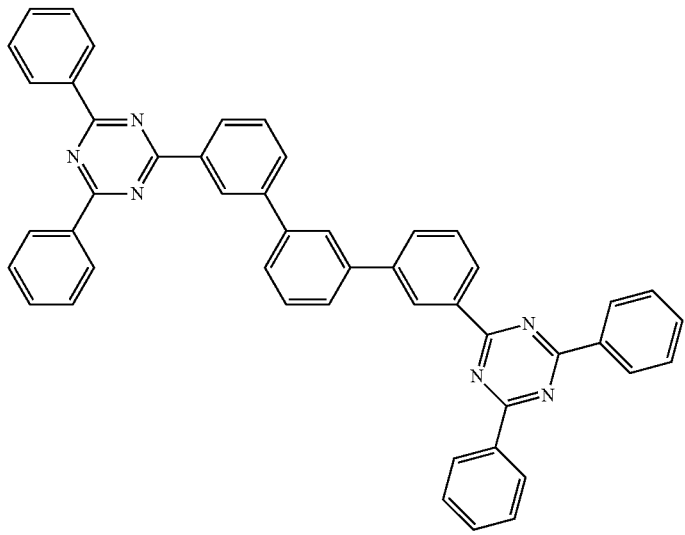
2
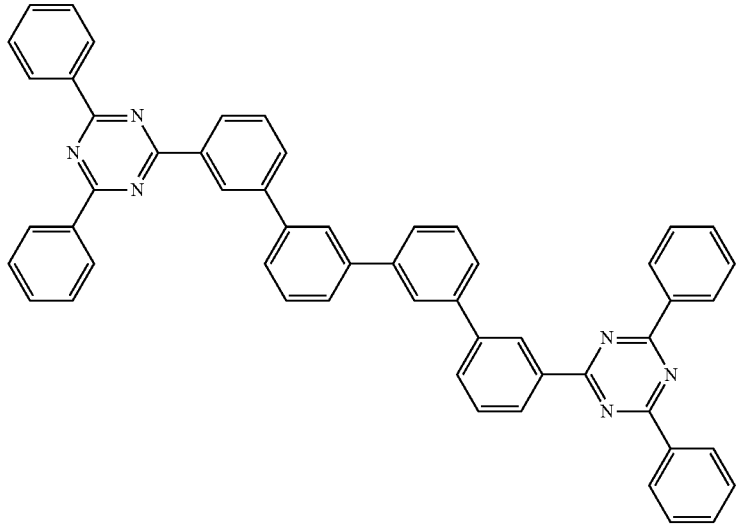
3

-continued
4
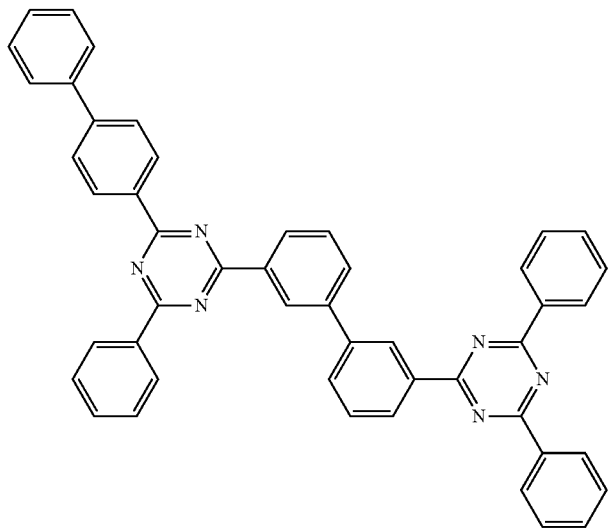
5
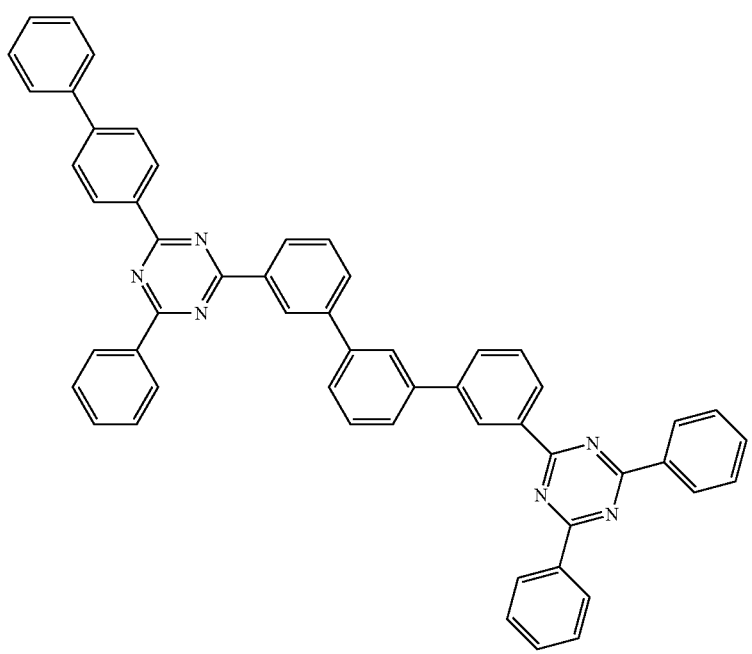

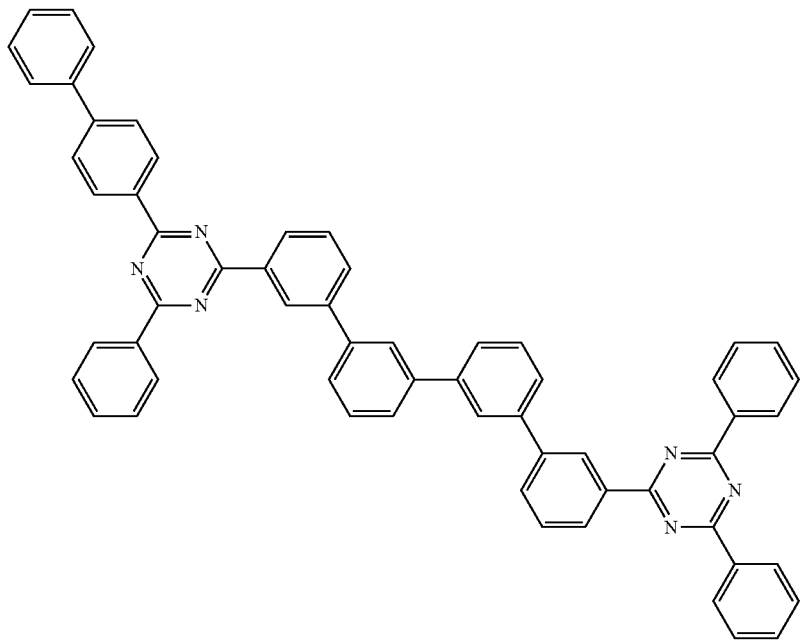
6
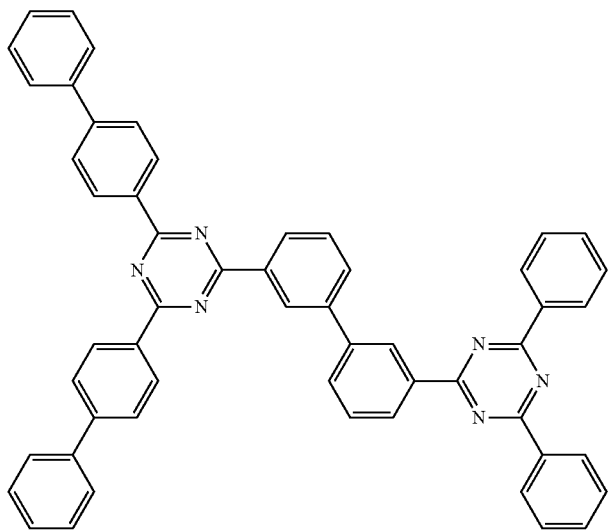
7

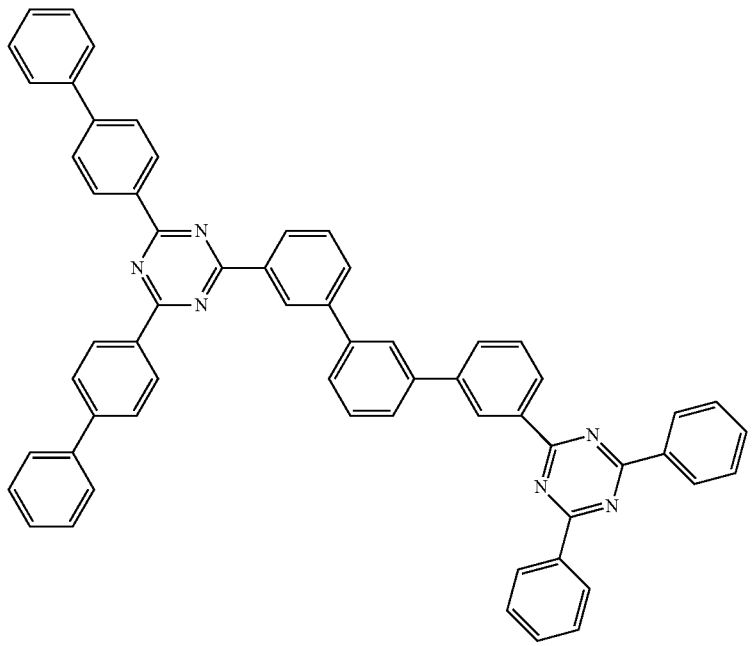
8
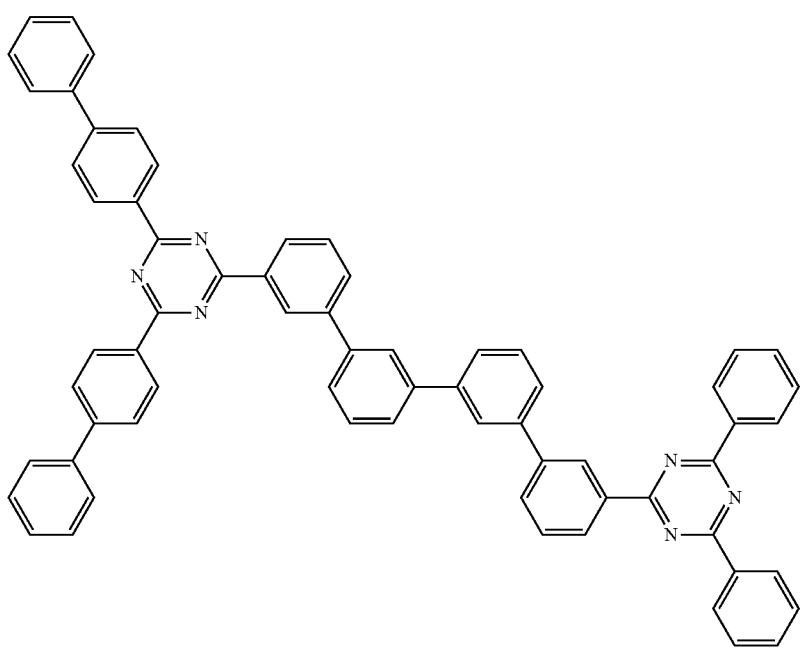
9

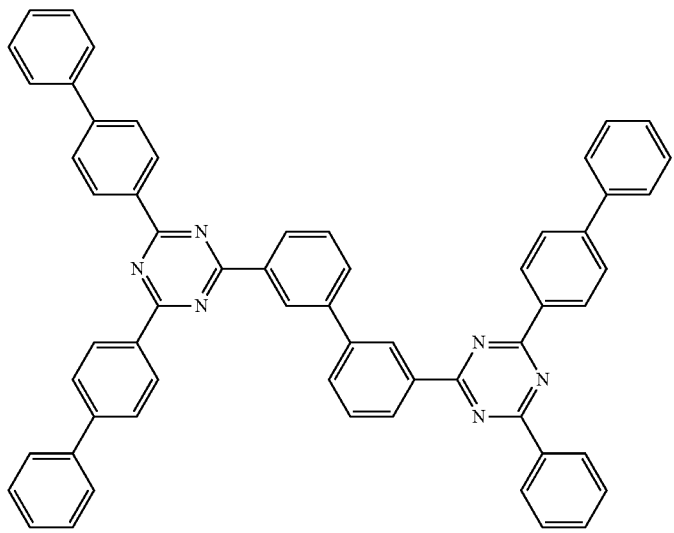
10
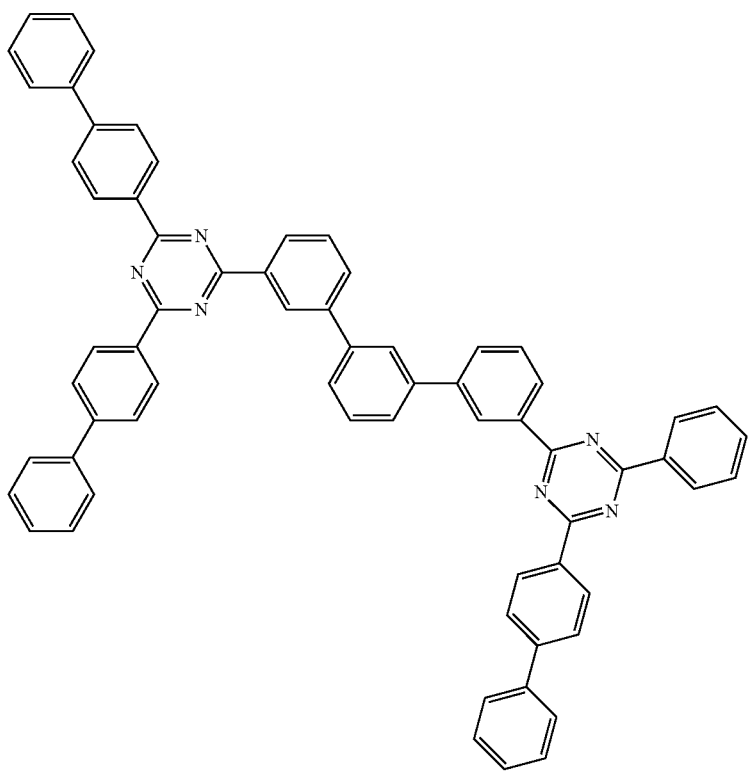
11

-continued
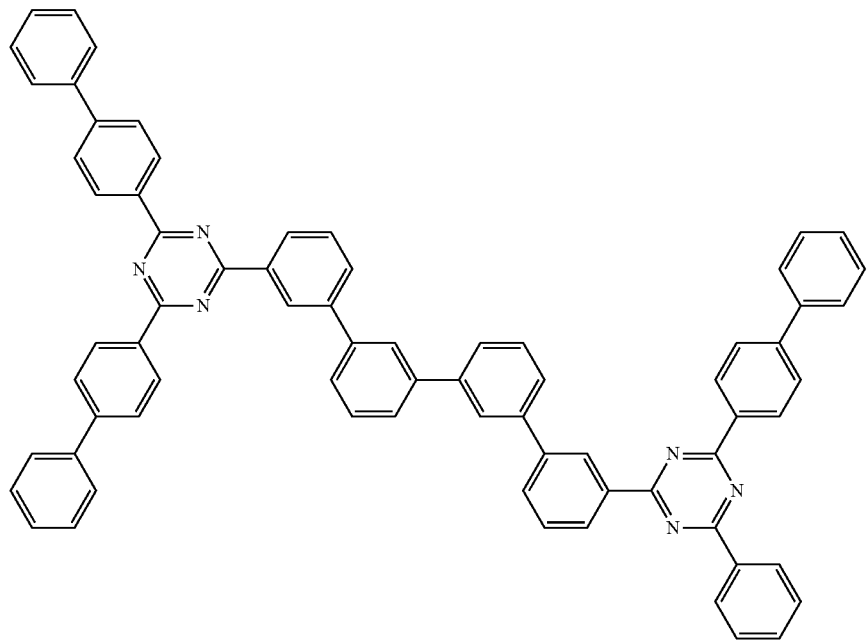
12
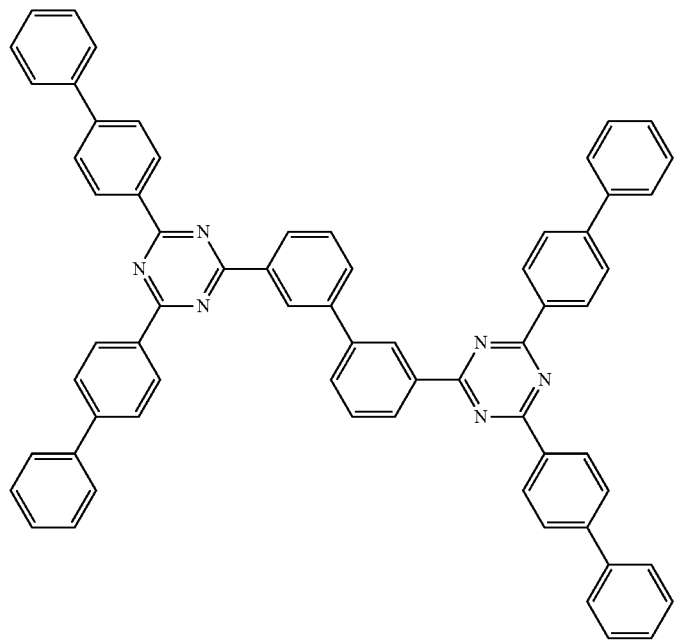
13

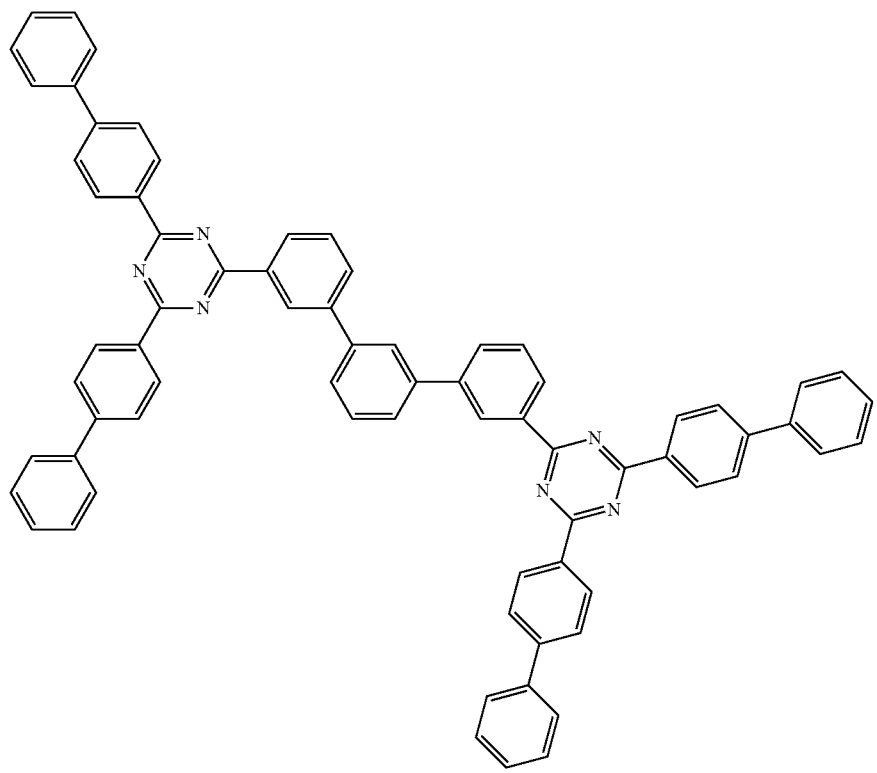
14
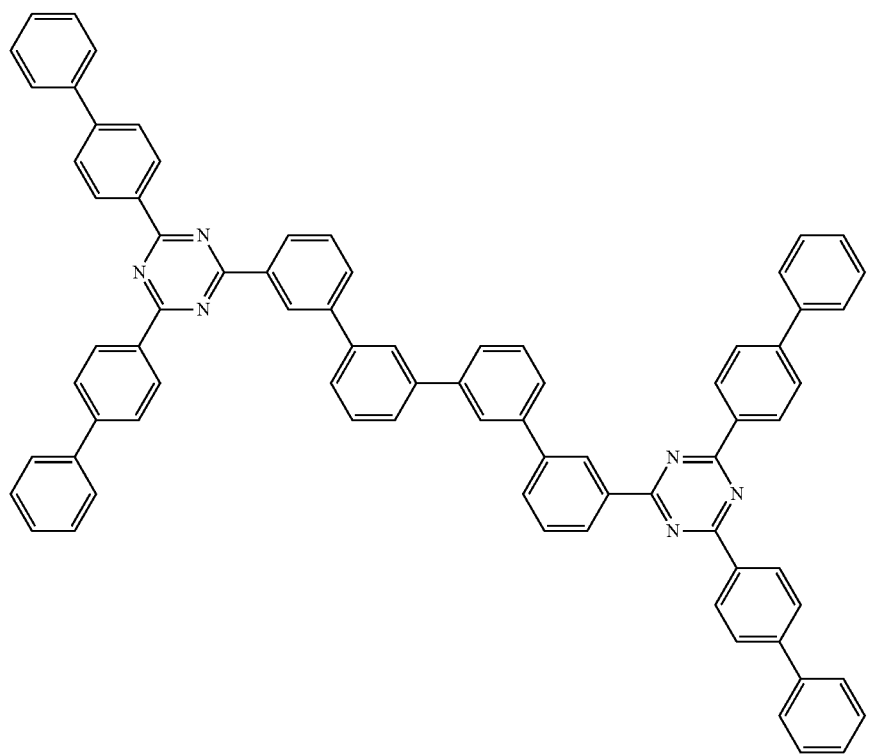
15

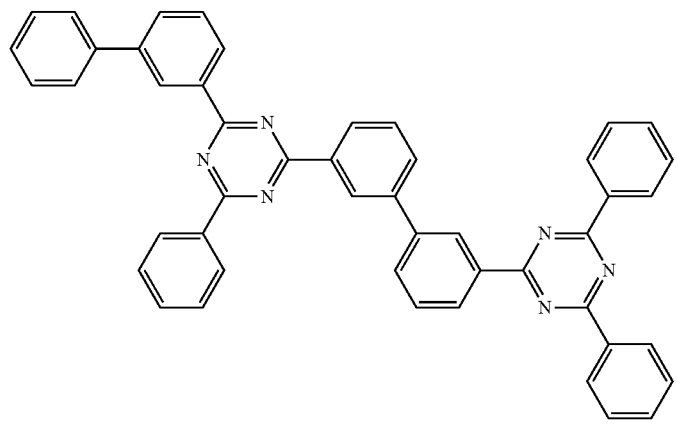
16
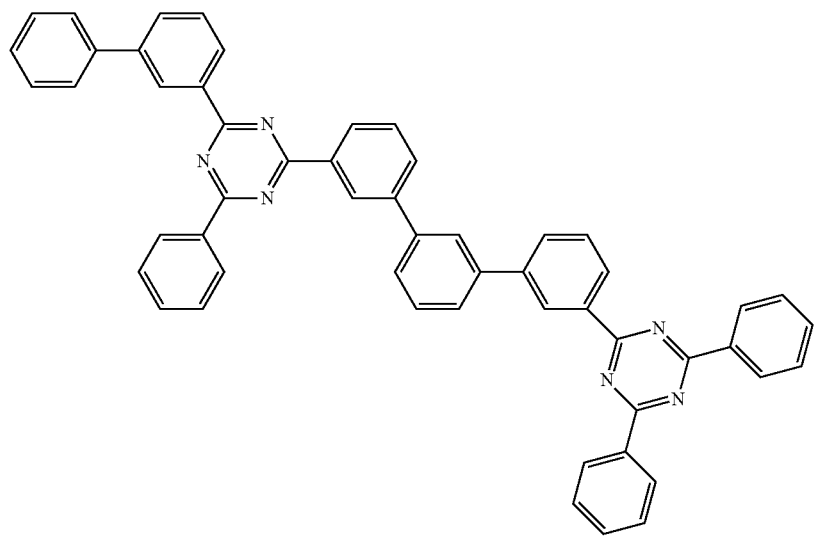
17
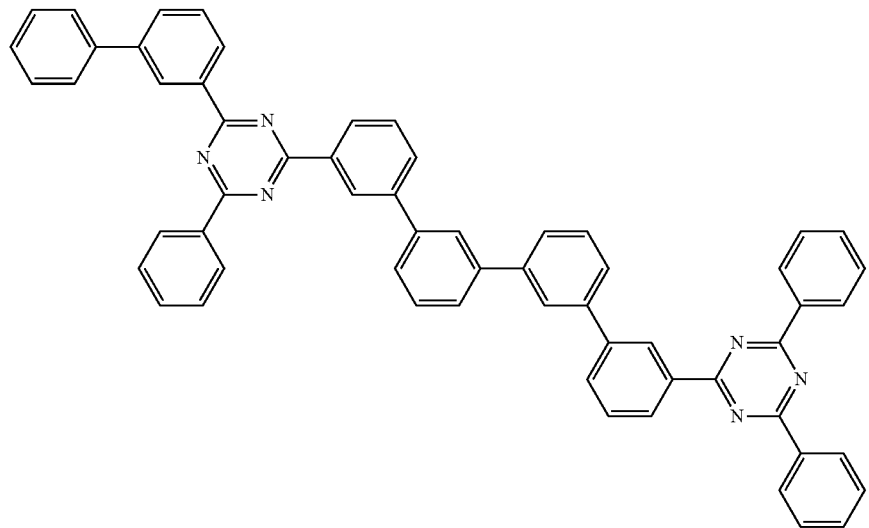
18

-continued
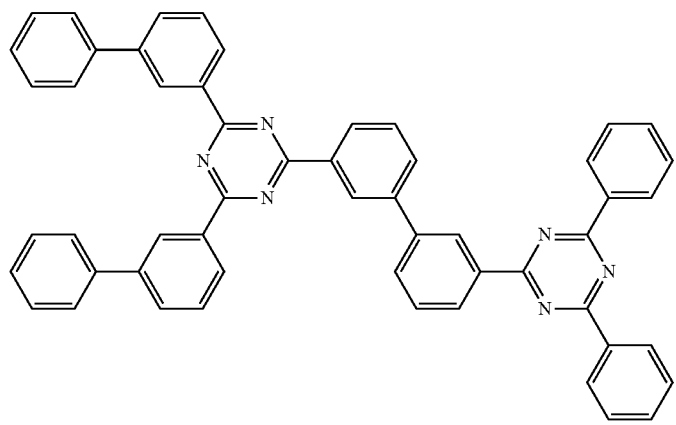
19
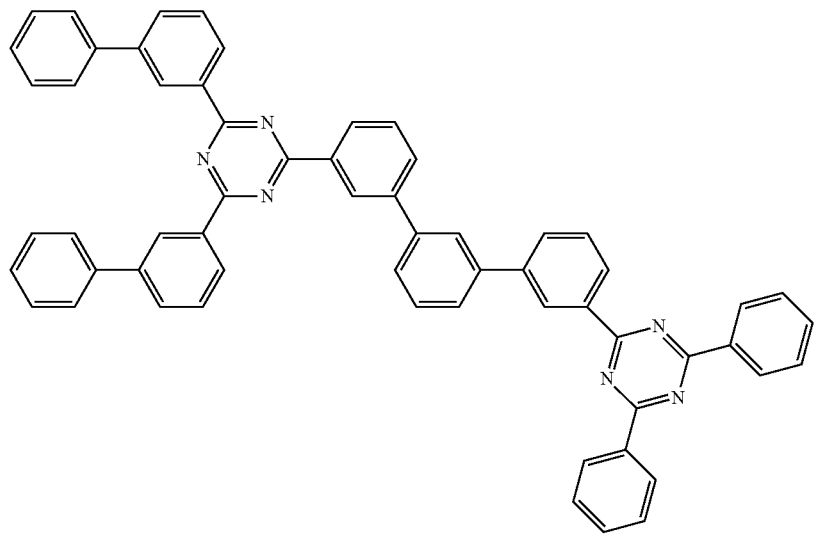
20
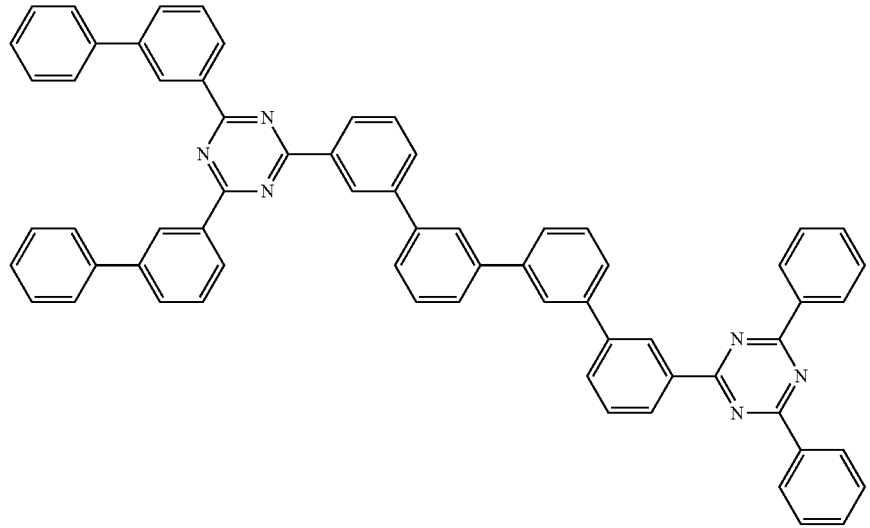
21

22
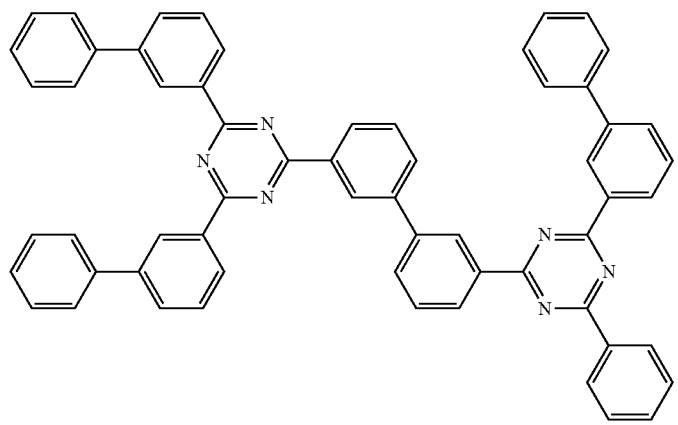
23
24
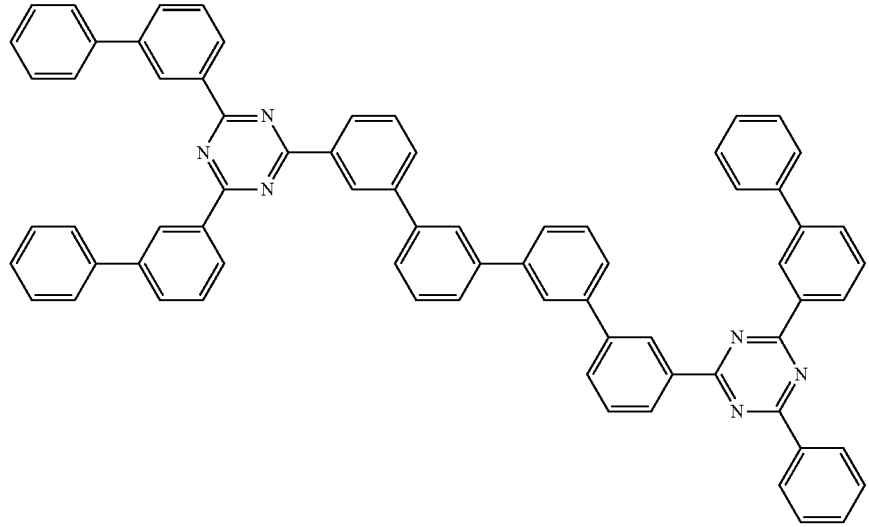

-continued
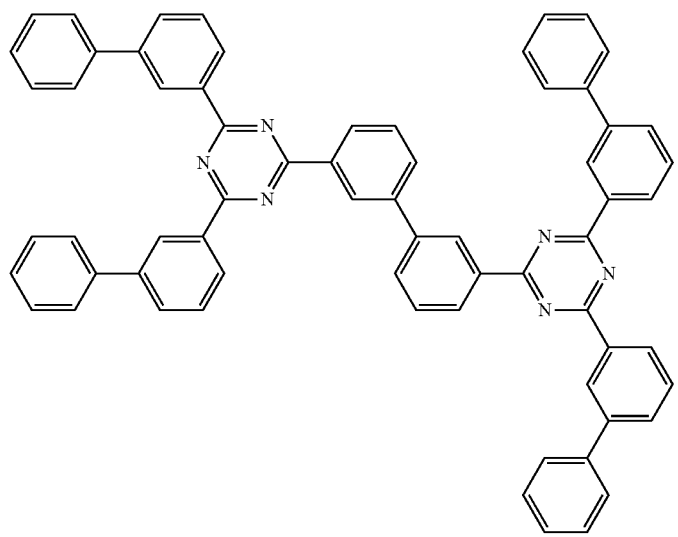
25
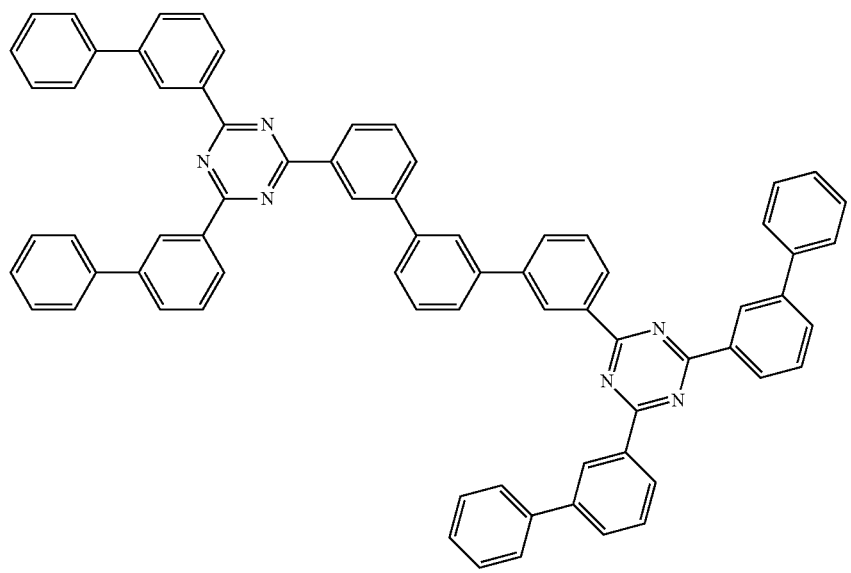
26
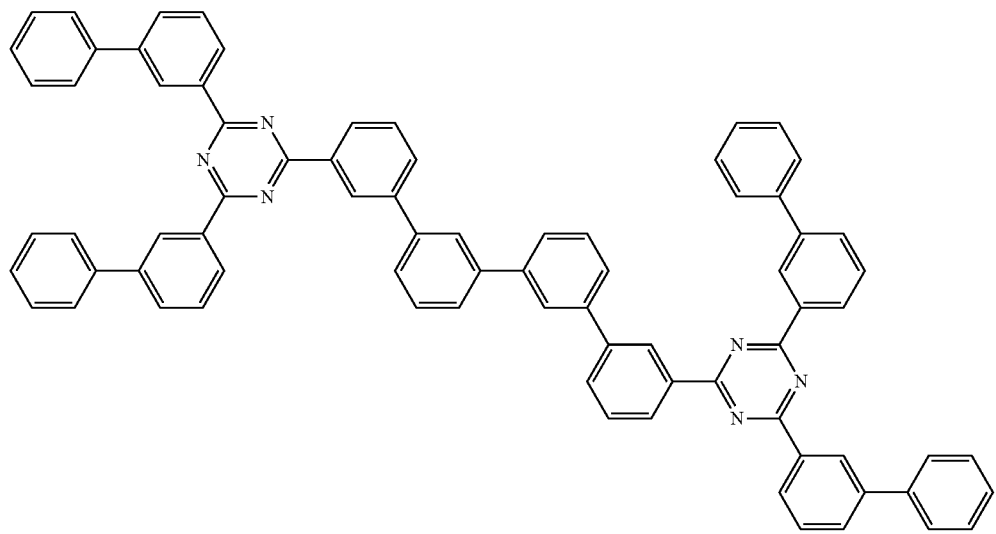
27

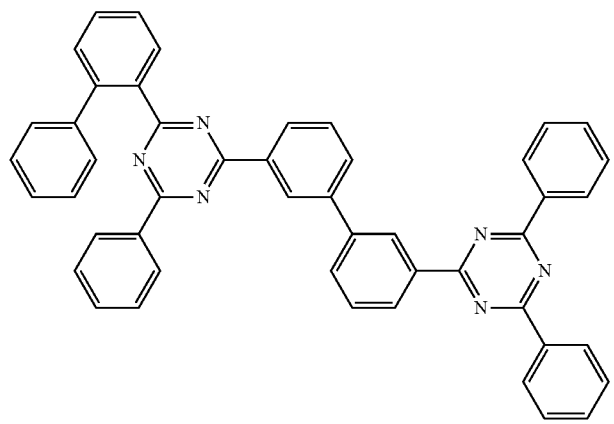
28
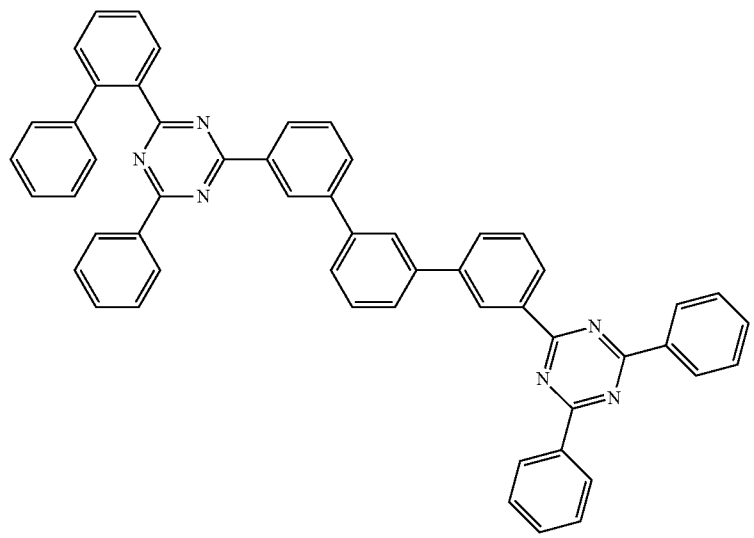
29
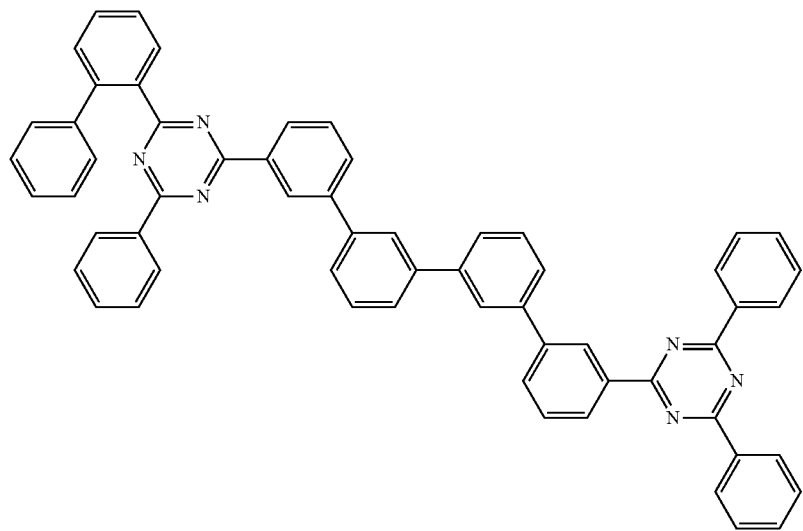
30

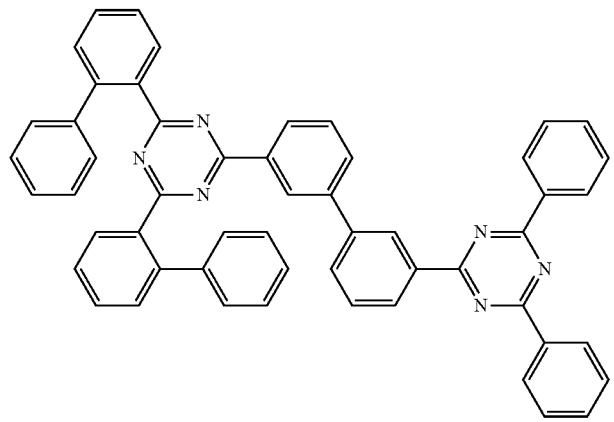
31
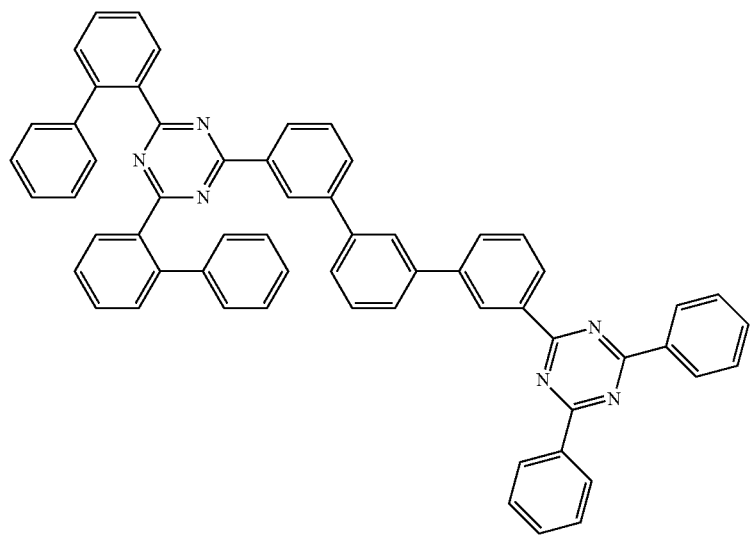
32
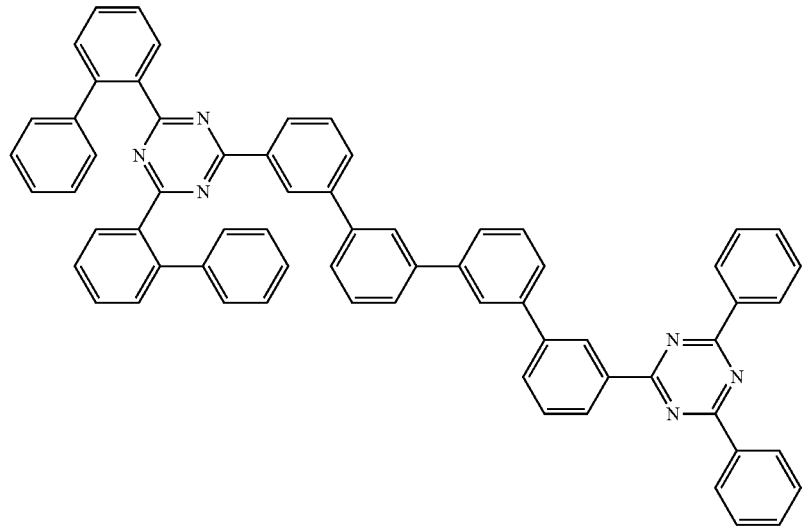
33

34
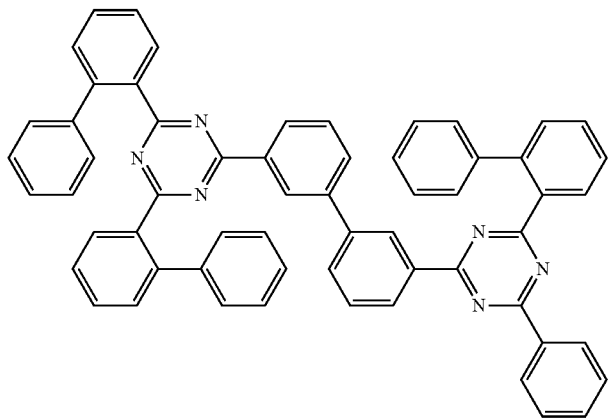
35
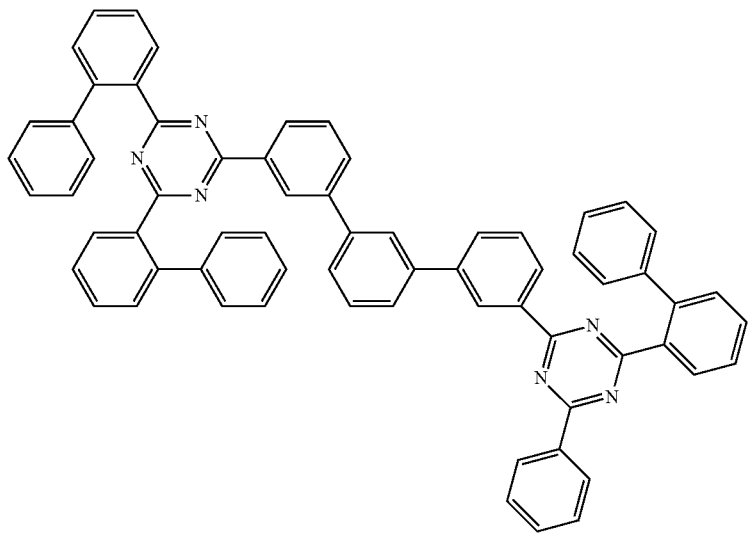
36
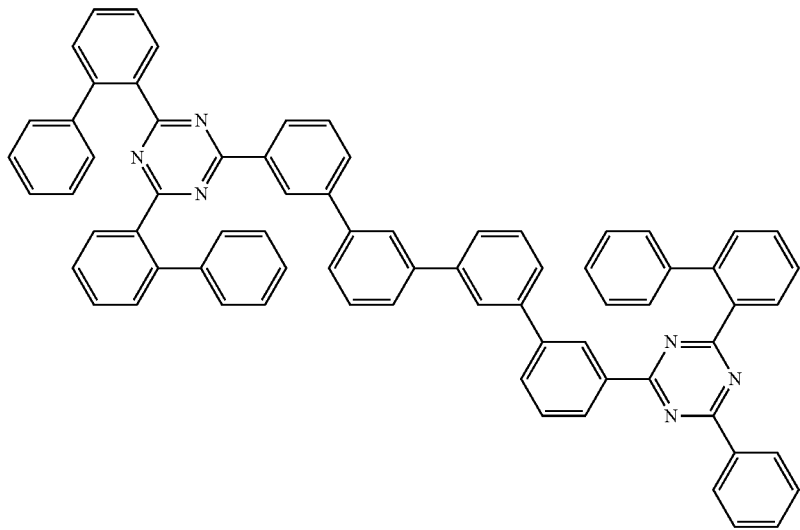

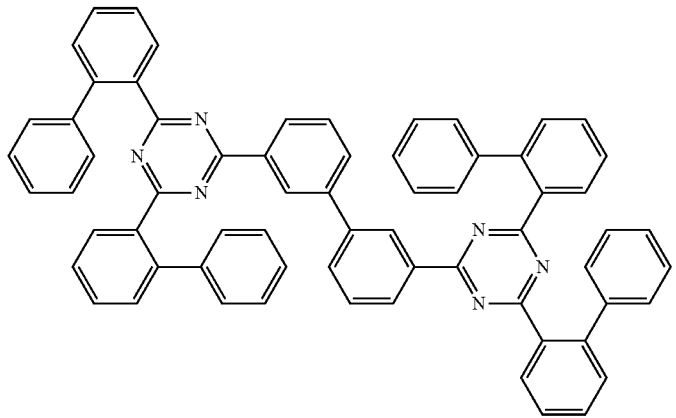
37
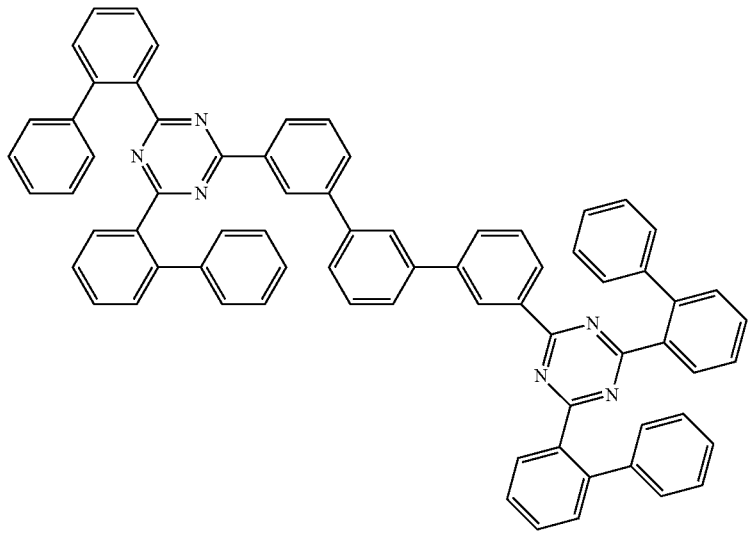
38
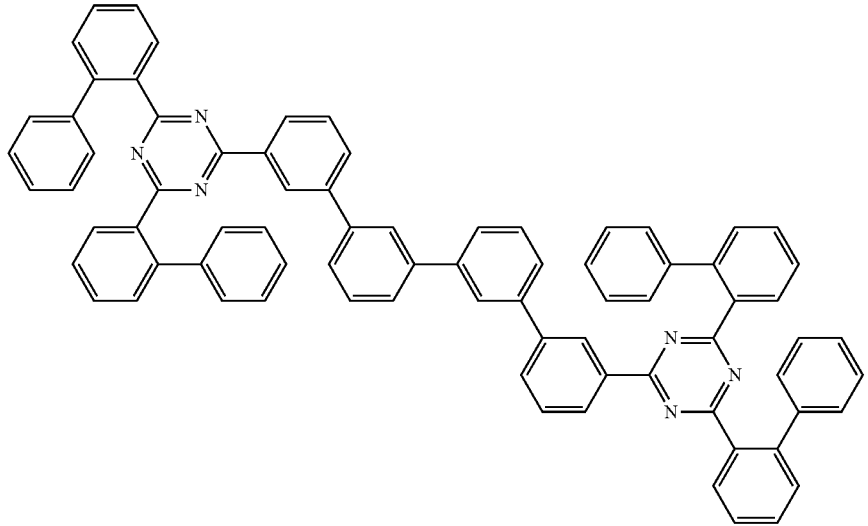
39

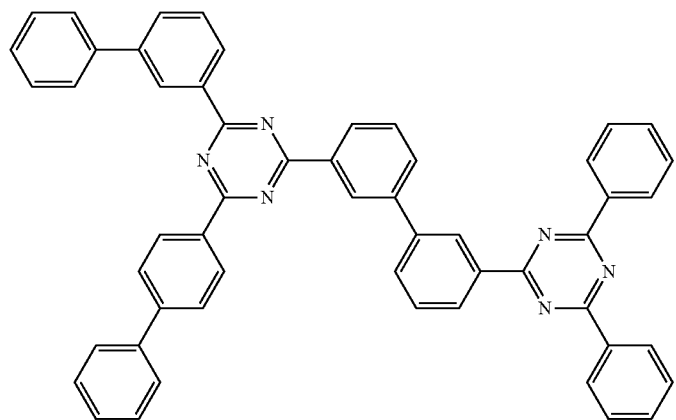
40
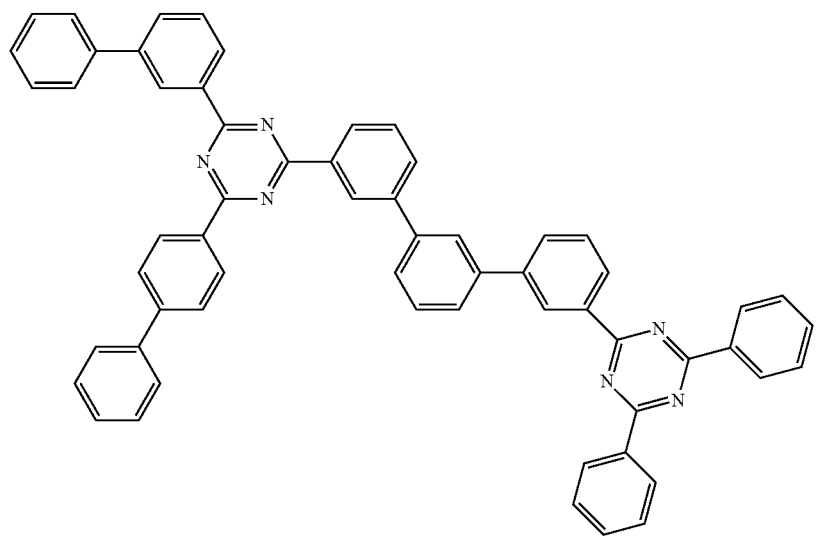
41
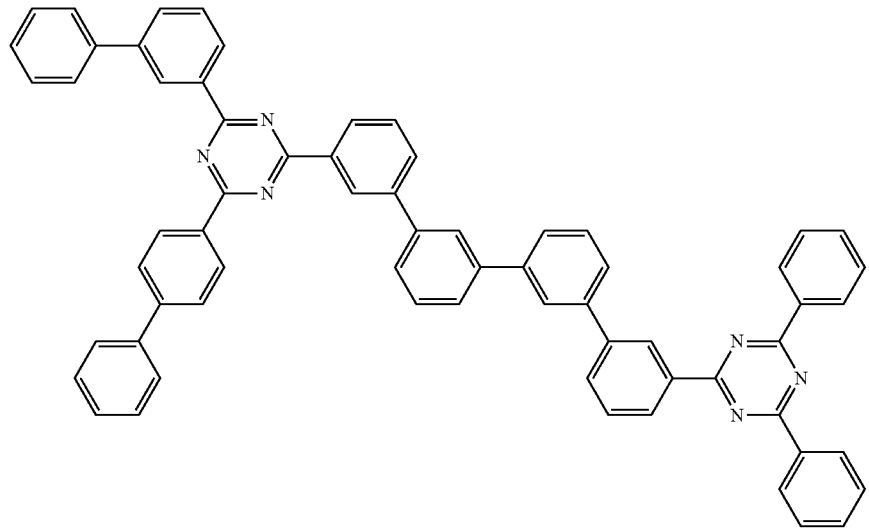
42

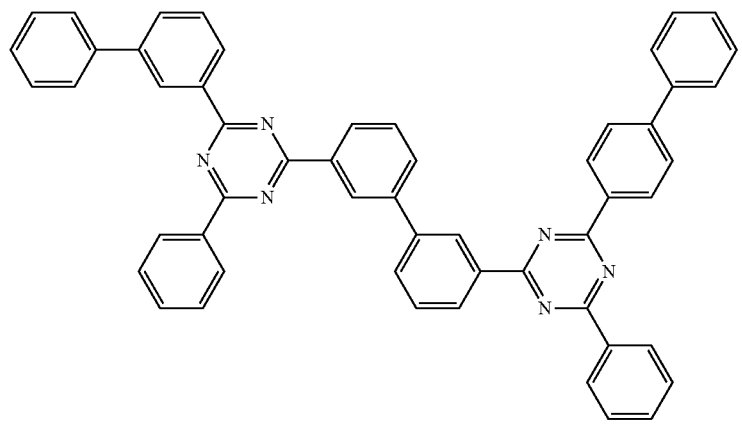
43
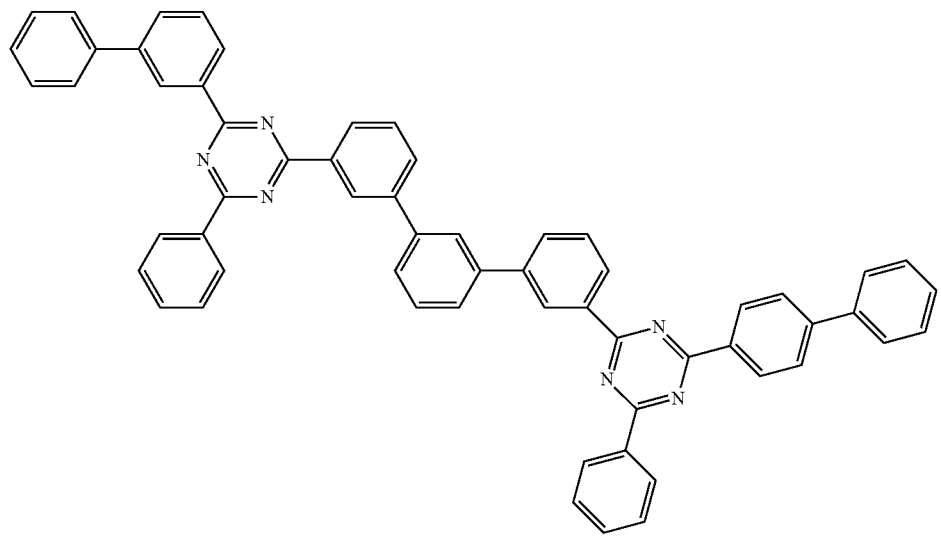
44
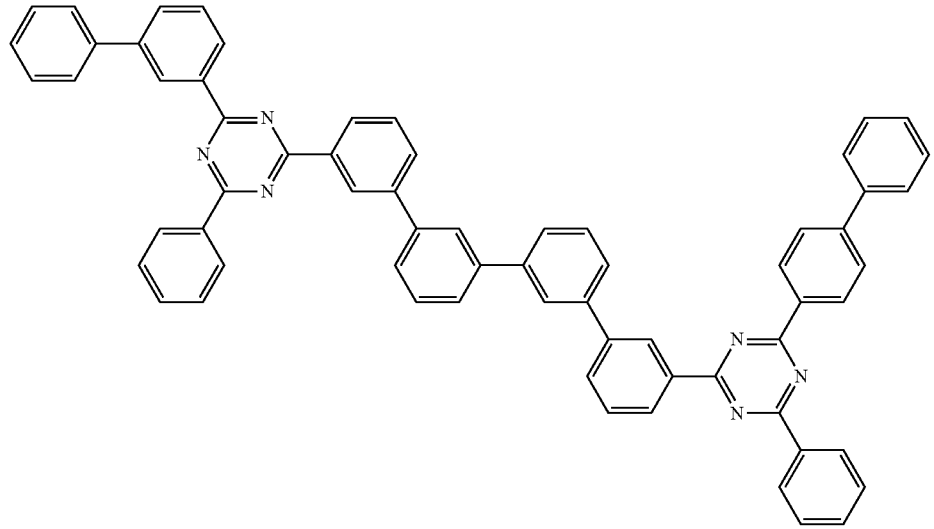
45

46
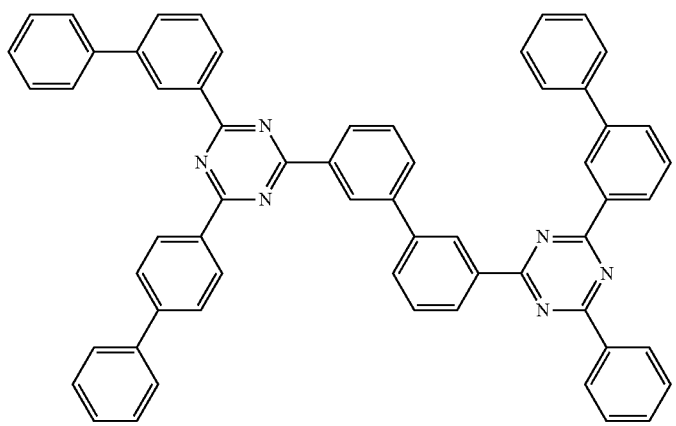
47
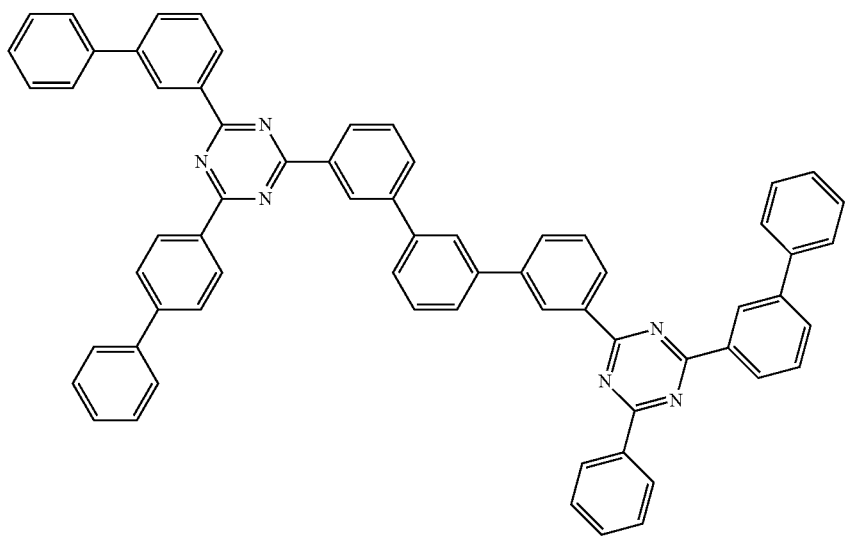
48
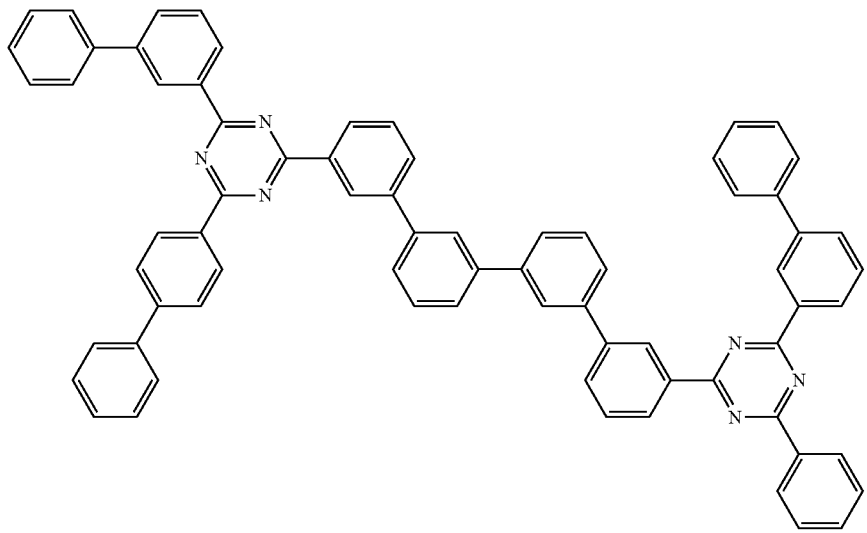

-continued
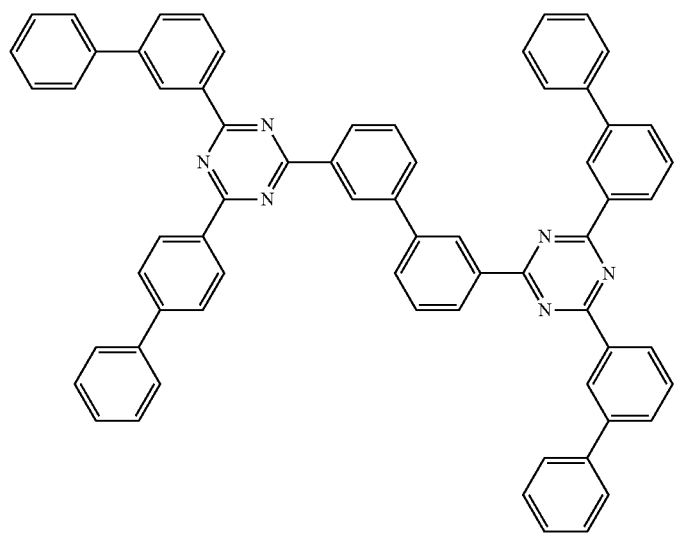
49
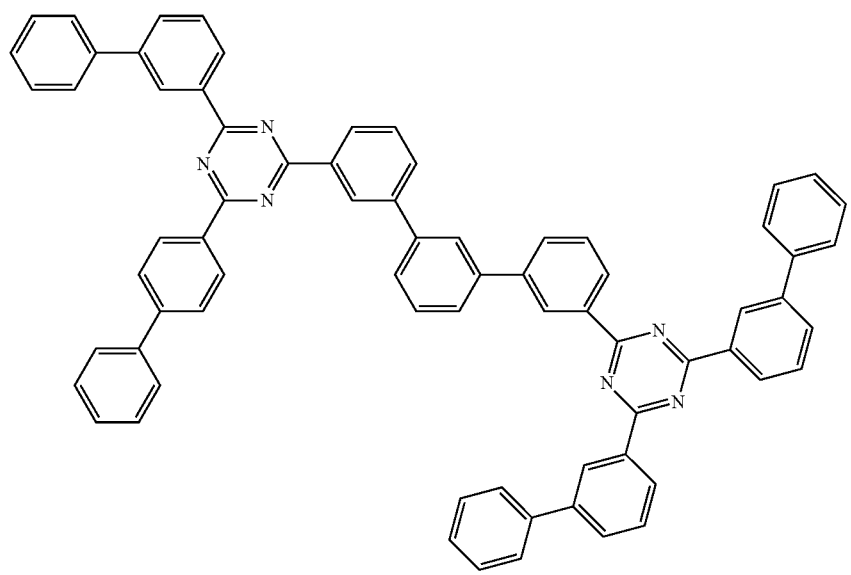
50
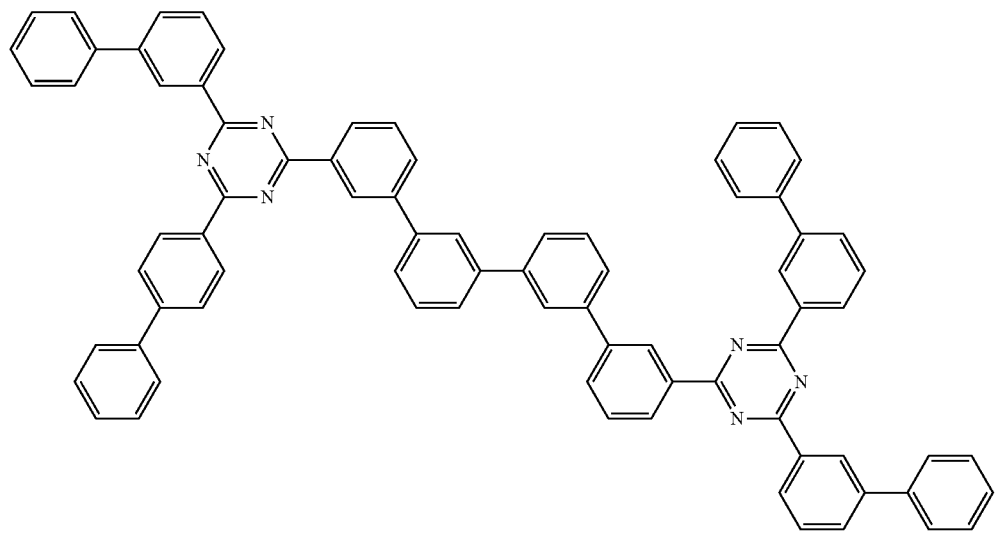
51

52
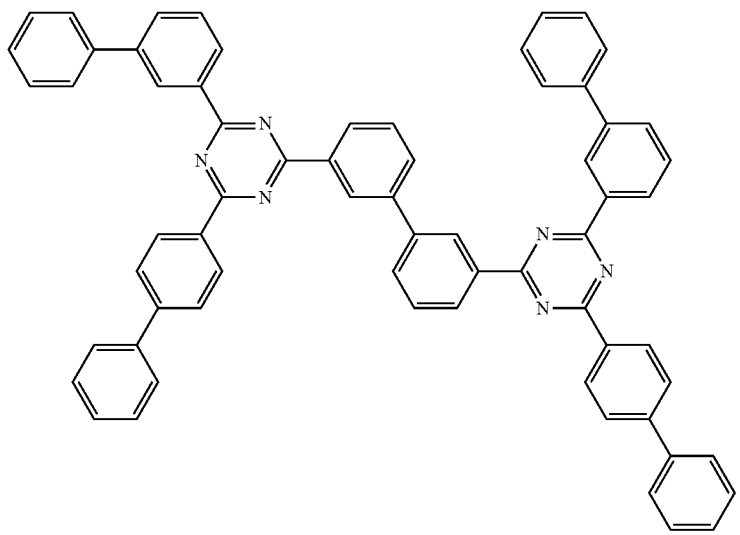
53
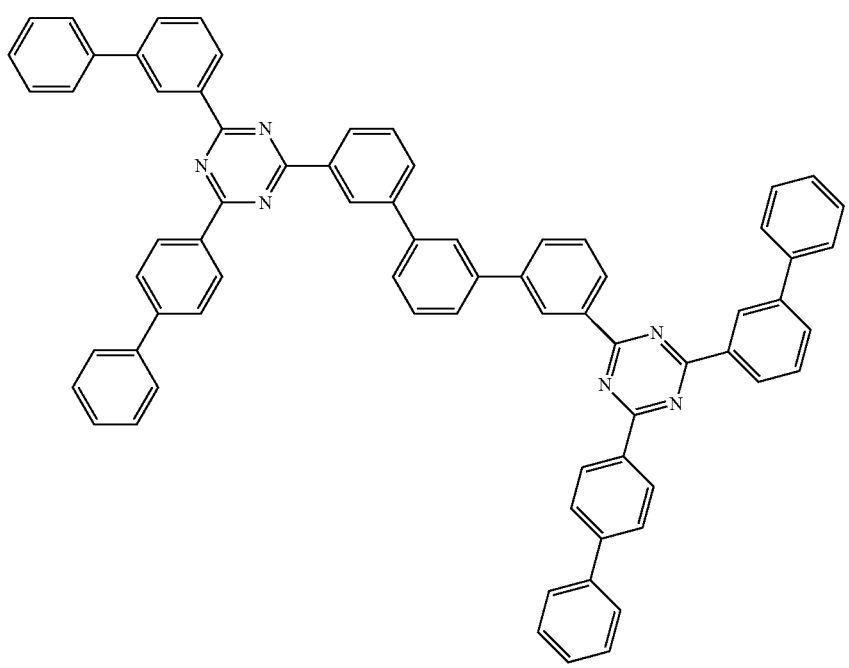

-continued
54
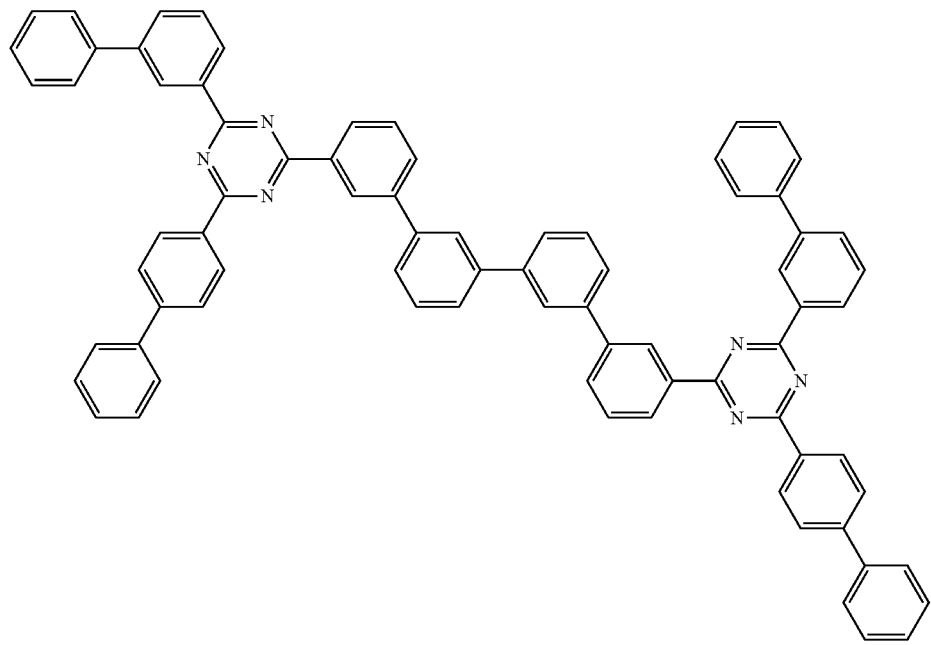
55
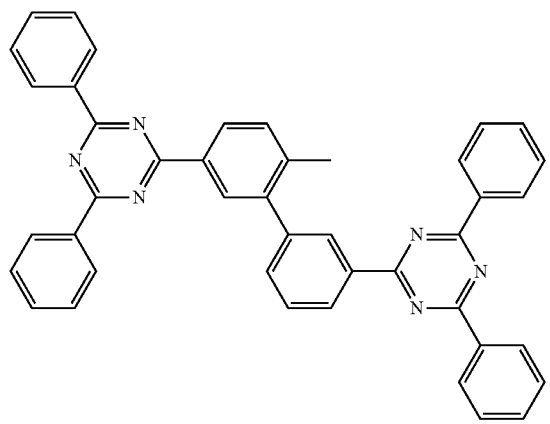
56
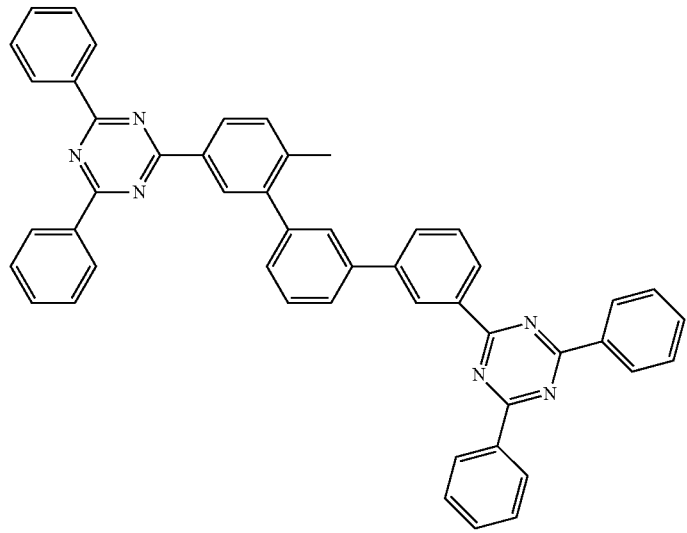

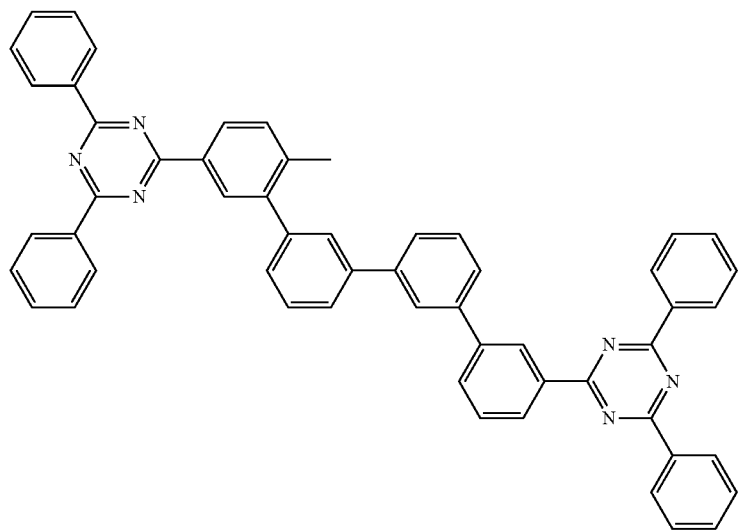
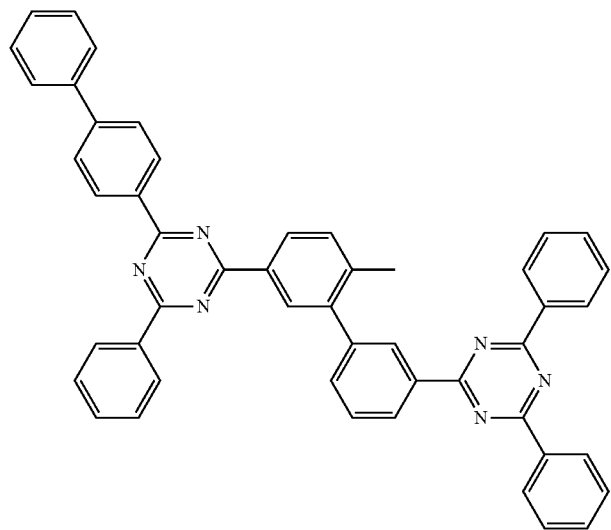

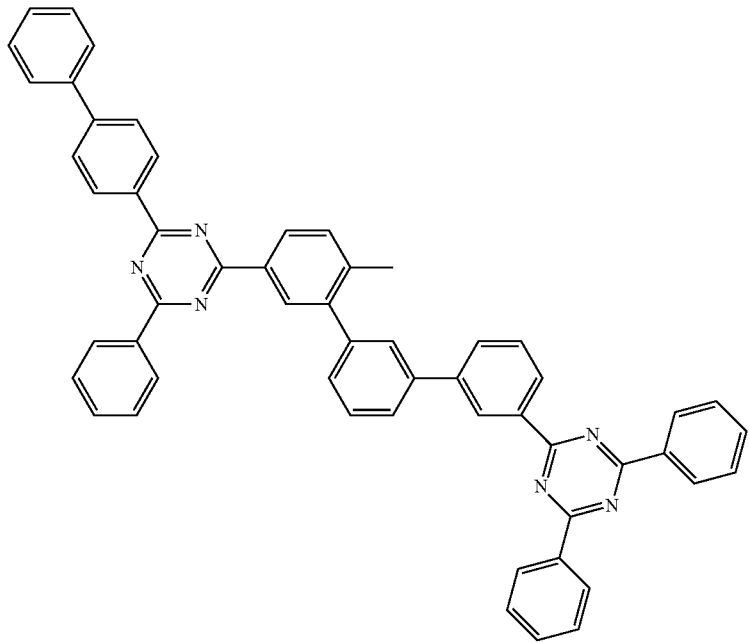
59
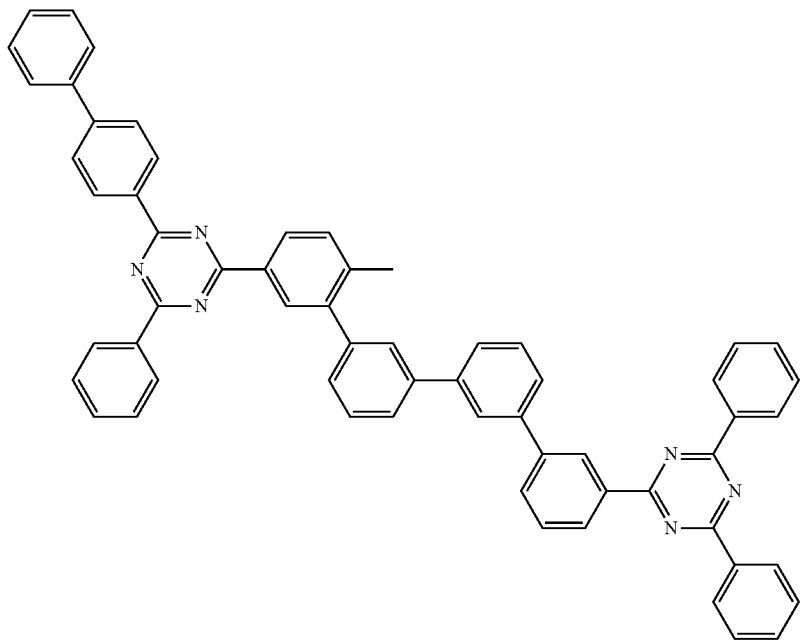
60

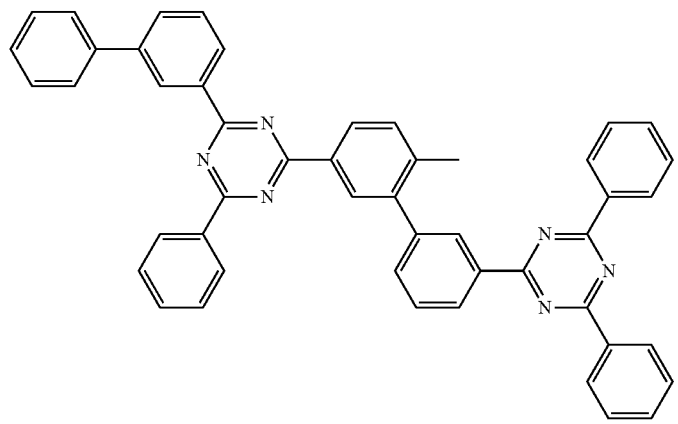
61
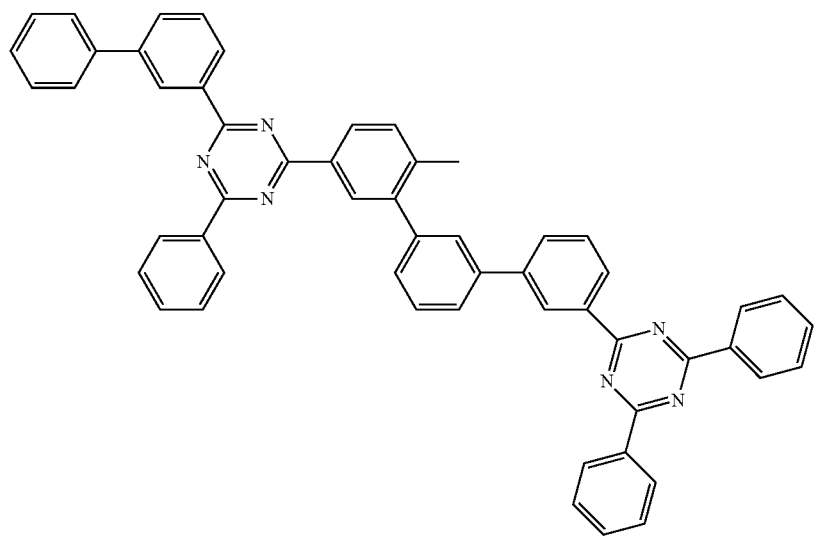
62
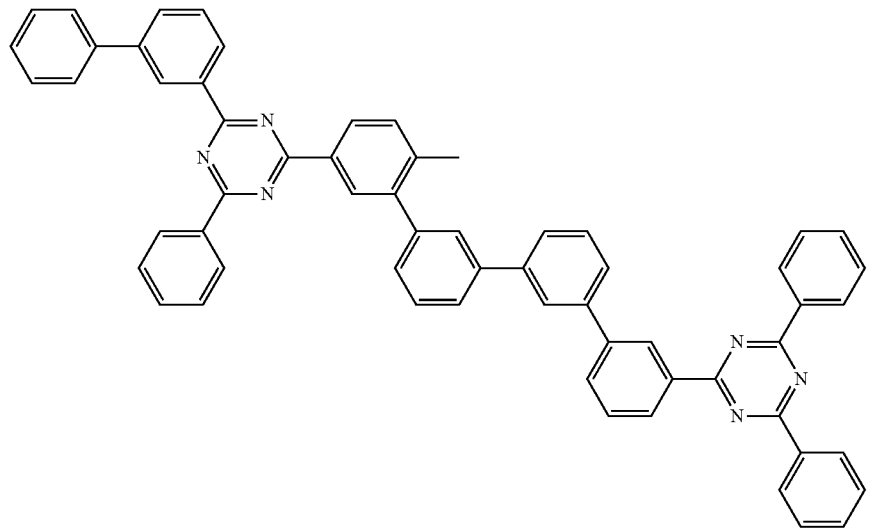
63

64
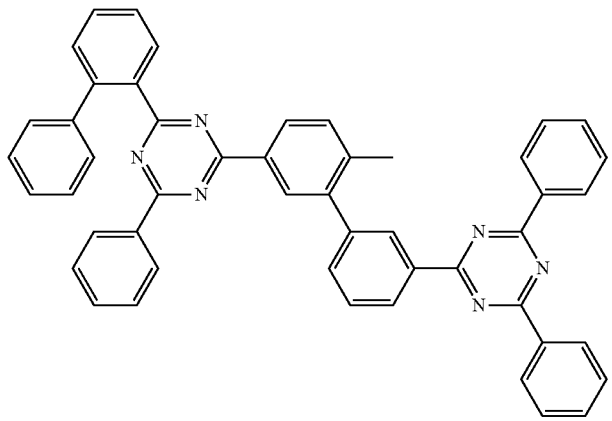
65
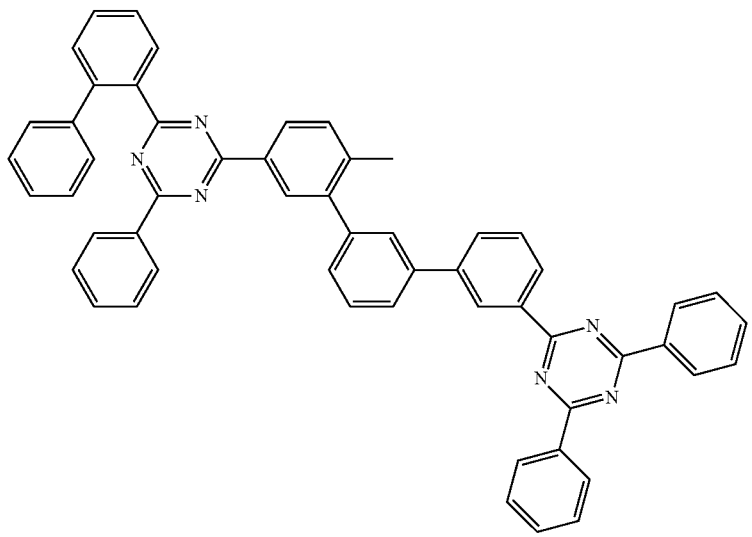
66
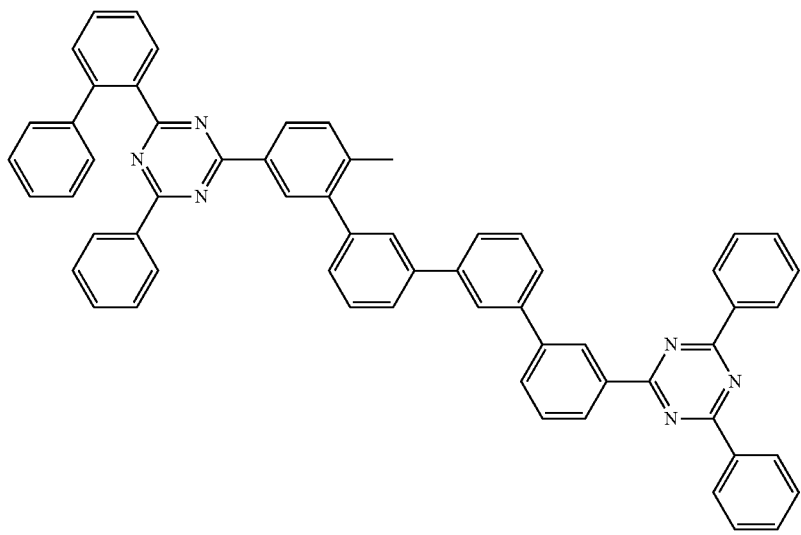

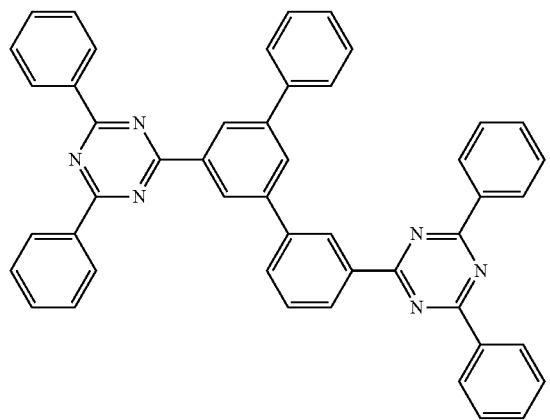
67
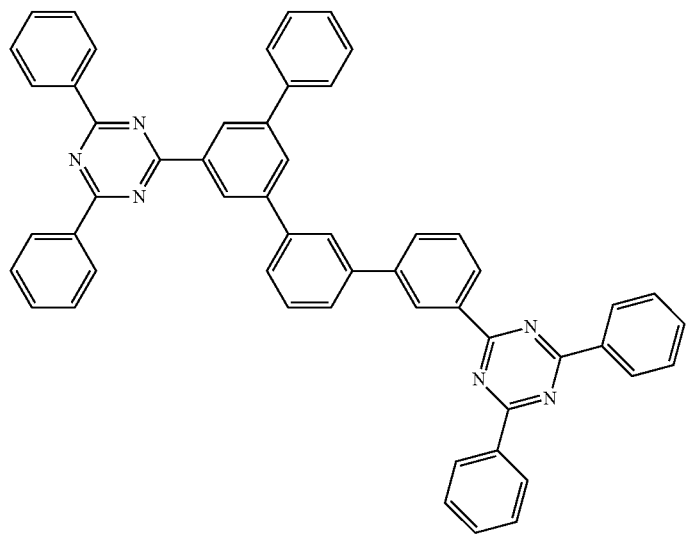
68
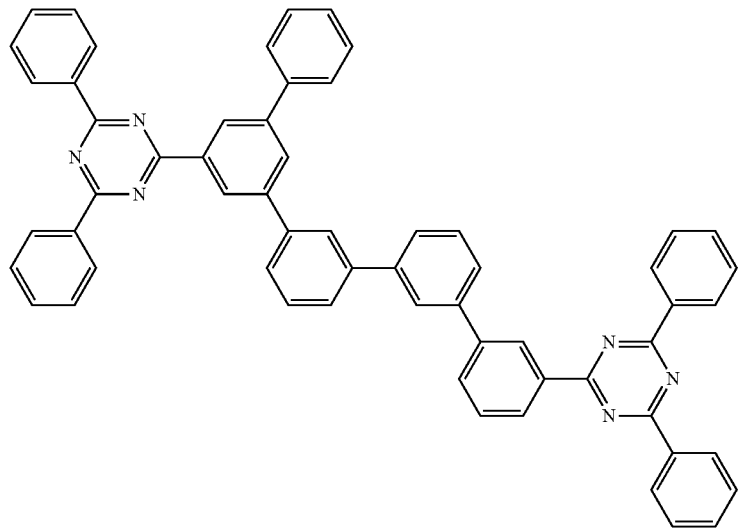
69

-continued
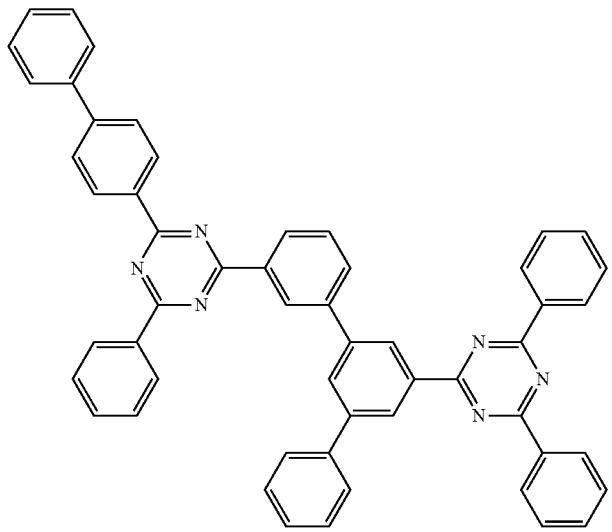
70
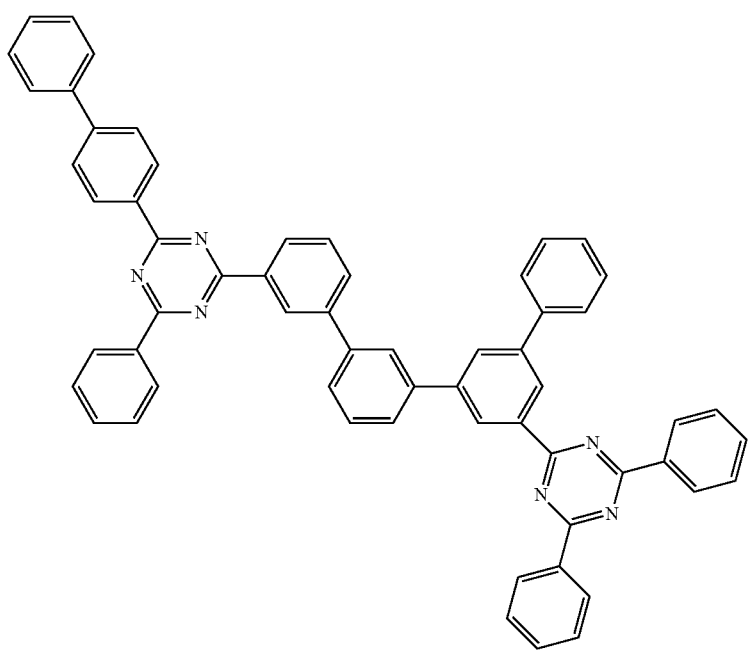
71

72
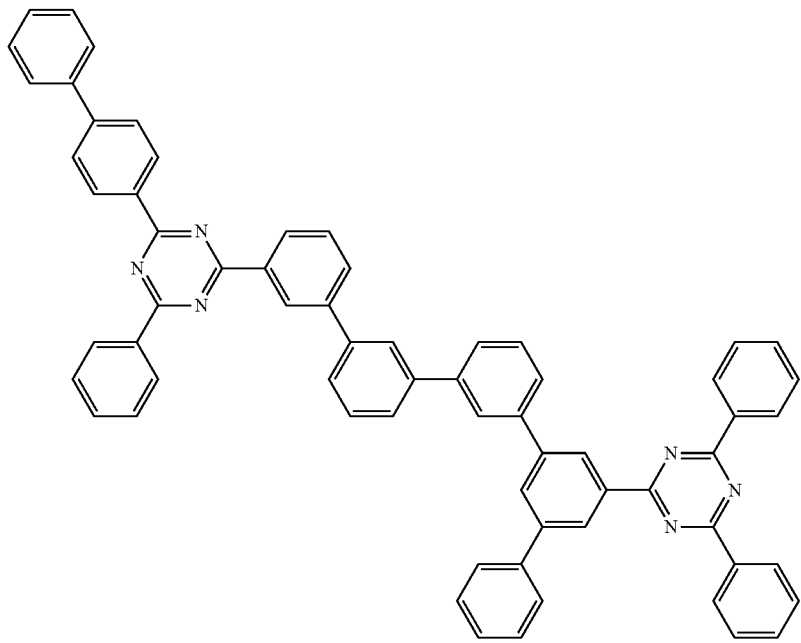
73
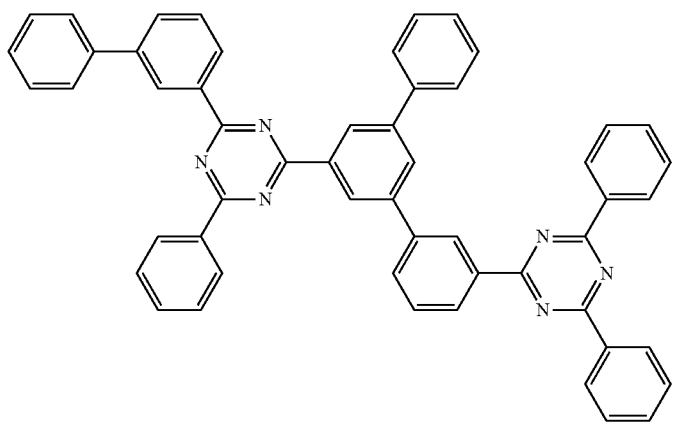
74
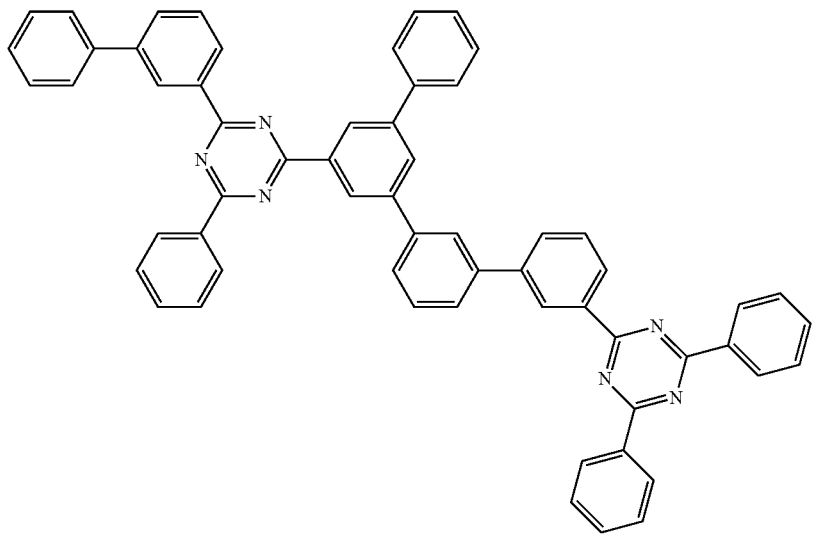

-continued
75
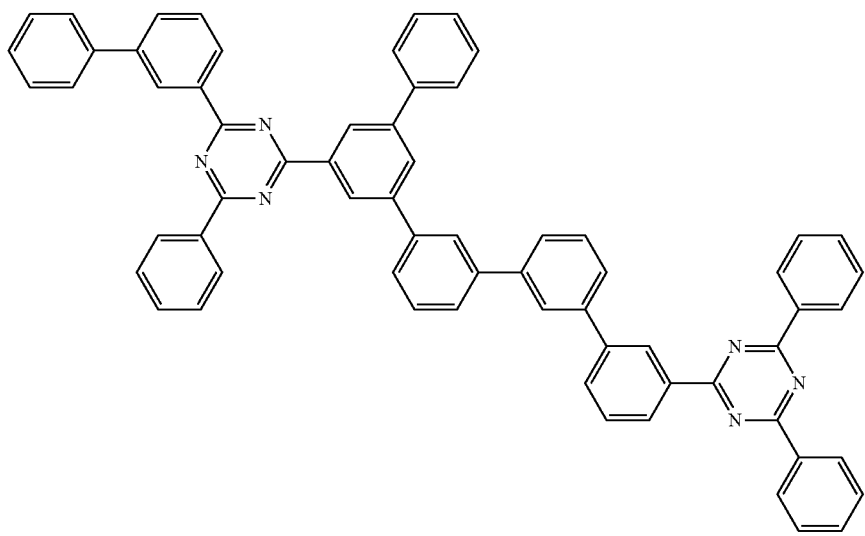
76
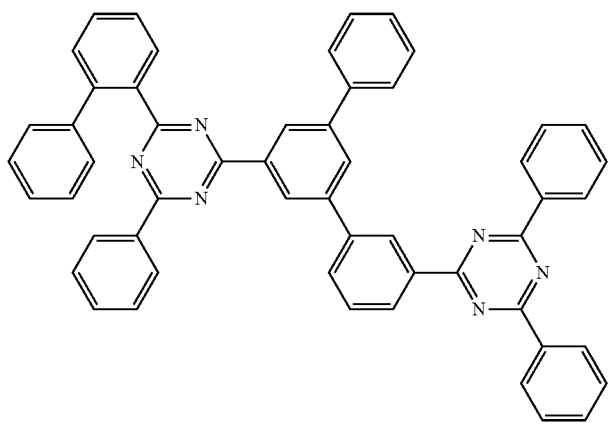
77
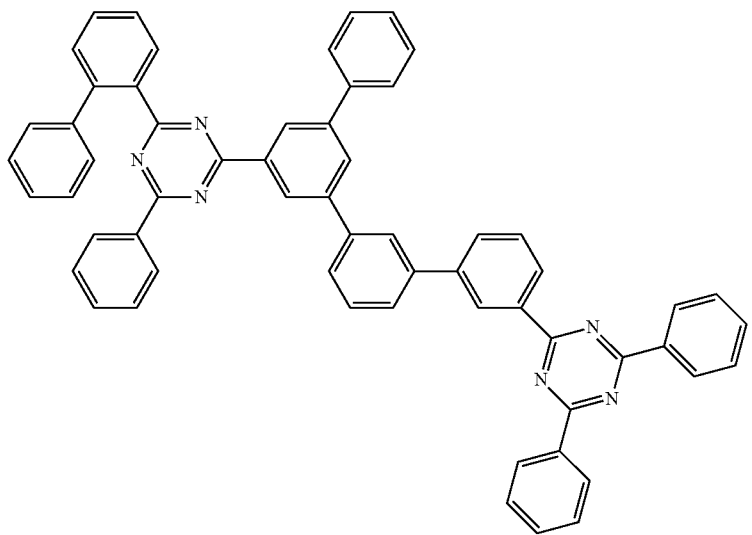

78
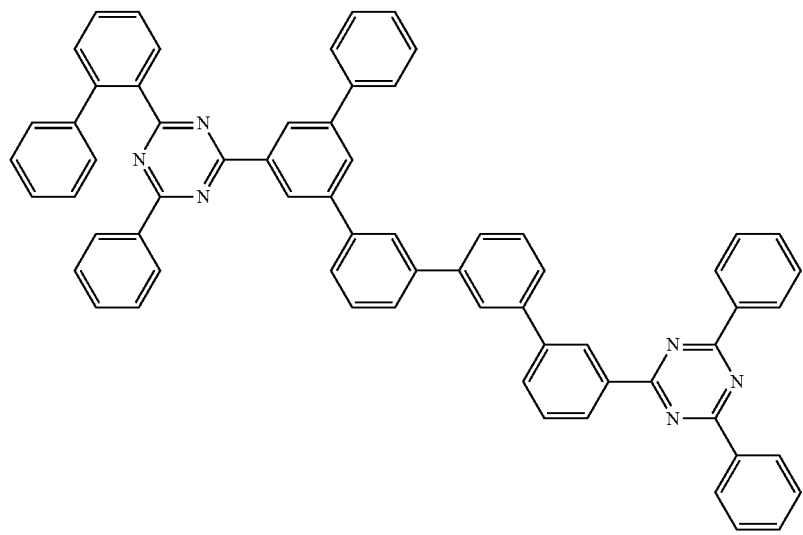
79
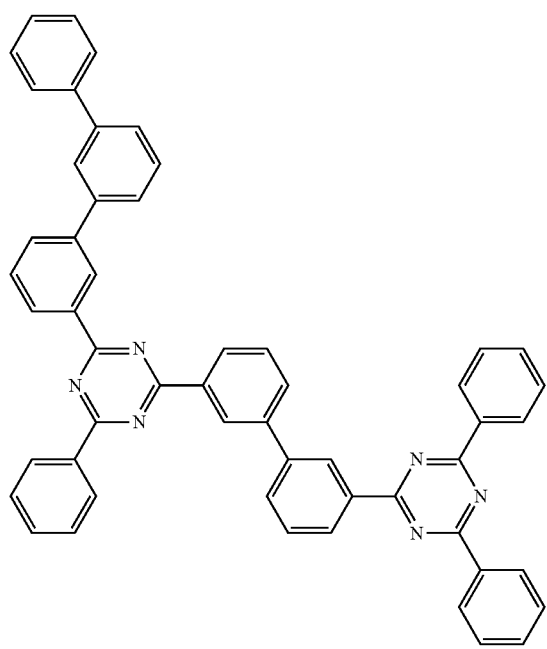

-continued
80
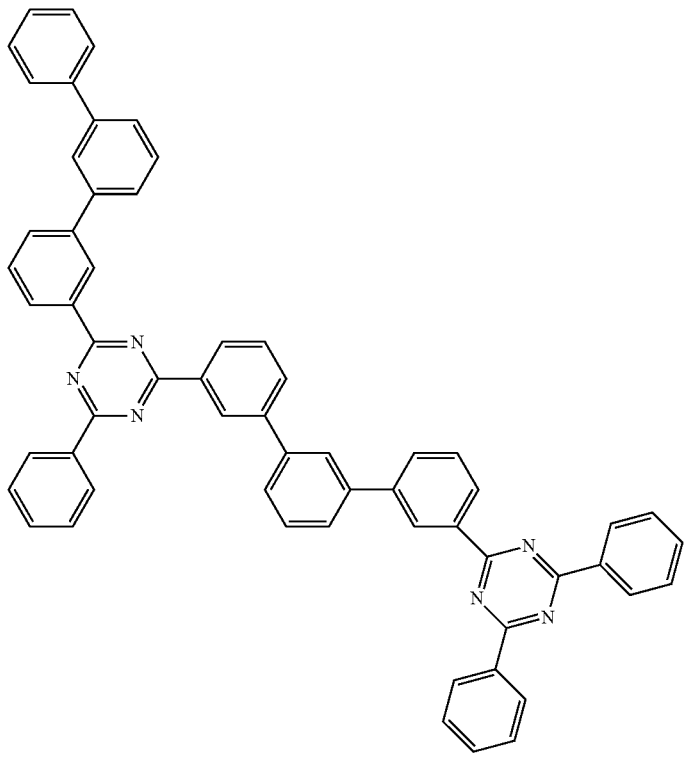
81
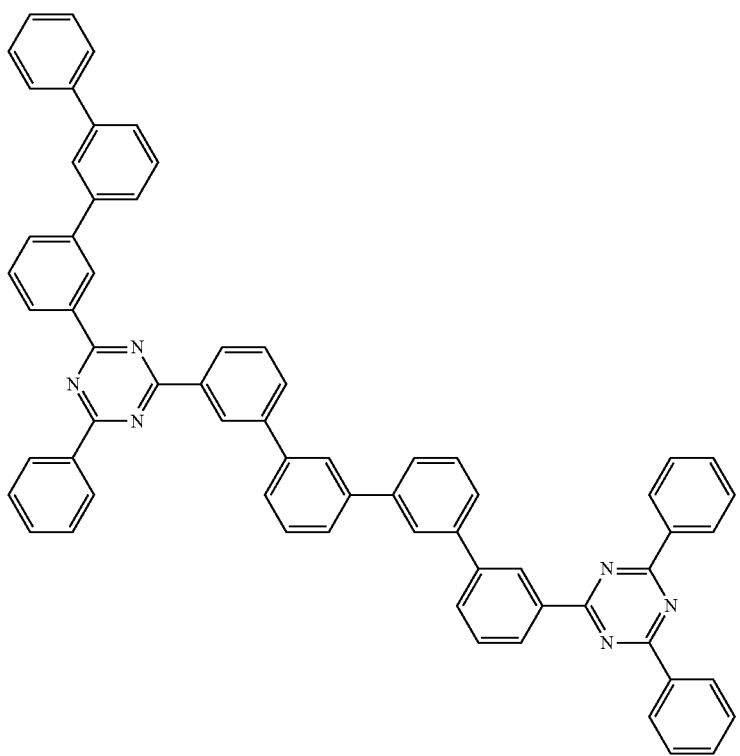

-continued
82
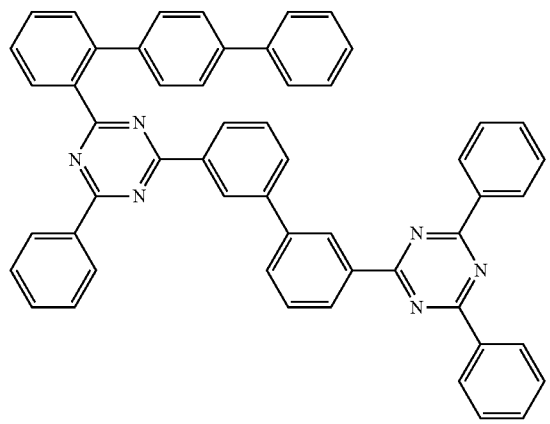
83
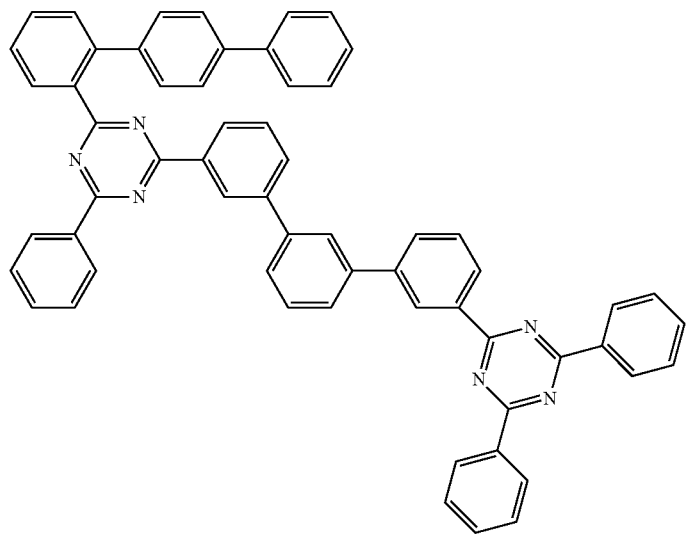
84
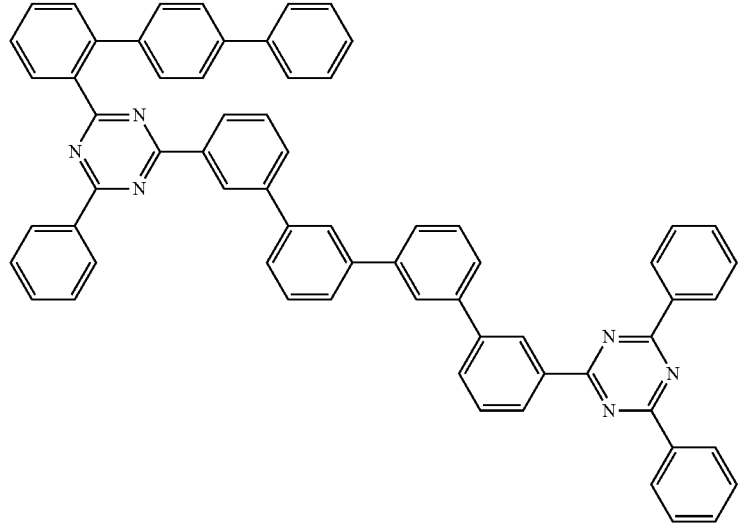

85
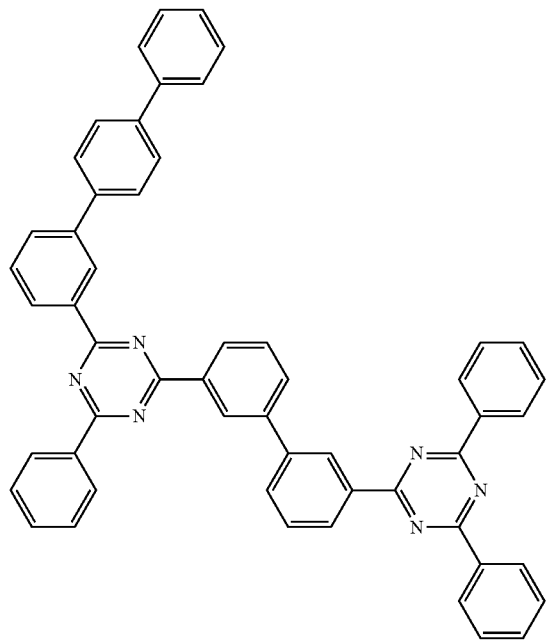
86
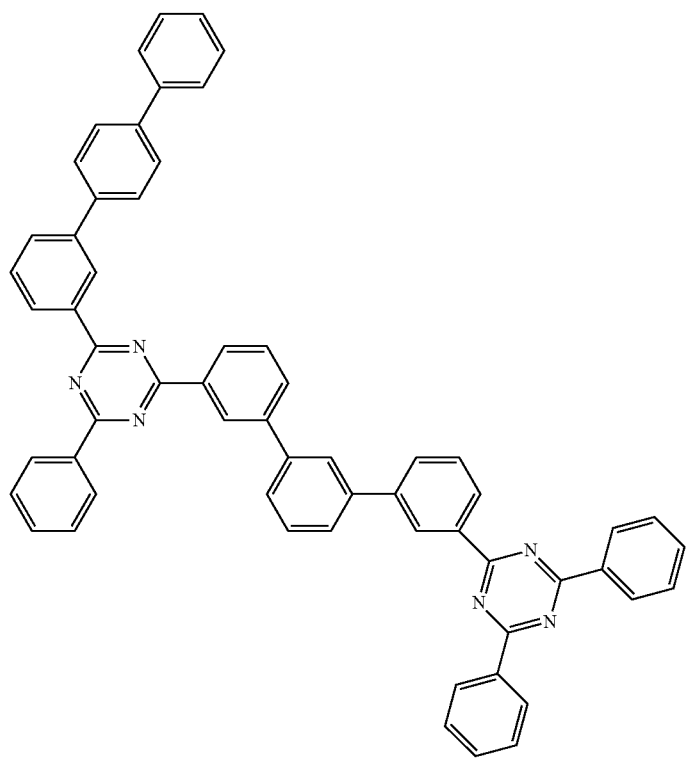

87
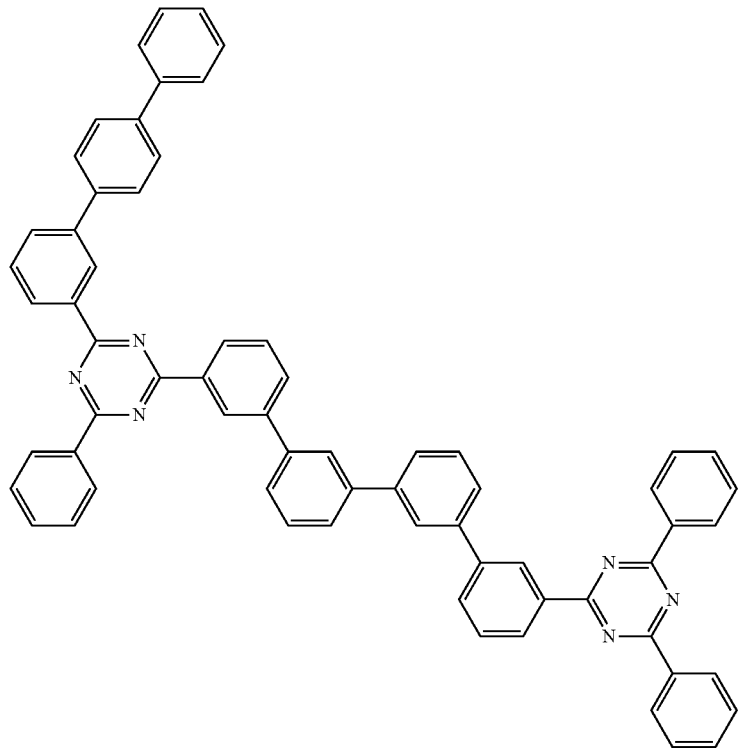
88
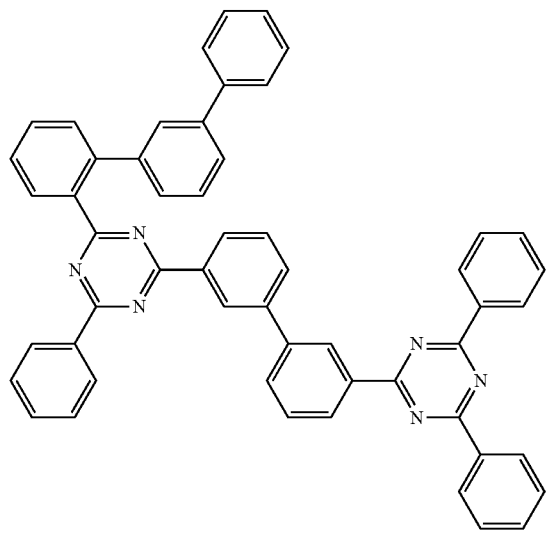

89
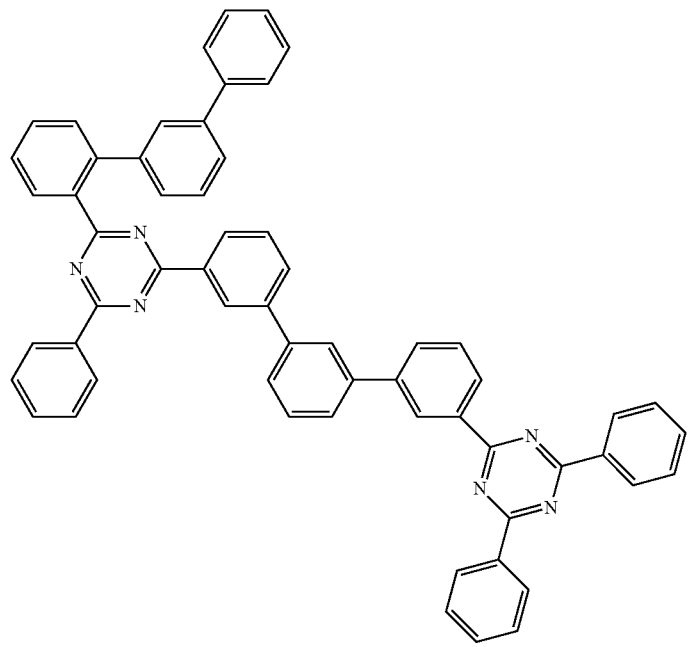
90
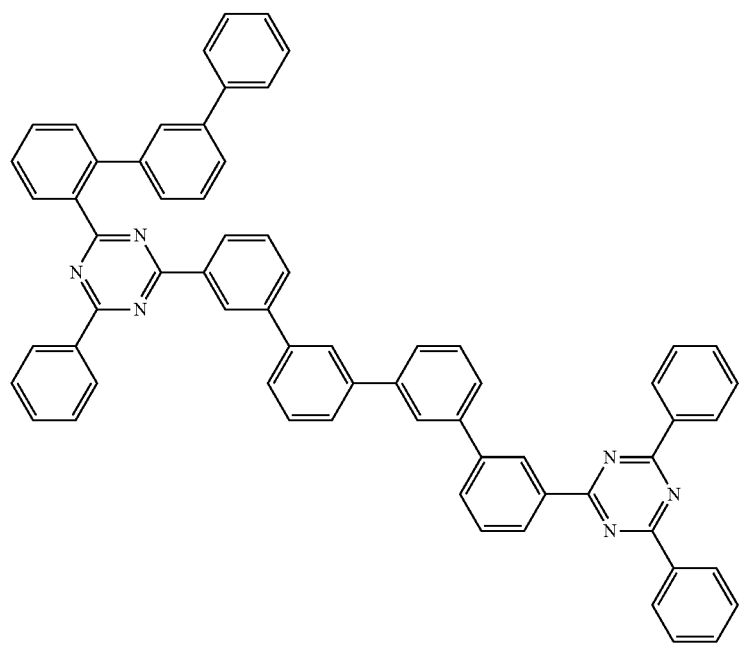

91
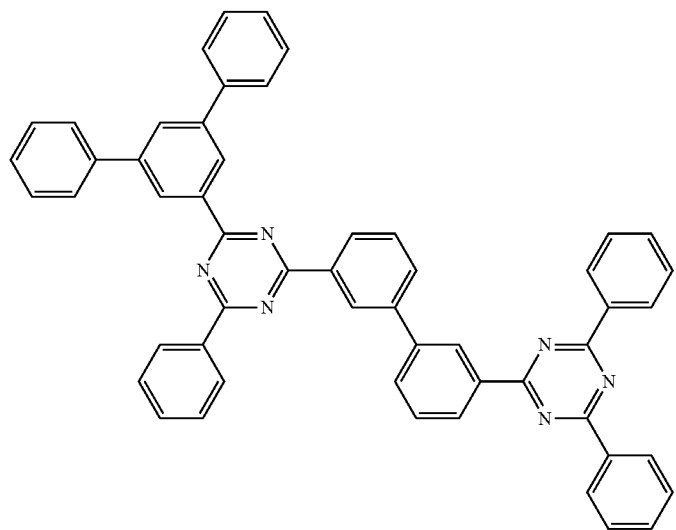
92
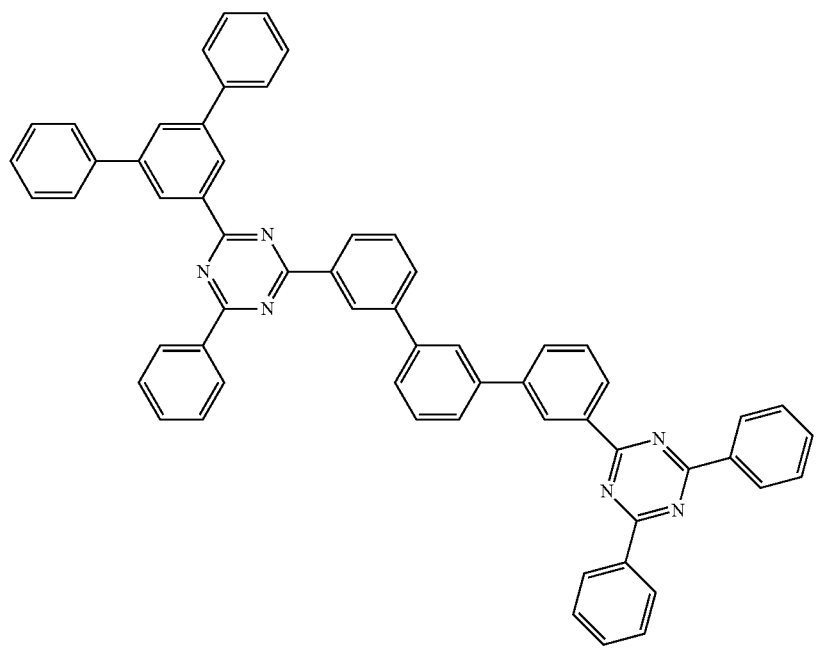

93
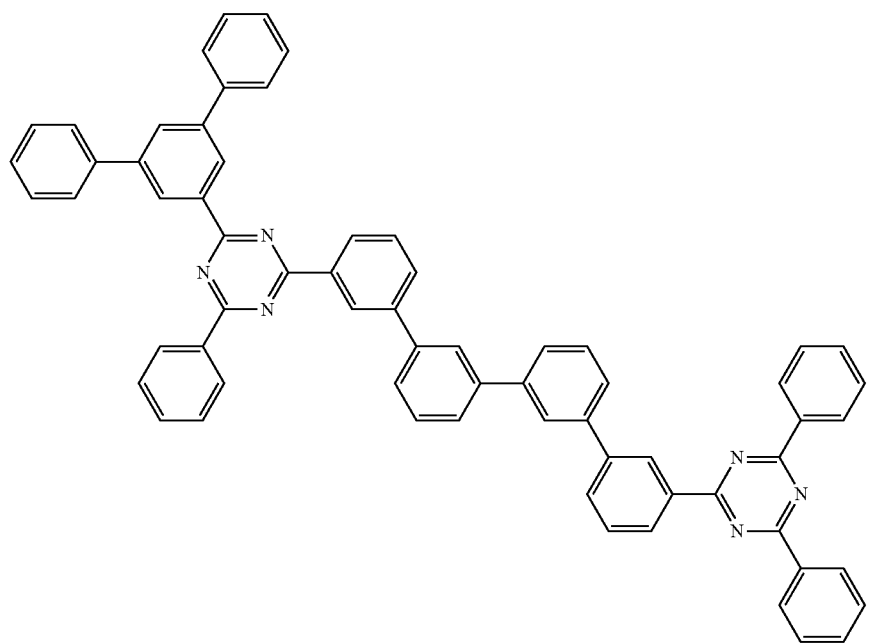
94
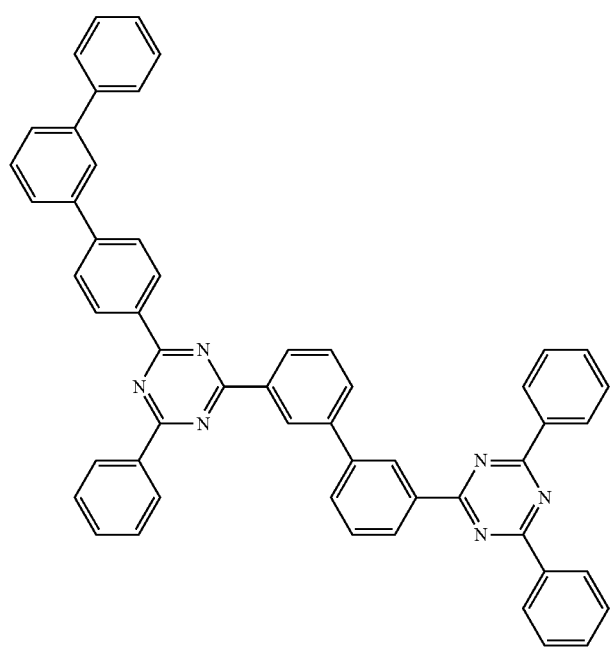

95
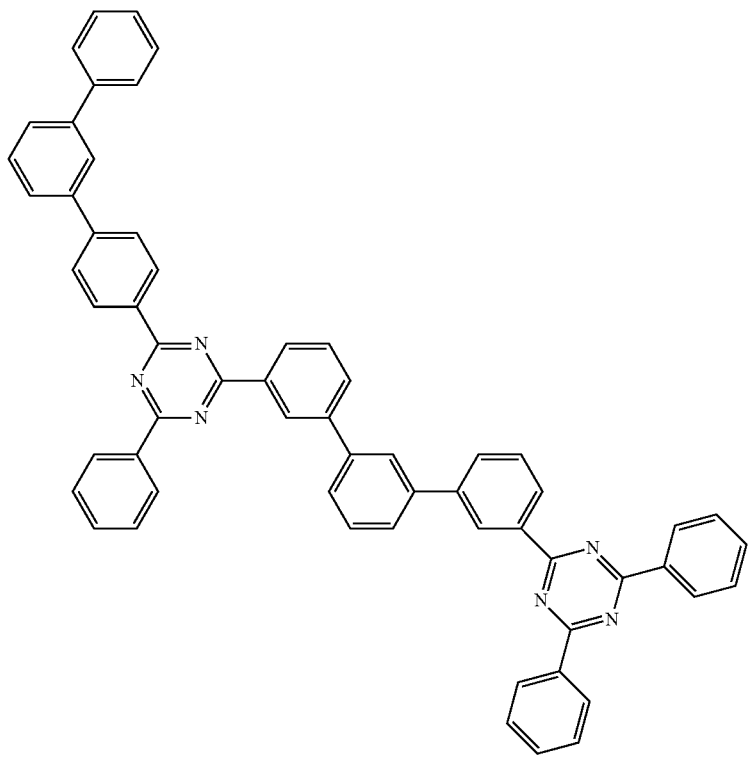
96
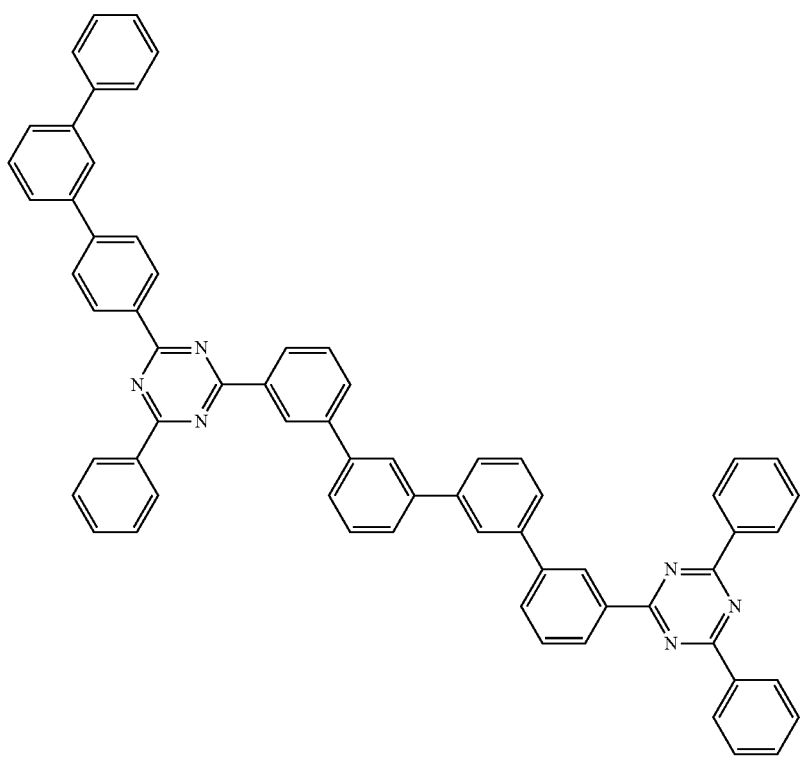

97
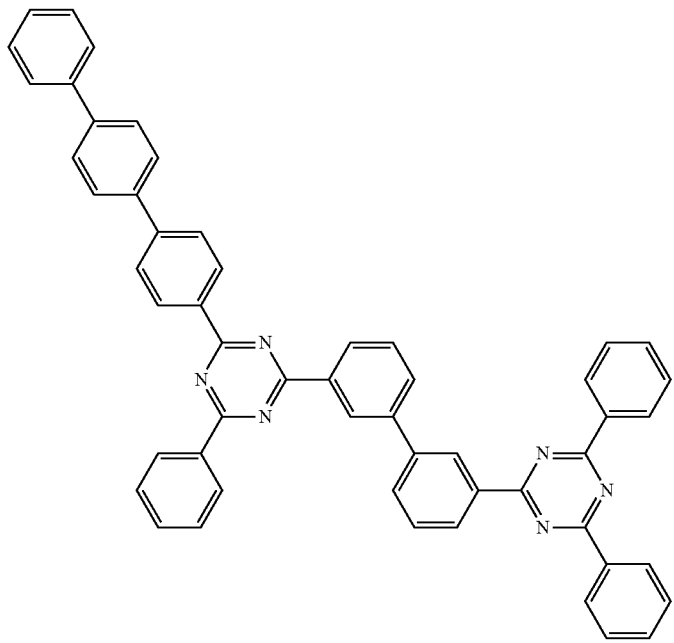
98
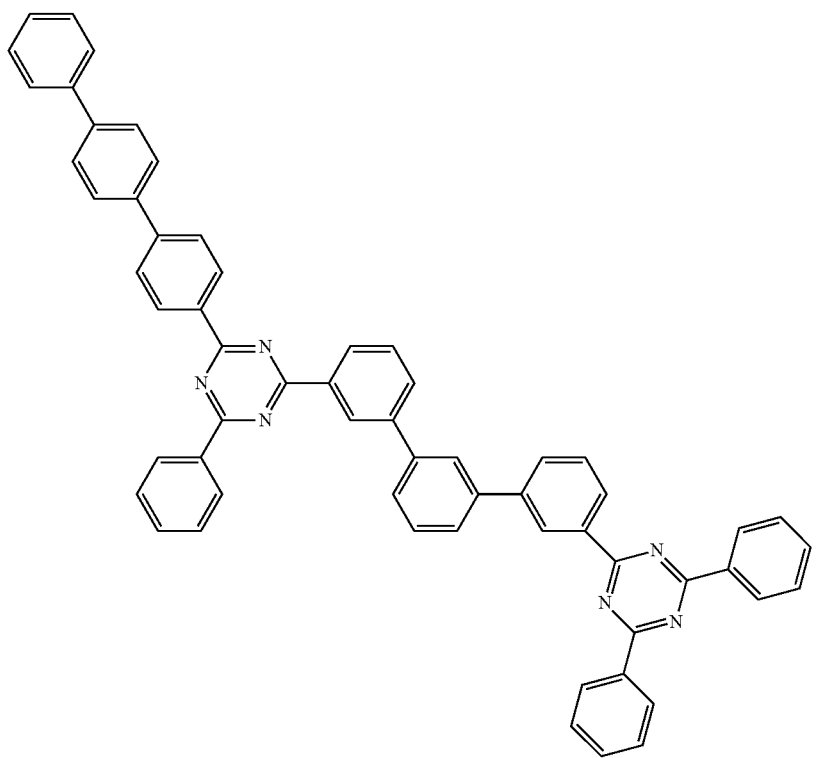

-continued
99
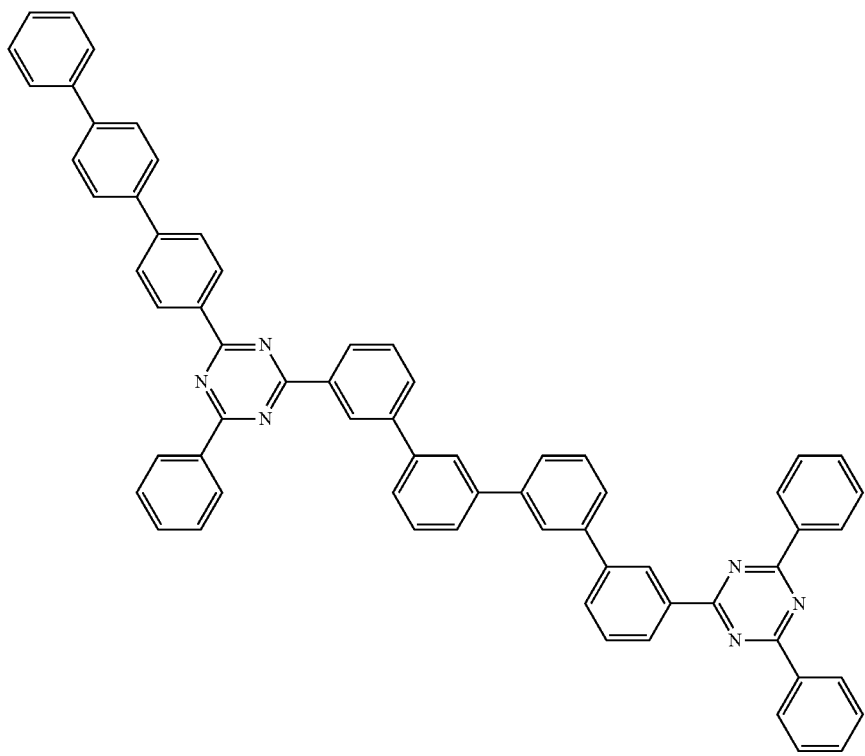
100
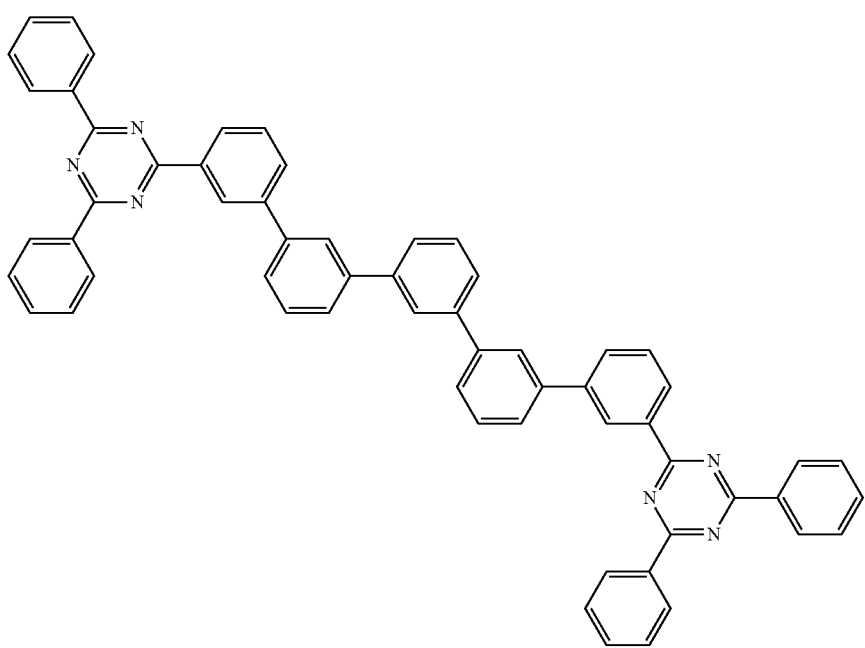

-continued
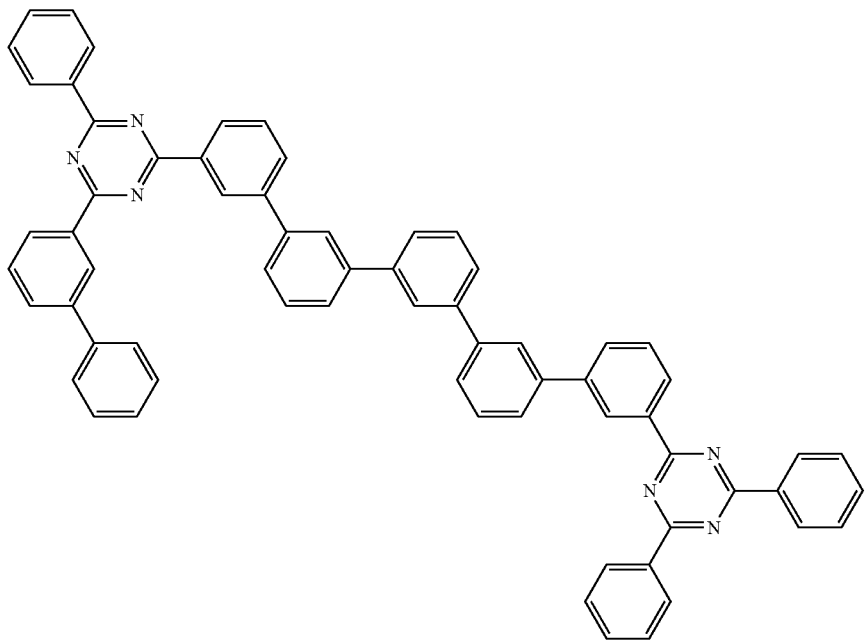
101
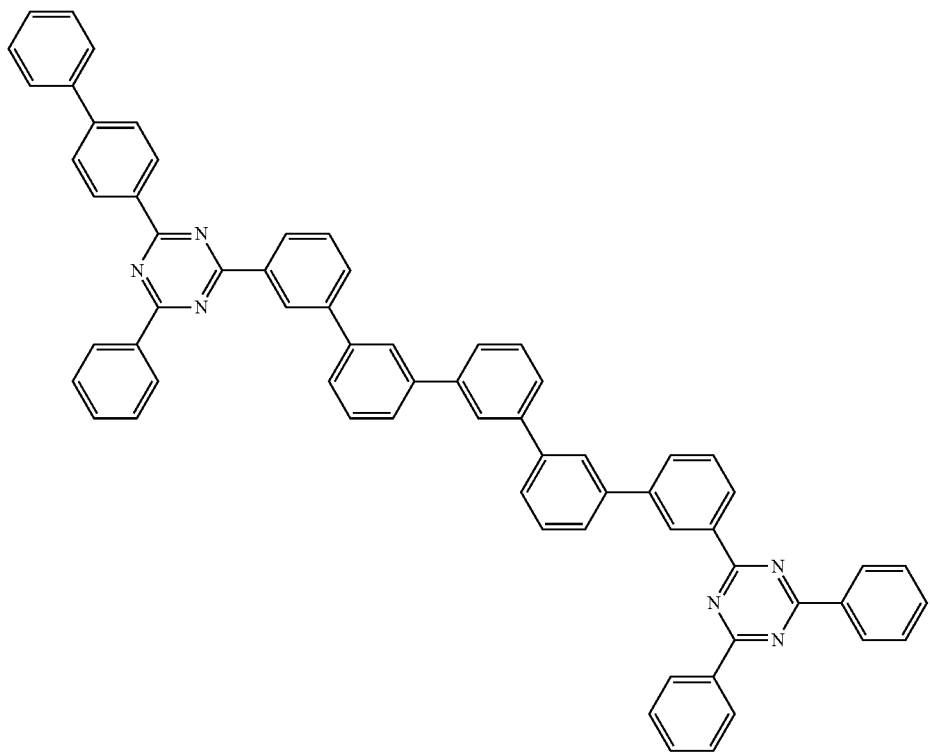
102

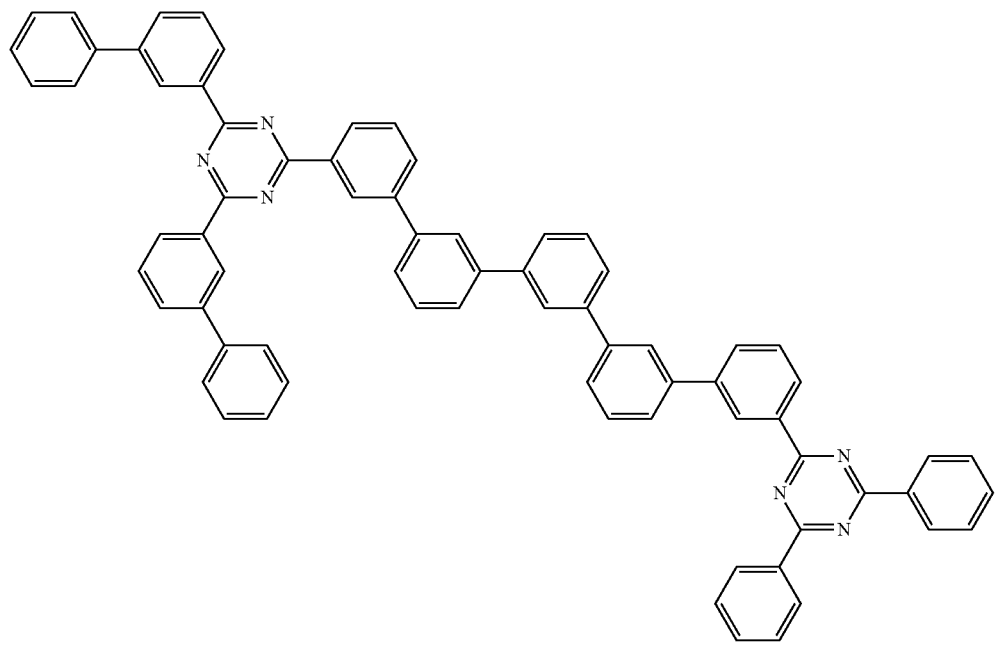
103
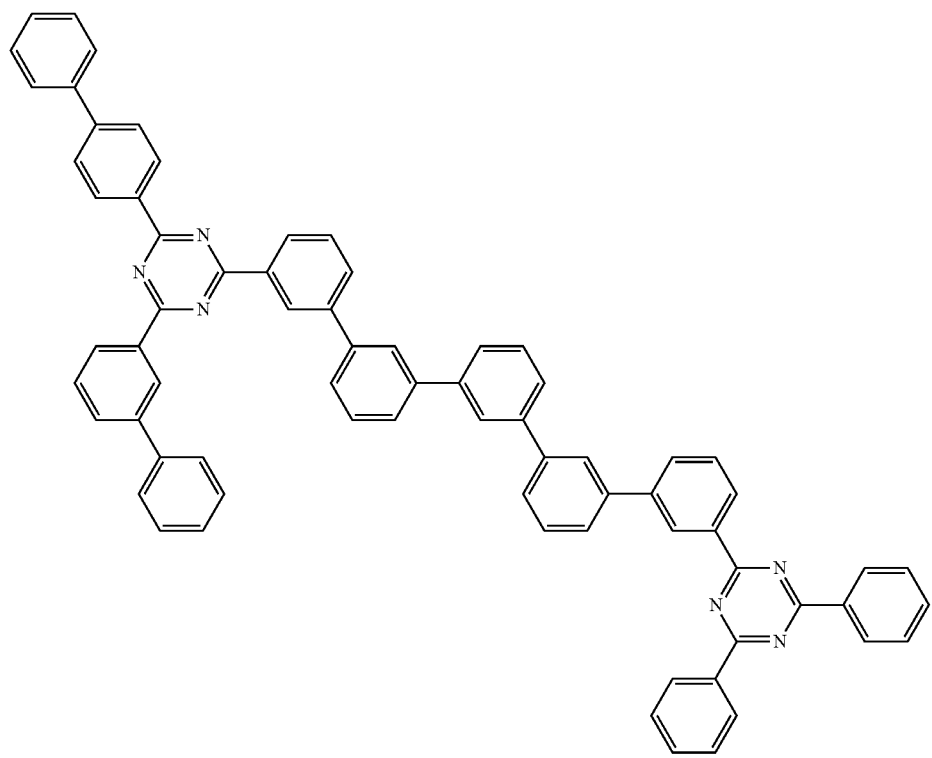
104

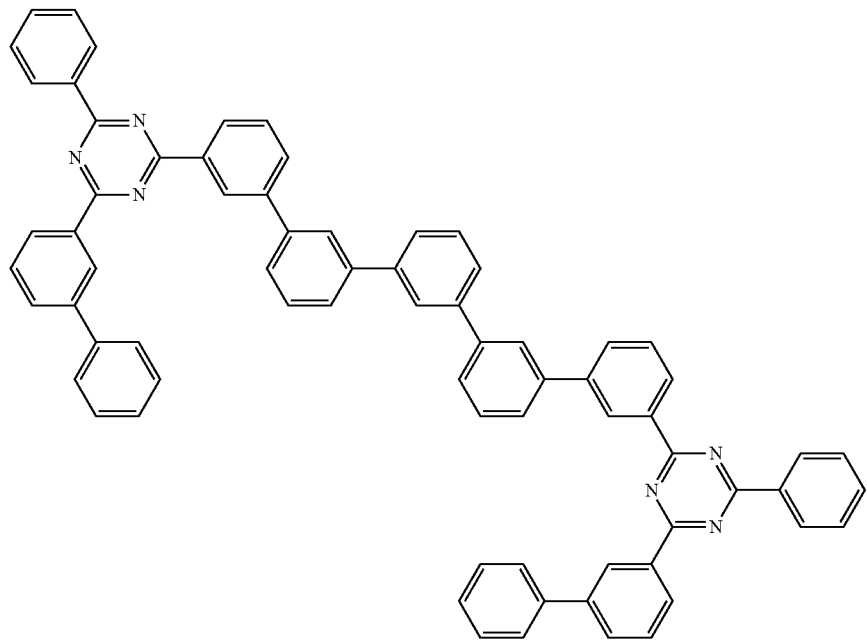
105
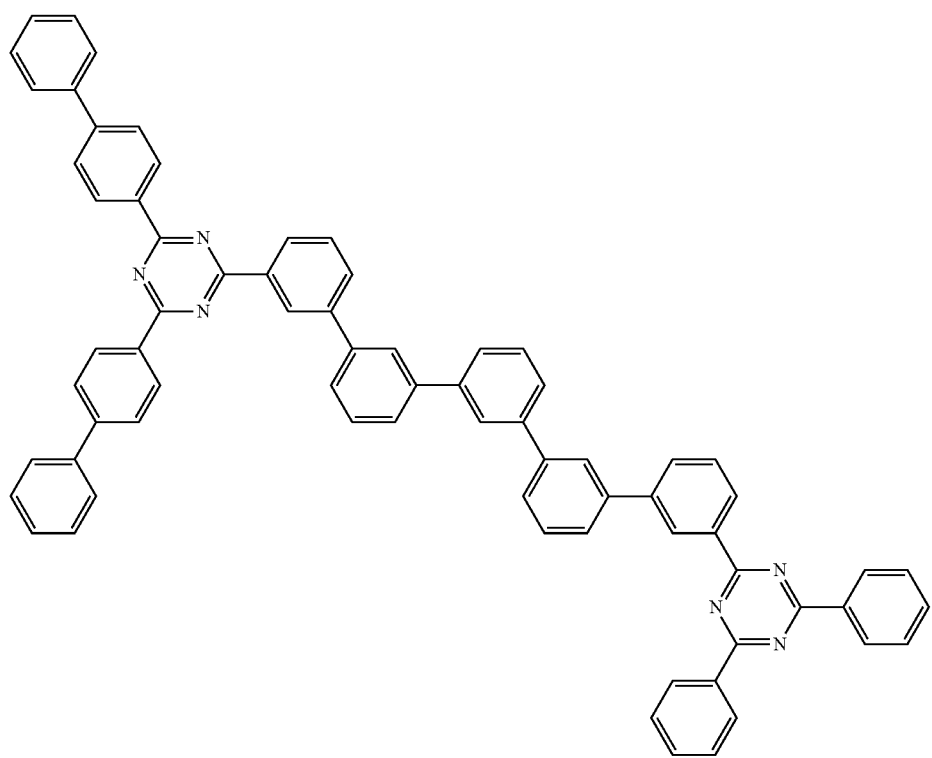
106

-continued
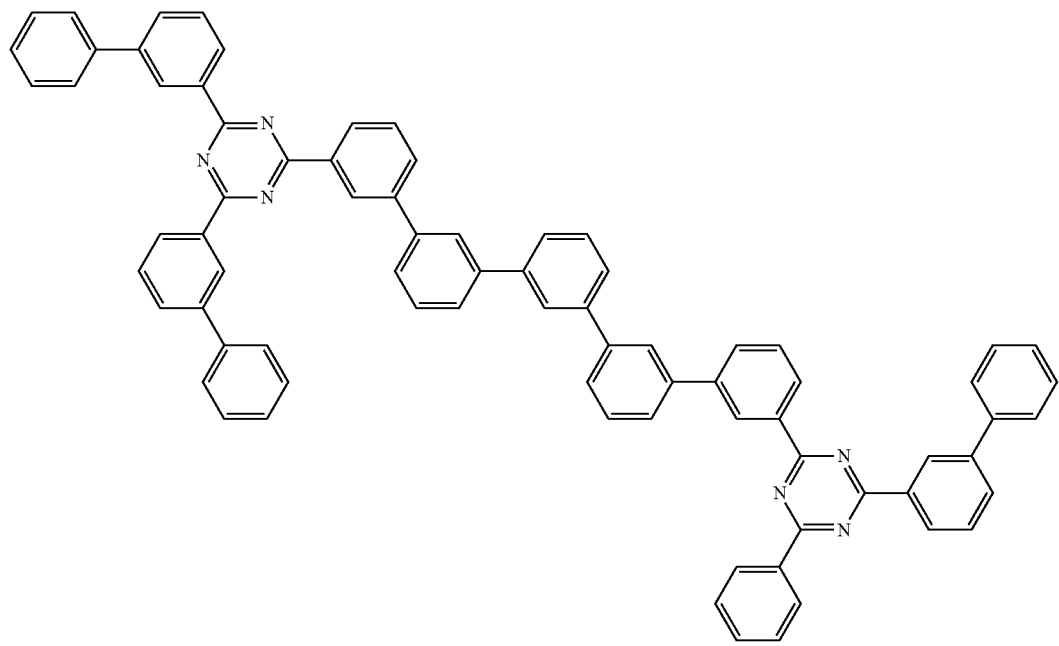
107
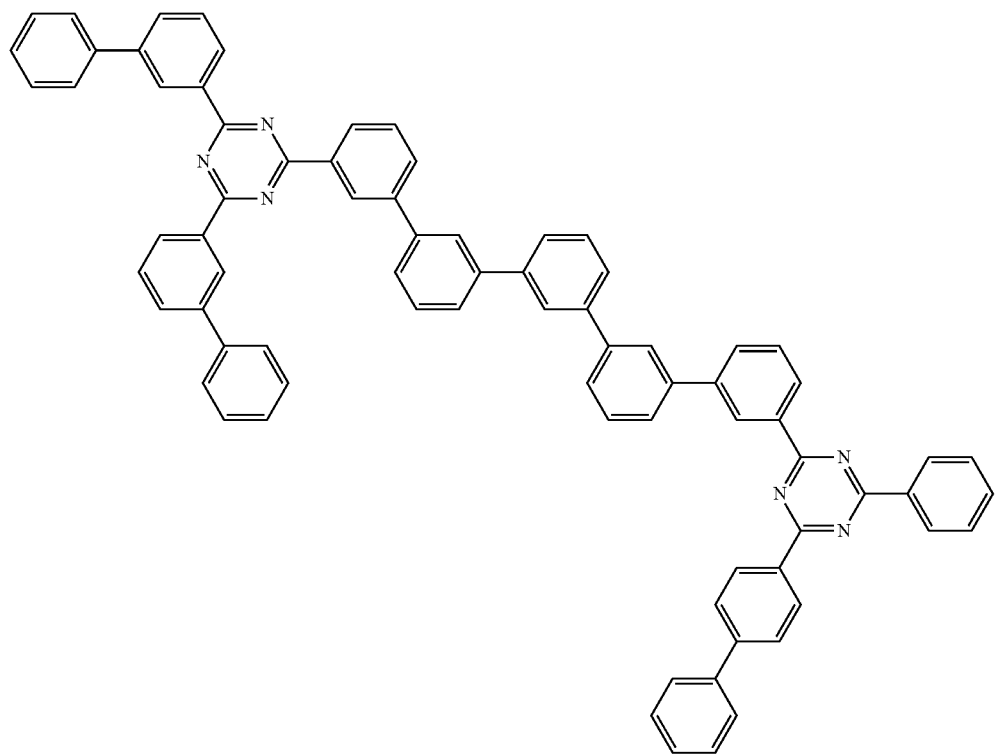
108

-continued
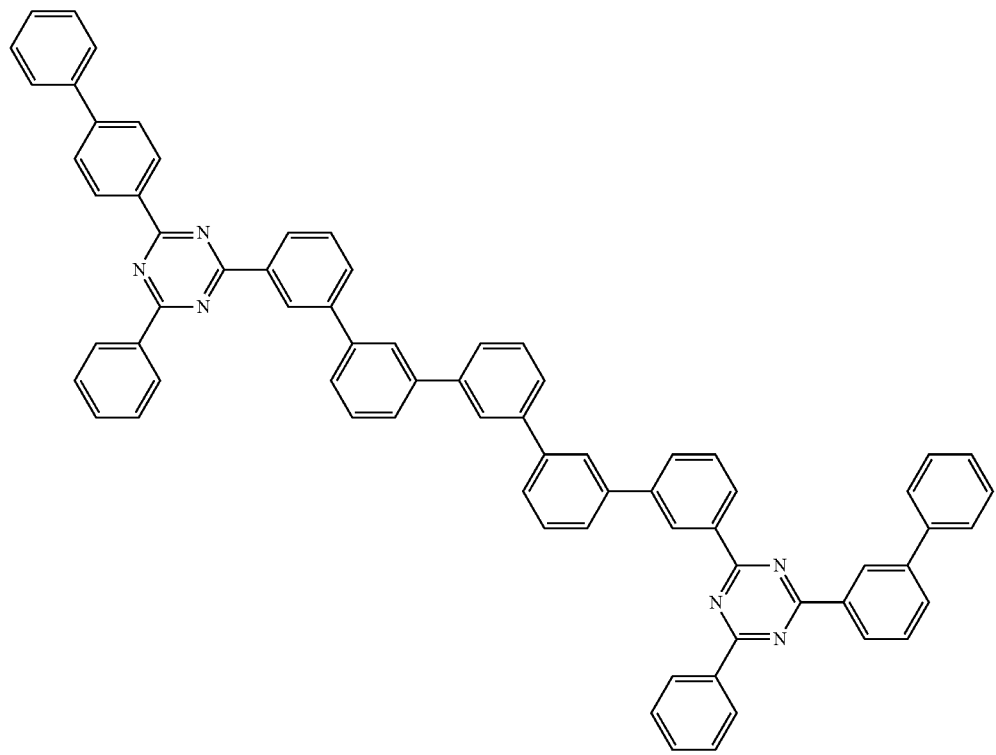
109
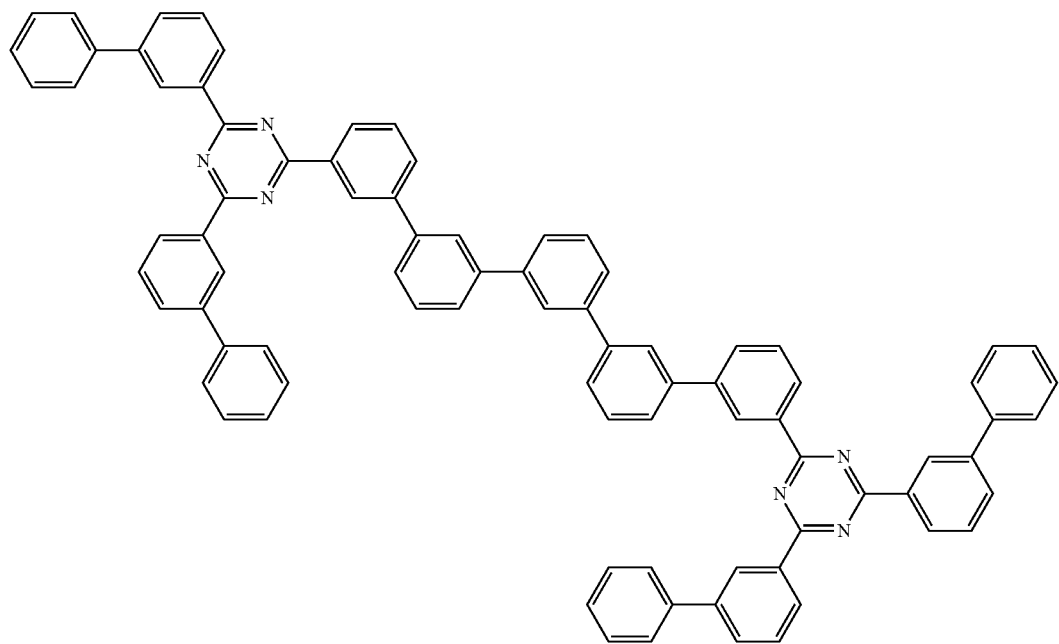
110

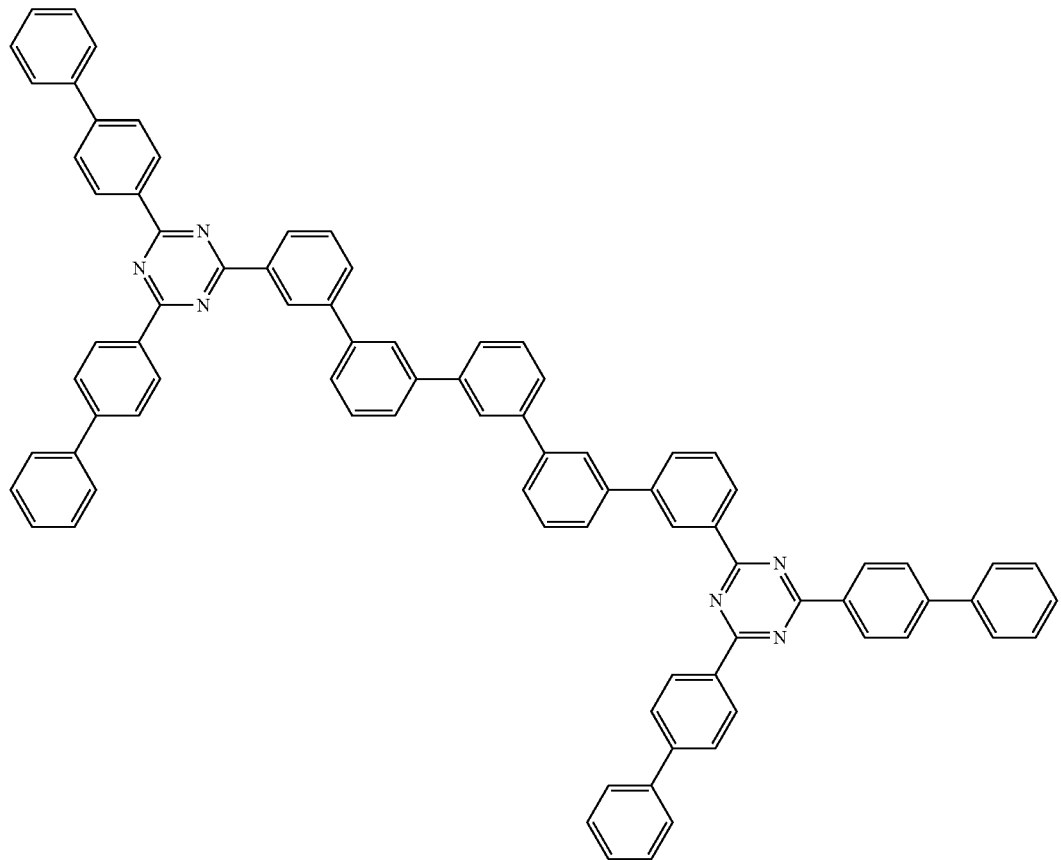
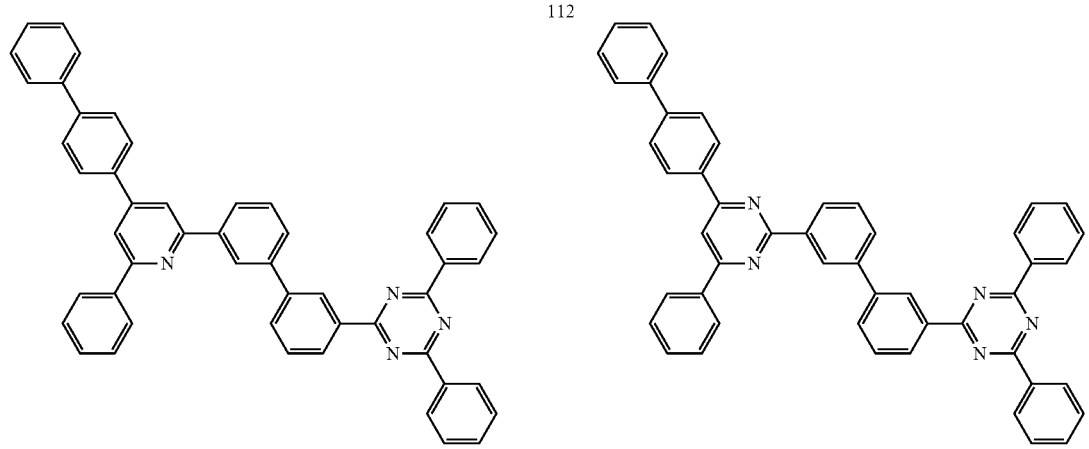

-continued
114
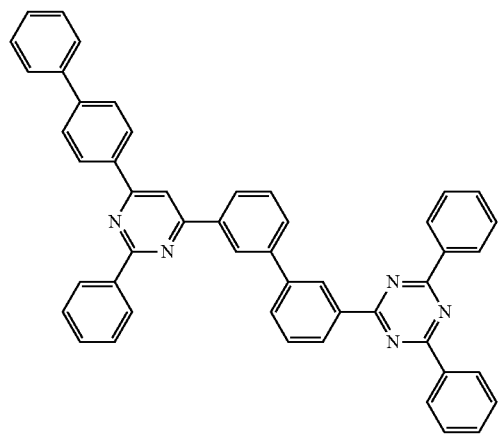
115
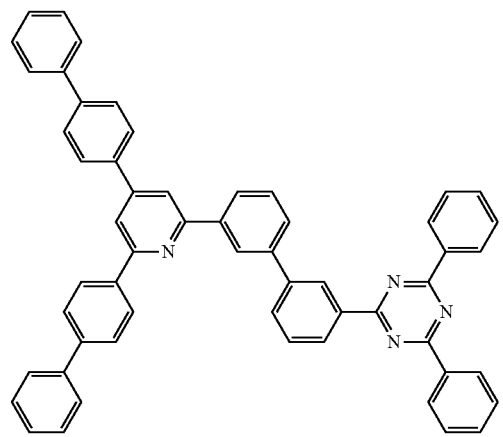
116
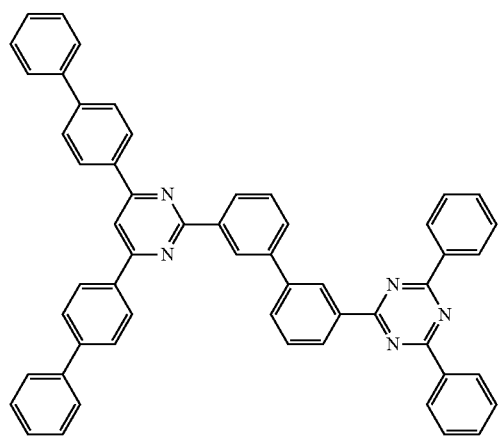
117
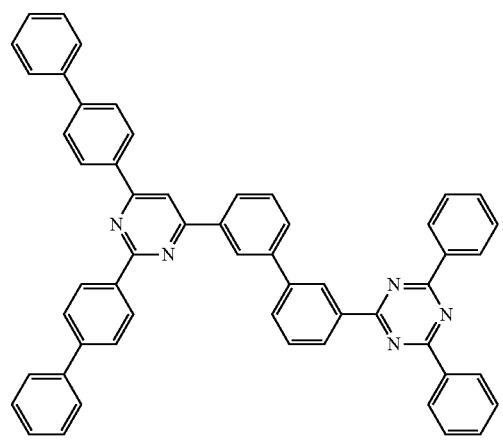
118
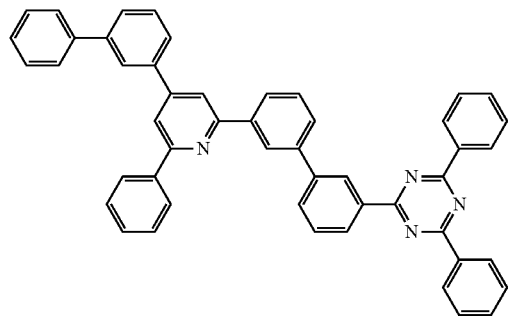
119
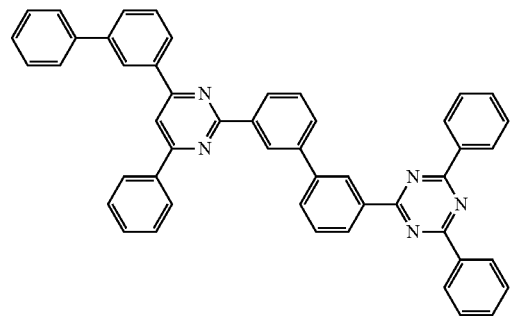
120
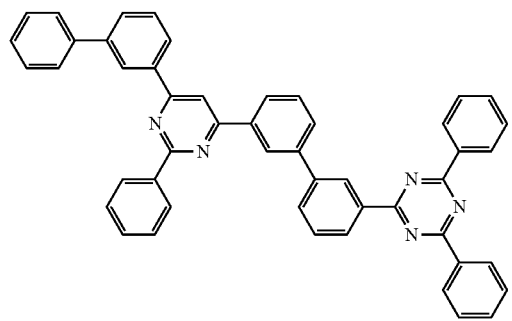
121
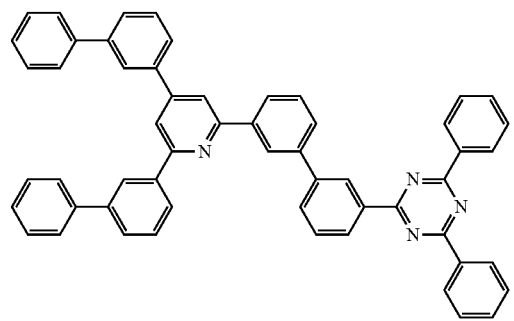

-continued
122
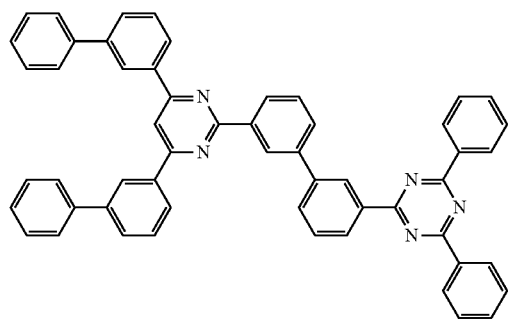
123
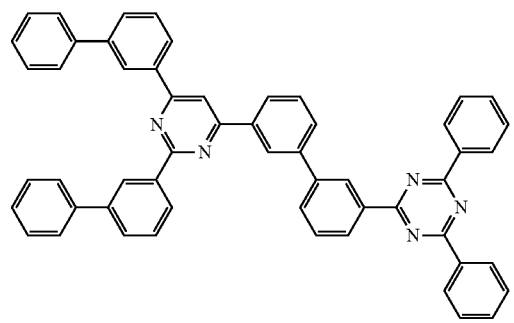
124
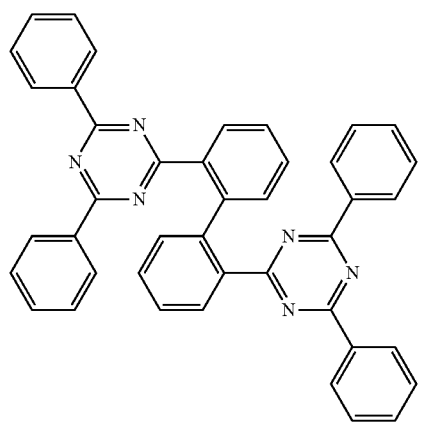
125
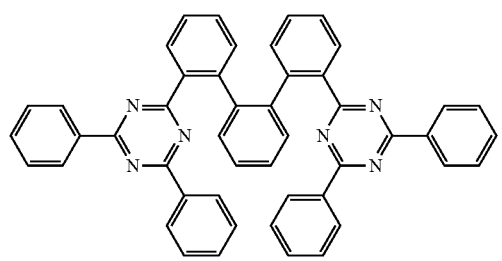
126
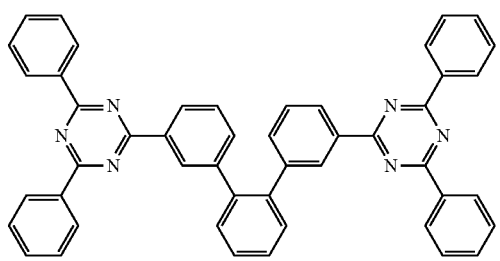
127
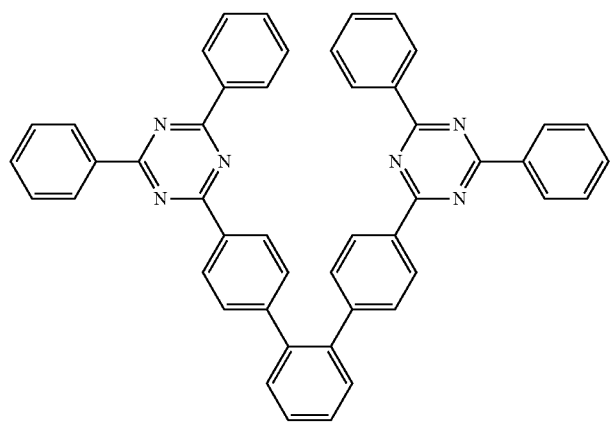

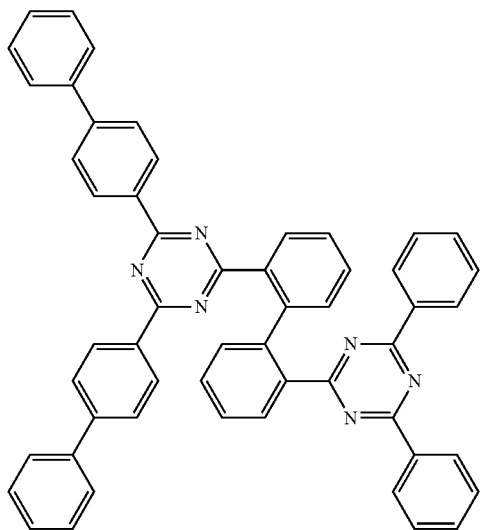
128
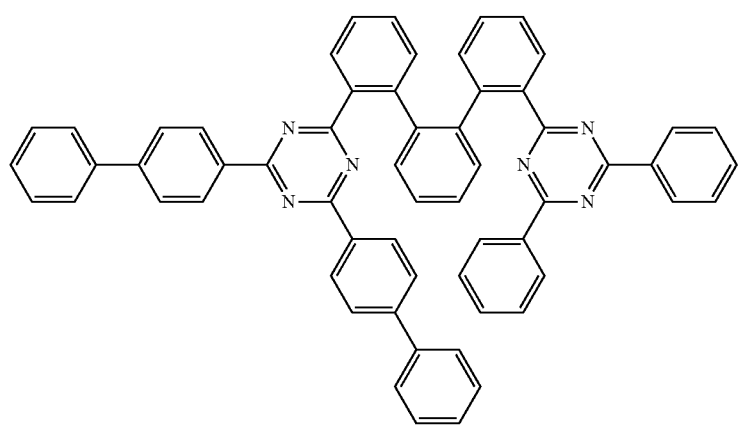
129
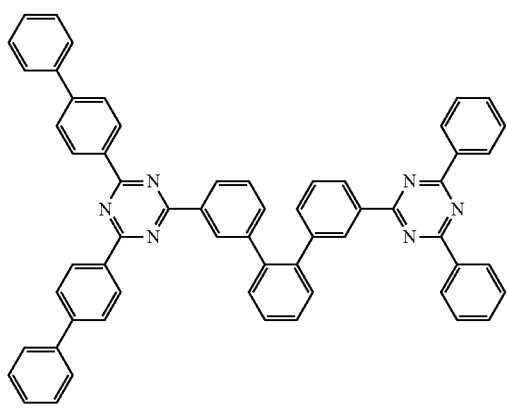
130
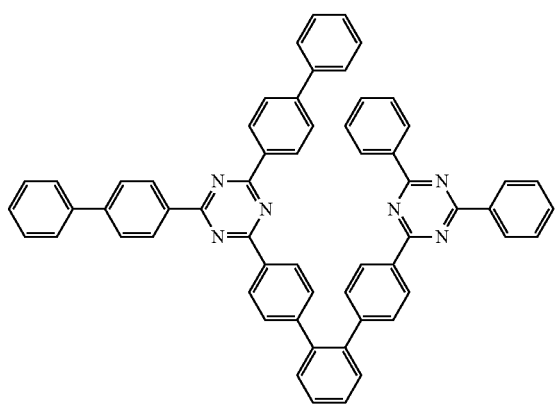
131

132
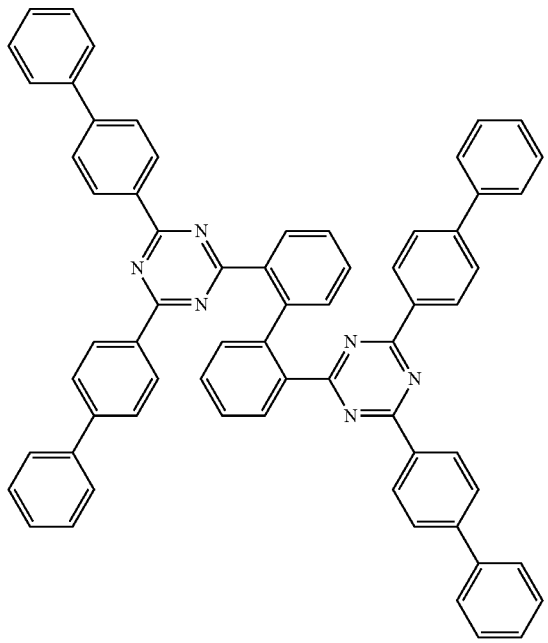
133
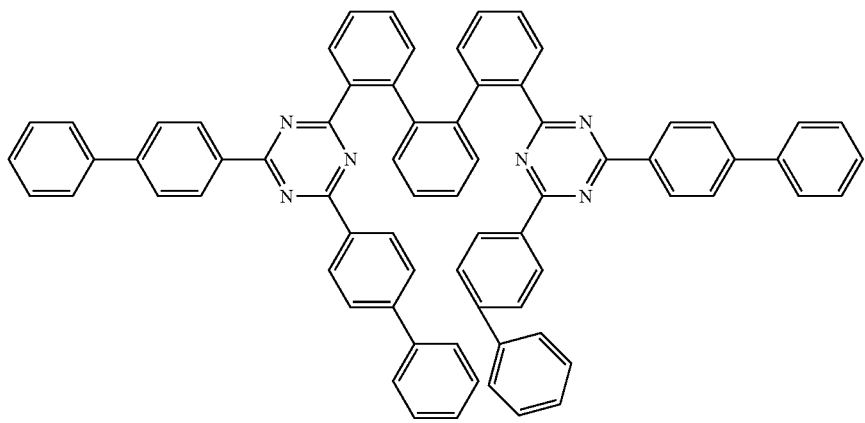
134
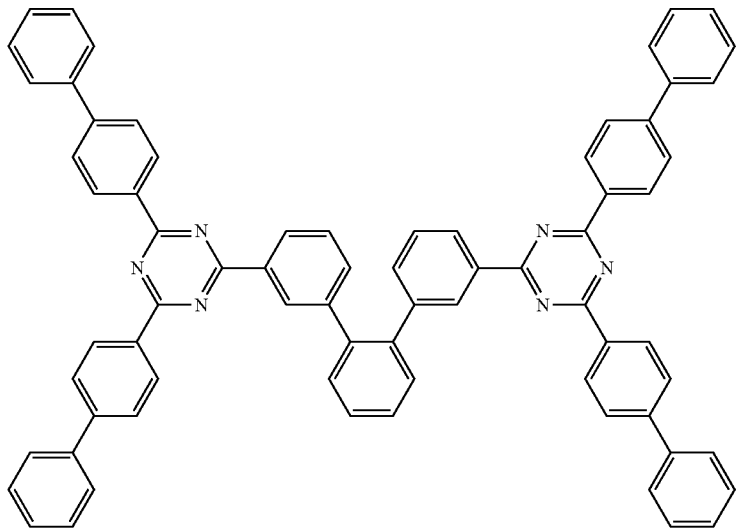

135
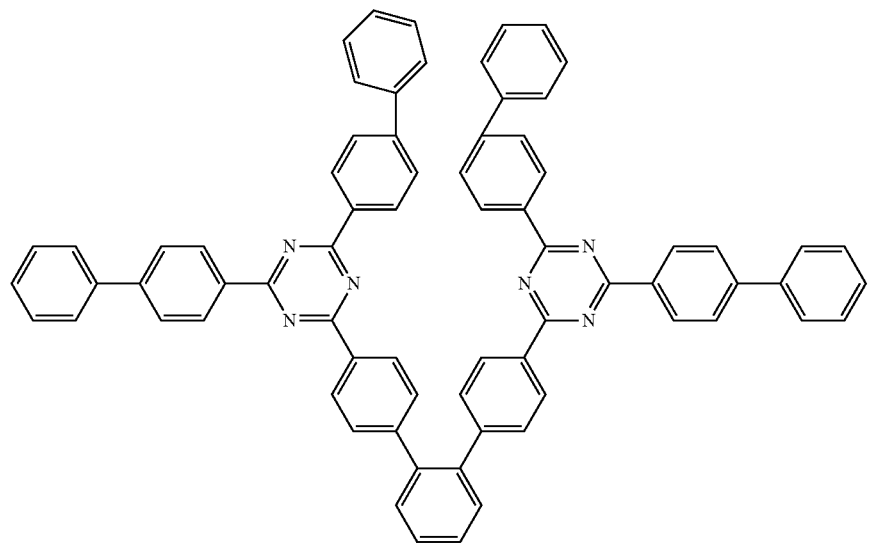
136
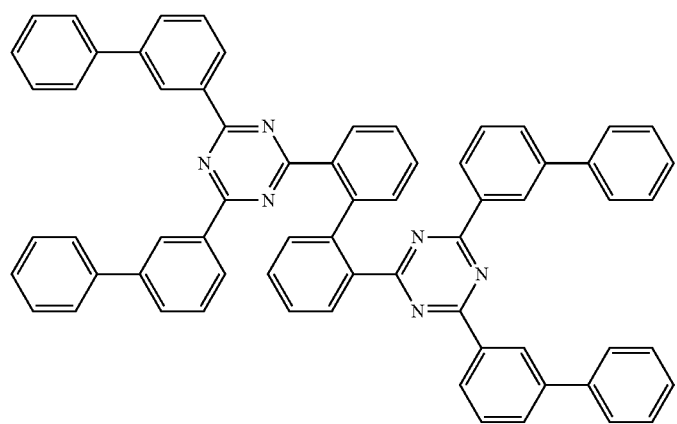
137
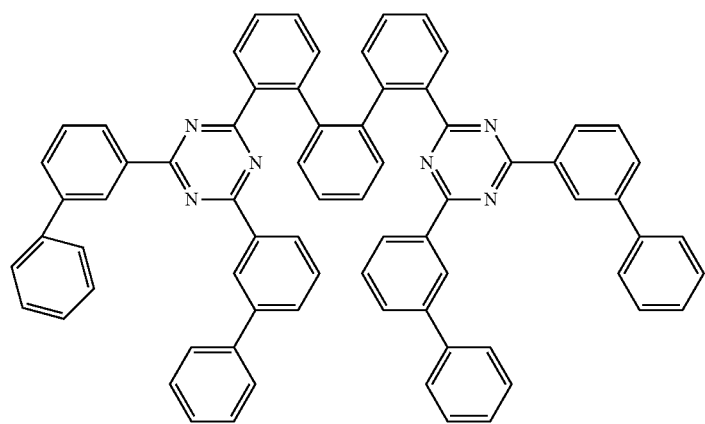

-continued
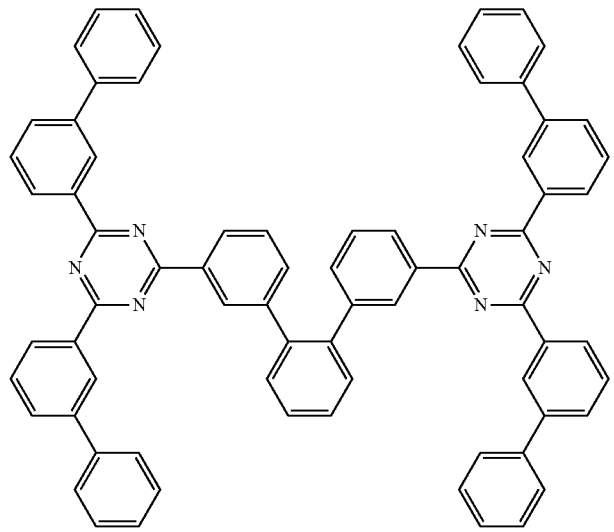
138
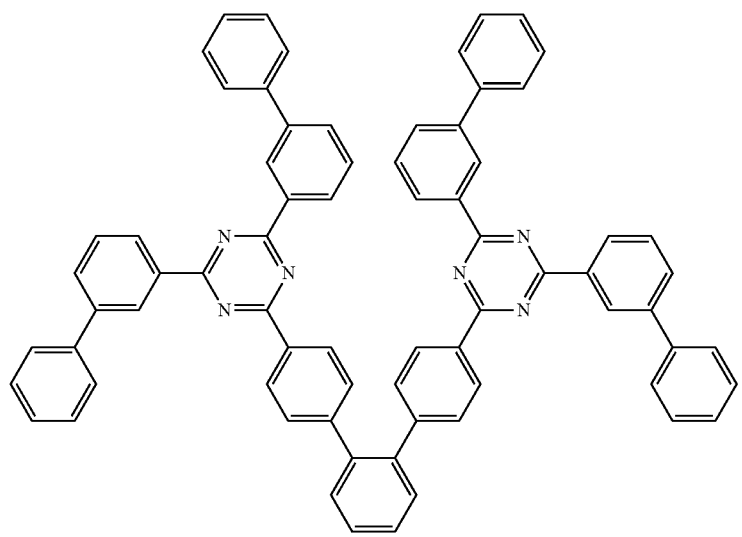
139
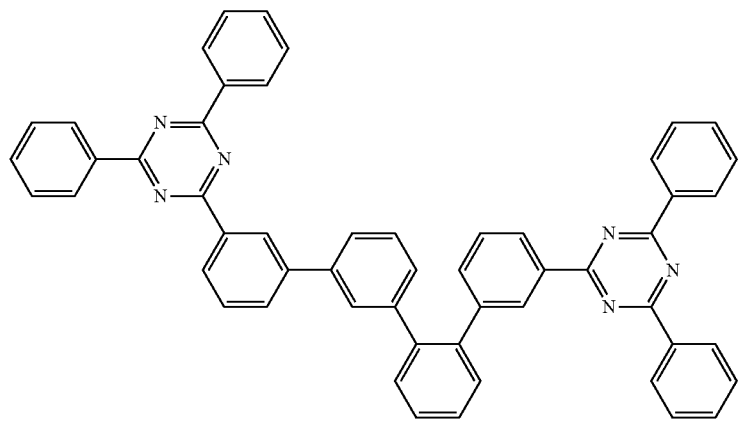
140

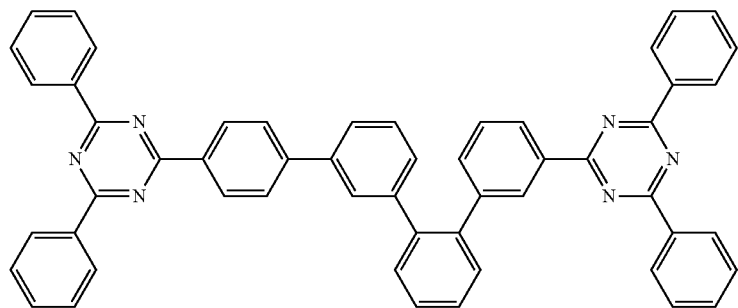
141
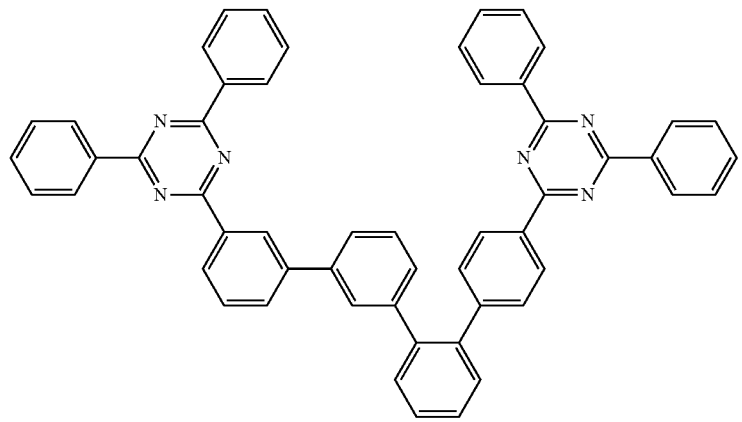
142
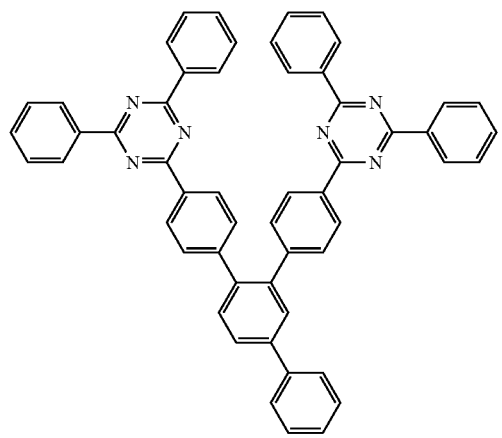
143
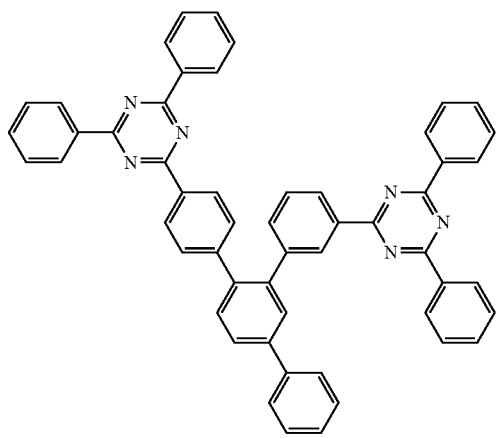
144
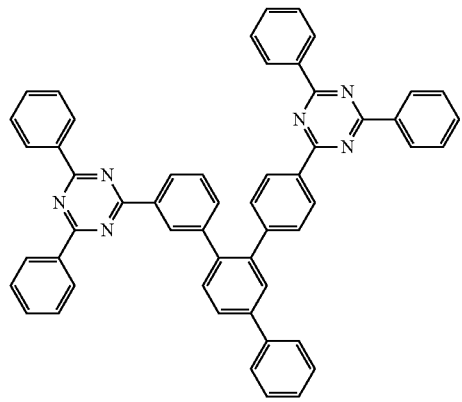
145
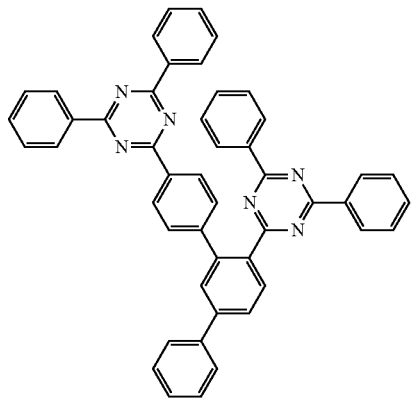
146

-continued
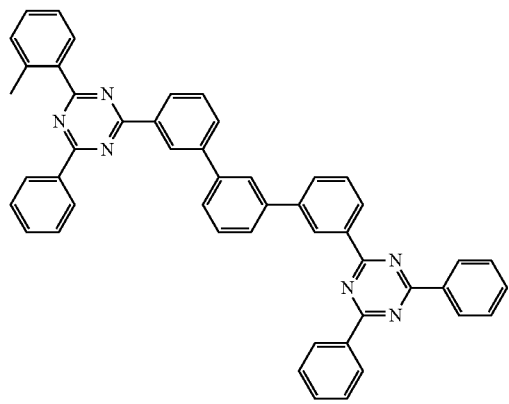
147
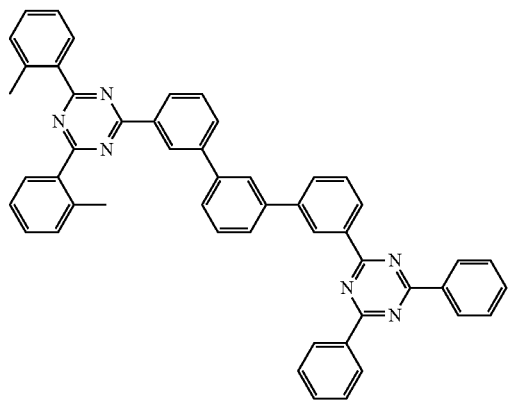
148
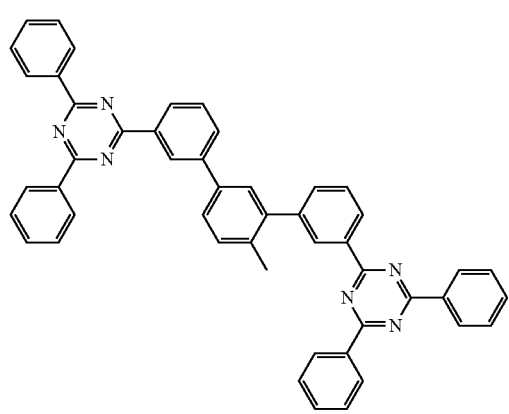
149
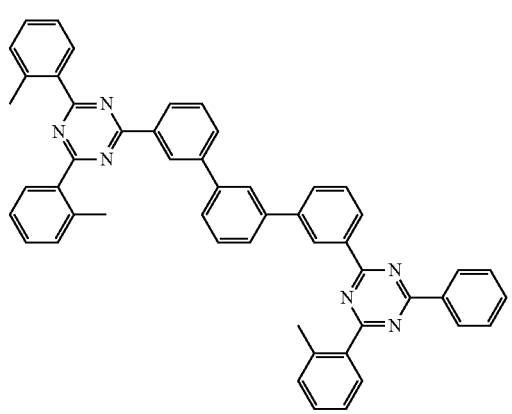
150
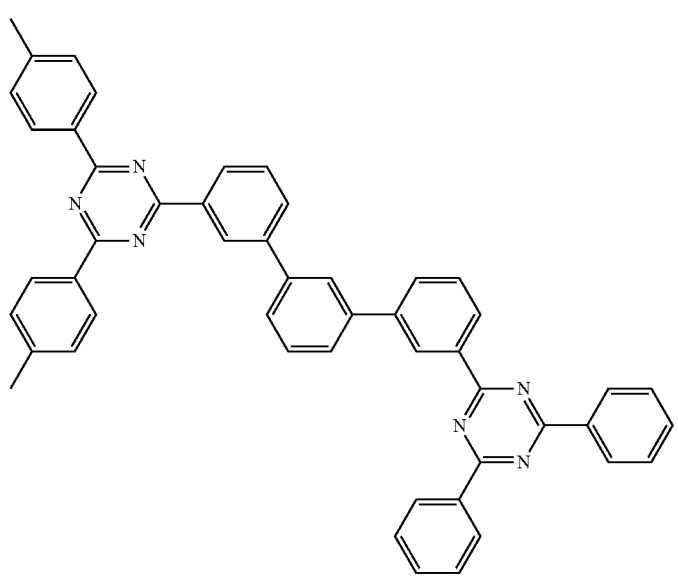
151

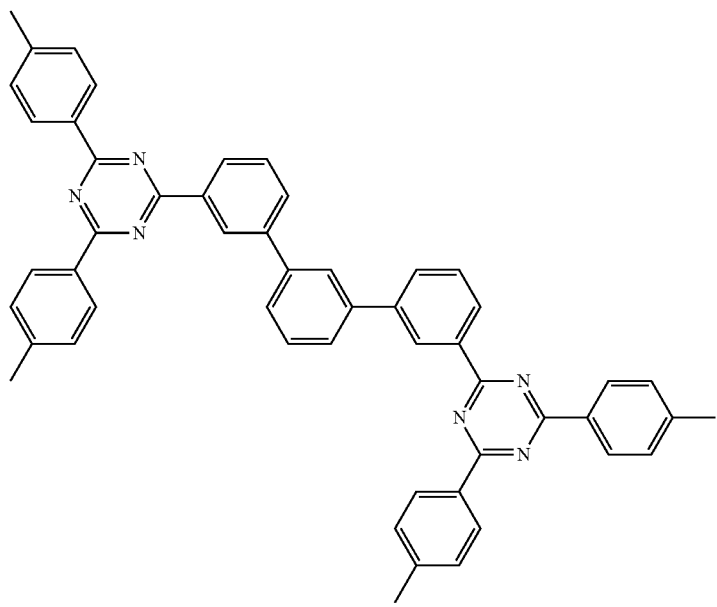
152
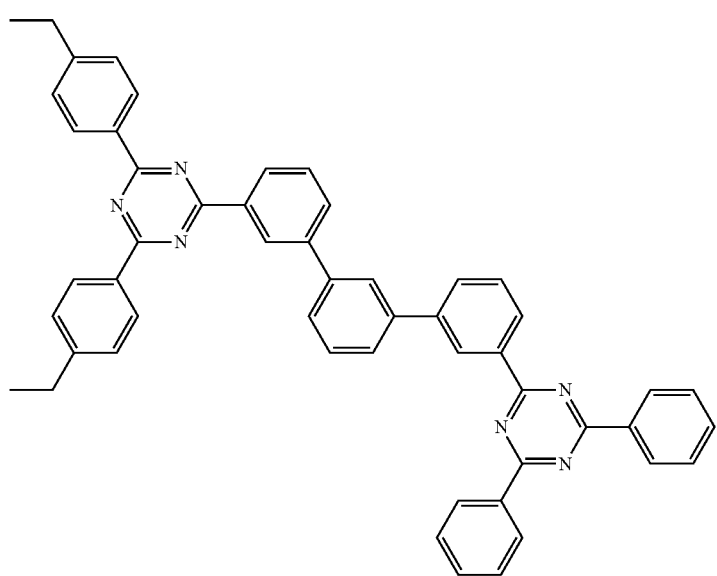
153

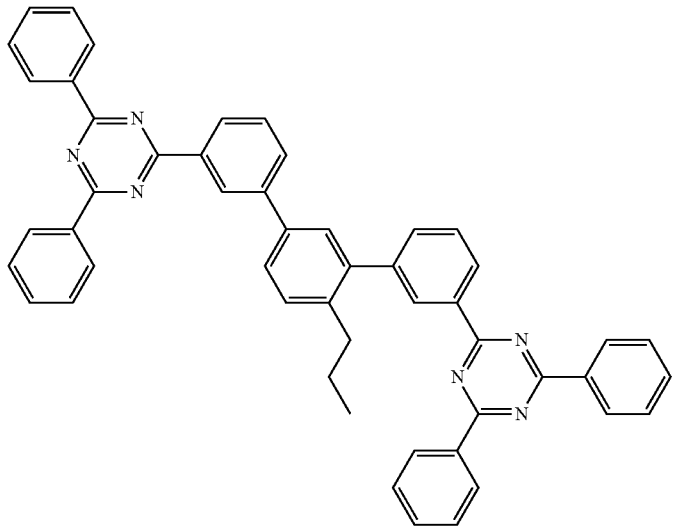

The first compound used in an emission layer has strong electron transport and inject characteristics, and thus crystallinity of a material may be increased.

Accordingly, the first compound may be used with a material having strong hole transport and injection characteristics rather than used alone to balance hole transport and injection characteristics/electron transport and injection characteristics.

The compound having strong hole transport and injection characteristics may be a second compound represented by Chemical Formula 2.

The second compound is used in an emission layer with the first compound including at least one carbazolyl group and thus having bipolar characteristics in which hole characteristics is relatively strong and thus may increase charge mobility and stability and remarkably improve luminous efficiency and life-span characteristics.

The Chemical Formula 2 may be represented by one of Chemical Formulas 2-I to 2-VI depending on a linking position of a carbazolyl group, whether a linking group is present or not, and whether the substituents of the carbazolyl group are linked and fused one another or not.

[Chemical Formula 2-I]

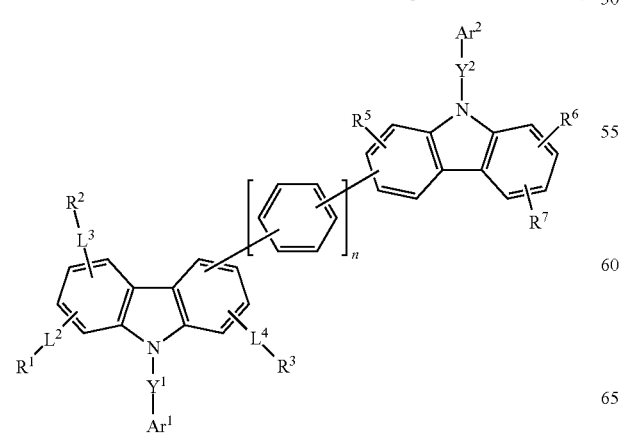

[Chemical Formula 2-II]

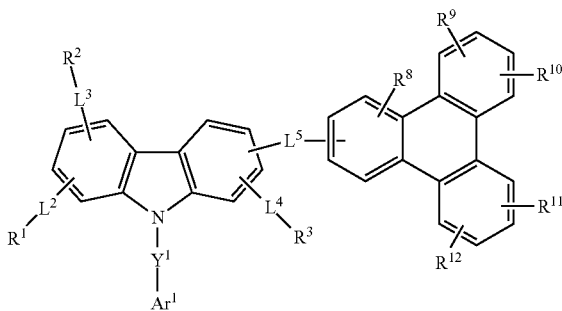

[Chemical Formula 2-III]

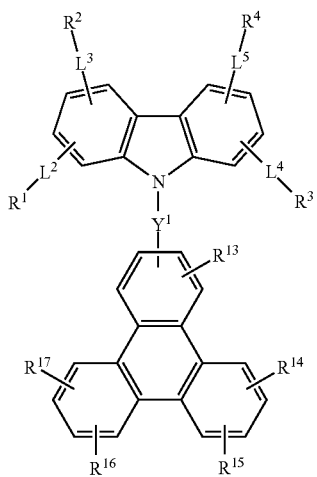

-continued

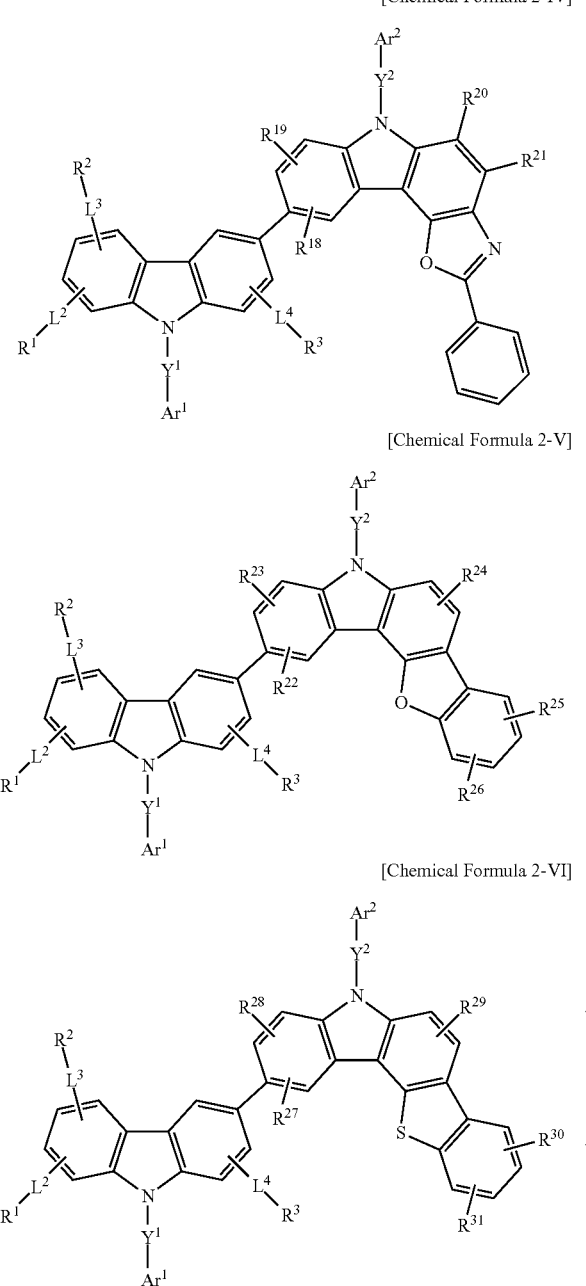

[Chemical Formula 2-IV]

[Chemical Formula 2-V]

[Chemical Formula 2-VI]

In Chemical Formulae 2-I to 2-VI, $L^2$ to $L^5$, $Y^1$, $Ar^1$ and $R^1$ to $R^4$ are the same as described above, $Y^2$ is the same as the definition of $Y^1$, and $Ar^2$ is the same as the definition of $Ar^1$.

$R^1$ or $R^2$ of Chemical Formula 2-I is not a substituted or unsubstituted carbazolyl group, $R^5$ to $R^{31}$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof, provided that all the $R^5$ to $R^7$ are not a carbazolyl group, and n is an integer of 0 to 5.

The Chemical Formula 2-I may be, for example, represented by one of Chemical Formulae 1a to 1j depending on absence or presence of a phenylene linking group linking two carbazolyl groups and linking points of two carbazolyl groups.

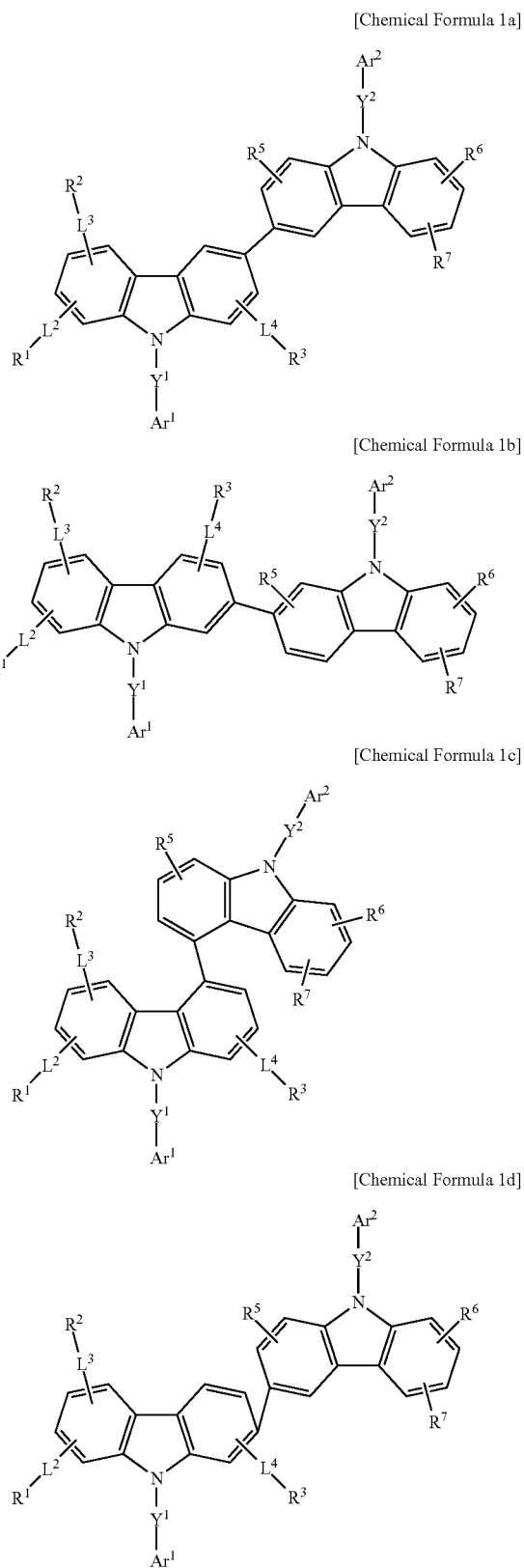

[Chemical Formula 1a]

[Chemical Formula 1b]

[Chemical Formula 1c]

[Chemical Formula 1d]

[Chemical Formula 1e]

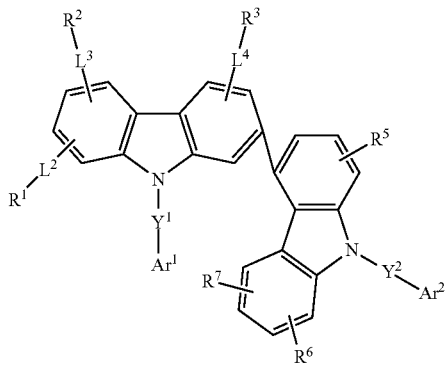

[Chemical Formula 1f]

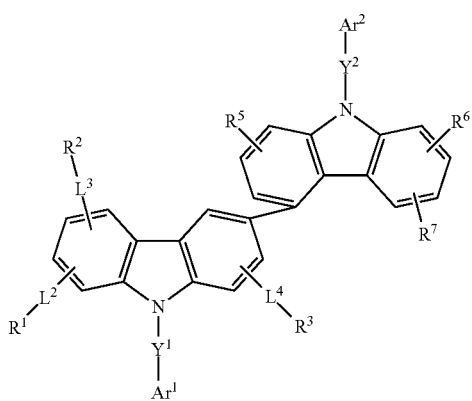

[Chemical Formula 1g]

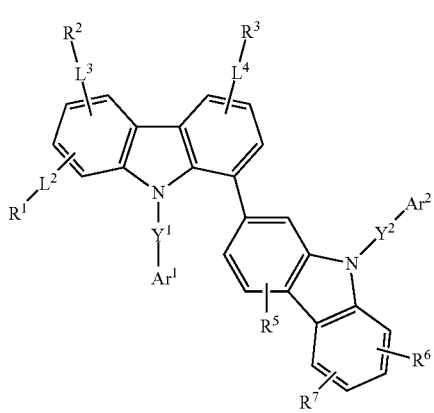

[Chemical Formula 1h]

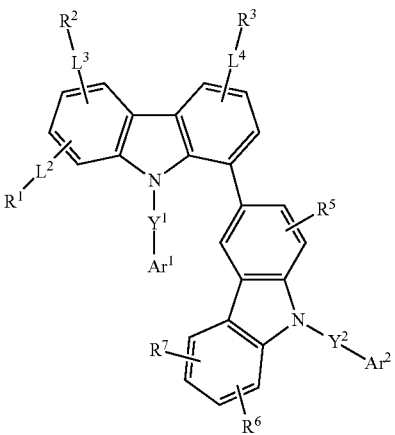

[Chemical Formula 1i]

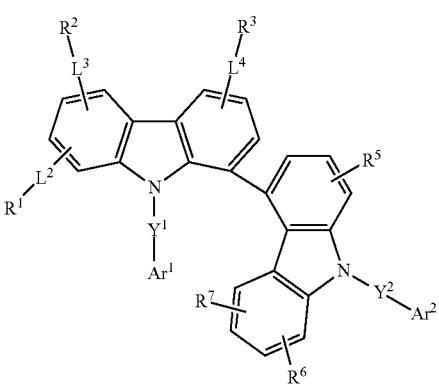

[Chemical Formula 1j]

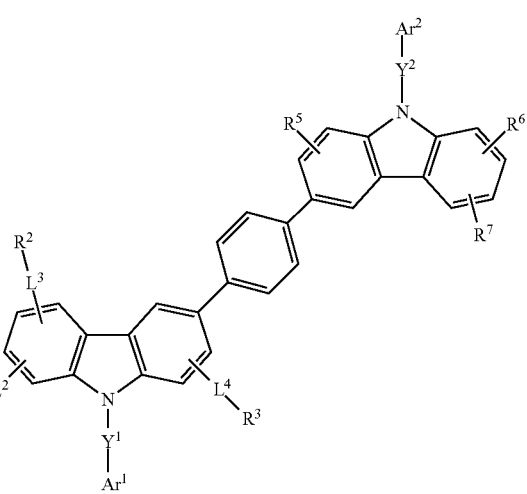

In Chemical Formulae 1a to 1j, $L^2$ to $L^4$, $Y^1$, $Y^2$, $Ar^1$, $Ar^3$, $R^1$ to $R^3$, and $R^5$ to $R^7$ are the same described above, provided that $R^1$ or $R^2$ is not a substituted or unsubstituted carbazolyl group, all the $R^5$ to $R^7$ are not a carbazolyl group.

The Chemical Formula 2-II may be, for example represented by Chemical Formula 2a according to a linking position of a triphenylene group, and

[Chemical Formula 2a]

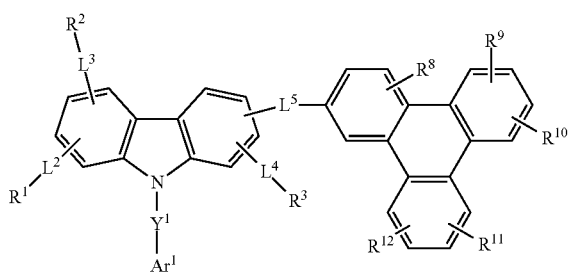

specifically, may be represented by one of Chemical Formulae 2a-1 to 2a-3.

[Chemical Formula 2a-1]

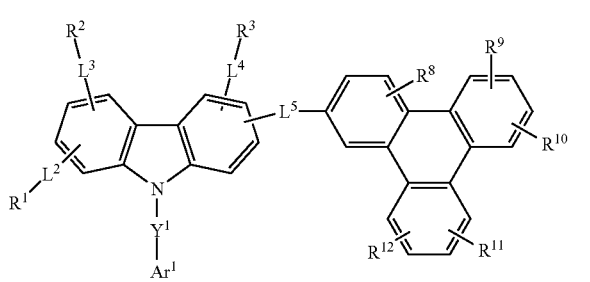

[Chemical Formula 2a-2]

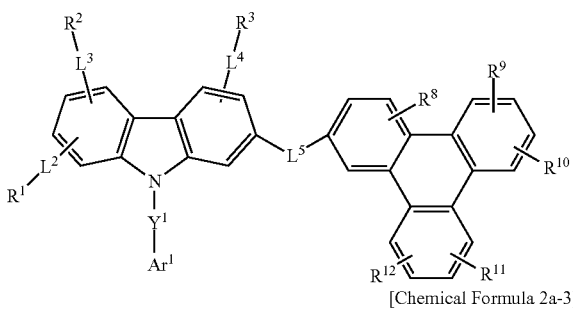

[Chemical Formula 2a-3]

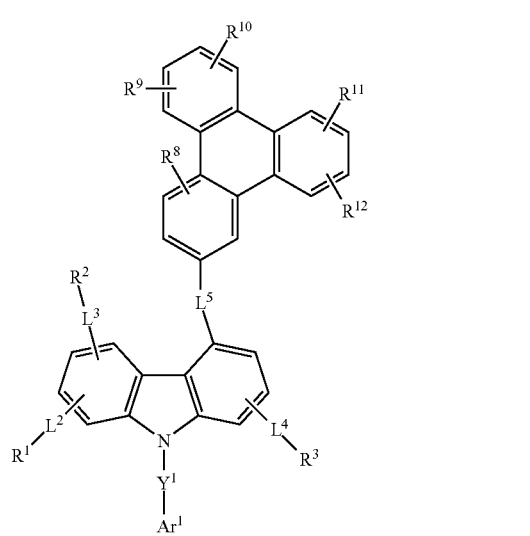

In Chemical Formulae 2a and 2a-1 to 2a-3, $L^2$ to $L^5$, $Y^1$, $Ar^1$, $R^1$ to $R^3$ and $R^8$ to $R^{12}$ are the same as described above.

The Chemical Formula 2-III may be, for example represented by Chemical Formula 3a according to a linking position of a triphenylene group.

[Chemical Formula 3a]

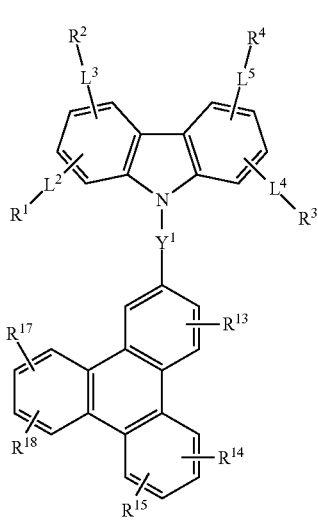

In Chemical Formula 3a, $L^2$ to $L^5$, $Y^1$, $R^1$ to $R^4$, and $R^{13}$ to $R^{17}$ are the same as described above.

$Ar^1$ and $Ar^2$ of Chemical Formulae 2-I to 2-VI according to an example embodiment of the present invention may independently be hydrogen, deuterium, a substituted or unsubstituted C1 to C30 alkyl group, a substituted or unsubstituted C1 to C30 alkenyl group, a substituted or unsubstituted C1 to C30 alkynyl group, a substituted or unsubstituted C6 to C30 aryl group, a substituted or unsubstituted C6 to C30 aryloxy group, a substituted or unsubstituted C6 to C30 arylthio group, a substituted or unsubstituted C2 to C30 heteroaryl group, a hydroxy group, a thiol group, or a combination thereof, and specifically, a substituted or unsubstituted C6 to C30 aryl group, or a substituted or unsubstituted C2 to C30 heteroaryl group.

When the $Ar^1$ and $Ar^2$ are a substituted or unsubstituted C6 to C30 aryl group, they may more specifically be a substituted or unsubstituted phenyl group, a substituted or unsubstituted biphenyl group, a substituted or unsubstituted terphenyl group, a substituted or unsubstituted naphthyl group, a substituted or unsubstituted triphenylenyl group, or a substituted or unsubstituted fluorenyl group, and when the $Ar^1$ and $Ar^2$ are a substituted or unsubstituted C2 to C30 heteroaryl group, they may more specifically be a substituted or unsubstituted pyridinyl group, a substituted or unsubstituted quinolinyl group, a substituted or unsubstituted isoquinolinyl group, a substituted or unsubstituted dibenzofuranyl group, or a substituted or unsubstituted dibenzothiophenyl group.

$Y^1$ and $Y^2$ of Chemical Formula 2 according to an example embodiment of the present invention may independently be a single bond, a substituted or unsubstituted C6 to C30 arylene group, a substituted or unsubstituted C2 to C30 heteroarylene group, or a combination thereof, and specifically, a single bond or a substituted or unsubstituted C6 to C30 arylene group.

For example, the $Y^1$ and $Y^2$ may independently be a single bond, a substituted or unsubstituted phenylene group, or a substituted or unsubstituted biphenylene group, and the $Ar^1$ and $Ar^2$ may independently be a substituted or unsubstituted groups of Group 4.

[Group 4]
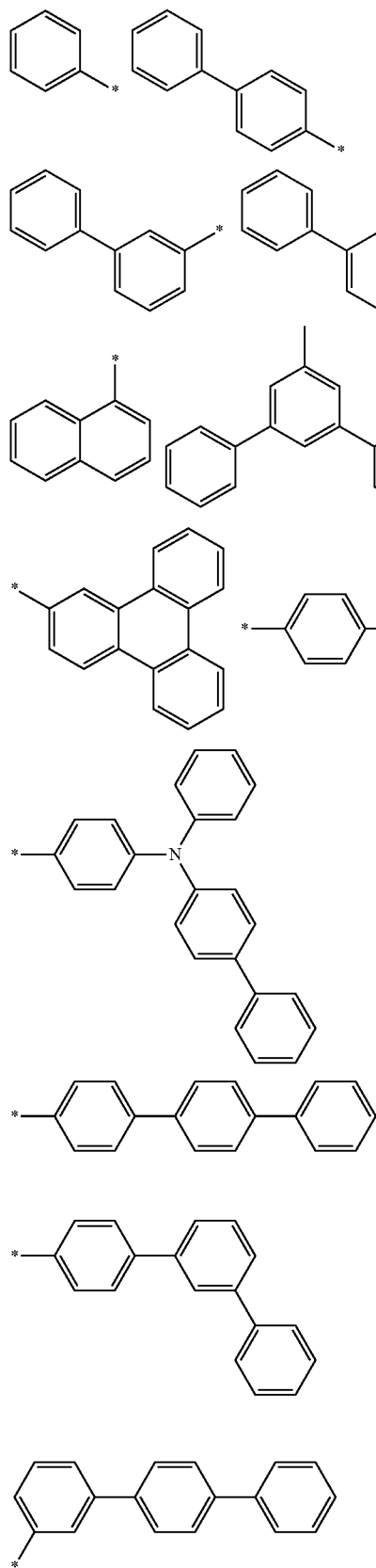
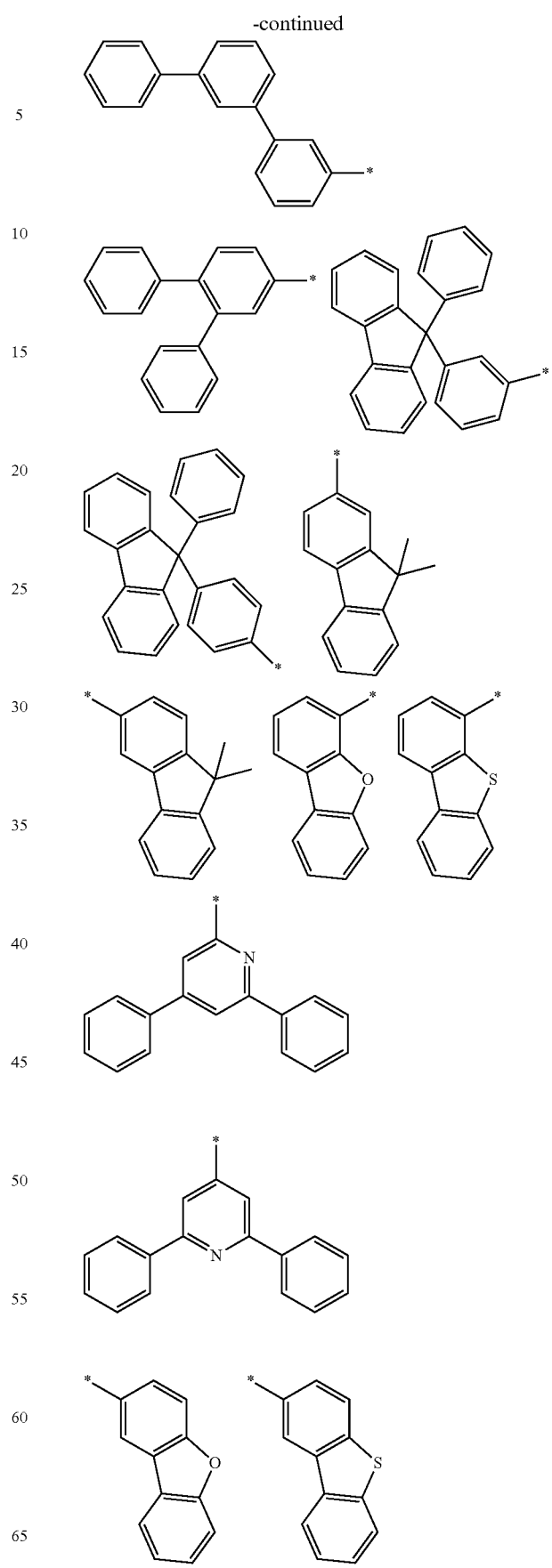

-continued

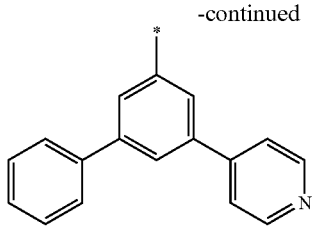

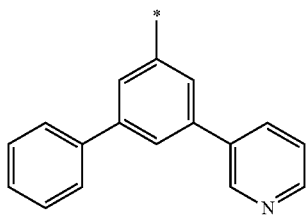

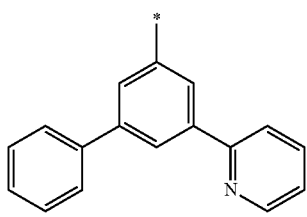

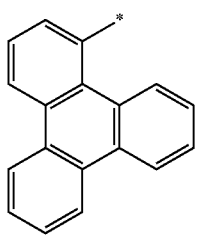

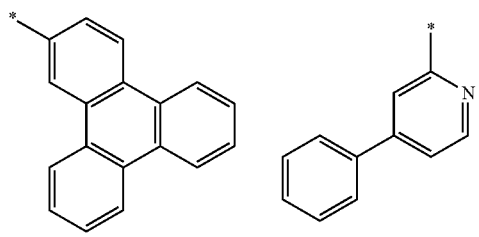

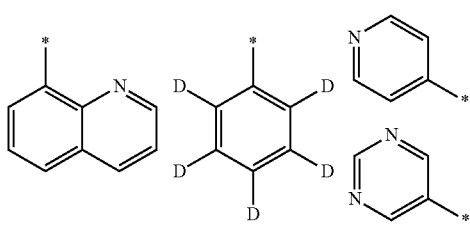

In Group 4, * is a linking point to an adjacent atom.

$R^1$ to $R^4$ of Chemical Formula 2 according to an example embodiment of the present invention may independently be hydrogen, deuterium, a substituted or unsubstituted C1 to C20 alkyl group, a substituted or unsubstituted C6 to C30 aryl group, a substituted or unsubstituted C2 to C30 heterocyclic group, a substituted or unsubstituted nitrile group, a substituted or unsubstituted isonitrile group, a hydroxy group, a thiol group, and specifically, hydrogen, a phenyl group, an o-biphenyl group, a m-biphenyl group, a p-biphenyl group, a pyridyl group, a methyl group, an ethyl group, a propyl group, an isopropyl group, and the like, and the phenyl group, o-biphenyl group, m-biphenyl group, p-biphenyl group, pyridyl group, methyl group, ethyl group, propyl group and isopropyl group may be further substituted with deuterium, a C6 to C30 aryl group, or a C1 to C30 alkyl group, and substituents may be linked to each other to form a fused ring.

For example, when one of $R^1$ to $R^4$ is a triphenylmethyl group, two adjacent phenyl group to the triphenylmethyl group are linked therewith to form a fluorene ring.

The second compound represented by Chemical Formula 2 may be, for example compounds of Group 5, but is not limited thereto.

[Group 5]

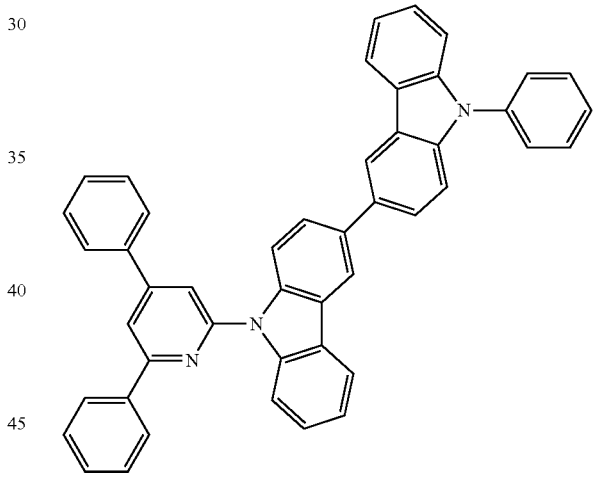

B-10

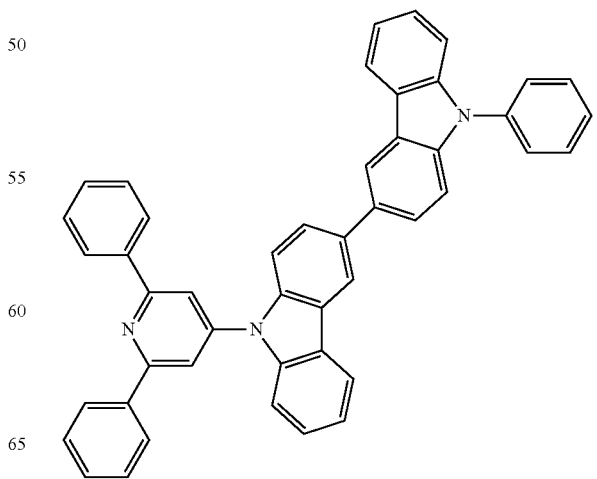

B-11

B-12
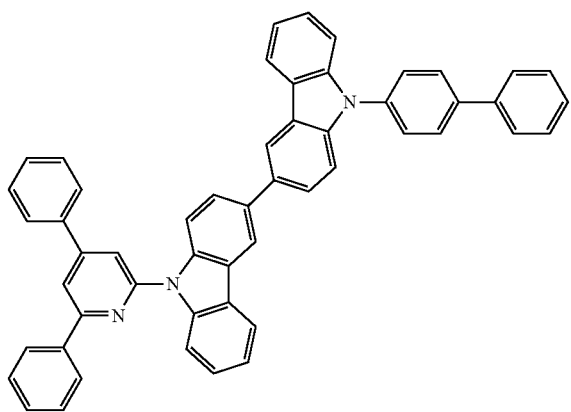
B-13
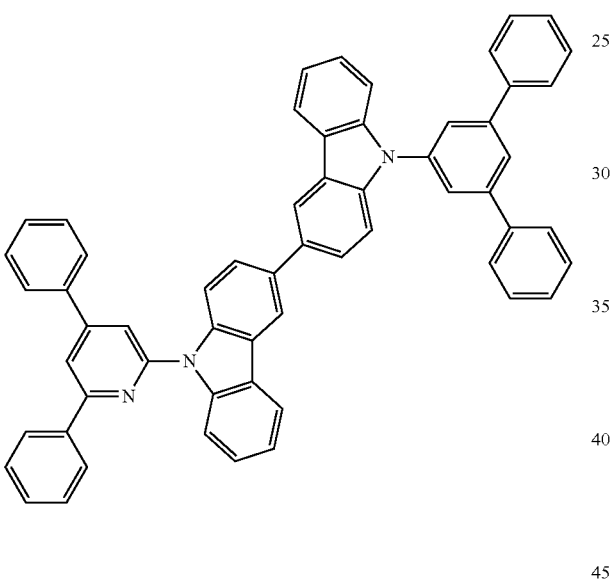
B-14
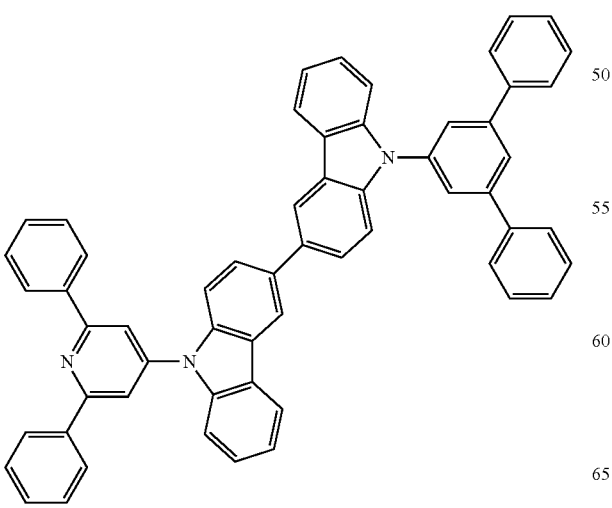
B-15
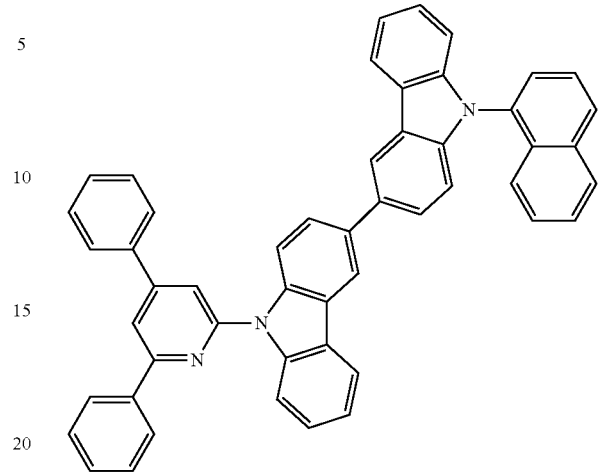
B-16
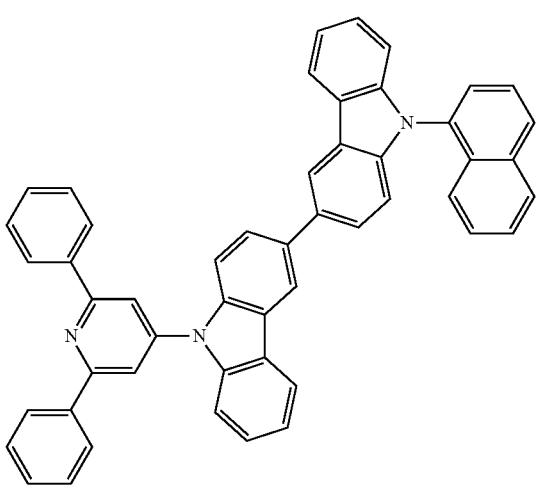
B-17
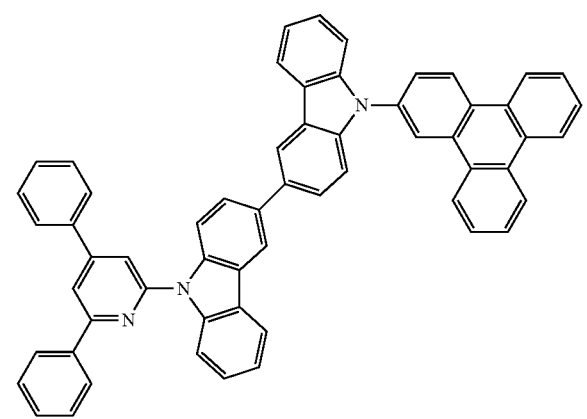

B-18
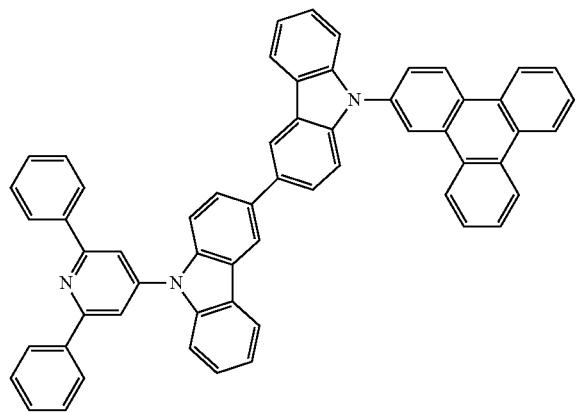
B-19
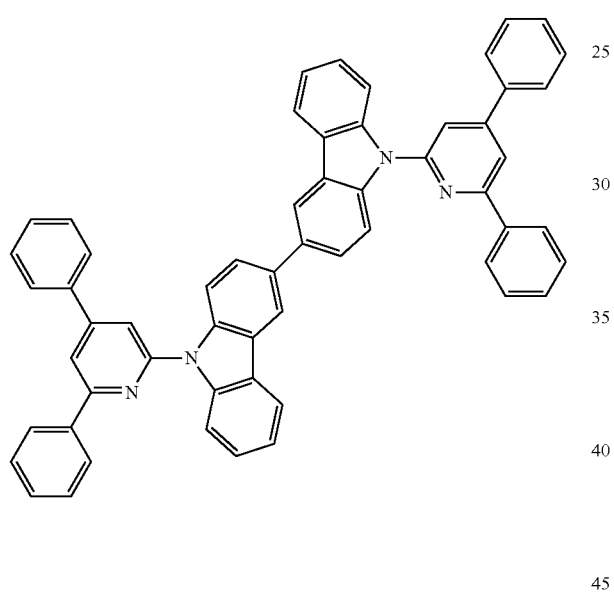
B-20
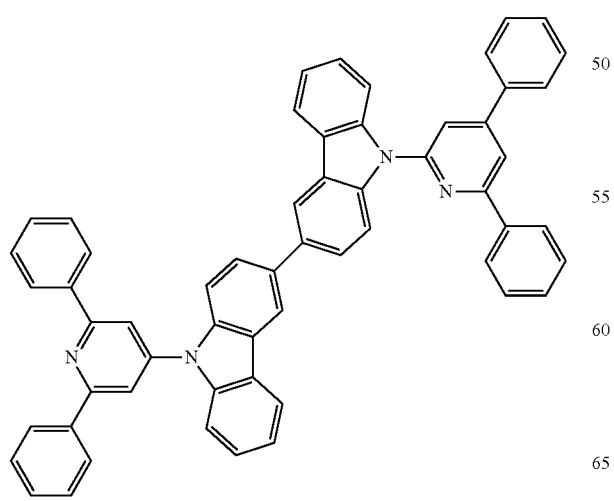
B-21
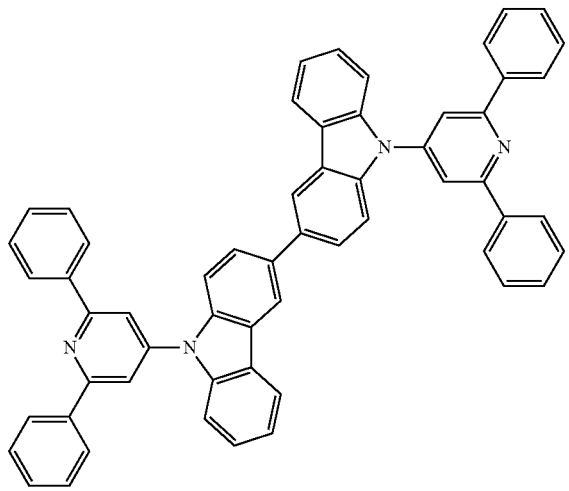
B-22
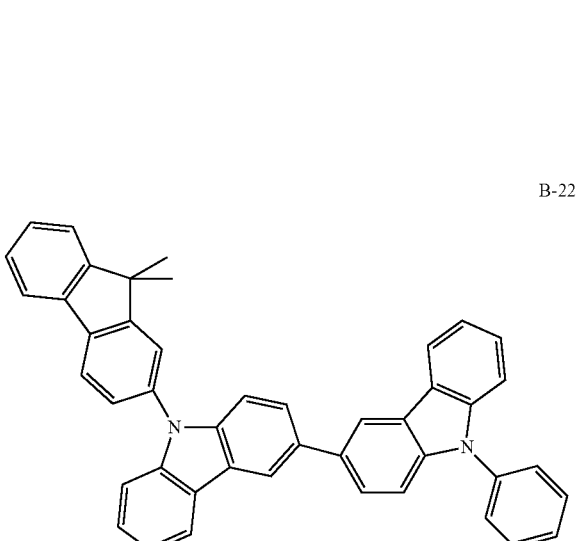
B-23
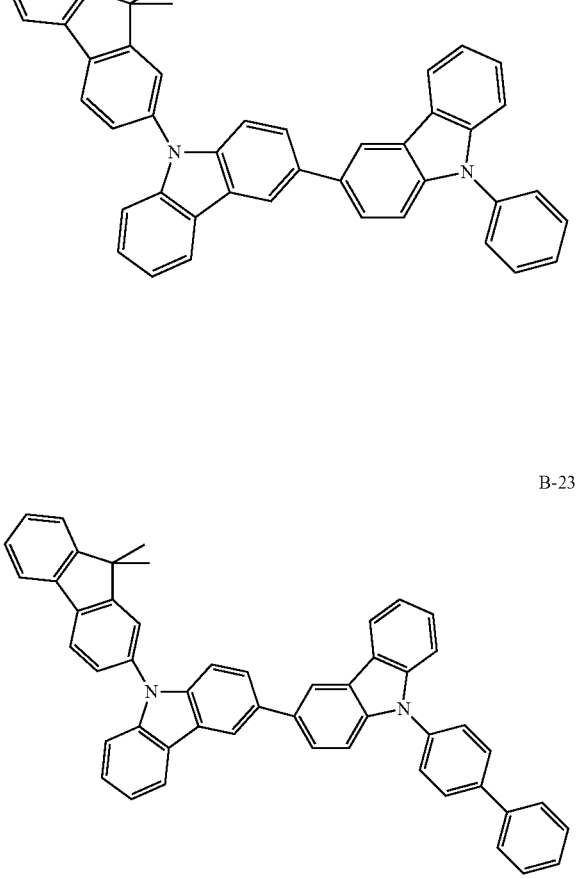

B-24
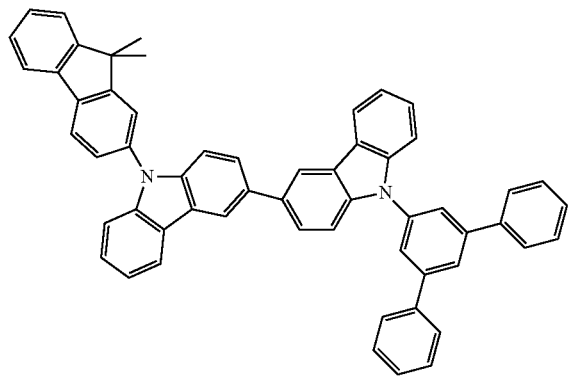
B-27
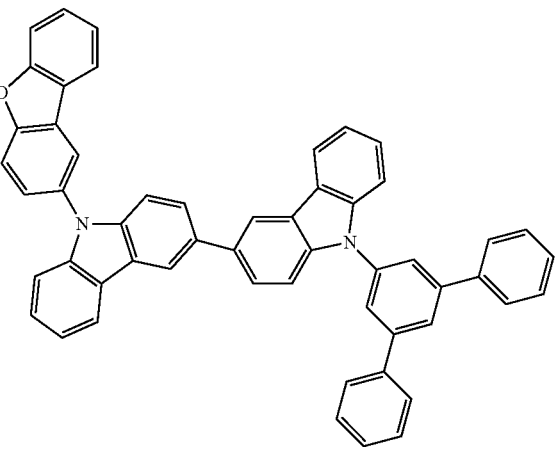
B-25
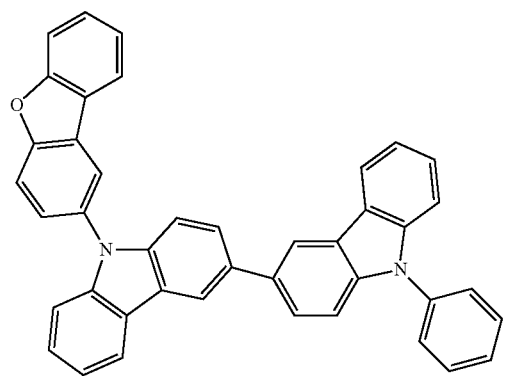
B-28
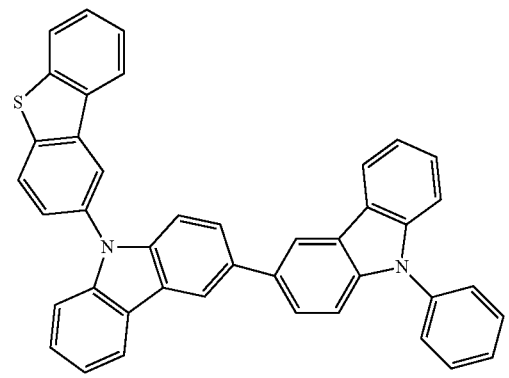
B-26
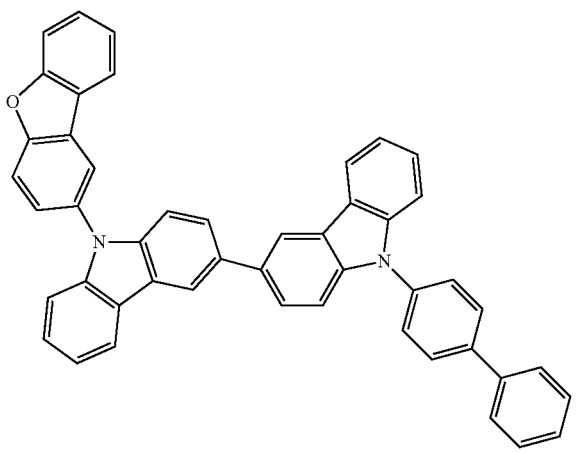
B-29
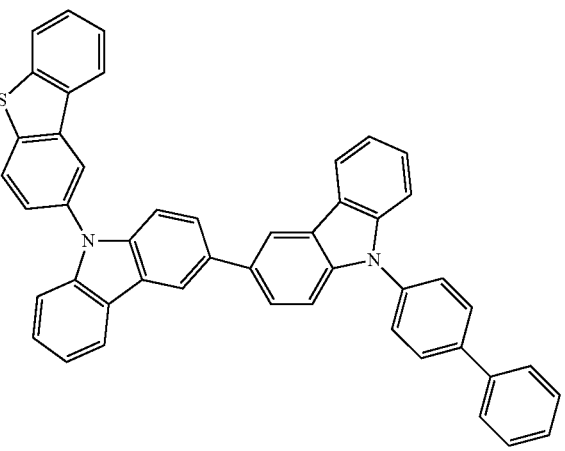

B-30
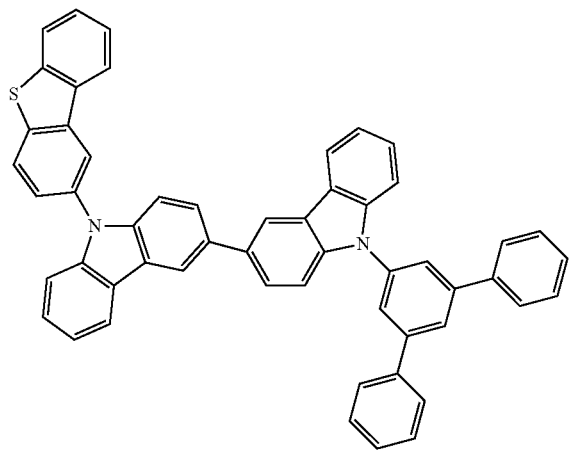
B-31
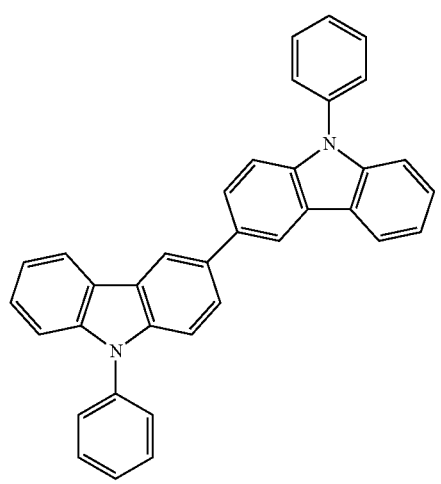
B-32
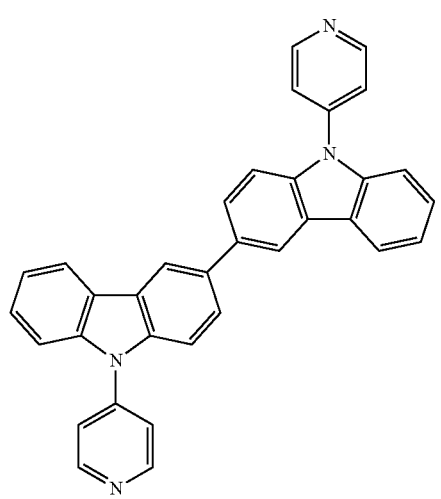
B-33
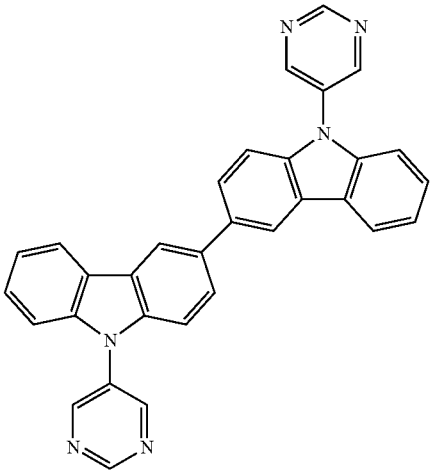
B-34
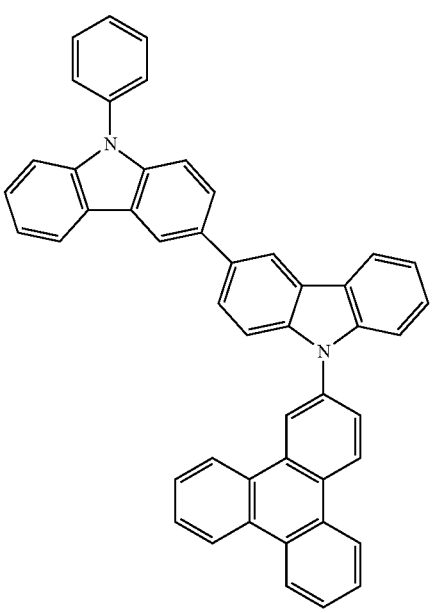

B-35
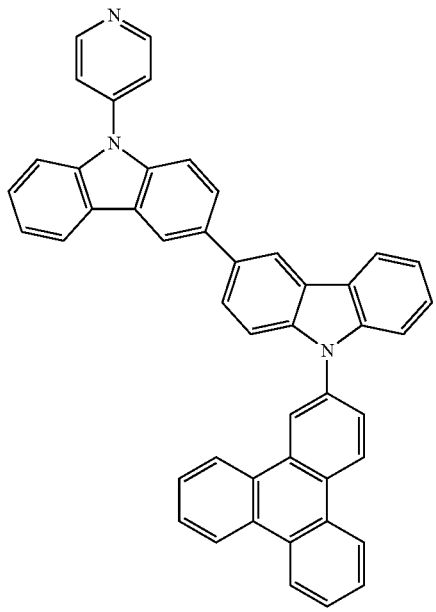
B-37
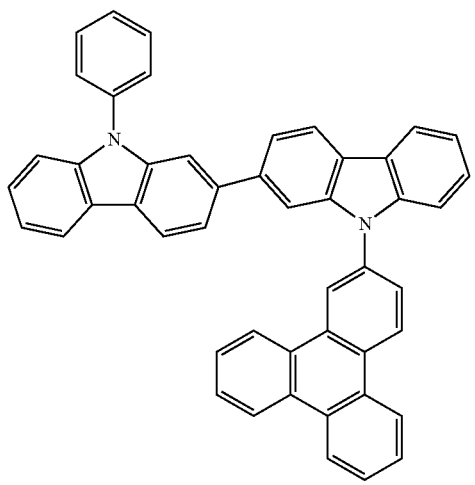
B-38
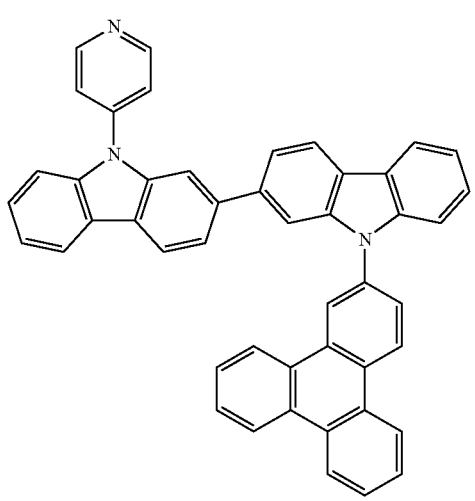
B-40
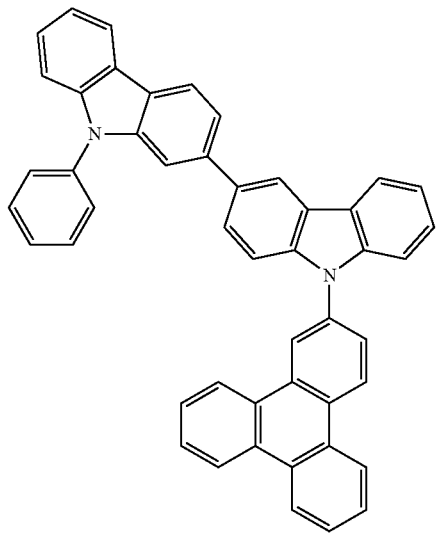
B-41
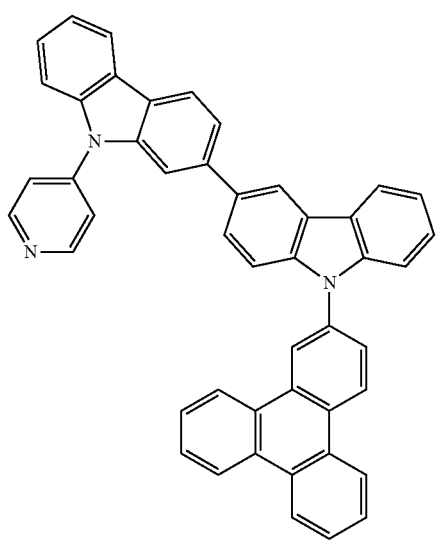

B-43
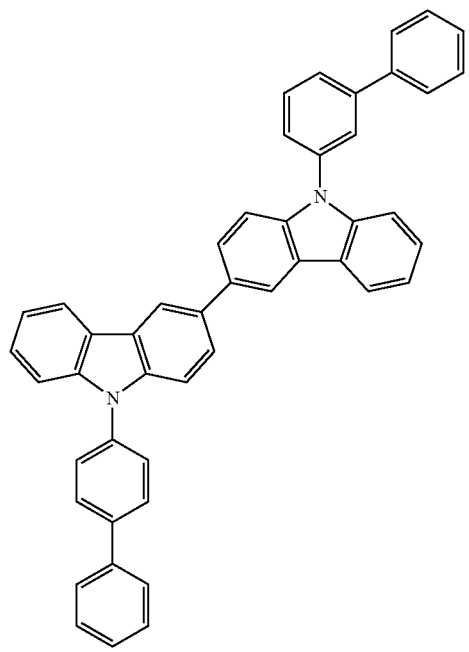
B-44
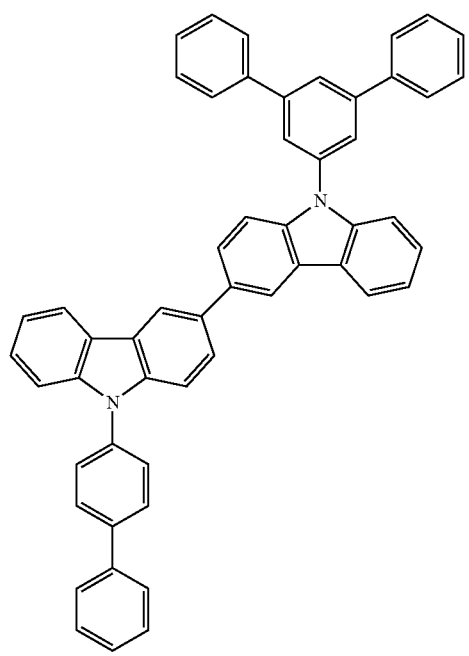
B-45
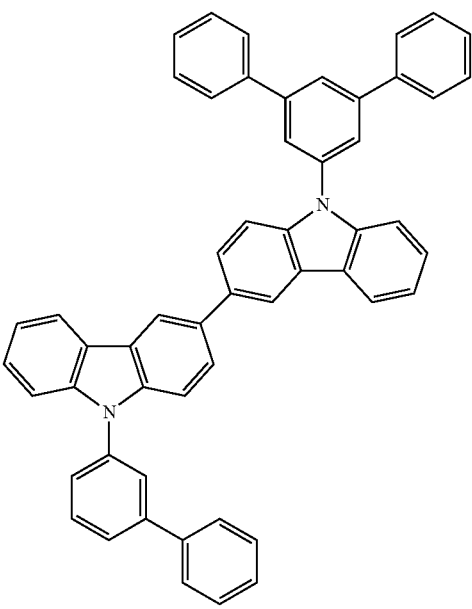
B-46
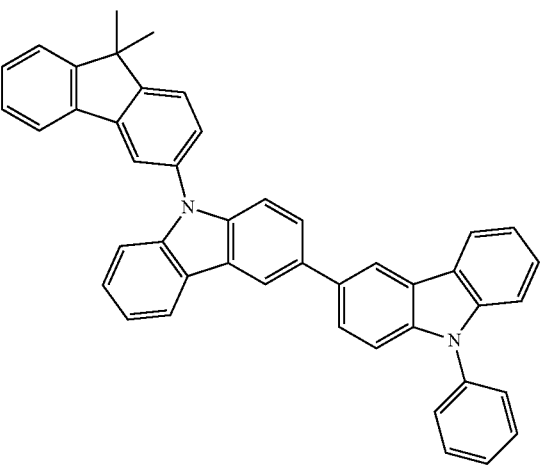

B-47
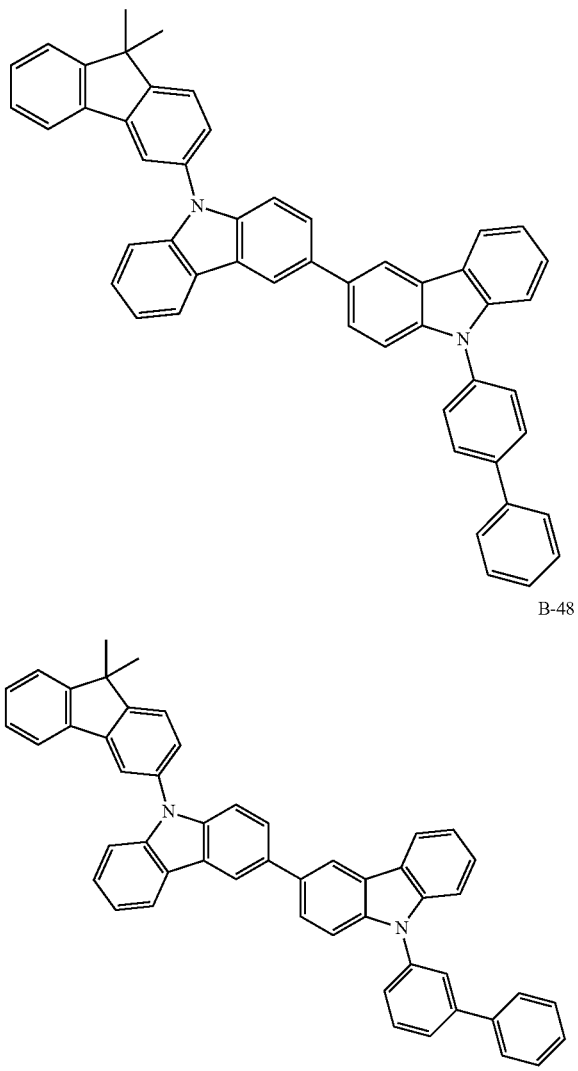
B-50
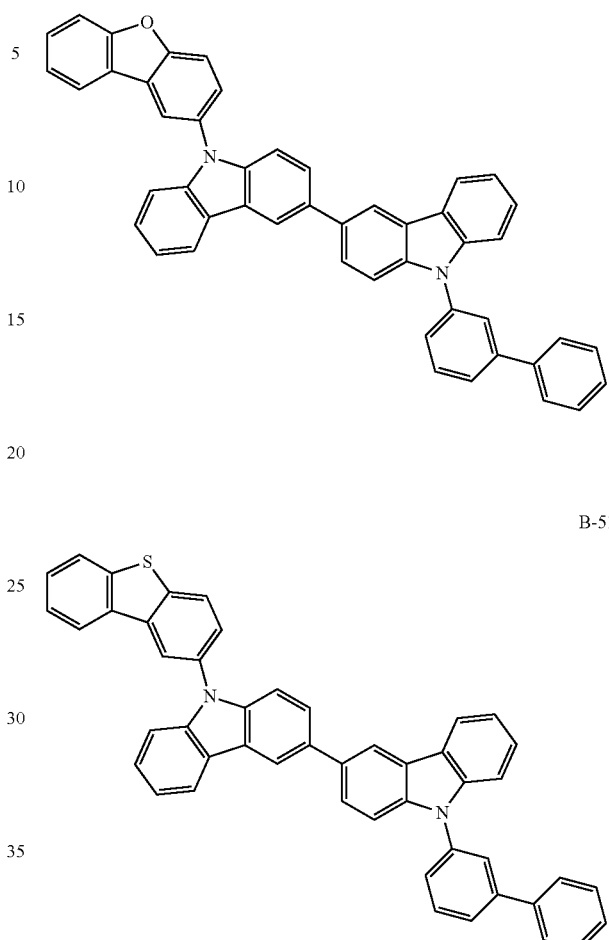
B-51
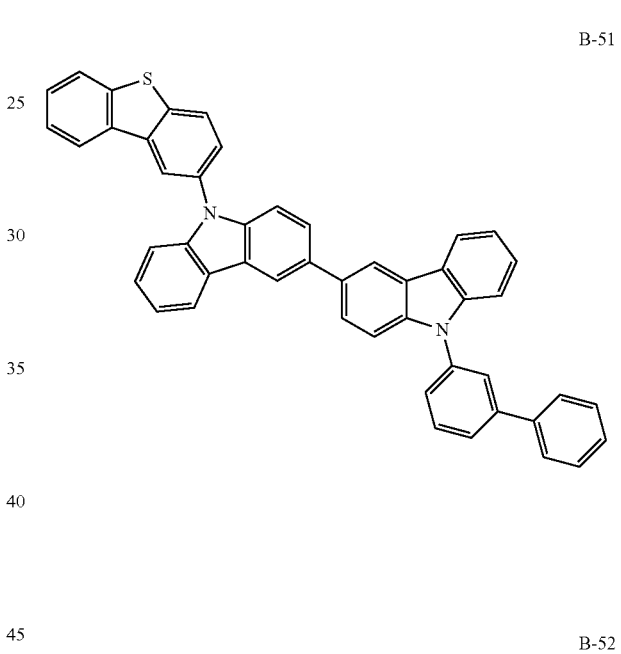
B-48
B-49
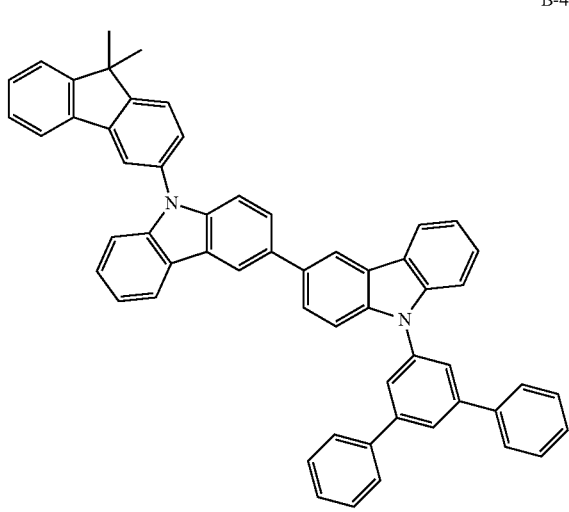
B-52
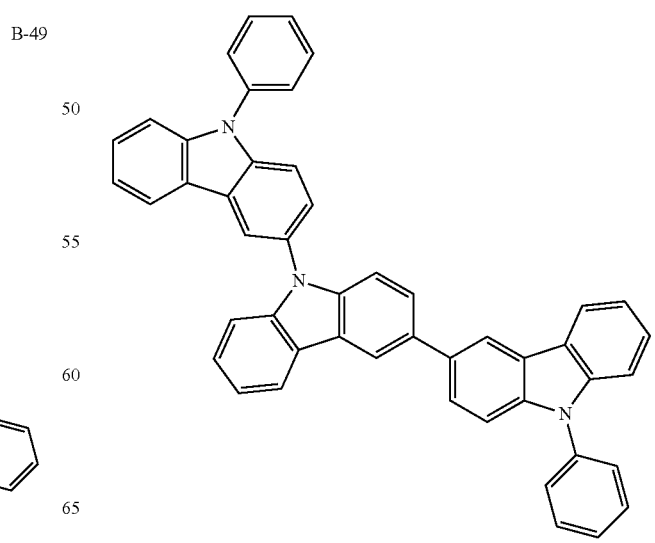

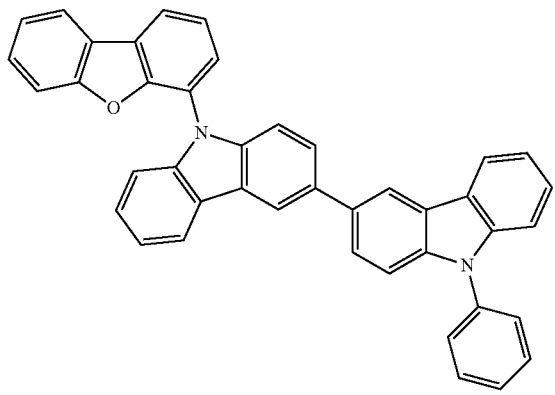
B-53
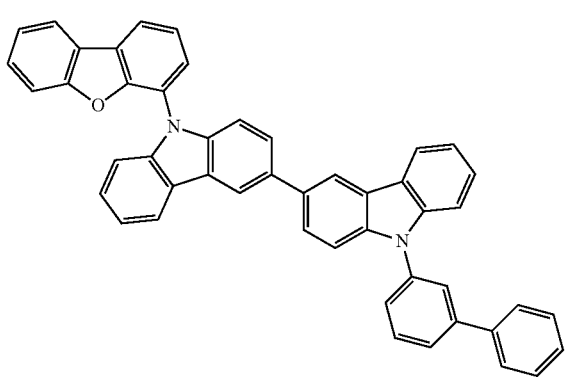
B-54
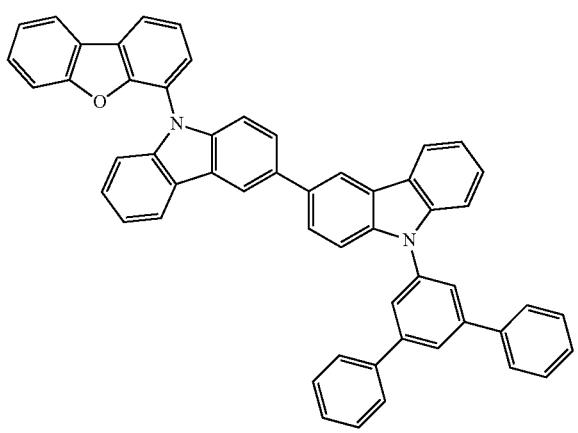
B-55
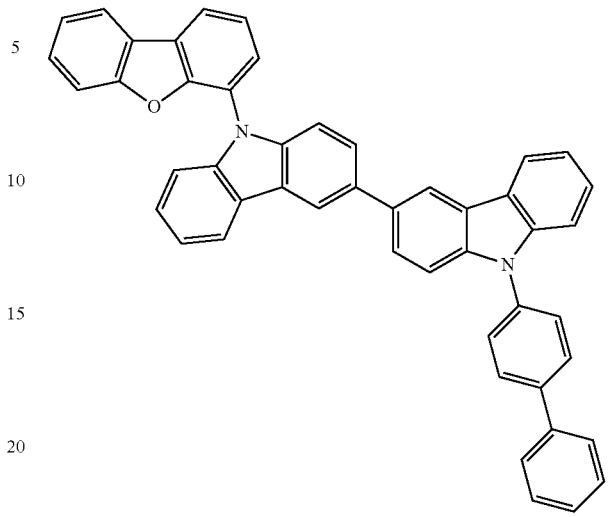
B-56
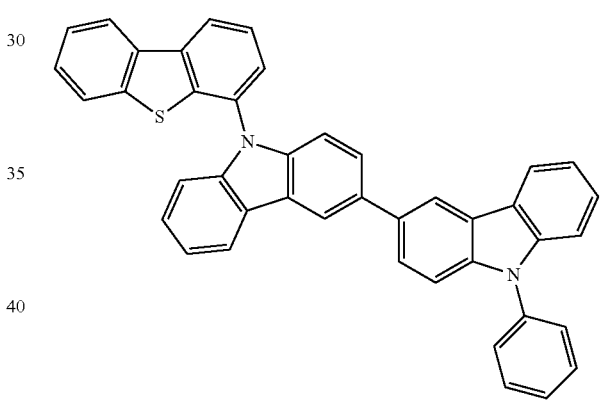
B-57
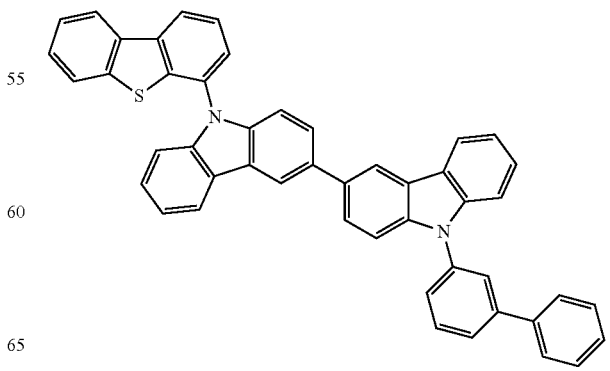
B-58

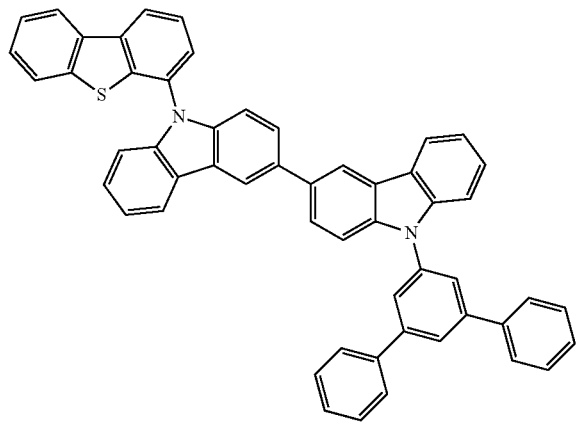
B-59
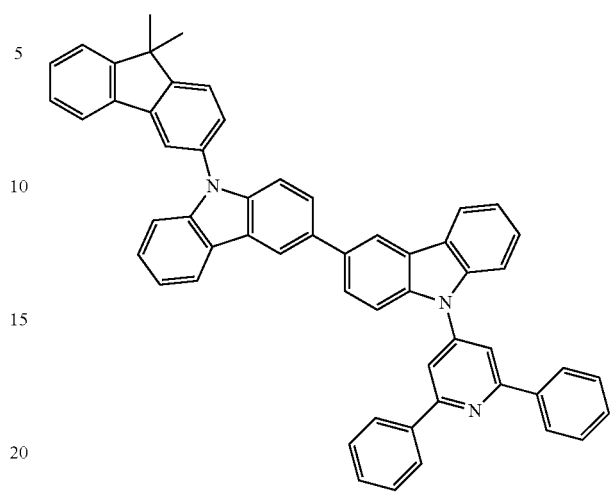
B-62
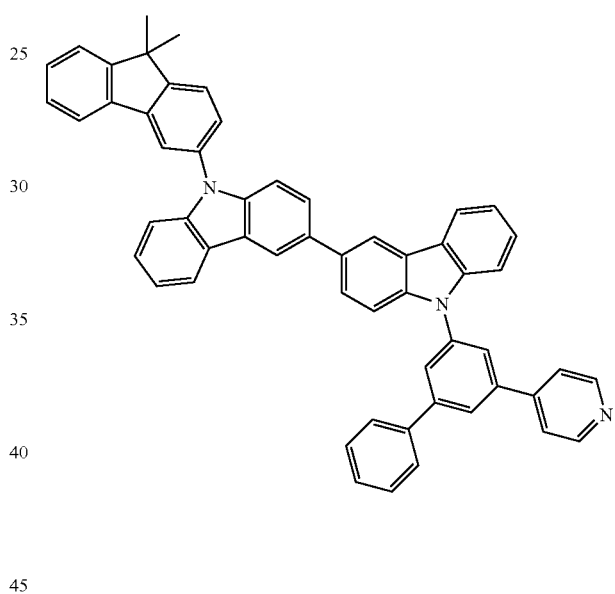
B-60, B-63
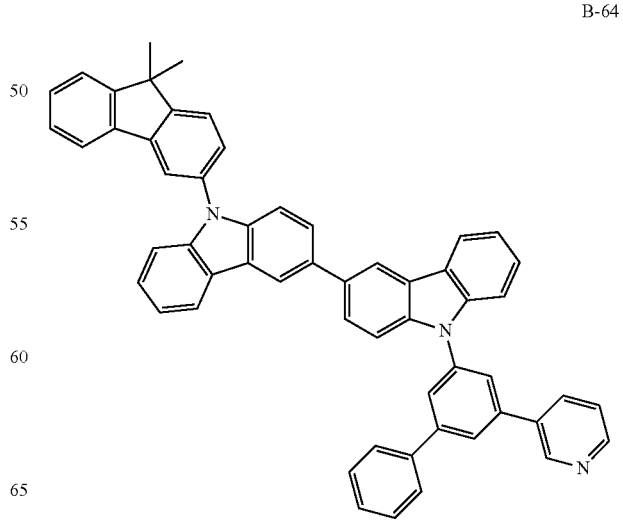
B-61, B-64

B-65
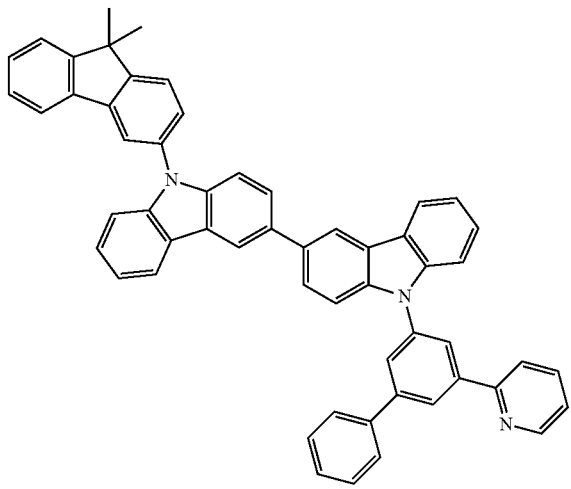
B-66
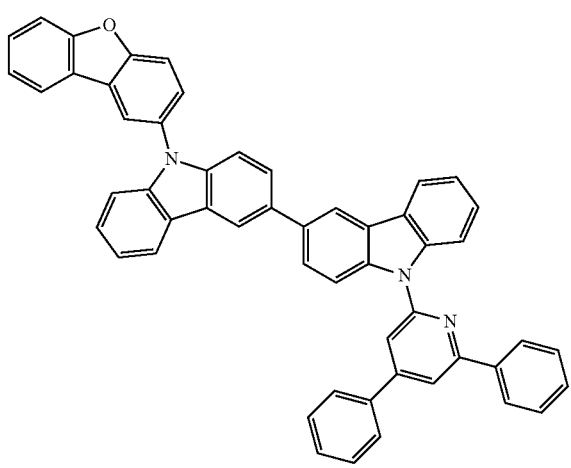
B-67
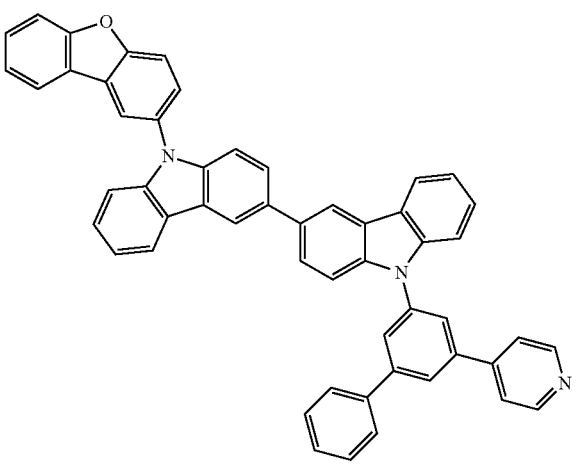
B-68
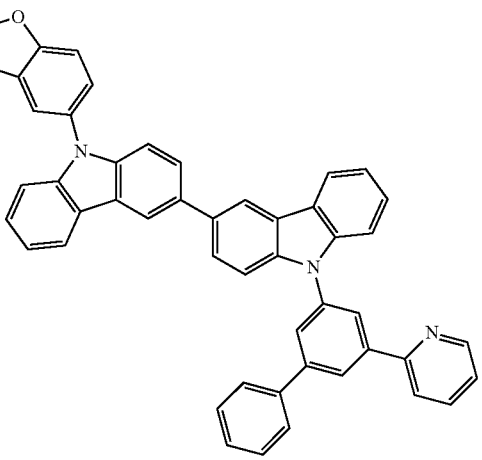
B-69
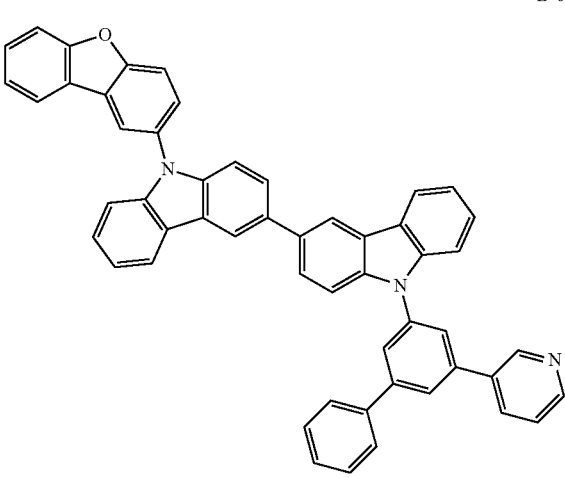
B-70
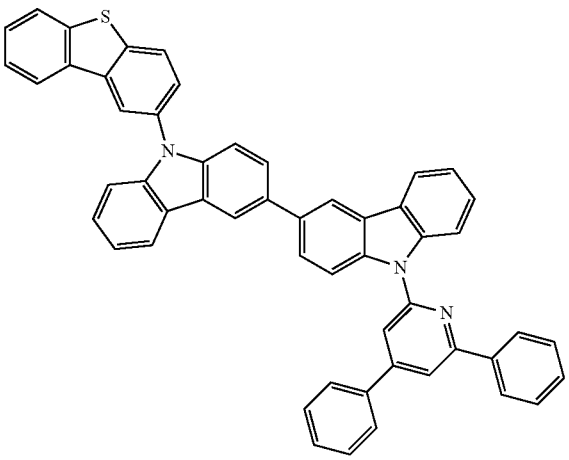

B-71
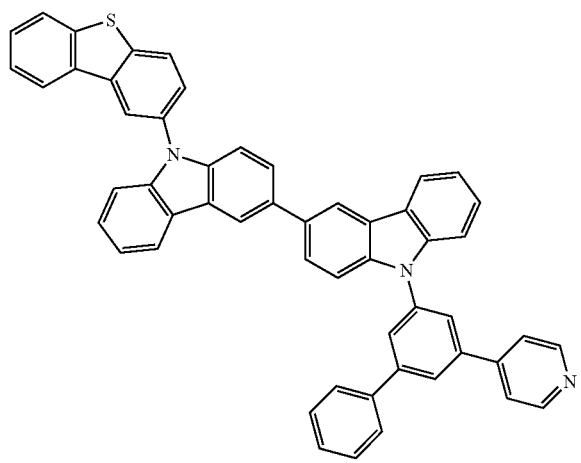
B-72
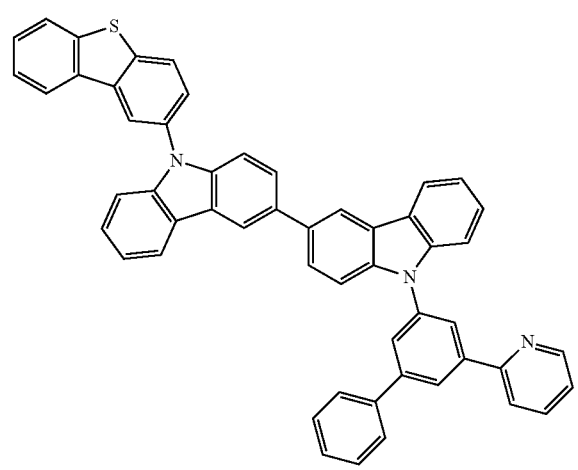
B-73
B-74
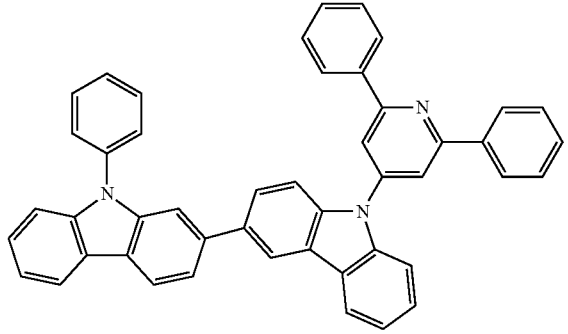
B-75
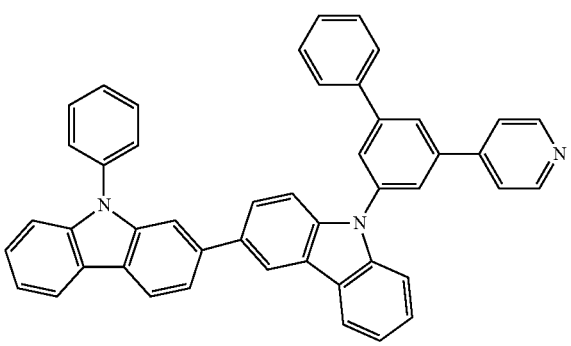
B-76
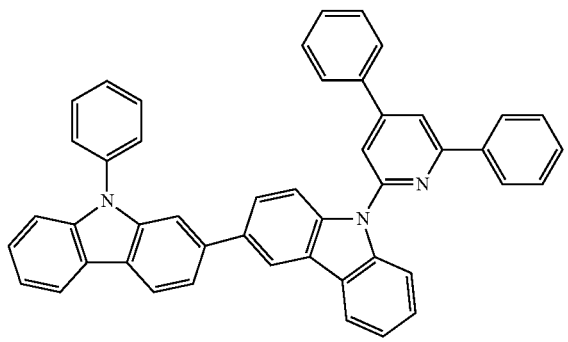
B-77
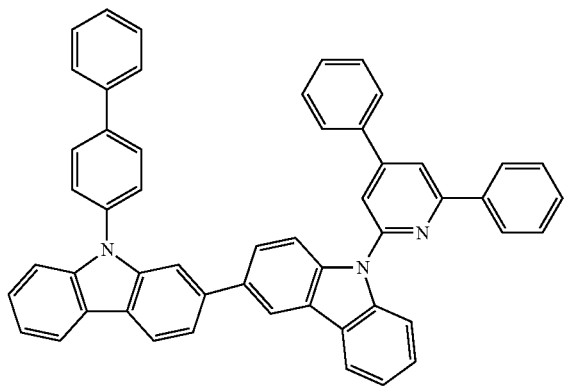

B-78
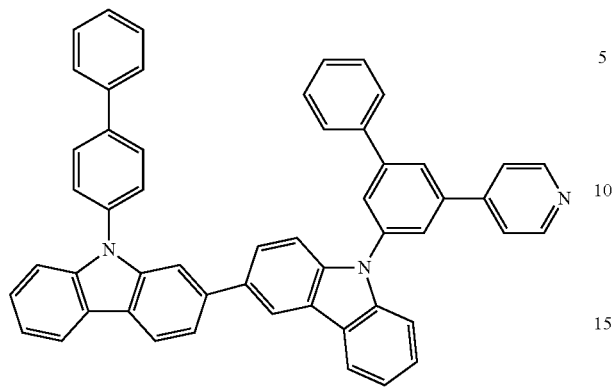
B-79
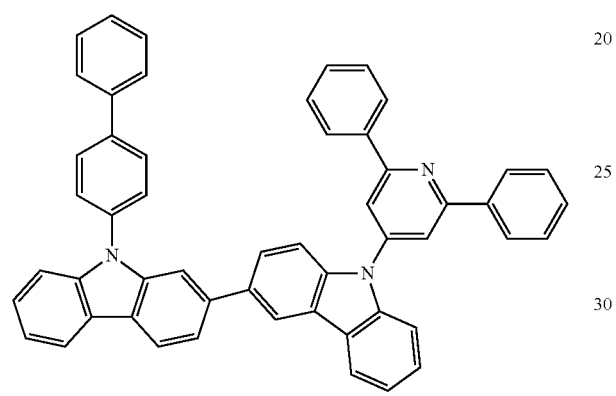
B-80
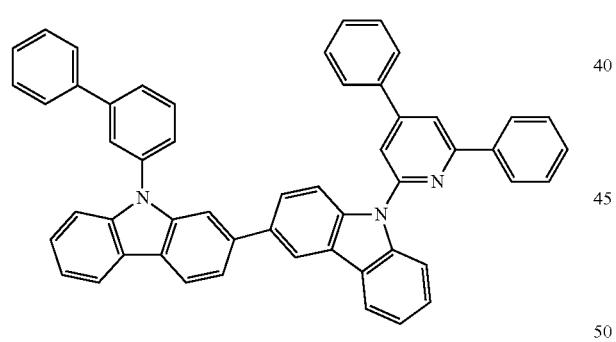
B-81
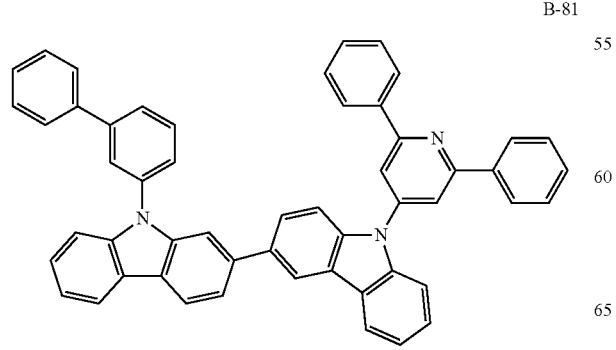
B-82
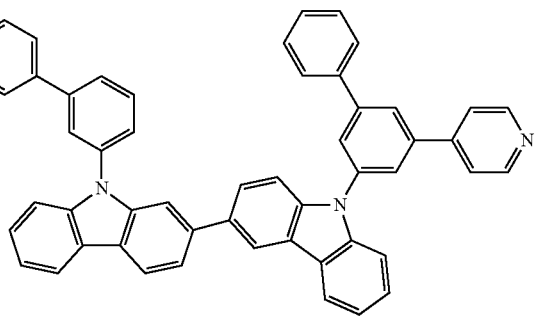
B-83
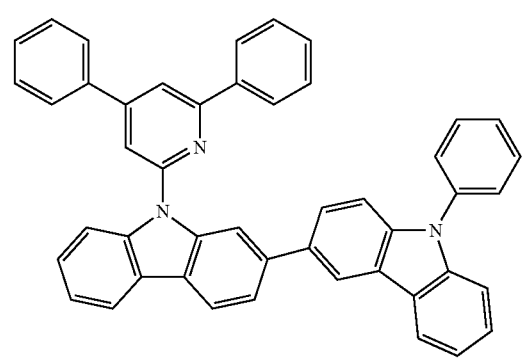
B-84
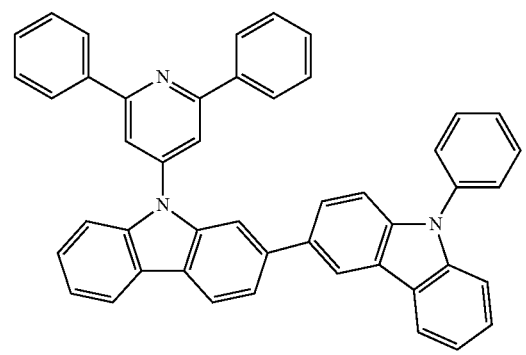
B-85
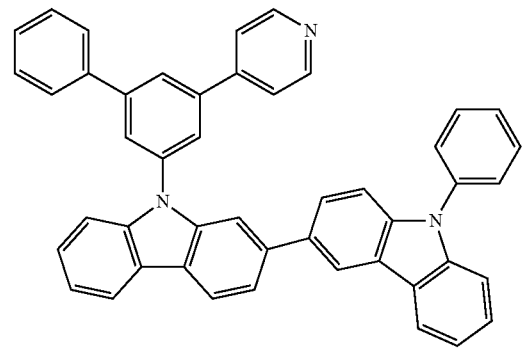

B-86 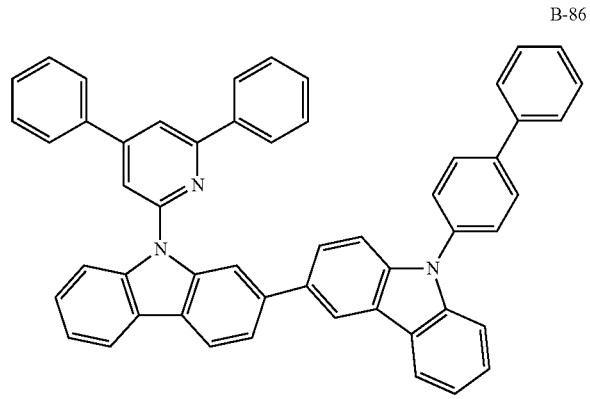
B-87 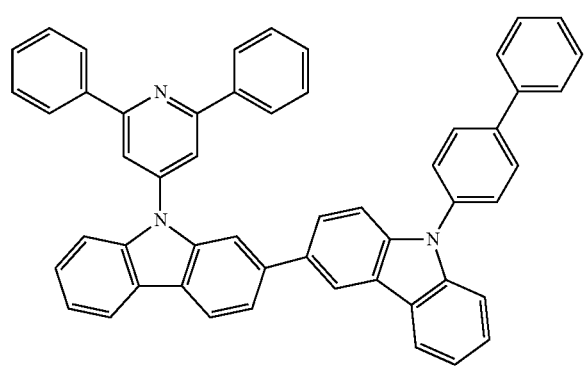
B-88 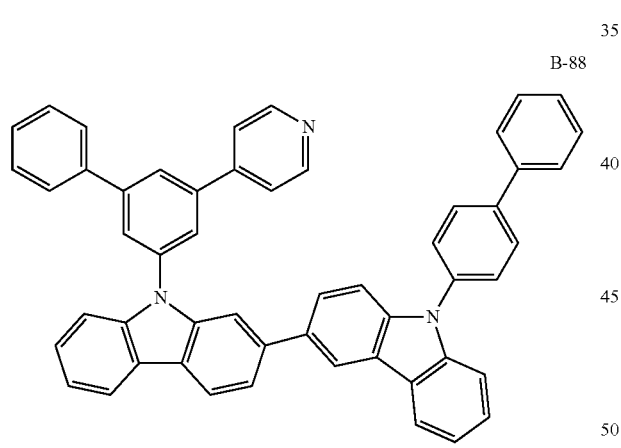
B-89 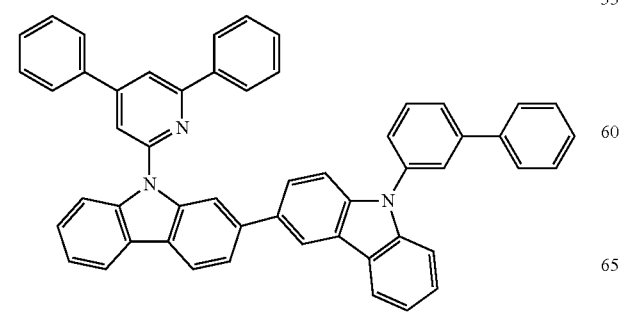
B-90 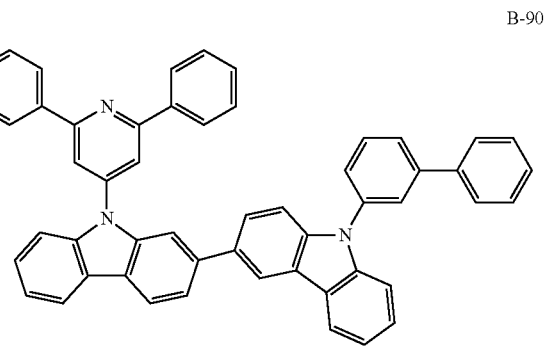
B-91 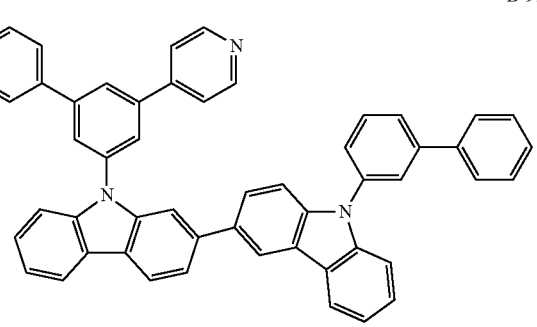
B-92 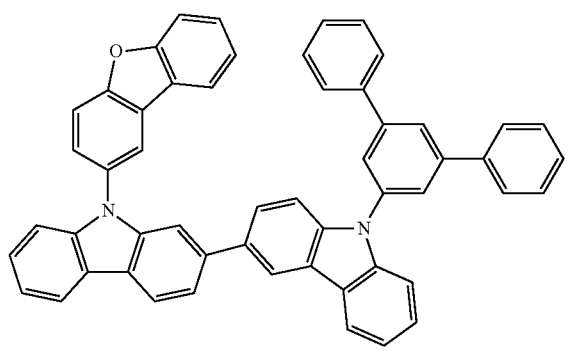
B-93 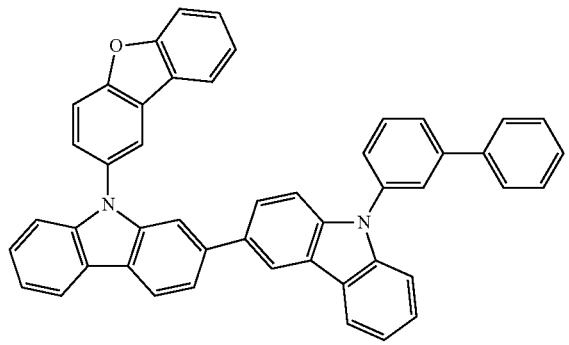

B-94
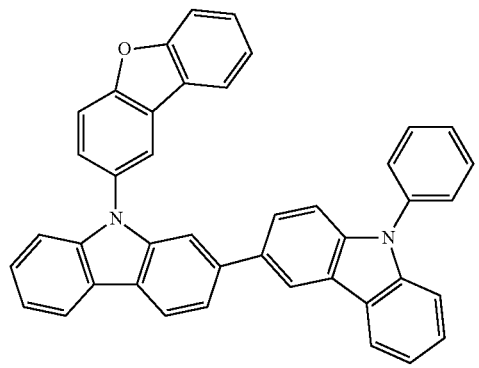
B-95
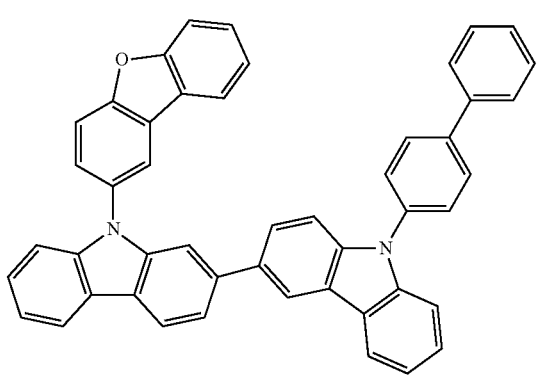
B-98
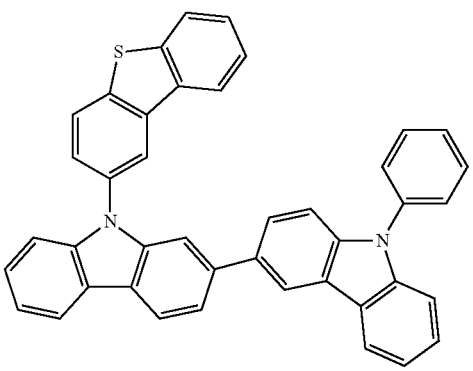
B-99
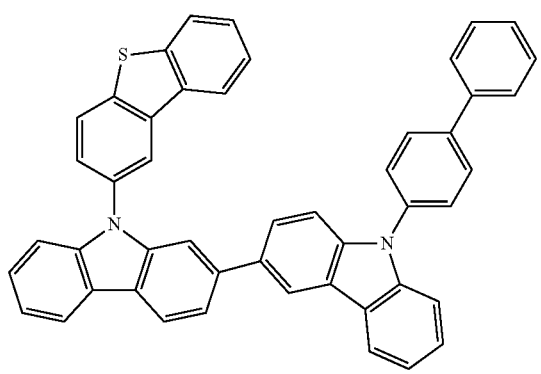
B-96
B-100
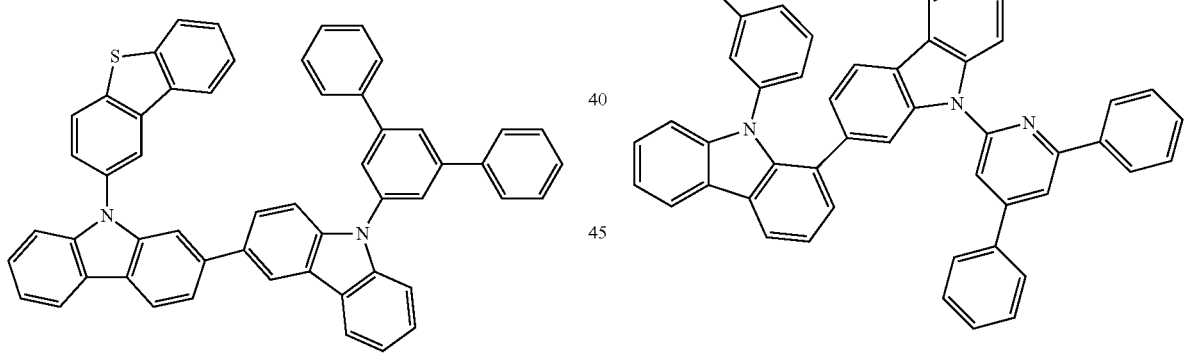
B-97
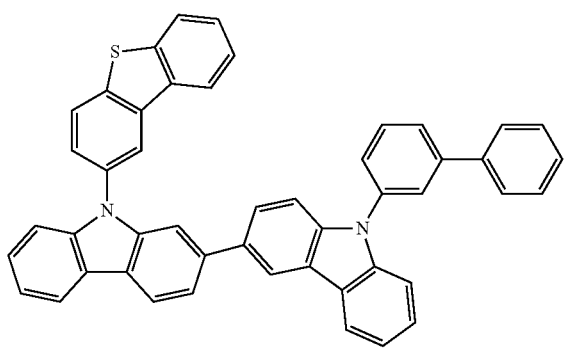
B-101
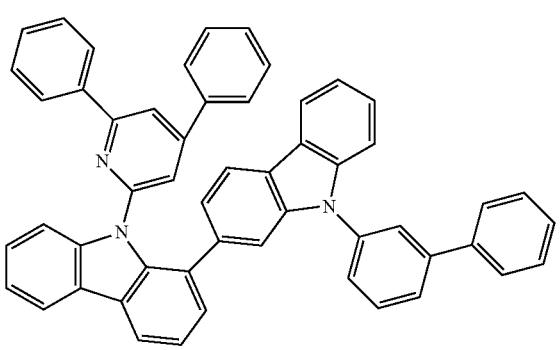

B-102
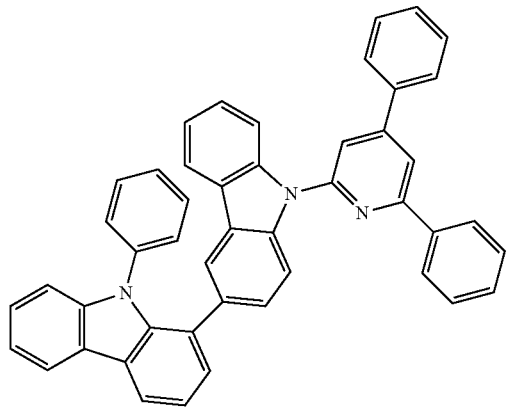
B-103
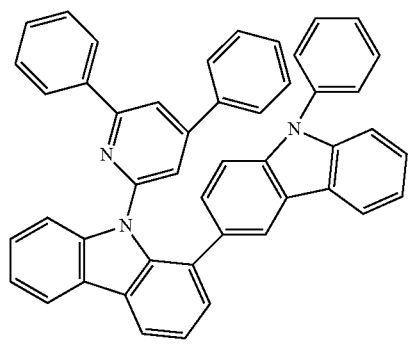
B-104
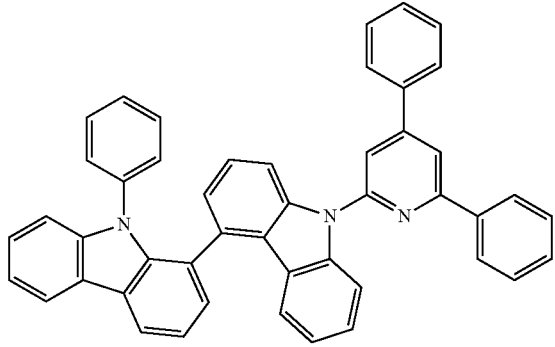
B-105
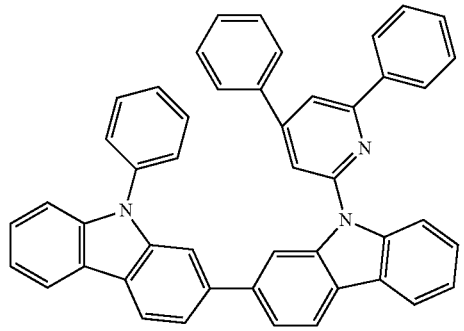
B-106
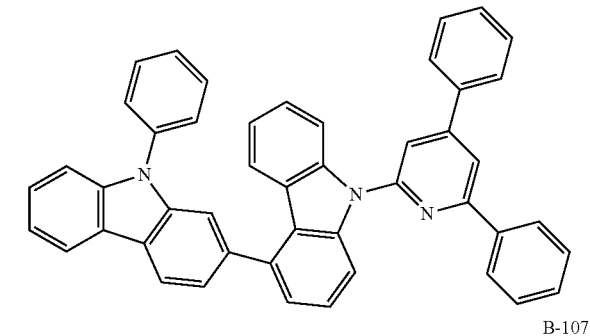
B-107
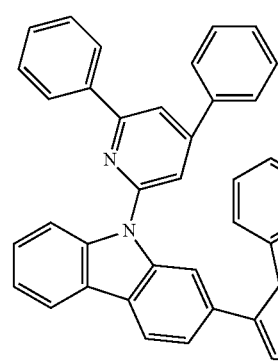
B-108
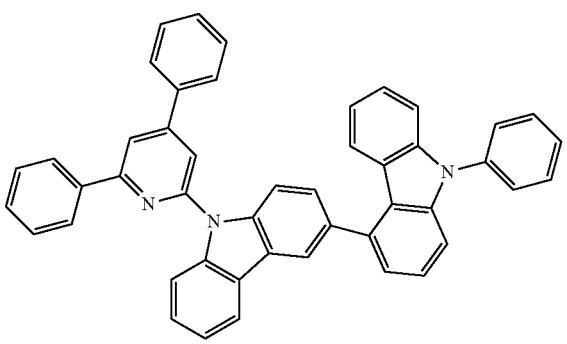
B-109
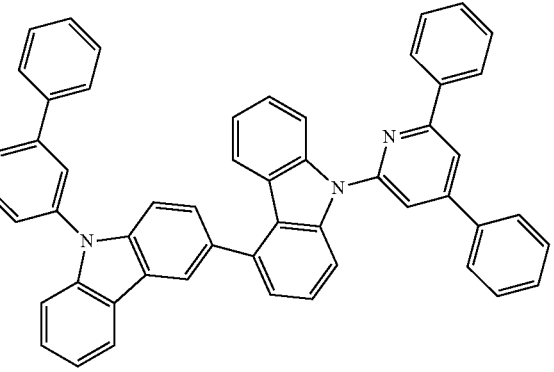

B-110
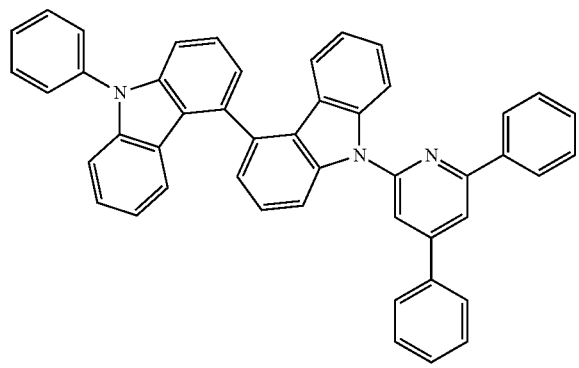
B-111
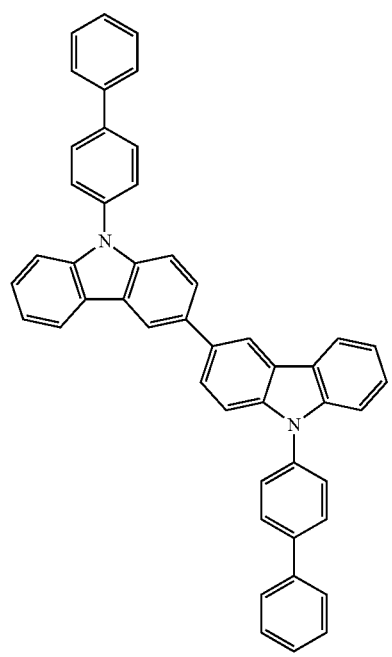
B-112
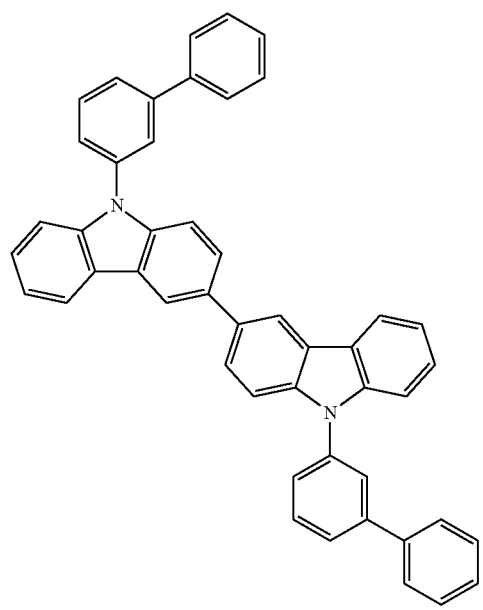
B-113
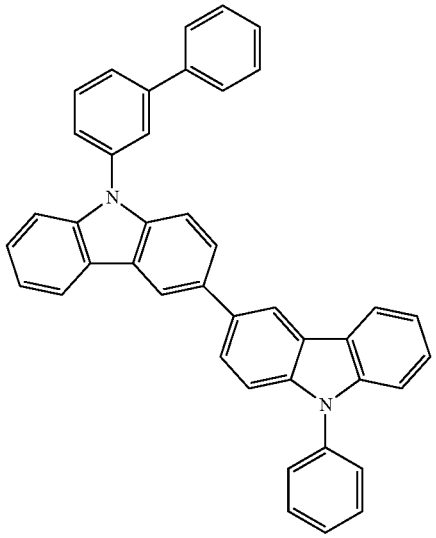
B-114
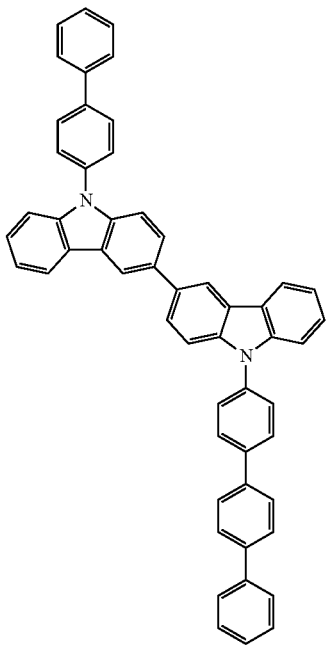

B-115
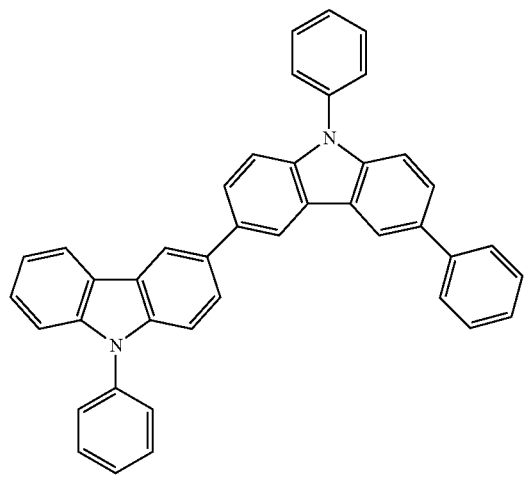
B-116
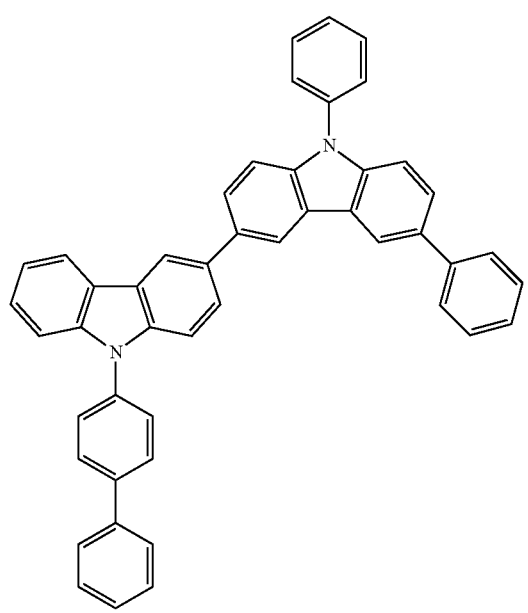
B-117
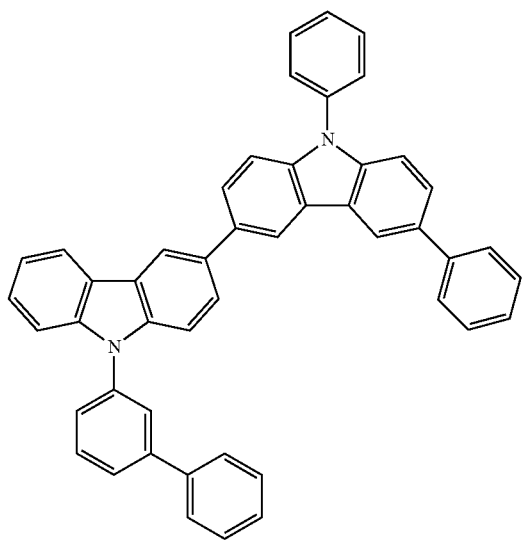
B-118
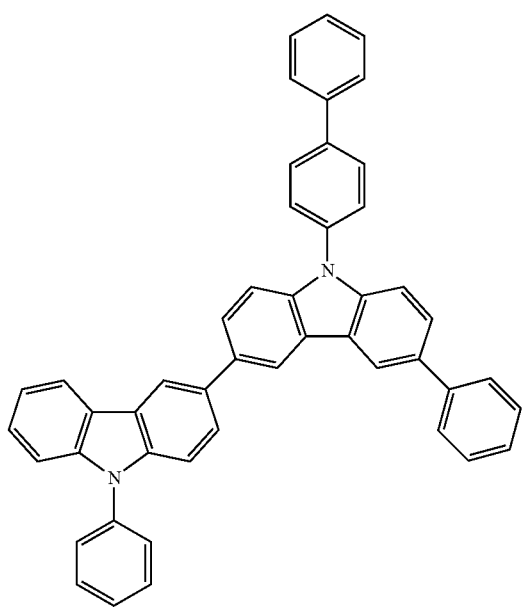
B-119
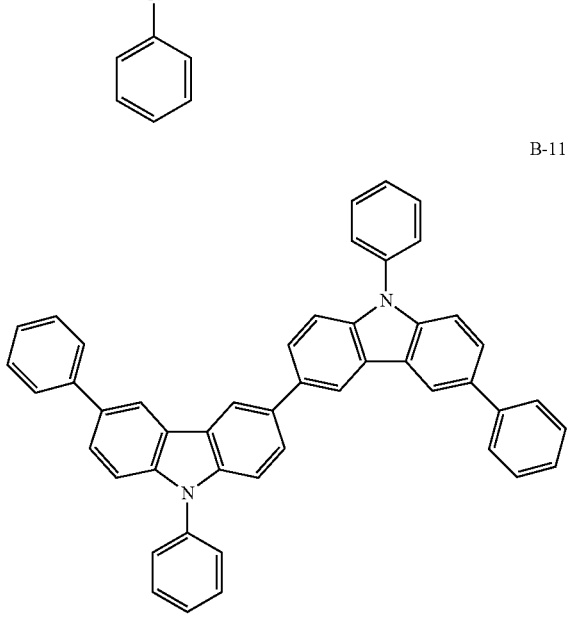

B-120
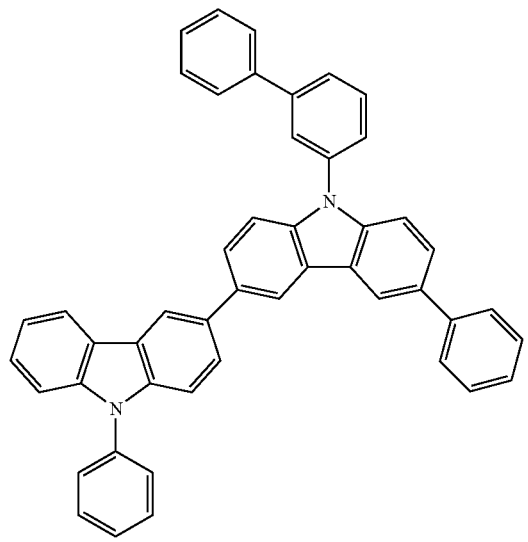
B-121
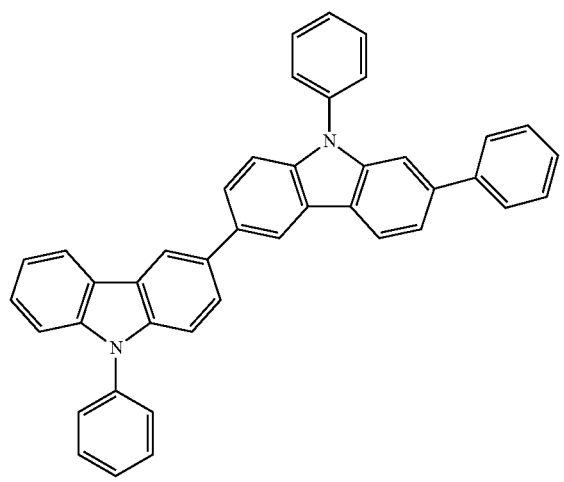
B-122
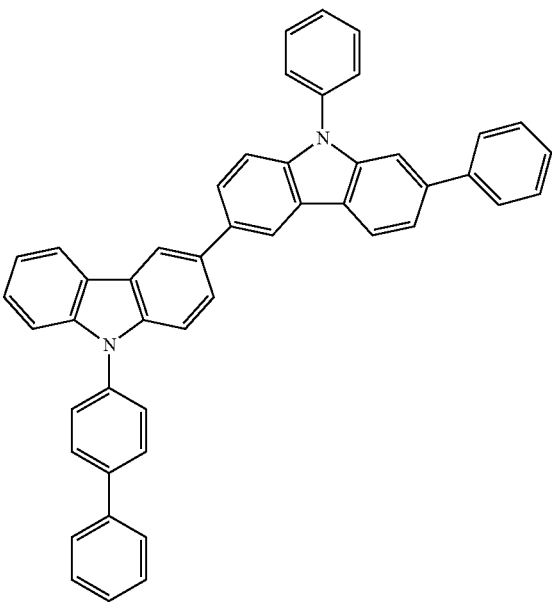
B-123
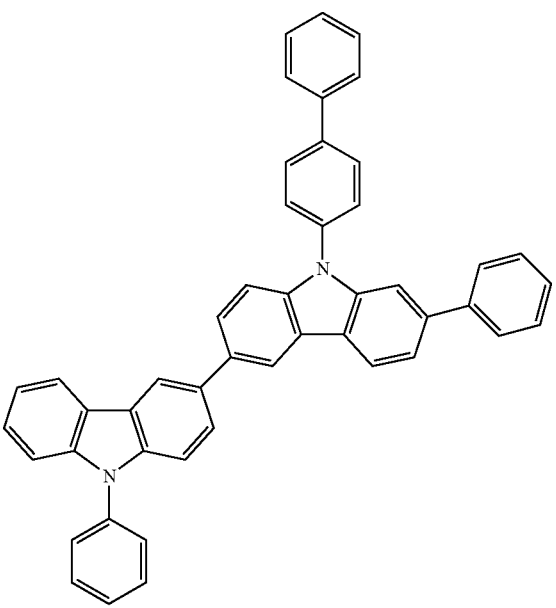

-continued
B-124
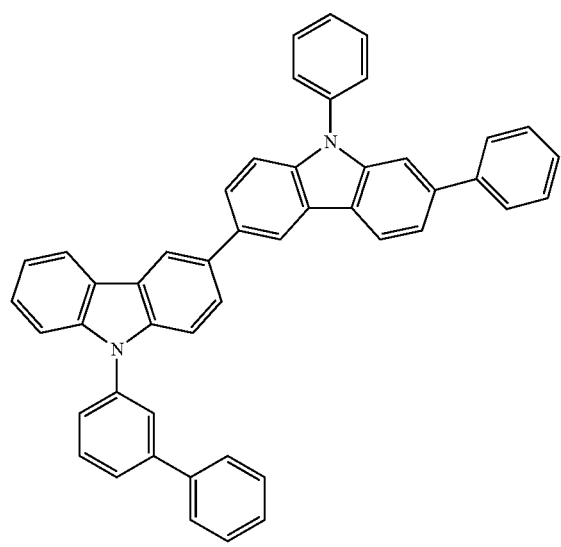
B-127
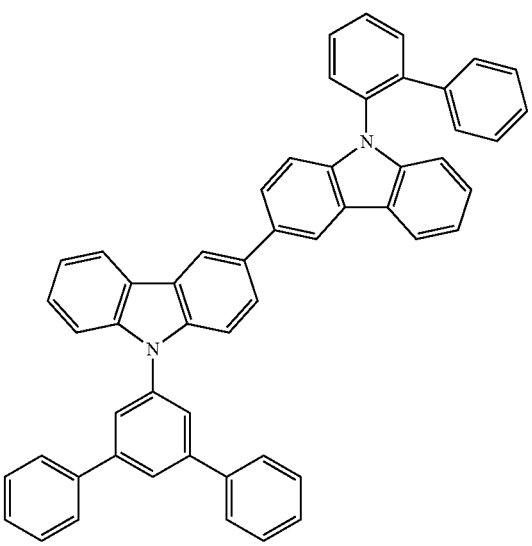
B-125
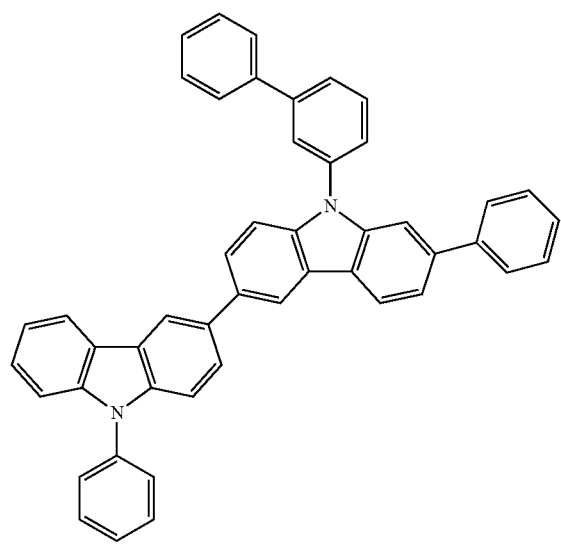
B-128
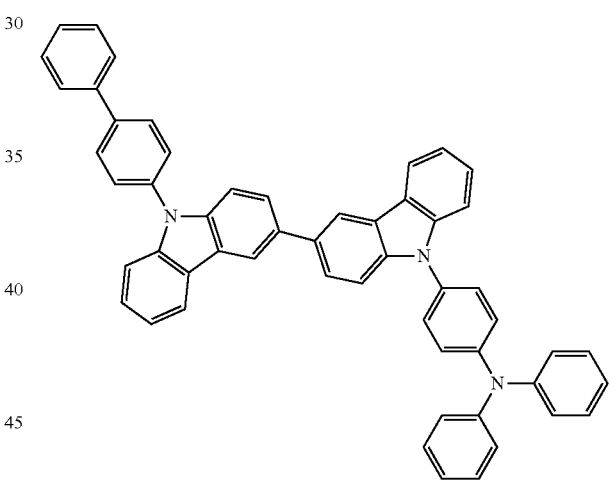
B-126
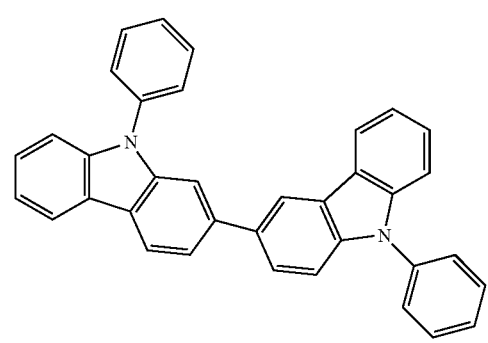
B-129
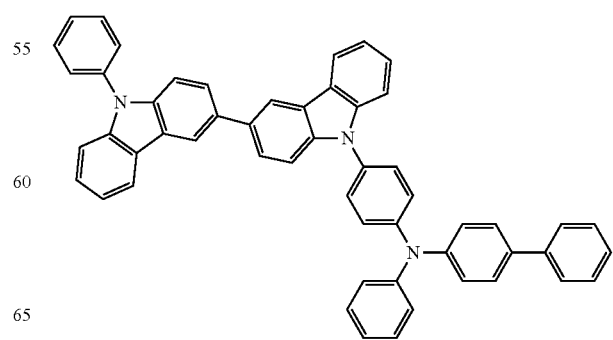

B-130
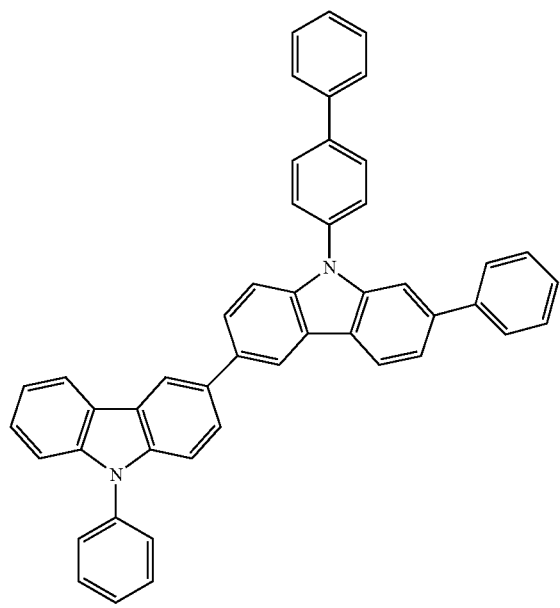
B-132
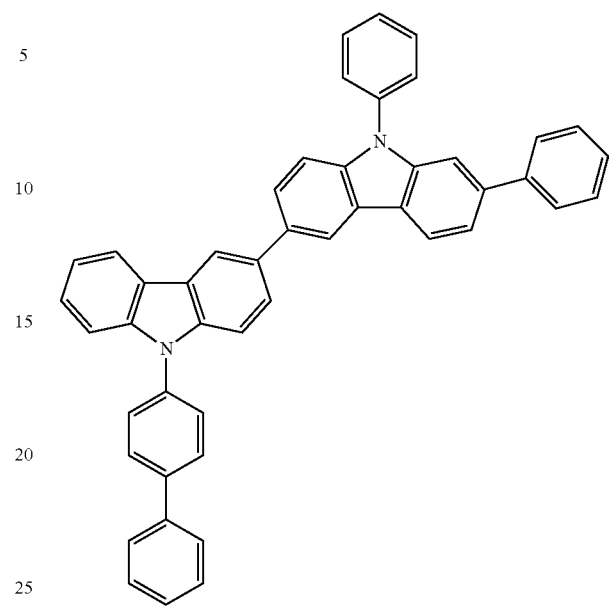
B-133
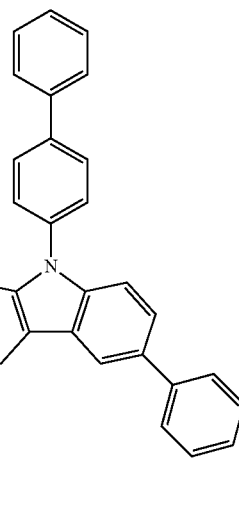
B-131
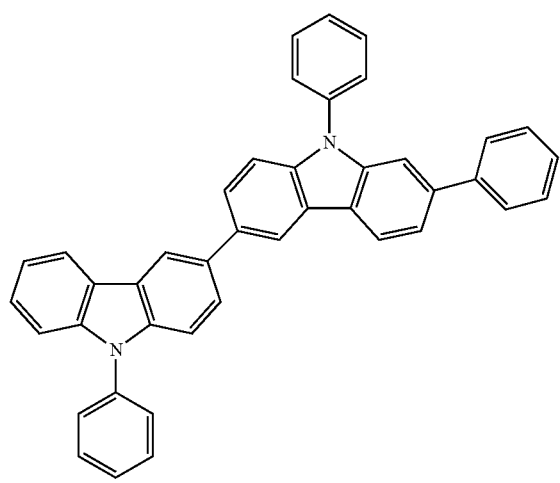
B-134

B-135
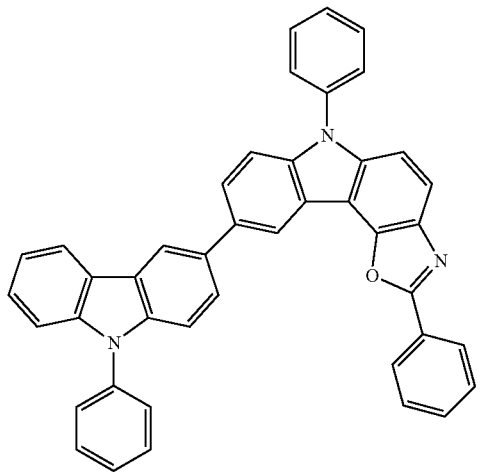
B-136
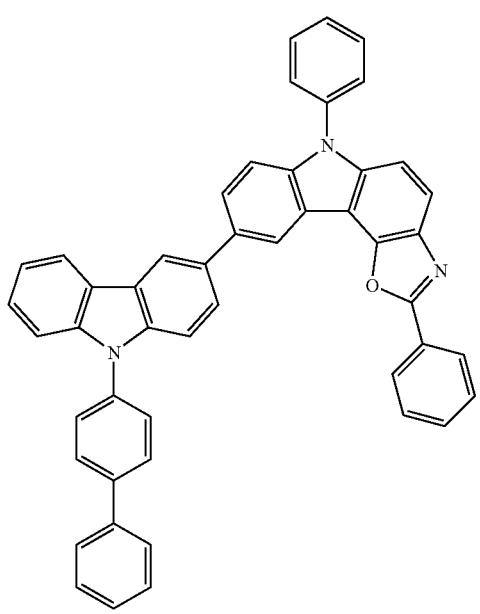
B-137
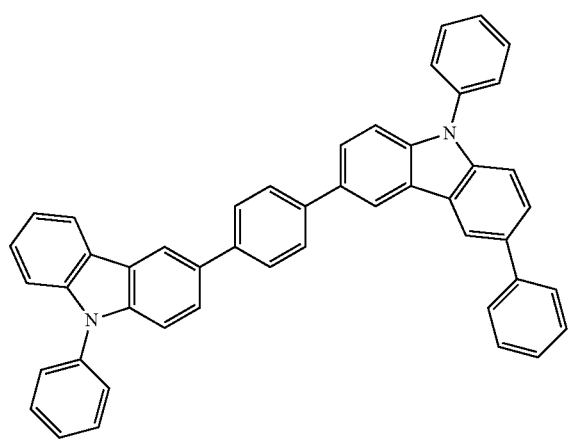
B-138
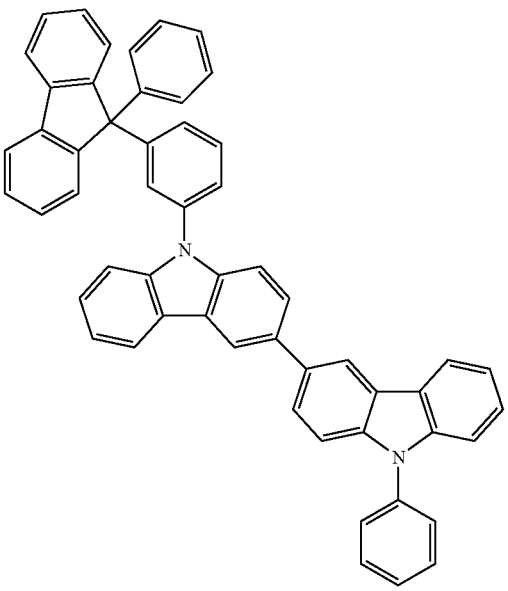
B-139
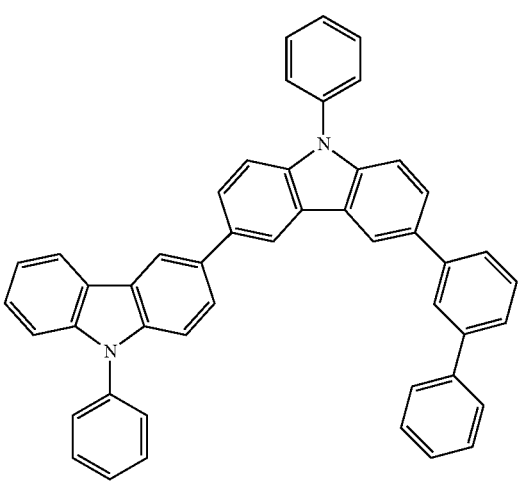
B-140
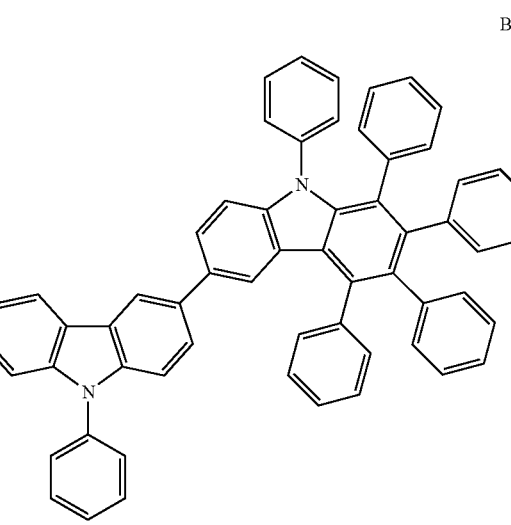

B-141
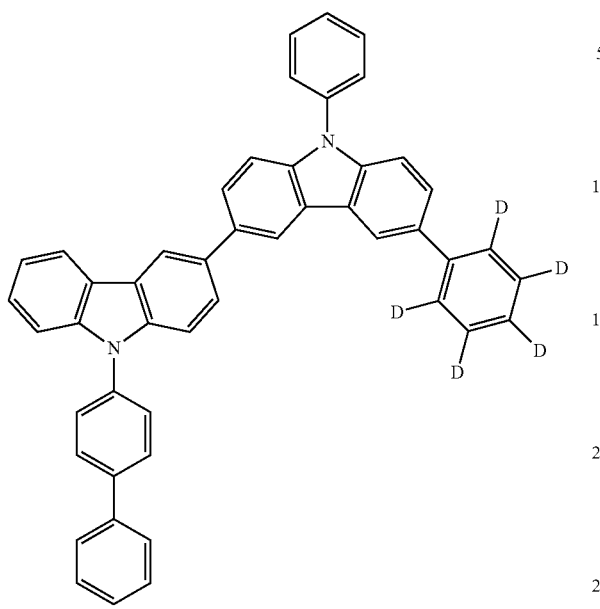
B-142
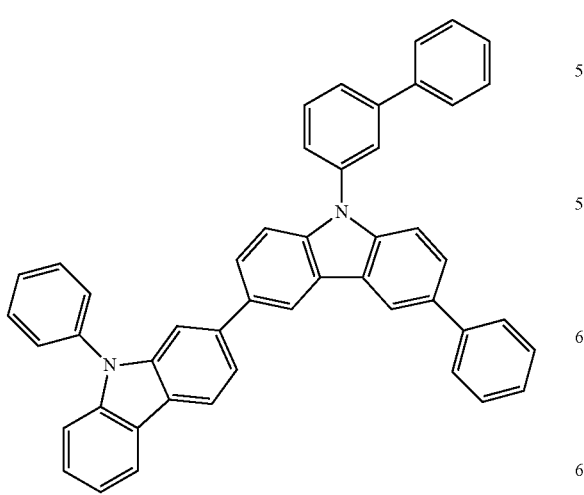
B-143
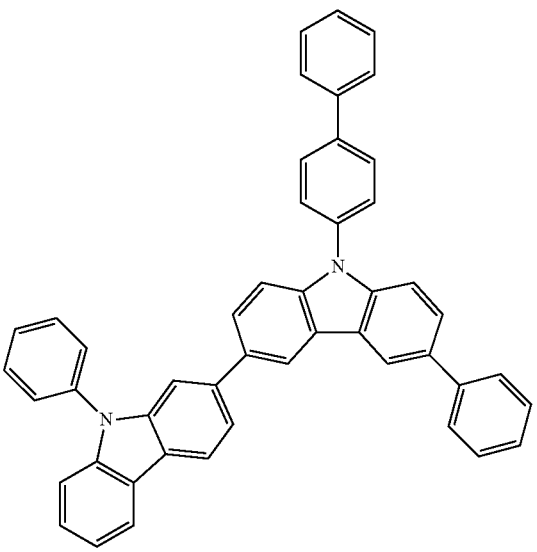
B-144
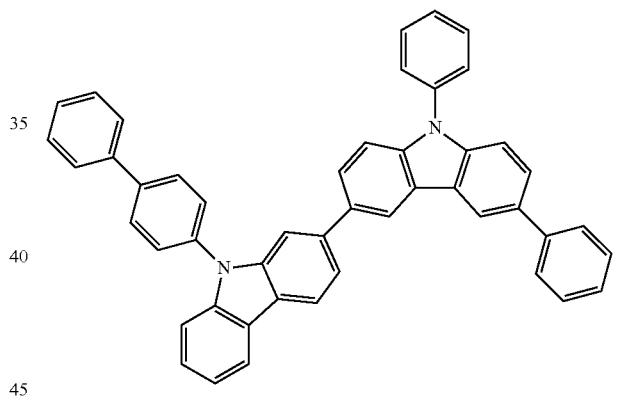
B-145
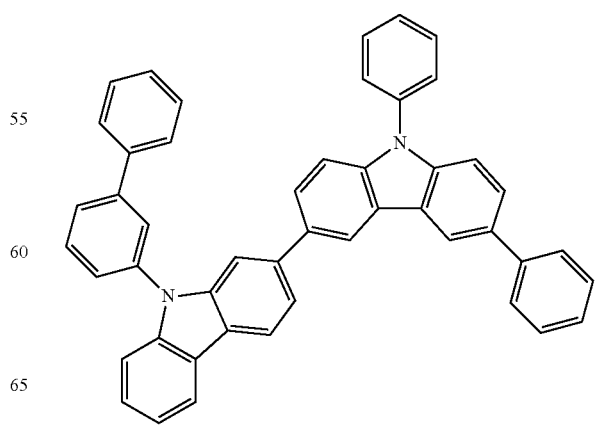

B-146
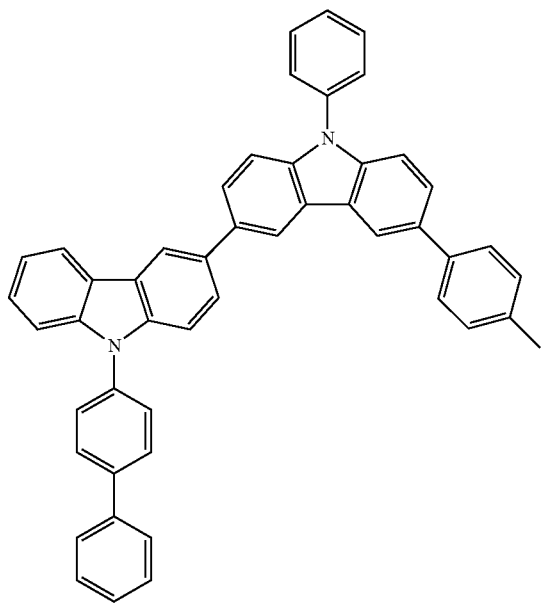
B-148
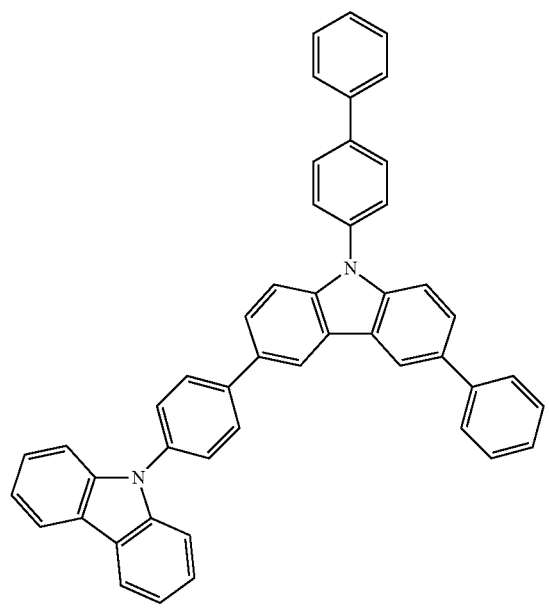
B-149
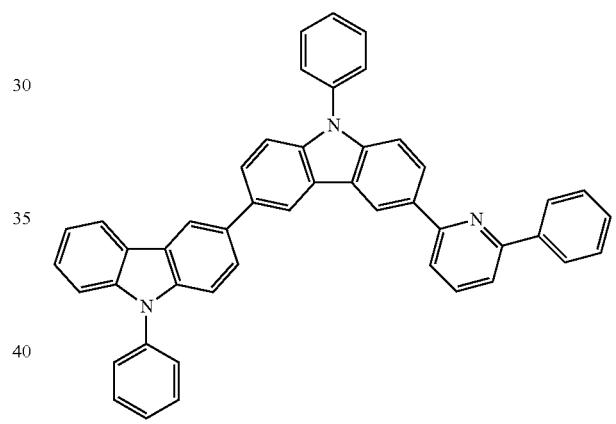
B-147
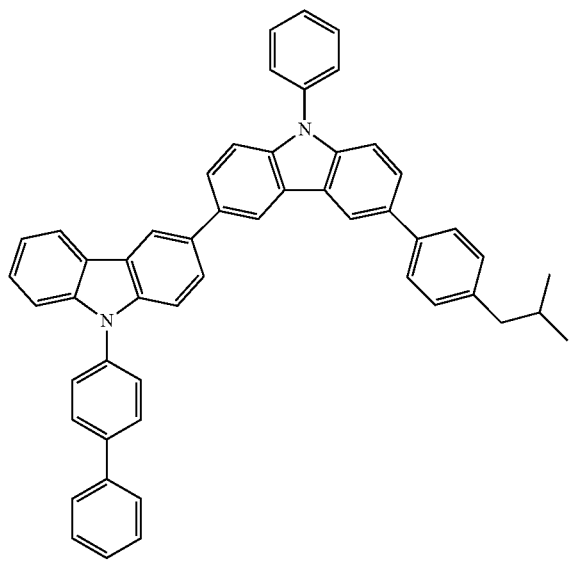
B-150
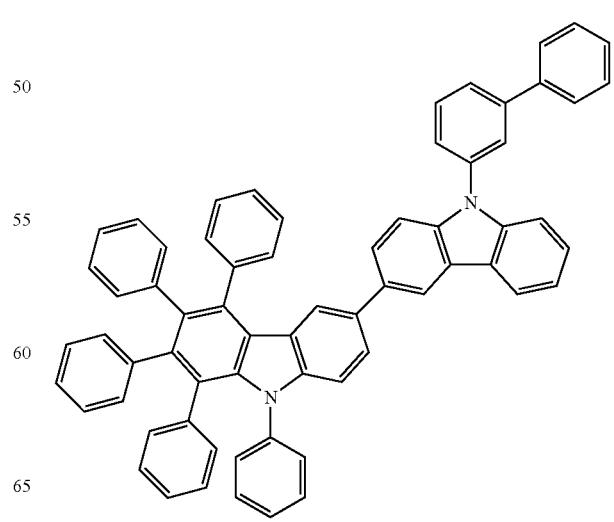

B-151
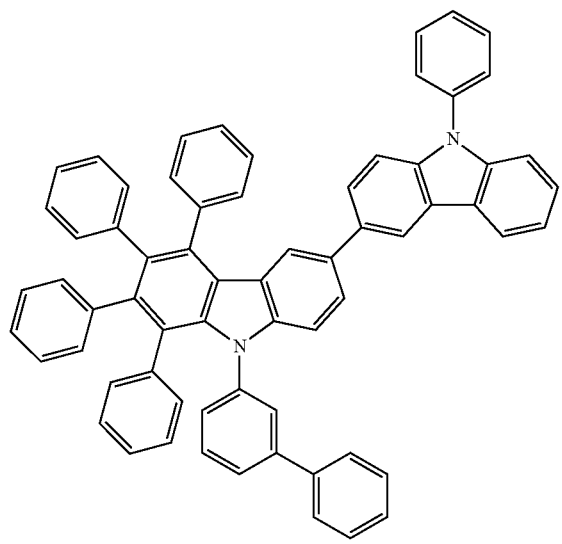
B-153
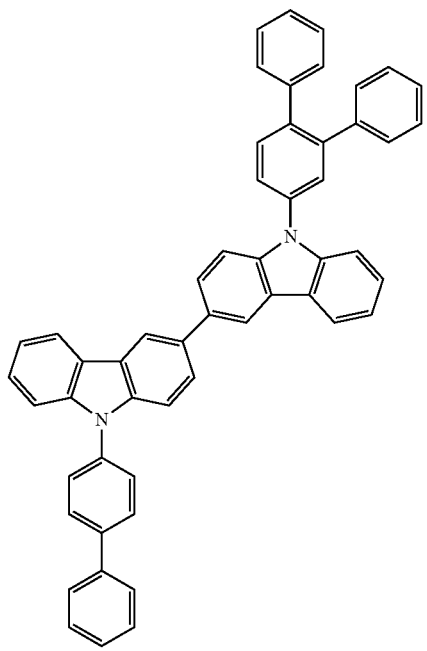
B-152
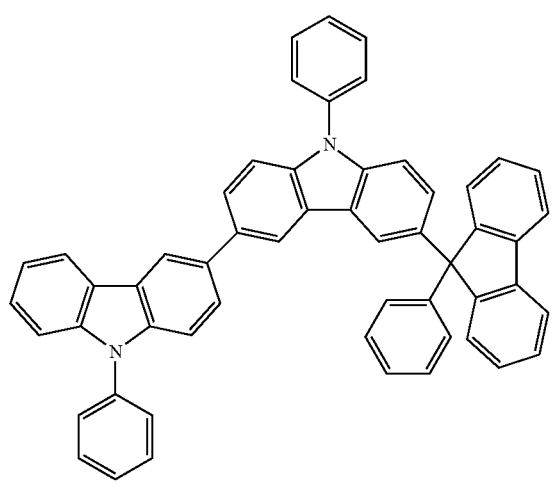
B-154
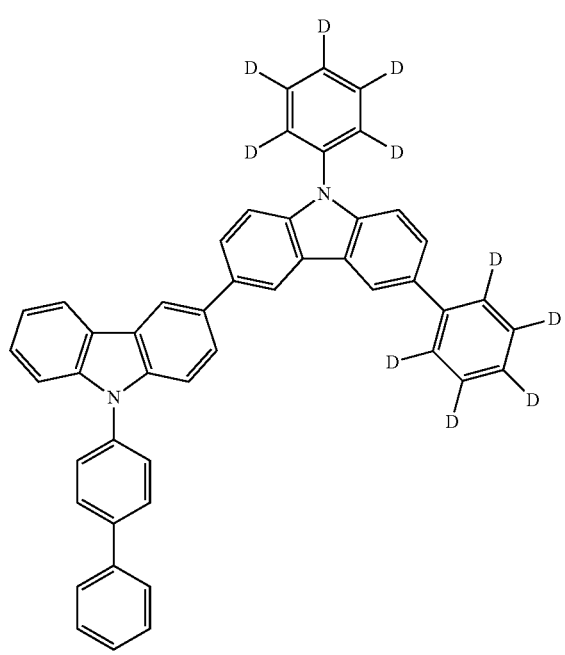

B-155
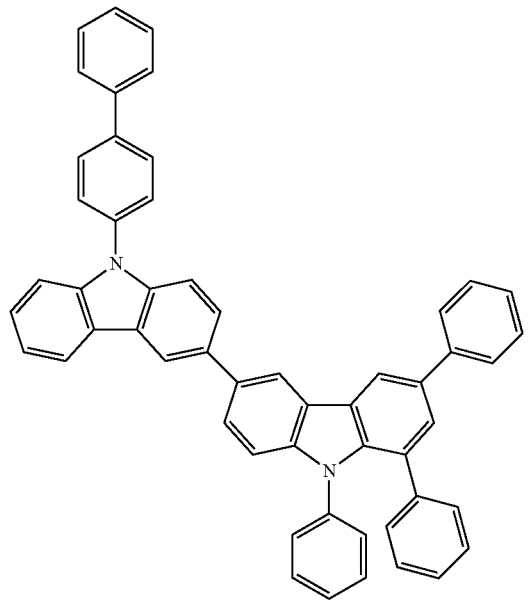
B-157
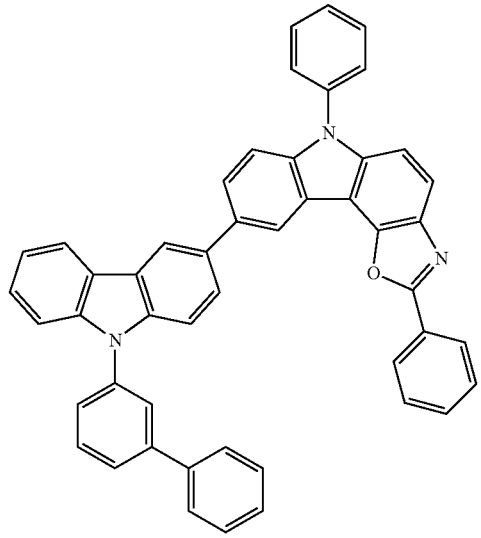
B-158
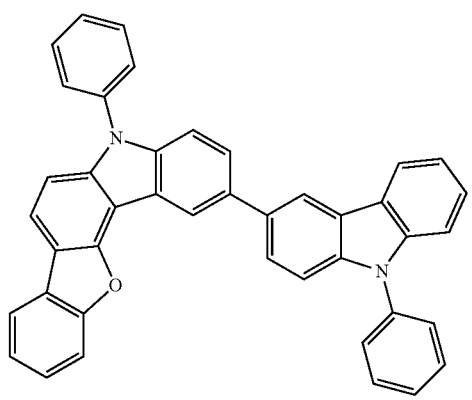
B-156
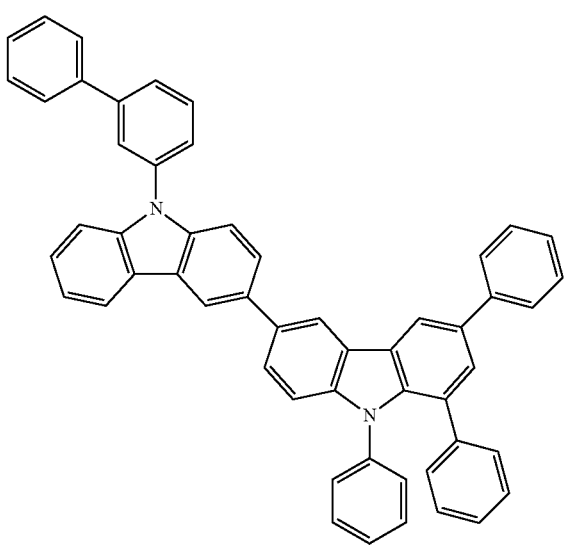
B-159
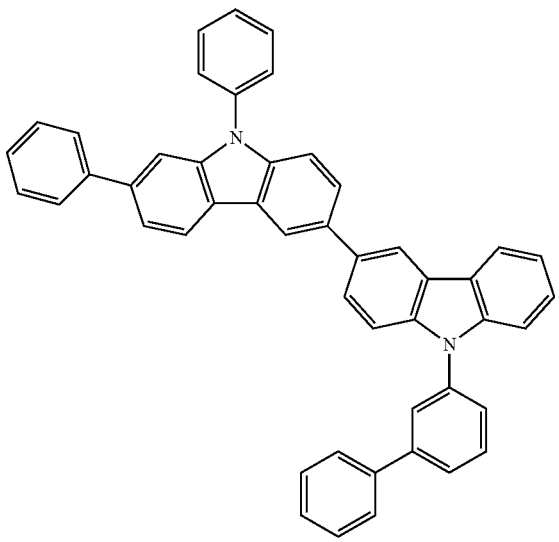

B-160
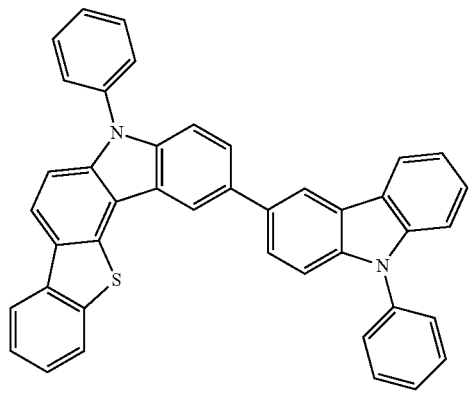
B-161
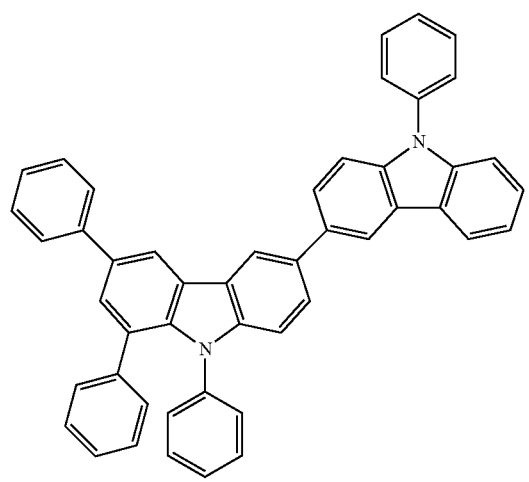
B-162
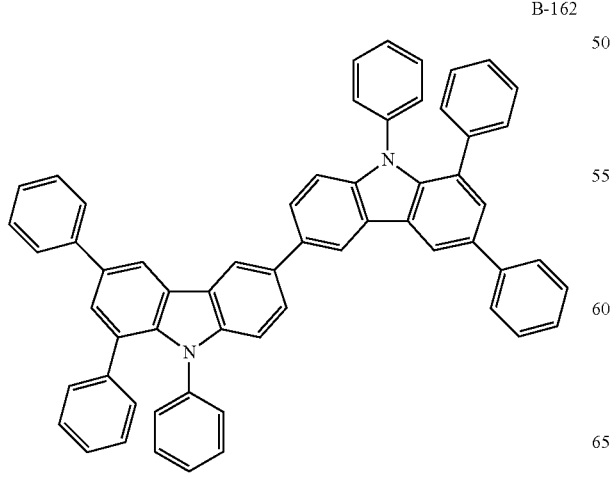
B-163
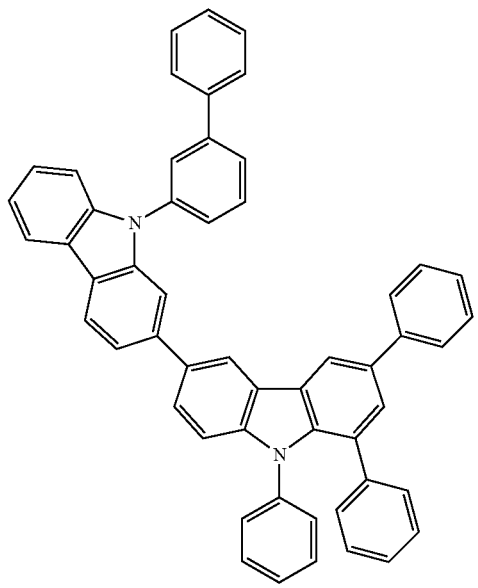
B-164
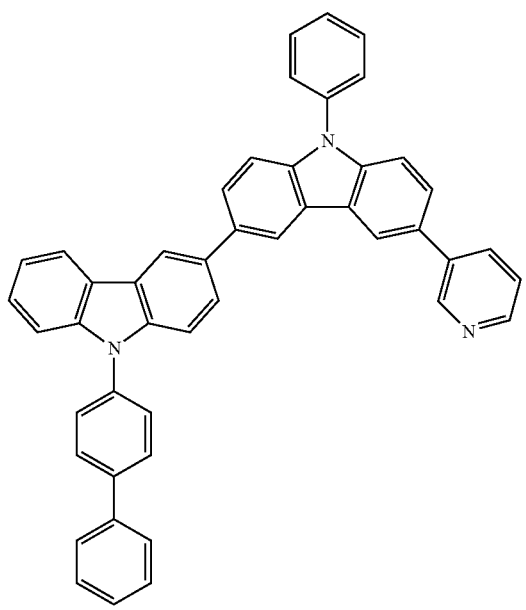

-continued
B-165
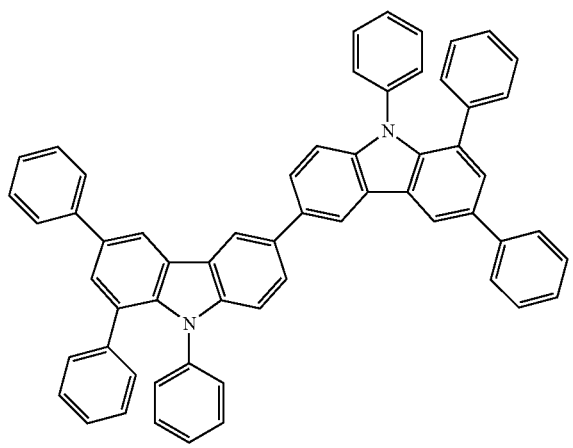
C-10
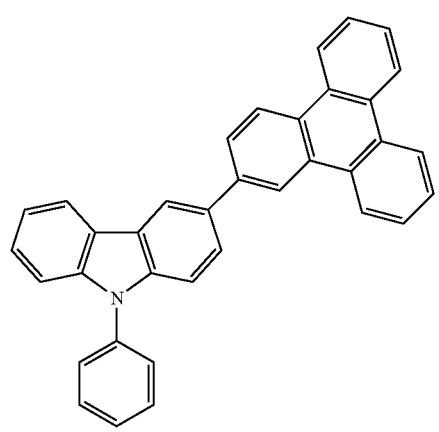
C-11
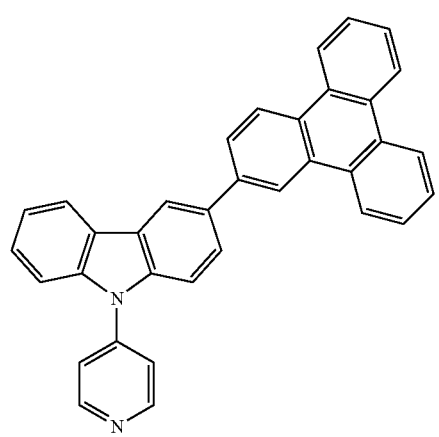
C-12
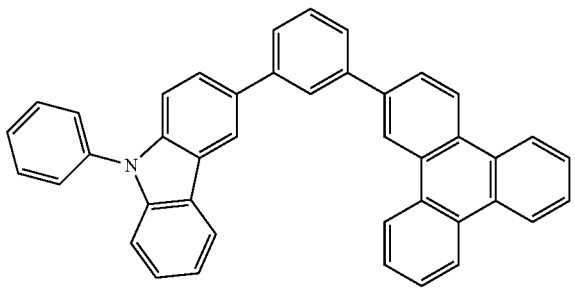
-continued
C-13
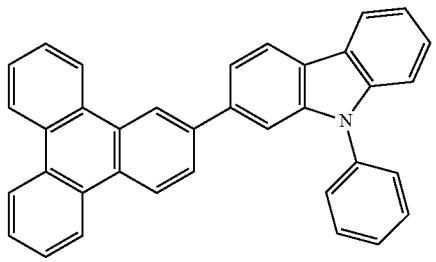
C-14
C-15
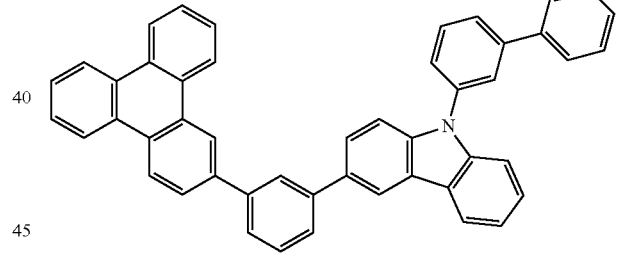
C-16
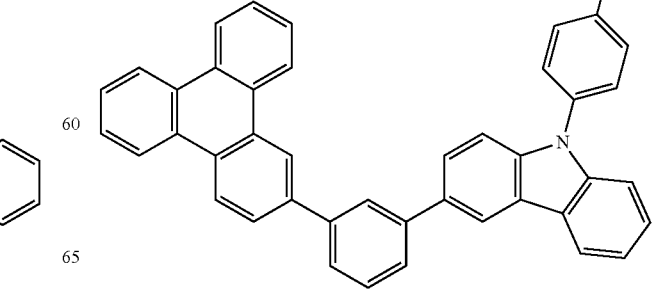

-continued
C-17
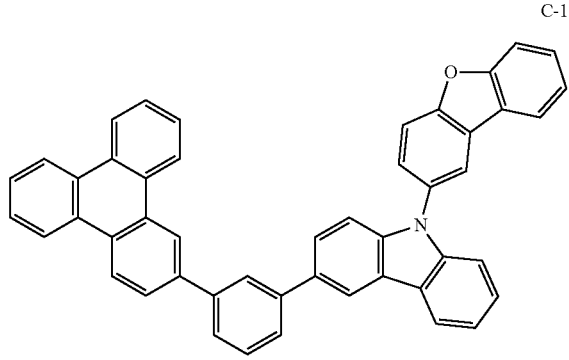
C-18
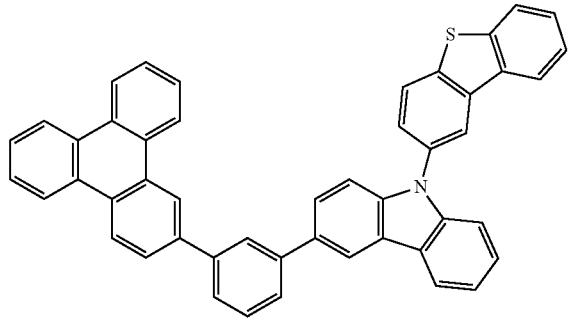
C-19
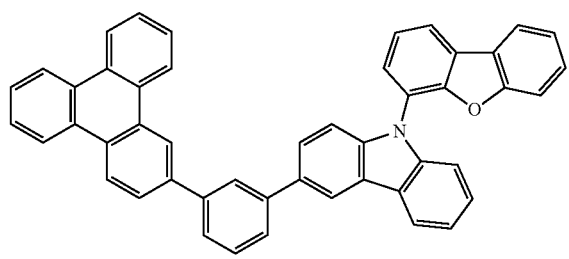
C-20
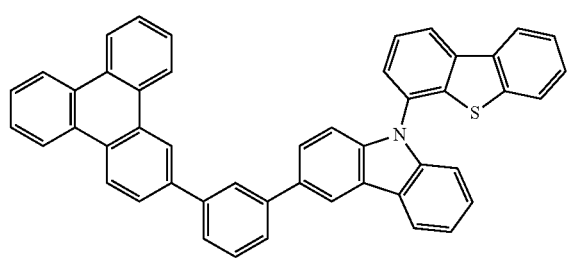
-continued
C-21
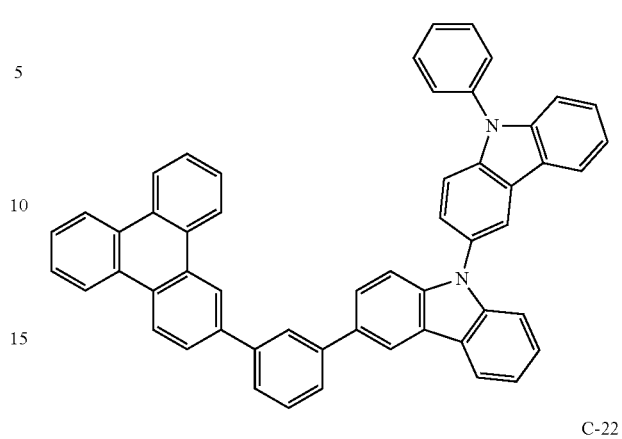
C-22
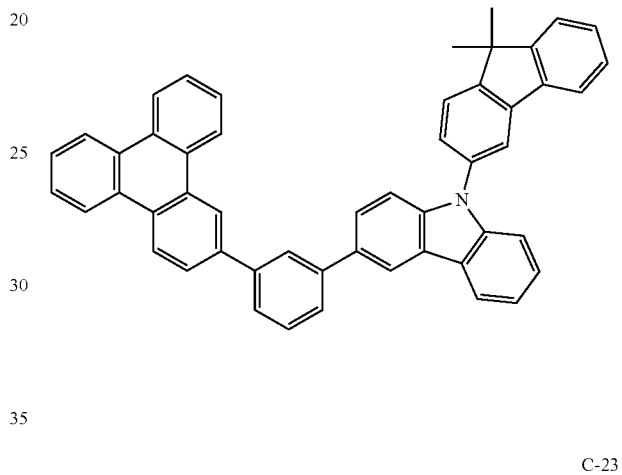
C-23
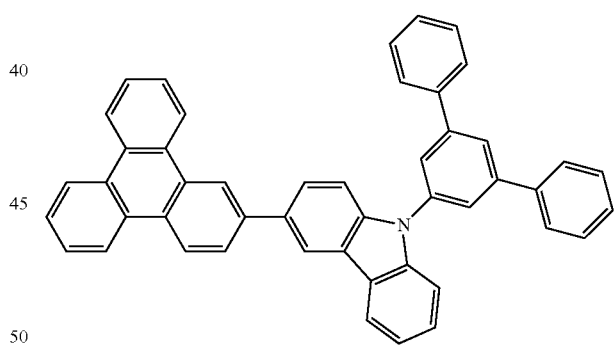
C-24
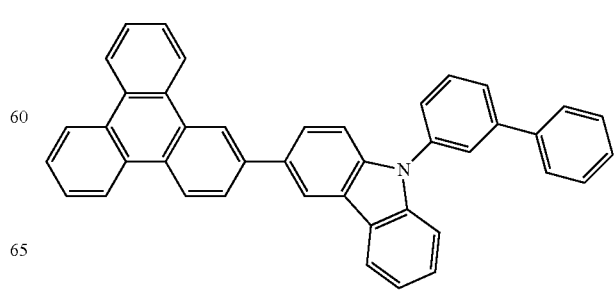

C-25
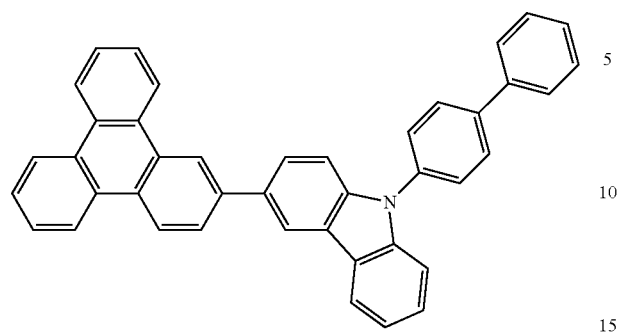
C-26
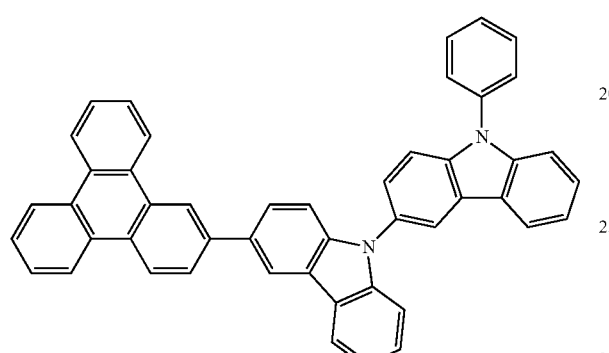
C-27
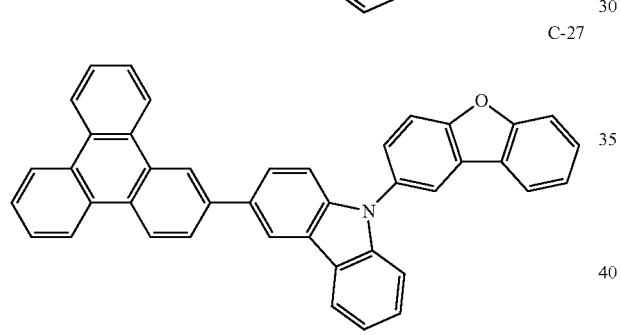
C-28
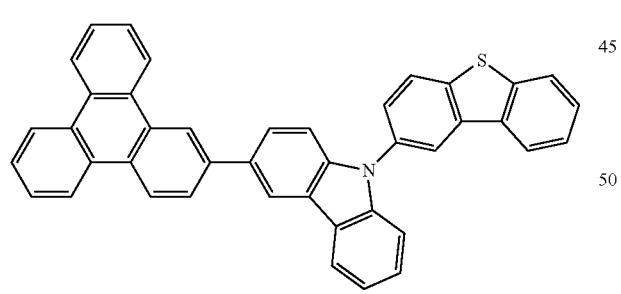
C-29
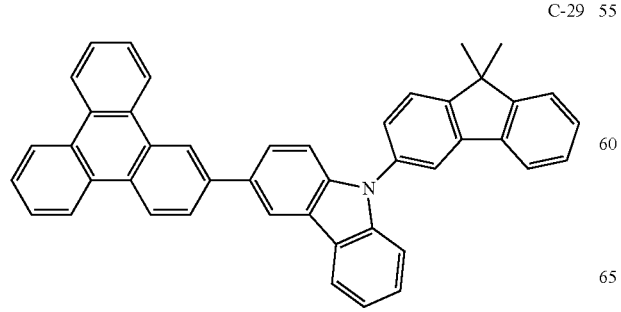
C-30
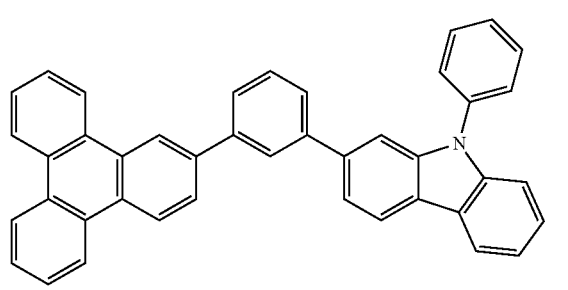
C-31
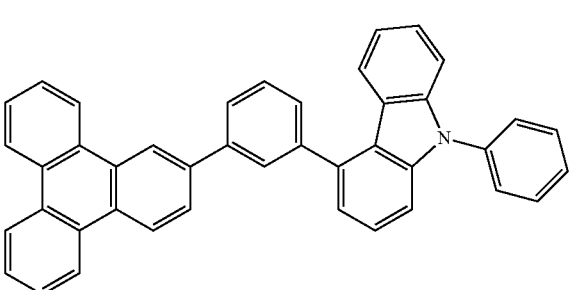
C-32
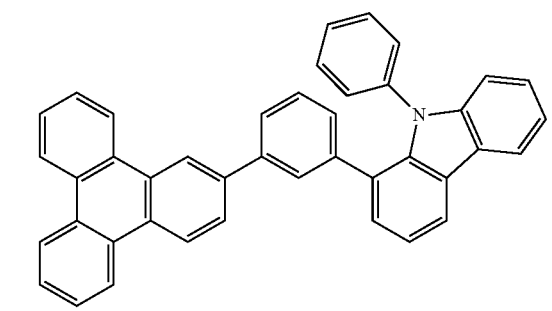
C-33
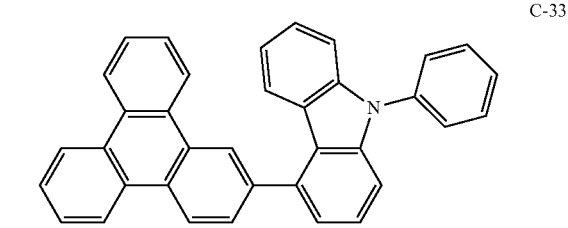
D-10
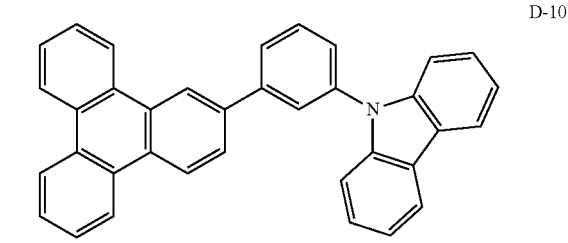

D-11
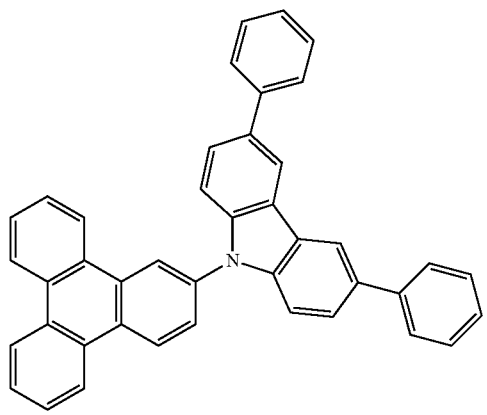
D-15
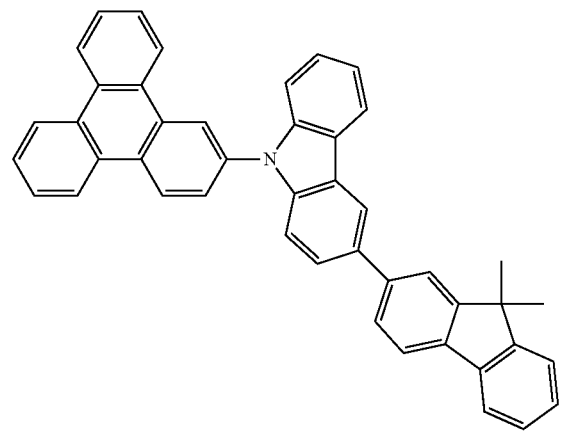
D-12
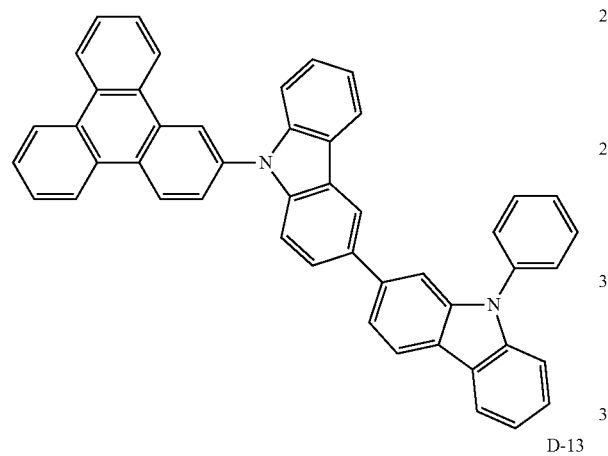
D-13
D-16
D-14
D-17
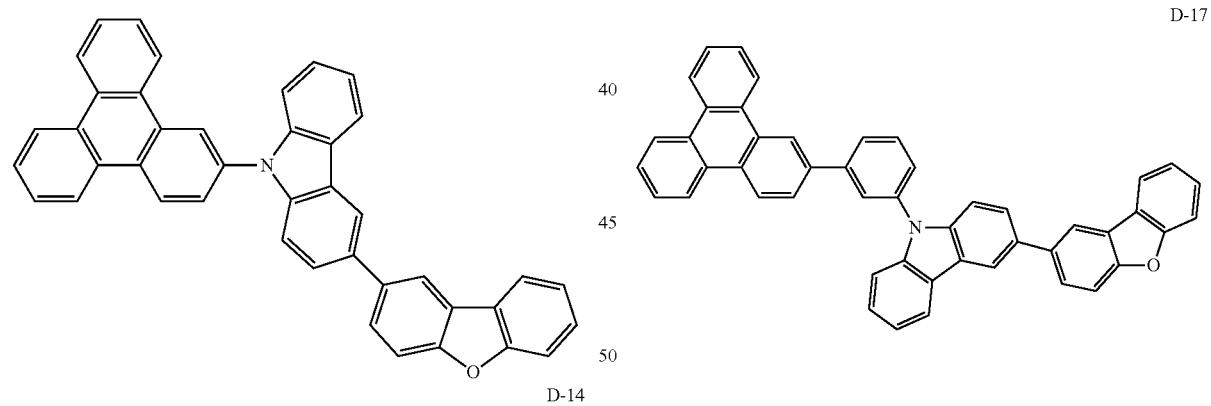
D-18
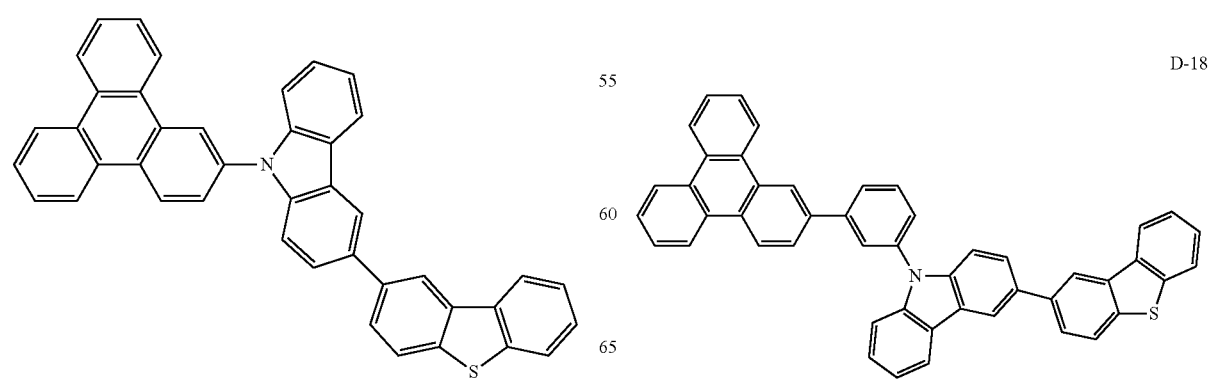

D-19
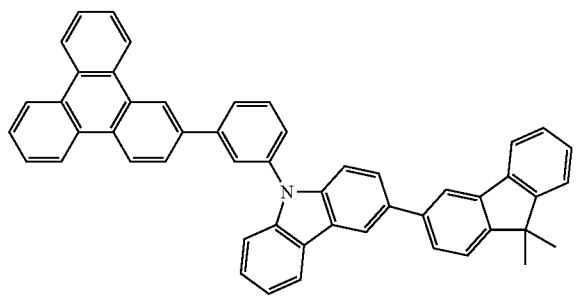
D-20
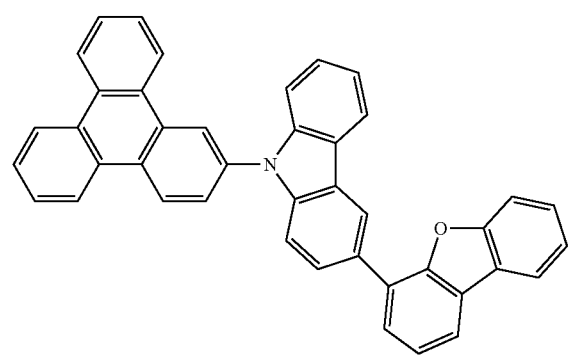
D-21
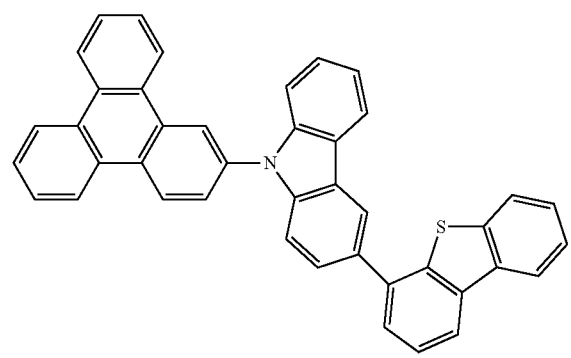
D-22
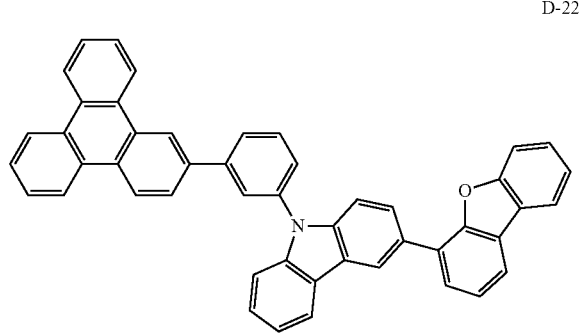
D-23
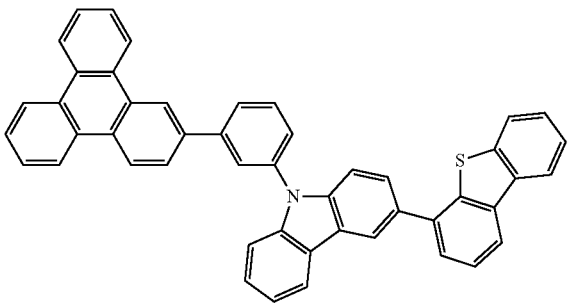
D-24
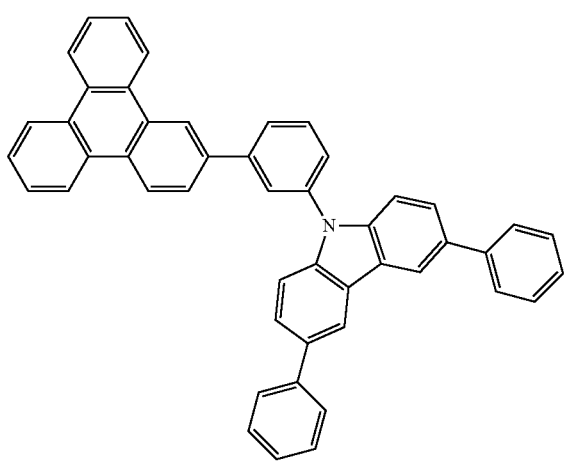
D-25
D-26
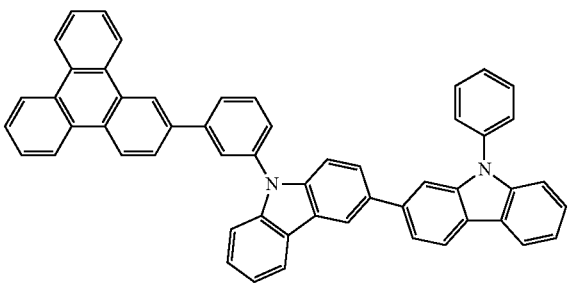

D-27

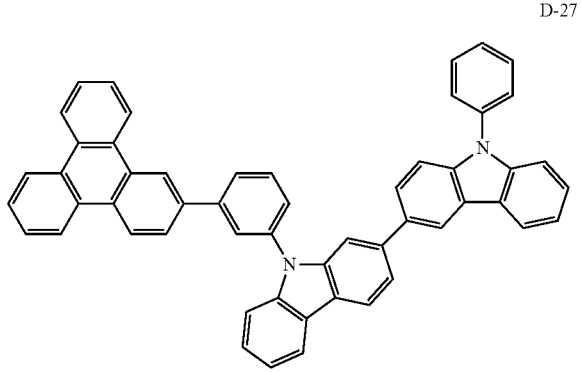

D-28

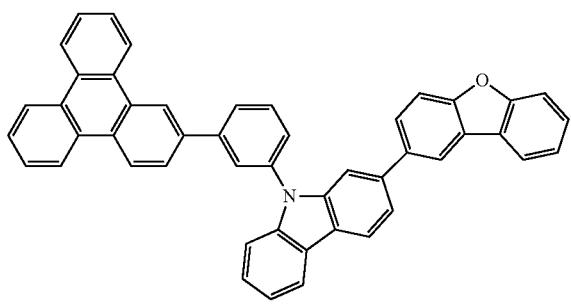

D-29

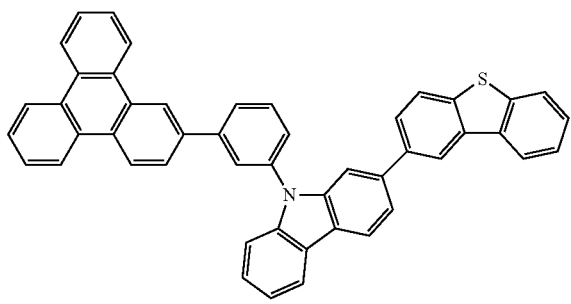

On the other hand, charge mobility may be adjusted by controlling a ratio between the second compound having hole characteristics and the first compound.

Since the hole characteristics of the second compound is relatively determined through a relationship with the first compound, a substituent having weak electron characteristics such as a substituted or unsubstituted pyridinyl group may be included in at least either one of $Ar^1$ and $Ar^2$ of Chemical Formula 2.

Herein, the second compound may have a LUMO energy level of greater than or equal to −1.7 eV.

Specifically, the second compound may have a LUMO energy level ranging from −1.7 to −0.850 eV.

In addition, the first and second compounds may be included for example in a weight ratio of about 1:9 to 9:1, specifically, 2:8 to 8:2, 3:7 to 7:3, 4:6 to 6:4, and 5:5. When used within the range, bipolar characteristics may be further effectively realized, and thus efficiency and life-span may be simultaneously improved.

Specifically, in an emission layer 130, the first compound and the second compound may be simultaneously included as a host, for example the first compound may be represented by Chemical Formula 1-Ia and the second compound may be represented by Chemical Formula 1a or 2a-1.

[Chemical Formula 1-Ia]

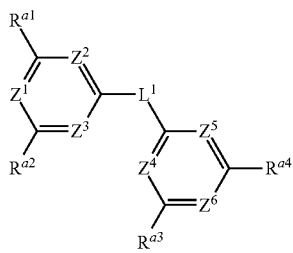

In Chemical Formula 1-I, $Z^1$ to $Z^6$ are independently N, or $CR^a$, at least two of $Z^1$ to $Z^3$ are N, at least two of $Z^4$ to $Z^6$ are N, $R^8$, and $R^{a1}$ to $R^{a4}$ are independently hydrogen, or a substituted or unsubstituted C6 to C30 aryl group, and $L^1$ is a C6 to C30 arylene group that is substituted or unsubstituted with deuterium, a C1 to C30 alkyl group, or a C6 to C30 aryl group;

$L^2$ to $L^5$, $Y^1$ and $Y^2$ of Chemical Formulae 1a and 2a-1 are independently a single bond, or a substituted or unsubstituted C6 to C30 arylene group, $Ar^1$ and $Ar^2$ are independently, a substituted or unsubstituted C6 to C30 aryl group, or a substituted or unsubstituted C2 to C30 heterocyclic group, $R^1$ to $R^3$ and $R^5$ to $R^{12}$ are independently, hydrogen, deuterium, or a substituted or unsubstituted C6 to C30 aryl group, and $R^1$ or $R^2$ of Chemical Formula 1a is not a substituted or unsubstituted carbazolyl group and all the $R^5$ to $R^7$ are not a carbazolyl group.

Herein, "substituted" is the same as described above.

The emission layer 130 may further include at least one compound in addition to the first compound and the second compound as a host. For example, aryl amine compound or aryl amine carbazole compound having excellent hole characteristics may be further included.

The emission layer 130 may further include a dopant. The dopant is mixed with a host in a small amount to cause light emission, and may be generally a material such as a metal complex that emits, light by multiple excitation into a triplet or more. The dopant may be, for example an inorganic, organic, or organic/inorganic compound, and one or more kinds thereof may be used.

The dopant may be a red, green, or blue dopant, for example phosphorescent dopant. Examples of the phosphorescent dopant may be an organic metal compound including Ir, Pt, Os, Ti, Zr, Hf, Eu, Tb, Tm, Fe, Co, Ni, Ru, Rh, Pd, or a combination thereof. The phosphorescent dopant may be, for example a compound represented by Chemical Formula Z, but is not limited thereto.

$L_2MX$ [Chemical Formula Z]

In Chemical Formula Z, M is a metal, and L and X are the same or different, and are a ligand to form a complex compound with M.

The M may be, for example Ir, Pt, Os, Ti, Zr, Hf, Eu, Tb, Tm, Fe, Co, Ni, Ru, Rh, Pd or a combination thereof, and the L and X may be, for example a bidendate ligand.

The composition may be applied to an organic layer of an organic optoelectronic device, for example an emission layer. For example, the composition may be applied to an emission layer as a host.

The composition may be formed using a dry film formation method or a solution process. The dry film formation method may be, for example a chemical vapor deposition (CVD) method, sputtering, plasma plating, and ion plating, and two or more compounds may be simultaneously formed into a film or compound having the same deposition temperature may be mixed and formed into a film. The solution process may be, for example inkjet printing, spin coating, slit coating, bar coating and/or dip coating.

Hereinafter, an organic optoelectronic device including the composition is described.

The organic optoelectronic device may be any device to convert electrical energy into photoenergy and vice versa without particular limitation, and may be selected from an organic light emitting diode, an organic photoelectric device, an organic solar cell, an organic transistor, an organic photo conductor drum, and an organic memory device.

The organic optoelectronic device includes an anode and a cathode facing each other, and at least one organic layer interposed between the anode and the cathode, wherein the organic layer includes the composition.

Herein, an organic light emitting diode as one example of an organic optoelectronic device is described referring to drawings.

FIG. 1 is a cross-sectional view showing an organic light emitting diode according to an embodiment.

Referring to FIG. 1, an organic light emitting diode 100 according to an embodiment includes an anode 120 and a cathode 110 facing each other and an organic layer 105 interposed between the anode 120 and cathode 110.

The anode 120 may be made of a conductor having a large work function to help hole injection, and may be for example metal, metal oxide and/or a conductive polymer. The anode 120 may be, for example a metal nickel, platinum, vanadium, chromium, copper, zinc, gold, and the like or, an alloy thereof; metal oxide such as zinc oxide, indium oxide, indium tin oxide (ITO), indium zinc oxide (IZO), and the like; a combination of metal and oxide such as ZnO and Al or $SnO_2$ and Sb; a conductive polymer such as poly(3-methylthiophene), poly(3,4-(ethylene-1,2-dioxy)thiophene) (PEDT), polypyrrole, and polyaniline, but is not limited thereto.

The cathode 110 may be made of a conductor having a small work function to help electron injection, and may be for example metal, metal oxide and/or a conductive polymer. The cathode 110 may be for example a metal or an alloy thereof such as magnesium, calcium, sodium, potassium, titanium, indium, yttrium, lithium, gadolinium, aluminum silver, tin, lead, cesium, barium, and the like; a multi-layer structure material such as LiF/Al, $LiO_2$/Al, LiF/Ca, LiF/Al and $BaF_2$/Ca, but is not limited thereto.

The organic layer 105 includes an emission layer 130 including composition.

FIG. 2 is a cross-sectional view showing an organic light emitting diode according to another embodiment.

Referring to FIG. 2, an organic light emitting diode 200 according to the present embodiment includes an anode 120 and a cathode 110 facing each other and an organic layer 105 between the anode 120 and the cathode 110 like the above embodiment.

The organic layer 105 includes an emission layer 130 and an auxiliary layer 140 between the emission layer 130 and the anode 120. The auxiliary layer 140 may help charge injection and transfer between the anode 120 and the emission layer 130. The auxiliary layer 140 may be, for example an electron transport layer (ETL), an electron injection layer (EIL), and/or an electron transport auxiliary layer.

In FIGS. 1 and 2, at least one auxiliary layer between the anode 120 and the emission layer 130 may be further included as an organic layer 105.

The organic light emitting diode may be applied to an organic light emitting diode (OLED) display.

Hereinafter, the embodiments are illustrated in more detail with reference to examples. These examples, however, are not in any sense to be interpreted as limiting the scope of the invention.

Hereinafter, a starting material and a reactant used in Synthesis Examples and Examples were purchased from Sigma-Aldrich Corporation or TCI Inc. unless there was particularly mentioned.

(Synthesis of First Compound)

Synthesis Example 1: Synthesis of Compound 1 a) Synthesis of Intermediate 1-1

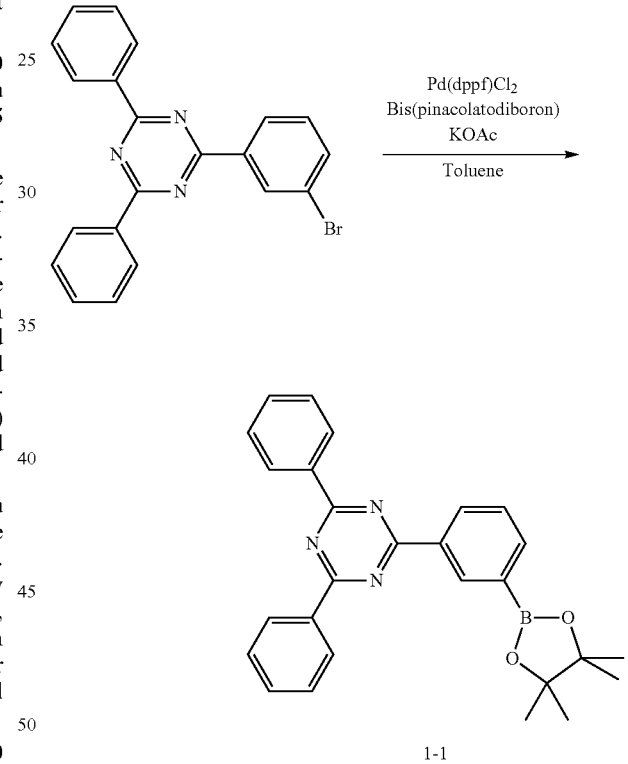

20 g (51.51 mmol) of 2-(3-bromophenyl)-4,5-diphenyl-1,3,5-triazine was dissolved in 250 mL of toluene in a 500 mL round-bottomed flask. Then, 0.05 equivalent of dichlorodiphenylphosphinoferrocene palladium, 1.2 equivalent of bis(pinacolato)diboron, and 2 equivalents of potassium acetate were added thereto, and the mixture was heated and refluxed under a nitrogen atmosphere for 18 hours. The reaction solution was cooled down, 100 mL of water was added thereto, and an organic layer was extracted therefrom. The organic layer was collected, treated with activated carbon, and filtered through silica gel, and the filtered solution was concentrated. The concentrated residue was collected and then, crystallized in 200 mL of toluene and 50 mL of acetone to obtain 19.1 g of an intermediate 1-1.

b) Synthesis of Compound 1

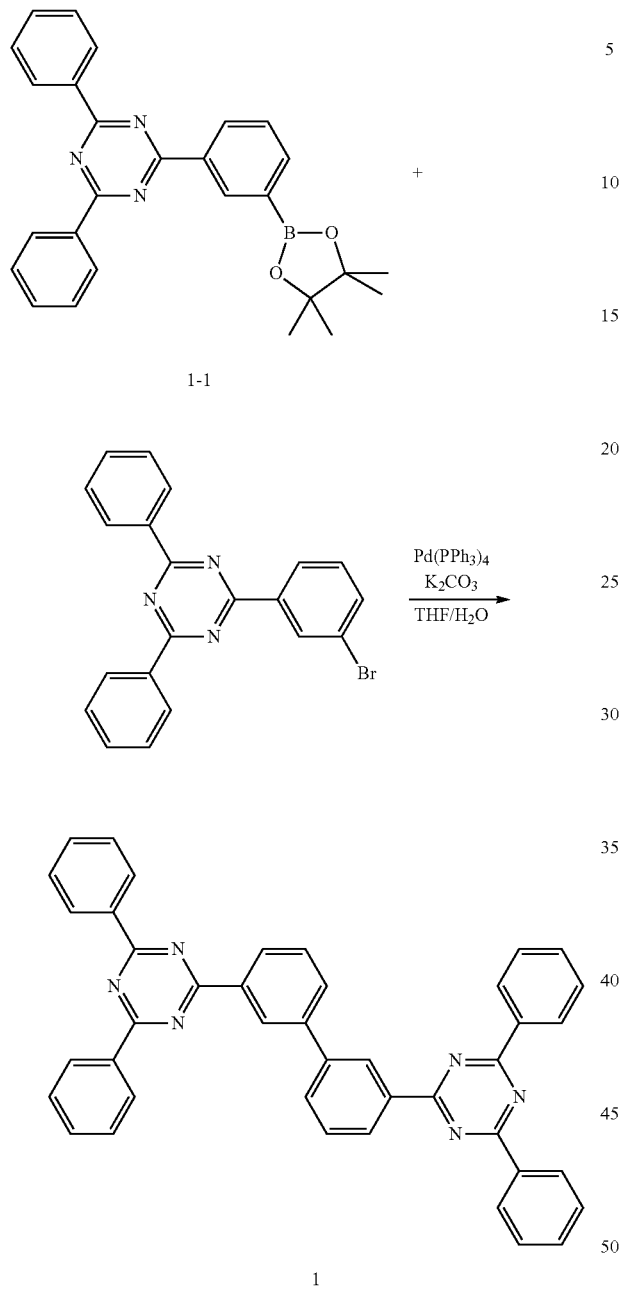

1-1

1

19 g (43.79 mmol) of the synthesized intermediate 1-1 was added to 200 mL of tetrahydrofuran and 50 mL of distilled water in a 500 mL round-bottomed flask, 1 equivalent of 2-(3-bromophenyl)-4,5-diphenyl-1,3,5-triazine, 0.03 equivalent of tetrakistriphenylphosphine palladium, and 2 equivalents of potassium carbonate were added thereto, and the mixture was heated and refluxed under a nitrogen atmosphere. After 18 hours, the reaction solution was cooled down, and a solid precipitated therein was filtered and washed with 500 mL of water. The solid was recrystallized with 500 mL of monochlorobenzene to obtain 22.41 g of a compound 1.

LC/MS calculated for: C42H28N6 Exact Mass: 616.2375 found for: 617.24 [M+H].

Synthesis Example 2: Synthesis of Compound 2

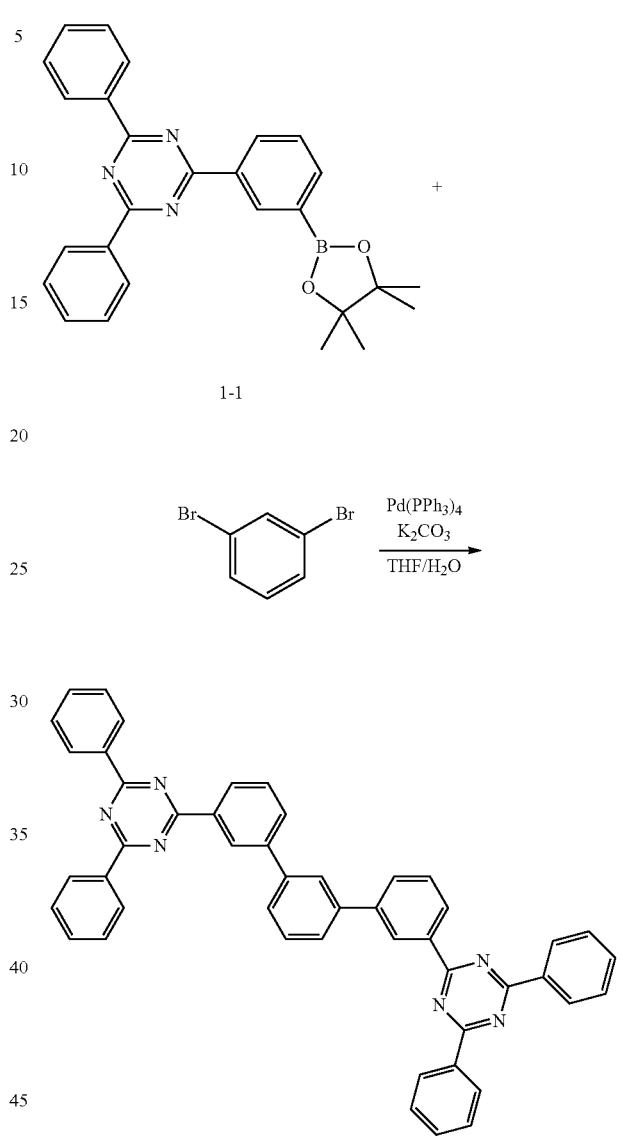

1-1

2

15 g (34.46 mmol) of the synthesized intermediate 1-1, 0.5 equivalent of 1,3-dibromobenzene, 0.03 equivalent of tetrakistriphenylphosphine palladium, 2 equivalents of potassium carbonate, 200 mL of tetrahydrofuran, and 50 mL of distilled water were put in a 500 mL round-bottomed flask and then, heated and refluxed under a nitrogen atmosphere. After 20 hours, the reaction solution was cooled down, and a solid precipitated therein was filtered and washed with 500 mL of water. The solid was recrystallized with 400 mL of dichlorobenzene to obtain 9.2 g of a compound 2.

LC/MS calculated for: C48H32N6 Exact Mass: 692.2688 found for: 693.27 [M+H].

Synthesis Example 3: Synthesis of Compound 3 a) Synthesis of Intermediate 3-1

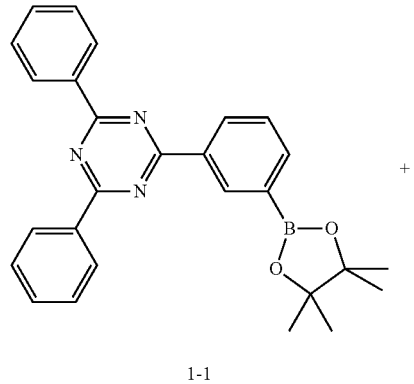

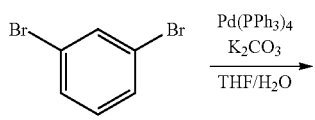

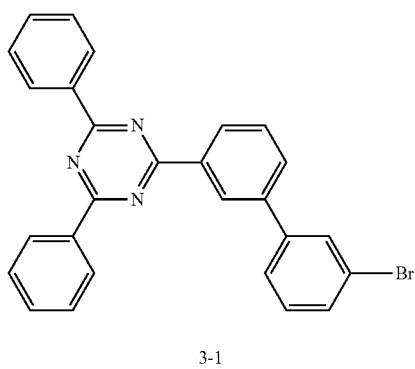

30 g (68.92 mmol) of the synthesized intermediate 1-1, 1.2 equivalent of 1,3-dibromobenzene, 0.03 equivalent of tetrakistriphenylphosphine palladium, 2 equivalents of potassium carbonate, 300 mL of tetrahydrofuran, and 100 mL of distilled water were put in a 500 mL round-bottomed flask and then, heated and refluxed under a nitrogen atmosphere. After 18 hours, the reaction solution was cooled down, suspended in 1 L of methanol, stirred, filtered, and washed with 500 mL of water. Then, a solid therein was recrystallized with 400 mL of dichlorobenzene to obtain 32 g of an intermediate 3-1.

b) Synthesis of Intermediate 3-2

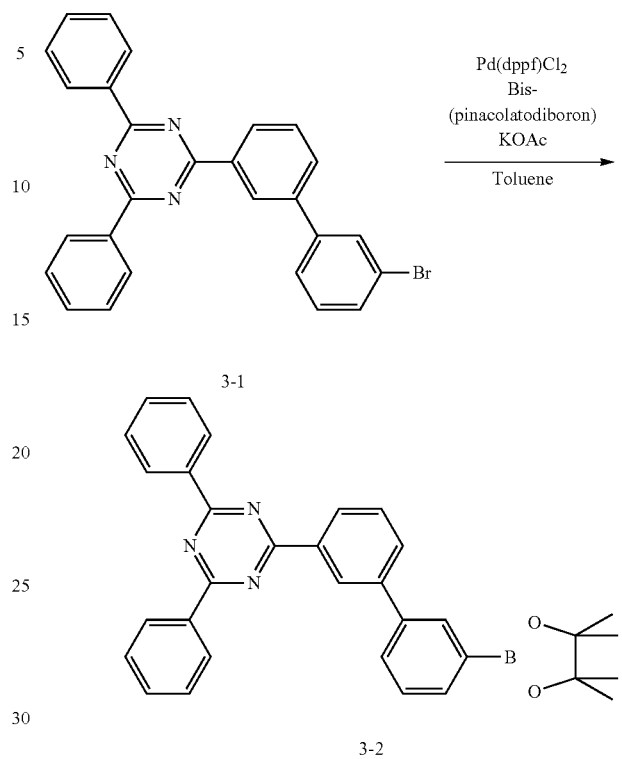

32 g (68.91 mmol) of the synthesized intermediate 3-1 was added to 350 mL of toluene, 0.05 equivalent of dichlorodiphenylphosphinoferrocene palladium, 1.2 equivalent of bis(pinacolato)diboron, and 2 equivalents of potassium acetate were put in a 500 mL round-bottomed flask and then, heated and refluxed under a nitrogen atmosphere for 18 hours. The reaction solution was cooled down, 100 mL of water was added thereto, and an organic layer was extracted therefrom. The organic layer was collected, treated with activated carbon, filtered through silica gel, and concentrated. The concentrated residue was collected, heated and dissolved in 1 L of toluene, treated with activated carbon, and filtered through silica gel. The filtered solution was cooled down to precipitate a solid. The precipitated solid was filtered to obtain 29.96 g of an intermediate 3-2.

c) Synthesis of Compound 3

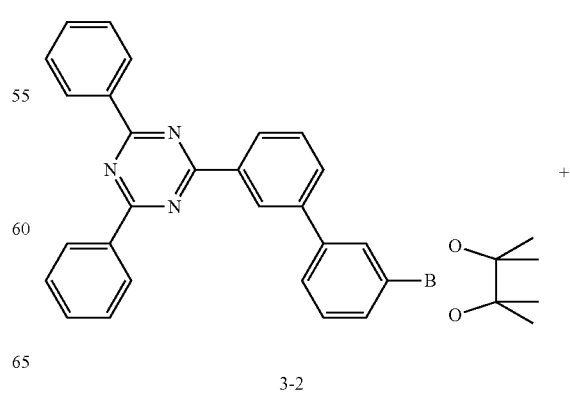

-continued

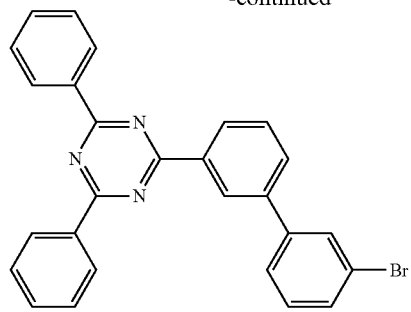

3-1

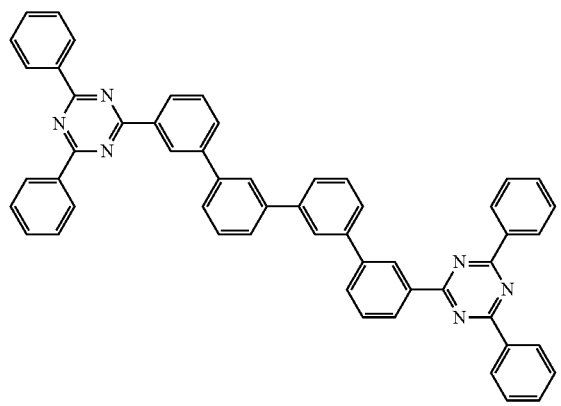

3

15 g (29.33 mmol) of the synthesized intermediate 3-2, 1 equivalent of the synthesized intermediate 3-1, 0.03 equivalent of tetrakistriphenylphosphine palladium, 2 equivalents of potassium carbonate, 200 mL of tetrahydrofuran, an 50 mL of distilled water were put in a 500 mL round-bottomed flask and then, heated and refluxed under a nitrogen atmosphere. After 18 hours, the reaction solution was cooled down, filtered, and washed with 500 mL of water. Then, a solid therein was recrystallized with 500 mL of dichlorobenzene to obtain 16.01 g of a compound 3.

LC/MS calculated for: C54H36N6 Exact Mass: 768.3001 found for: 769.3 [M+H].

Synthesis Example 4: Synthesis of Compound 100 a) Synthesis of Intermediate 100-1

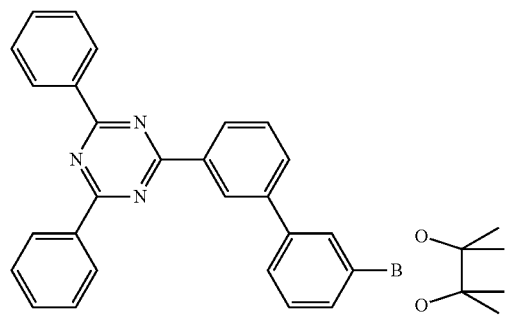

3-2

-continued

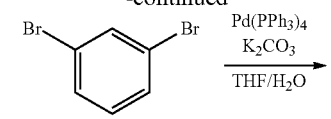

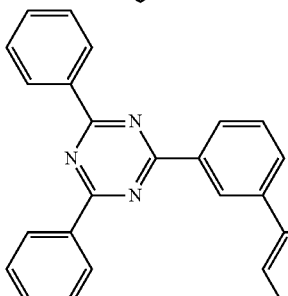

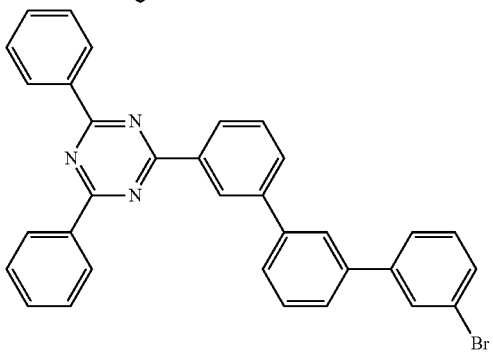

100-1

15 g (29.33 mmol) of the synthesized intermediate 3-2, 1.2 equivalent of 1,3-dibromobenzene, 0.03 equivalent of tetrakistriphenylphosphine palladium, 2 equivalents of potassium carbonate, 300 mL of tetrahydrofuran, and 100 mL of distilled water were put in a 500 mL round-bottomed flask and then, heated and refluxed under a nitrogen atmosphere. After 18 hours, the reaction solution was cooled down, suspended in 1 L of methanol, stirred and filtered, and washed with 500 mL of water. Then, a solid therefrom was recrystallized with 300 mL of dichlorobenzene to obtain 12.84 g of an intermediate 100-1.

b) Synthesis of Compound 100

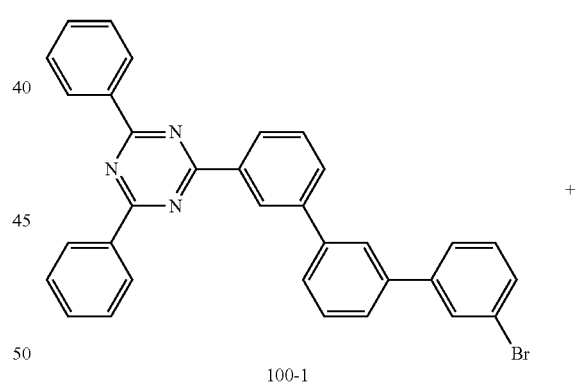

100-1

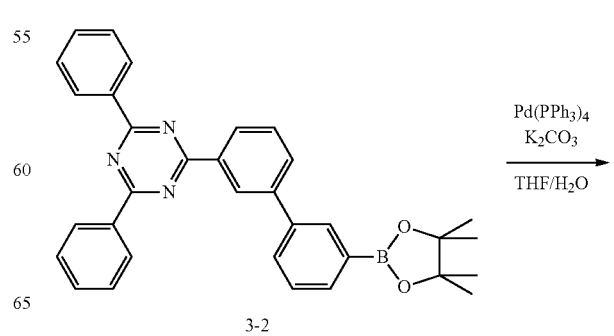 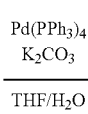

3-2

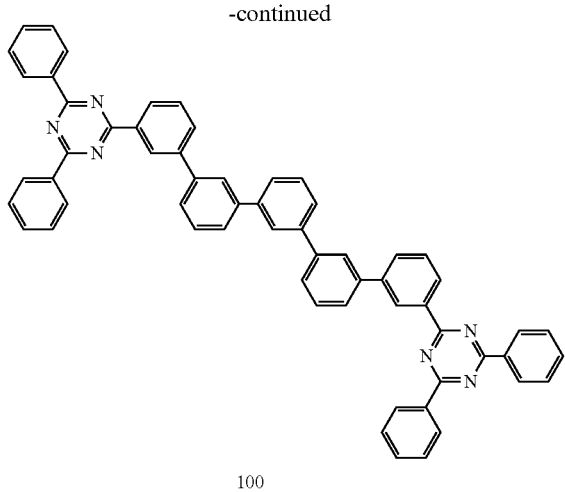

100

12 g (22.2 mmol) of the synthesized intermediate 100-1, 1.2 equivalent of the synthesized intermediate 3-2, 0.03 equivalent of tetrakistriphenylphosphine palladium, 2 equivalent of potassium carbonate, 150 mL of tetrahydrofuran, and 50 mL of distilled water were put in a 500 mL round-bottomed flask and then, heated and refluxed under a nitrogen atmosphere. After 18 hours, the reaction solution was cooled down, suspended in 1 L of methanol, stirred and filtered, and then, washed with 500 mL of water. Then, a solid therefrom is recrystallized with 500 mL of dichlorobenzene to obtain 13.3 g of a compound 100.

LC/MS calculated for: C60H40N6 Exact Mass: 844.3314 found for 845.34 [M+H].

Synthesis Example 5: Synthesis of Compound 4 a) Synthesis of Intermediate 4-2

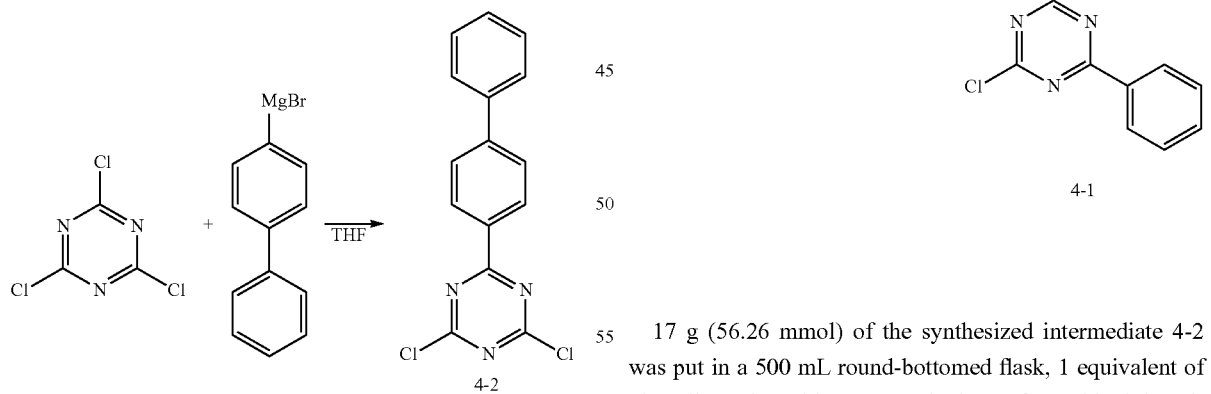

15 g (81.34 mmol) of cyanuric chloride was dissolved in 200 mL of anhydrous tetrahydrofuran in a 500 mL round-bottomed flask, 1 equivalent of a 4-biphenyl magnesium bromide solution (0.5 M tetrahydrofuran) was added thereto in a dropwise fashion under a nitrogen atmosphere at 0° C., and the mixture was slowly heated up to room temperature. Then, the reaction solution was stirred at room temperature for 1 hour, stirred, and then, poured into 500 mL of ice water to separate a layer. The separated organic layer was treated with anhydrous magnesium sulfate and concentrated. The concentrated residue was recrystallized with tetrahydrofuran and methanol to obtain 17.2 g of an intermediate 4-2.

b) Synthesis of Intermediate 4-1

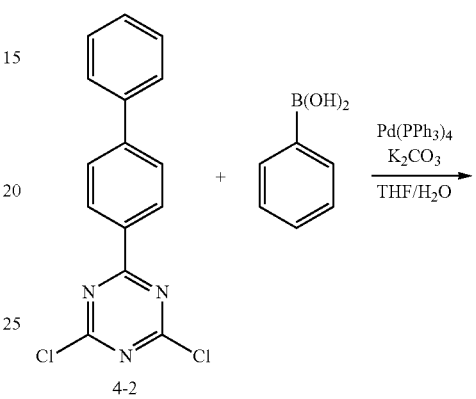

4-1

17 g (56.26 mmol) of the synthesized intermediate 4-2 was put in a 500 mL round-bottomed flask, 1 equivalent of phenylboronic acid, 0.03 equivalent of tetrakistriphenylphosphine palladium, 2 equivalents of potassium carbonate, 150 mL of tetrahydrofuran, and 50 mL of distilled water were added thereto, and the mixture was heated and refluxed under a nitrogen atmosphere. After 18 hours, the reaction solution was cooled down, suspended in 1 L of methanol, stirred and filtered, washed with 500 mL of water, and dried to obtain 12.57 g of an intermediate 4-1.

c) Synthesis of Compound 4

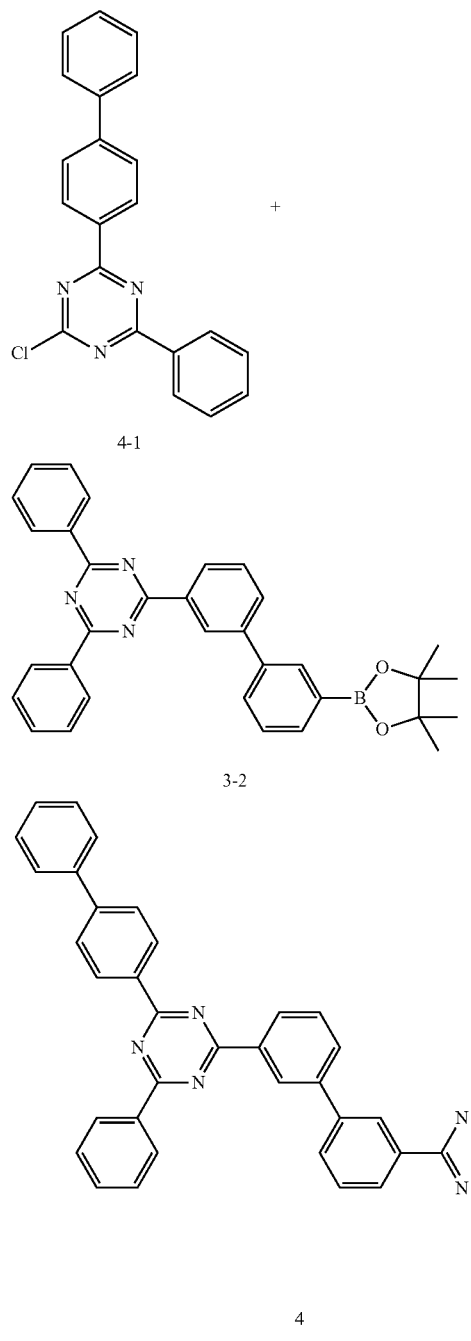

12 g (34.9 mmol) of the synthesized intermediate 4-1 was put in a 500 mL round-bottomed flask, 1.1 equivalent of the synthesized intermediate 3-2, 0.03 equivalent of tetrakistriphenylphosphine palladium, 2 equivalents of potassium carbonate, 150 mL of tetrahydrofuran, and 50 mL of distilled water were added thereto, and the mixture was heated and refluxed under a nitrogen atmosphere. After 18 hours, the reaction solution was cooled down, suspended in 1 L of methanol, stirred and filtered, and washed with 500 mL of water. Then, a solid produced therein was recrystallized with 500 mL of dichlorobenzene to obtain 17.8 g of a compound 4.

LC/MS calculated for: C48H32N6 Exact Mass: 692.2688 found for 692.27 [M+H].

Synthesis Example 6: Synthesis of Compound 16 a) Synthesis of Intermediate 16-2

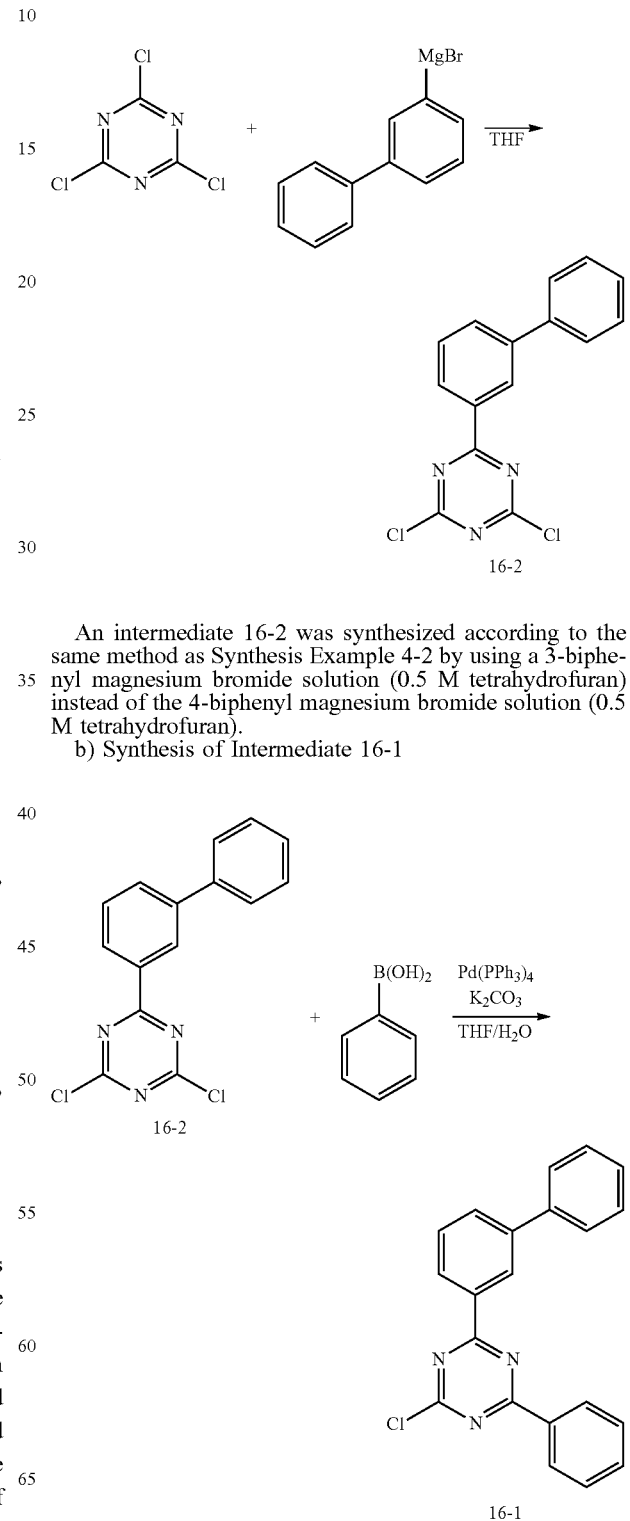

An intermediate 16-2 was synthesized according to the same method as Synthesis Example 4-2 by using a 3-biphenyl magnesium bromide solution (0.5 M tetrahydrofuran) instead of the 4-biphenyl magnesium bromide solution (0.5 M tetrahydrofuran).

b) Synthesis of Intermediate 16-1

An intermediate 16-1 was synthesized according to the same method as the (b) of Synthesis Example 5 by using the intermediate 16-2 instead of the intermediate 4-2.

c) Synthesis of Compound 16

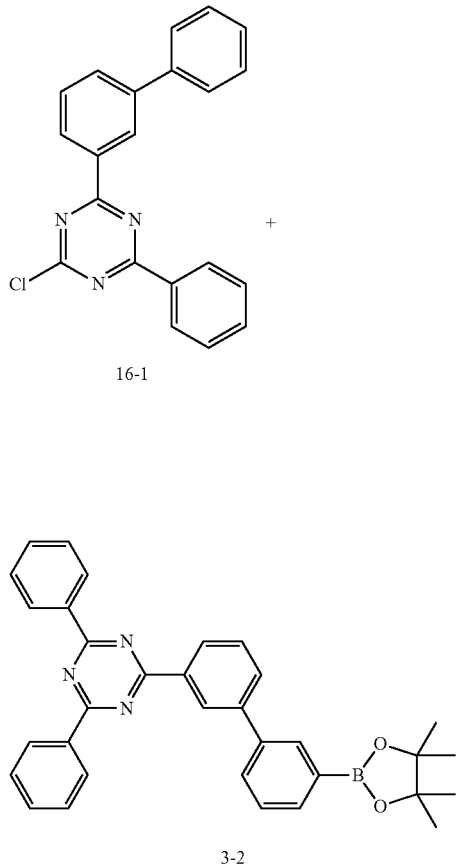

Synthesis Example 7: Synthesis of Compound 126

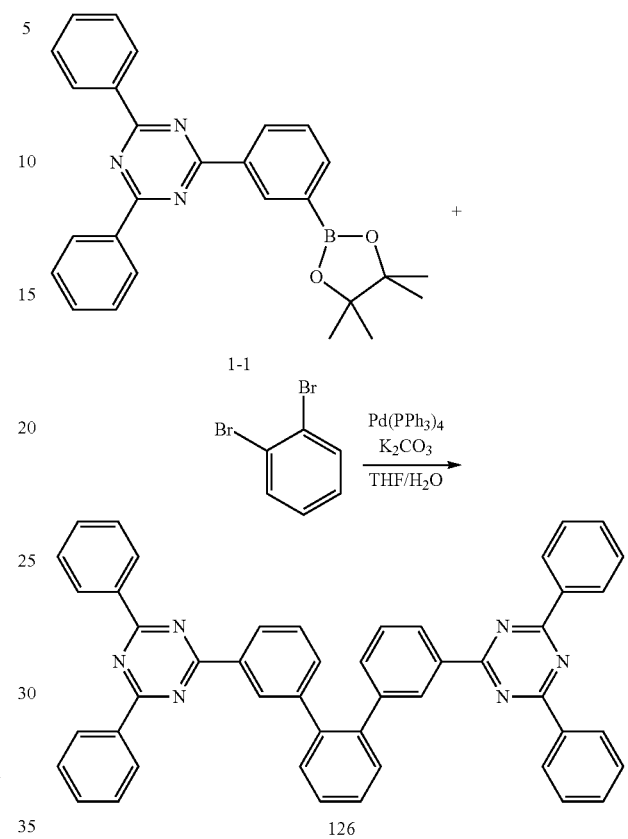

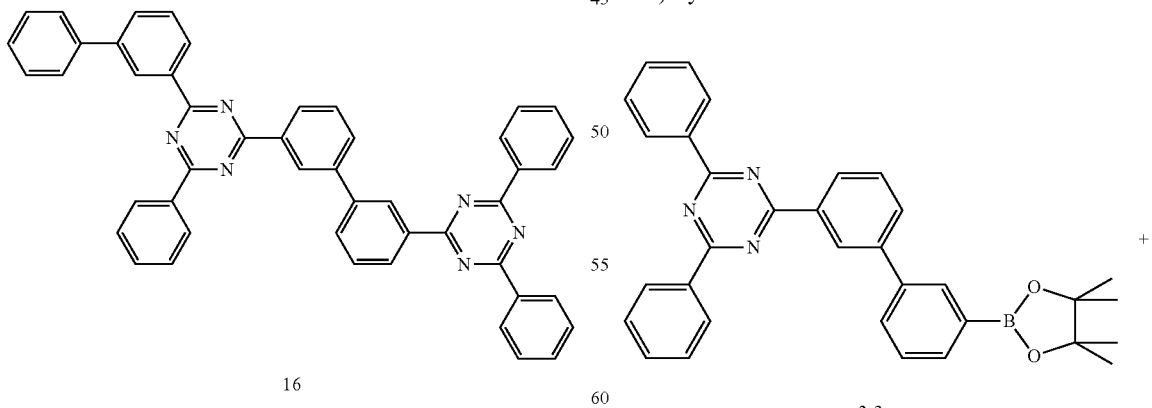

A compound 126 was synthesized according to the same method as Synthesis Example 2 by using 1,2-dibromobenzene as an intermediate.

LC/MS calculated for: C48H32N6 Exact Mass: 692.2688, found for 693.28 [M+H].

Synthesis Example 8: Synthesis of Compound 140 a) Synthesis of Intermediate 140-1

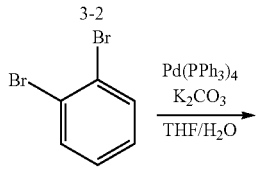

A compound 16 was synthesized according to the same method as the (c) of Synthesis Example 5 by using the intermediate 16-1 instead of the intermediate 4-2.

LC/MS calculated for: C48H32N6 Exact Mass: 692.2688 found for 692.27 [M+H].

213
-continued

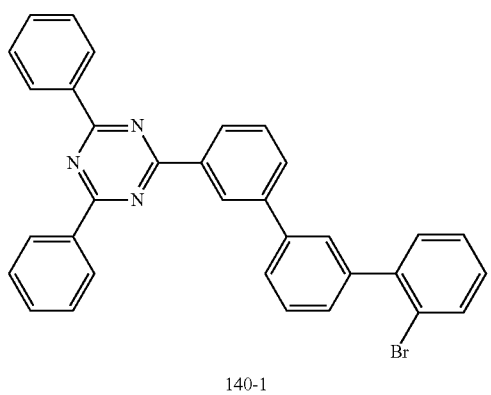
140-1

20 g (39.11 mmol) of the intermediate 3-2 was put in a 500 mL round-bottomed flask, 1.1 equivalent of 1,2-dibromobenzene, 0.03 equivalent of tetrakistriphenylphosphine palladium, 2 equivalents of potassium carbonate, 200 mL of tetrahydrofuran, and 50 mL of distilled water were added thereto, and the mixture was heated and refluxed under a nitrogen atmosphere. After 18 hours, the reaction solution was cooled down, suspended in 500 mL of methanol, stirred and filtered, and washed with 500 mL of water. Then, a solid produced therein was recrystallized with 500 mL of monochlorobenzene to obtain 18.4 g of an intermediate 140-1.

b) Synthesis of Compound 140

214
-continued

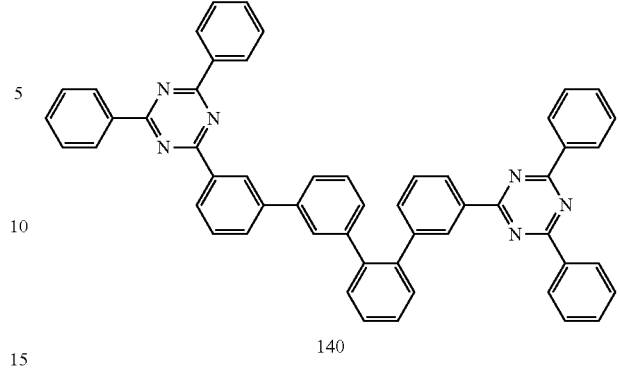
140

18 g (33.31 mmol) of the synthesized intermediate 140-1 was put in a 500 mL round-bottomed flask, 1.1 equivalent of the synthesized intermediate 1-1, 0.03 equivalent of tetrakistriphenylphosphine palladium, 2 equivalents of potassium carbonate, 200 mL of tetrahydrofuran, and 50 mL of distilled water were added thereto, and the mixture was heated and refluxed under a nitrogen atmosphere. After 18 hours, the reaction solution was cooled down, suspended in 500 mL of methanol, stirred and filtered, and washed with 500 mL of water. Then, a solid obtained therein was collected, silica gel column purified with a mixed solvent of normal hexane and ethyl acetate to obtain 19.2 g of a compound 140.

LC/MS calculated for: C54H36N6 Exact Mass: 768.3001, found for 769.3 [M+H].

Synthesis Example 9: Synthesis of Compound 113 a) Synthesis of Intermediate 113-3

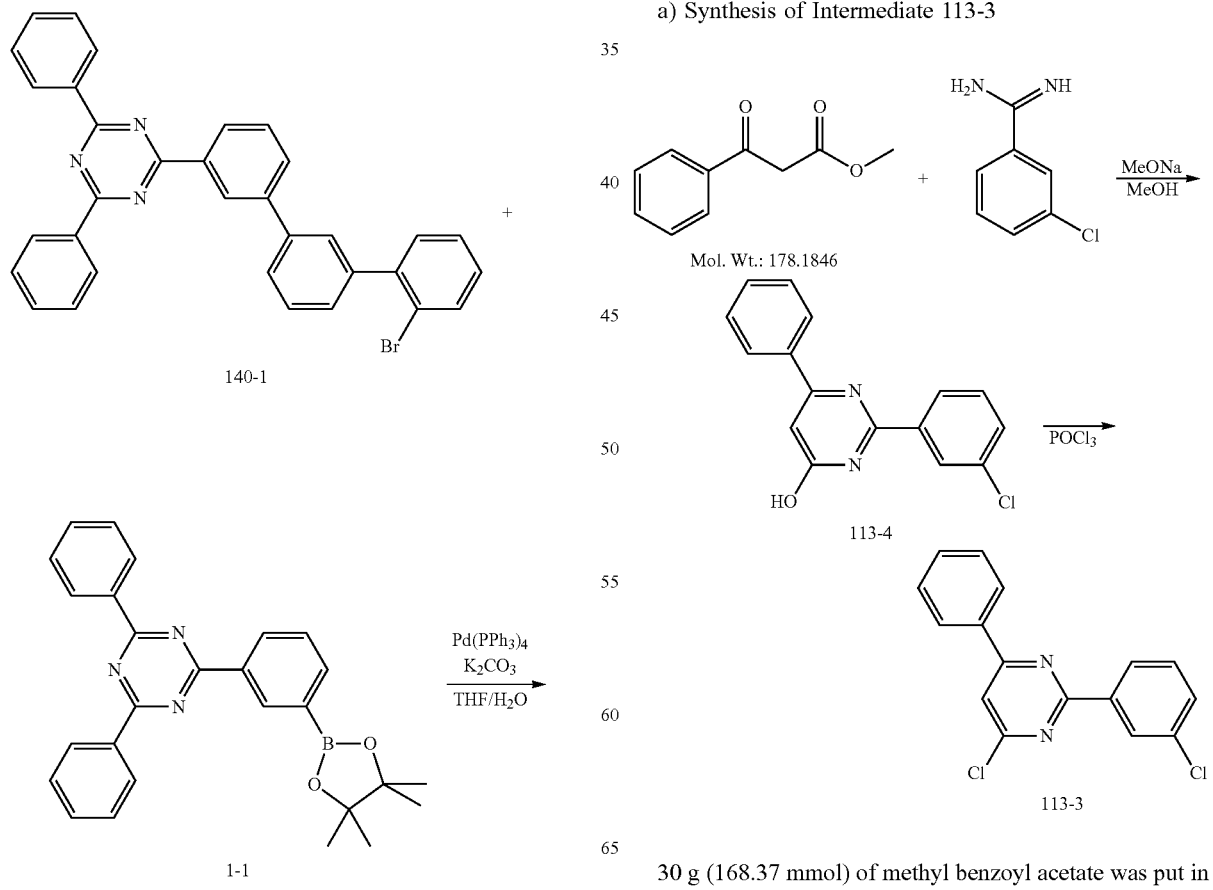

30 g (168.37 mmol) of methyl benzoyl acetate was put in a 500 mL round-bottomed flask, 1.1 equivalent of 3-chlorophenyl amidine, 1.2 equivalent of sodium methoxide, and 200 mL of methanol were added thereto, and the mixture heated and refluxed for 6 hours. The reaction solution was cooled down, a 1 N hydrochloric acid solution was added thereto, and chloridemethane was used for an extraction. The extracted solution was concentrated to obtain an intermediate 113-4, which itself is used for the following reaction.

The intermediate 113-4 was put in a 500 mL round-bottomed flask, 250 mL of phosphorylchloride was added thereto, and the mixture was heated and refluxed for 5 hours. The reaction solution was cooled down and slowly added to 1 L of ice water, and the mixture is stirred. Then, an aqueous layer is extracted with 500 mL of methane chloride, dried with anhydrous magnesium sulfate, and concentrated. The concentrated residue was purified through a silica gel column by using normal hexane and ethyl acetate to obtain 39 g of an intermediate 113-3.

b) Synthesis of Intermediate 113-2

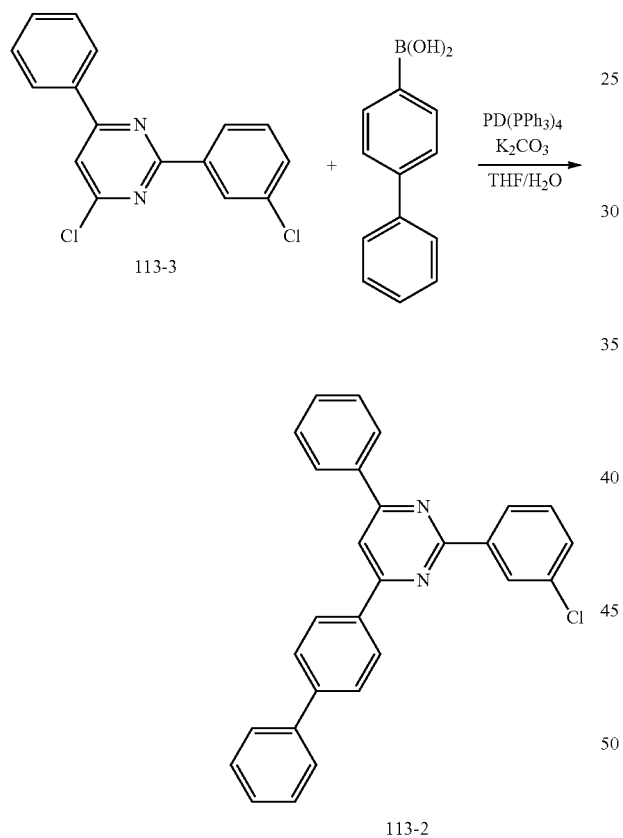

30 g (99.6 mmol) of the synthesized intermediate 113-3 was put in a 500 mL round-bottomed flask, 1.2 equivalent of biphenyl boronic acid, 0.03 equivalent of tetrakistriphenylphosphine palladium, 2 equivalents of potassium carbonate, 250 mL of tetrahydrofuran, and 70 mL of distilled water were added thereto, and the mixture was heated and refluxed under a nitrogen atmosphere. After 18 hours, the reaction solution was cooled down, suspended in 500 mL of methanol, stirred and filtered, and washed with 500 mL of water. Then, a solid produced therein was collected and then, heated and recrystallized with 500 mL of toluene to obtain 35.9 g of an Intermediate 113-2.

c) Synthesis of Intermediate 113-1

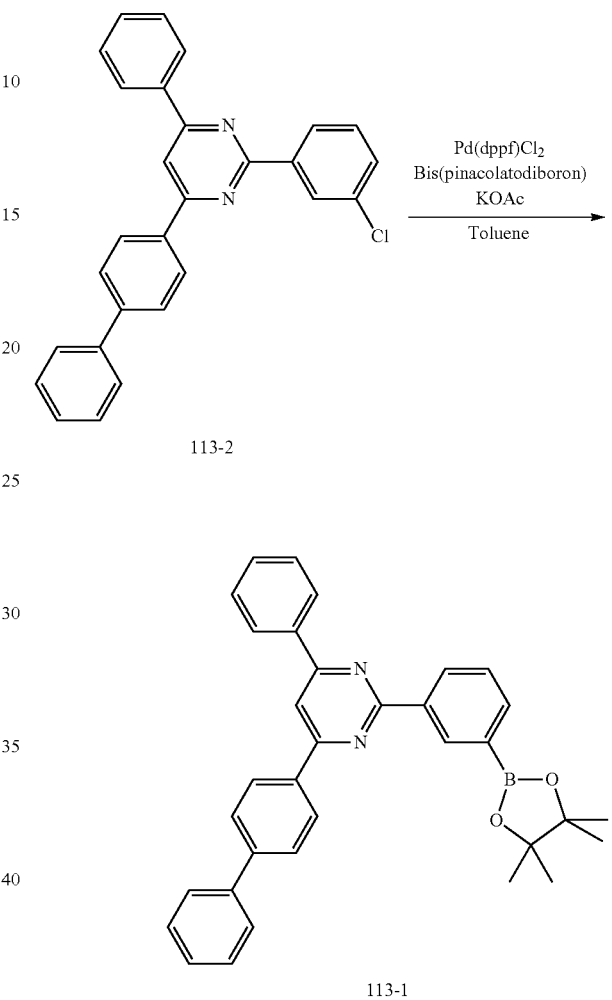

35 g (83.5 mmol) of the synthesized intermediate 113-2 was put in a 500 mL round-bottomed flask, 250 mL of toluene, 0.05 equivalent of dichlorodiphenylphosphinoferrocene palladium, 1.2 equivalent of bis(pinacolato)diboron, and 2 equivalents of potassium acetate were added thereto, and the mixture was heated and refluxed for 18 hours under a nitrogen atmosphere. The reaction solution was cooled down, and 100 mL of water was added thereto to extract an organic layer. The organic layer was collected, treated with activated carbon, filtered through silica gel, and concentrated. The concentrated residue was collected, heated and dissolved in 1 L of toluene, treated with activated carbon, filtered through silica gel. The filtered solution was cooled down and stirred to precipitate a solid. The precipitated solid was filtered to obtain 35.8 g of an intermediate 113-1.

d) Synthesis of Compound 113

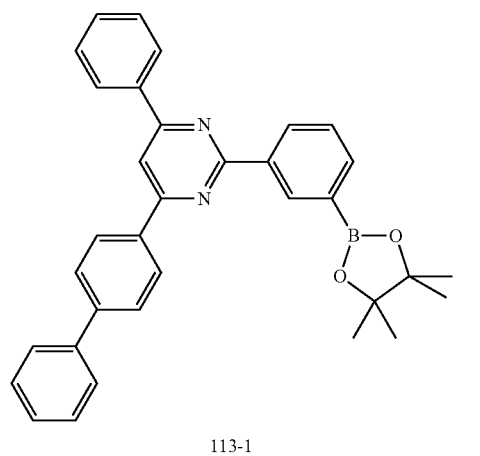

113-1

+

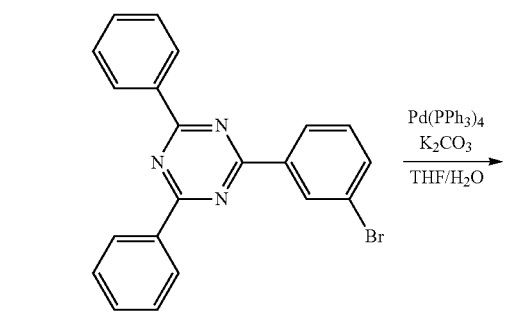

Pd(PPh₃)₄
K₂CO₃
THF/H₂O

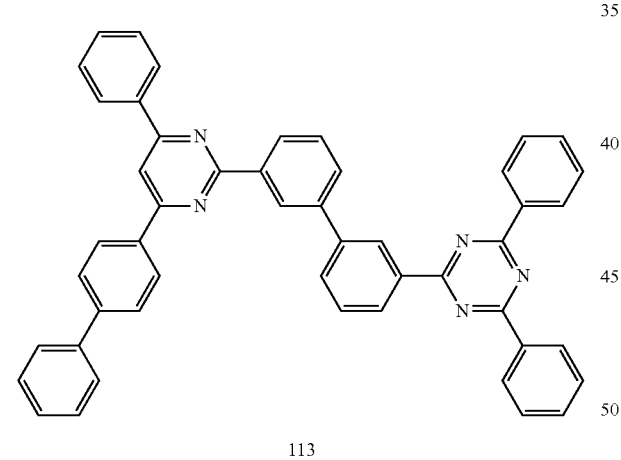

113

35 g (68.6 mmol) of the synthesized 113-1, 1 equivalent of 2-(3-bromophenyl)-4,6-diphenyl-1,3,5-triazine, 0.03 equivalent of tetrakistriphenylphosphine palladium, 2 equivalents of potassium carbonate, 250 mL of tetrahydrofuran, and 70 mL of distilled water were put in a 500 mL round-bottomed flask and then, heated and refluxed under a nitrogen atmosphere. After 16 hours, the reaction solution was cooled down, suspended in 500 mL of methanol, stirred and filtered, and washed with 500 mL of water. Then, a solid produced therein was collected and then, heated and recrystallized with 500 mL of dichlorobenzene to obtain 32 g of a compound 113.

LC/MS calculated for: C49H33N5 Exact Mass: 691.2736, found for: 692.29 [M+H].

Synthesis Example AD-1: Synthesis of Compound 119 a) Synthesis of Intermediate 119-2

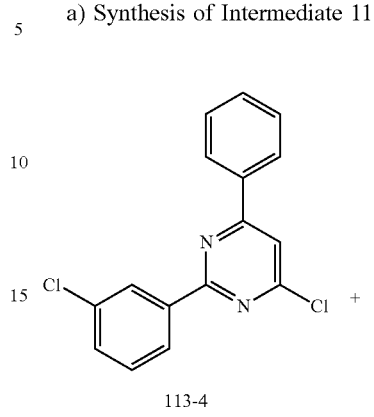

113-4

+

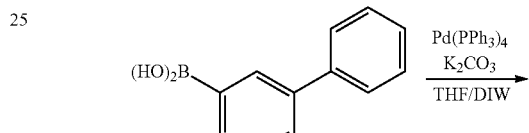

Pd(PPh₃)₄
K₂CO₃
THF/DIW

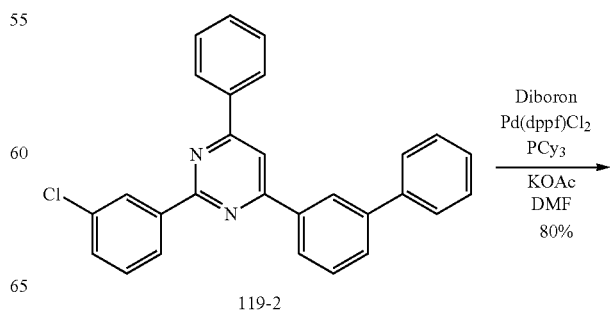

119-2

An intermediate 119-2 was synthesized according to the same method as the method of synthesizing the intermediate 113-2 according to Synthesis Example 9.

b) Synthesis of Intermediate 119-1

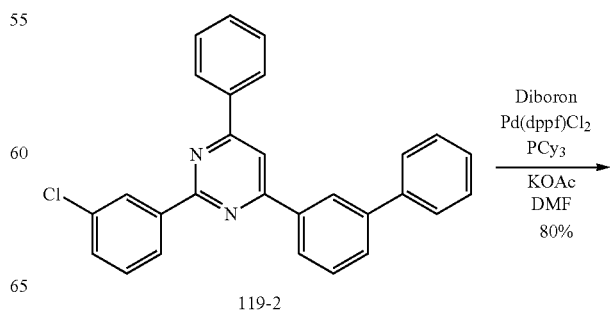

119-2

Diboron
Pd(dppf)Cl₂
PCy₃
KOAc
DMF
80%

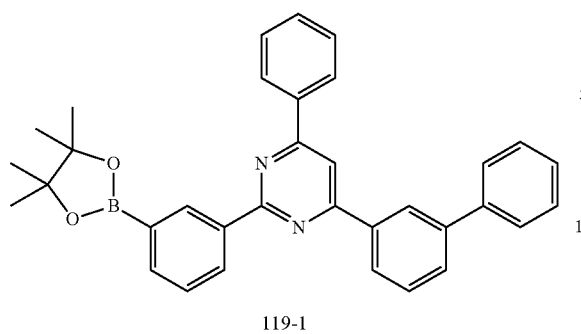

119-1

An intermediate 119-1 was synthesized according to the same method as the method of synthesizing the intermediate 113-1 according to Synthesis Example 9.

c) Synthesis of Compound 119

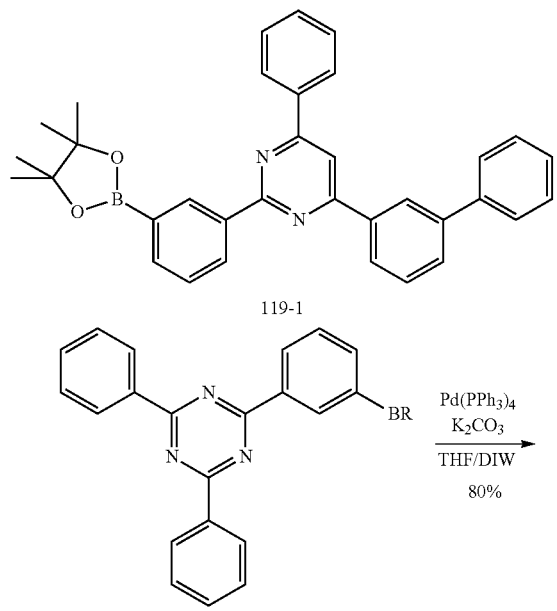

An intermediate 119 was synthesized according to the same method as the method of synthesizing the intermediate 113 according to Synthesis Example 9.

LC/MS calculated for: C49H33N5 Exact Mass: 691.27 found for: 692.33 [M+H].

Synthesis Example AD-2: Synthesis of Compound 146 a) Synthesis of Intermediate 146-6

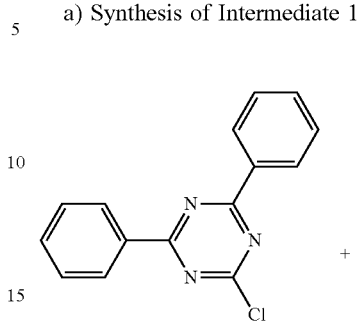

20 g of 2-chloro-4,6-diphenyl-1,3,5-triazine was dissolved in 250 mL of a mixed solution of tetrahydrofuran/distilled water (3/1) in a 500 mL round-bottomed flask. Then, 1.2 equivalent of 4-chlorophenyl boronic acid, 0.05 equivalent of tetrakistriphenylphosphine palladium, and 3 equivalents of potassium carbonate were added thereto, and the mixture was heated and refluxed under a nitrogen atmosphere for 18 hours. When the reaction was complete, the reaction solution was cooled down, and 100 mL of water was added thereto to extract an organic layer. The organic layer was collected, treated with activated carbon, and filtered through silica gel, and the filtered solution was concentrated. The concentrated residue was collected and crystallized in 200 mL of toluene and 50 mL of acetone to obtain 16 g of an intermediate 146-6.

b) Synthesis of Intermediate 146-5

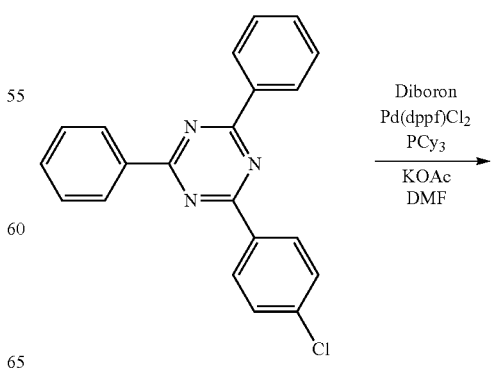

146-6

-continued

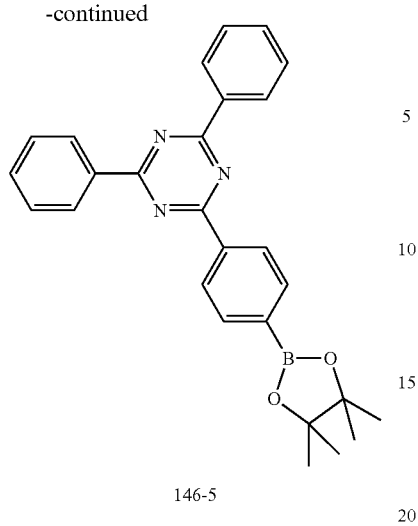

146-5

15 g of the synthesized intermediate 146-6 was dissolved in 200 mL of dimethyl formamide in a 500 mL round-bottomed flask. Then, 0.0.05 equivalent of dichlorodiphenylphosphinoferrocene palladium, 1.2 equivalent of bis(pinacolato)diboron, 2 equivalents of potassium acetate, and 0.2 equivalent of tricyclohexyl phosphine were added thereto, and the mixture was heated and refluxed under a nitrogen atmosphere for 18 hours. The reaction solution was cooled down and then, added to 500 mL of water and suspended therein to produce a solid, and the solid was filtered after stirring. The filtered solid was twice washed with 100 mL of water. The solid was collected and then, heated and dissolved in 500 mL of toluene, and filtered through activated carbon/silica gel, and the filtered solution was concentrated. The concentrated residue was solidified with 300 mL of a mixed solution of normal hexane and ethyl acetate in a ratio of 5:1 (V/V) to obtain 16 g of an intermediate 146-5.

c) Synthesis of Intermediate 146-4

-continued

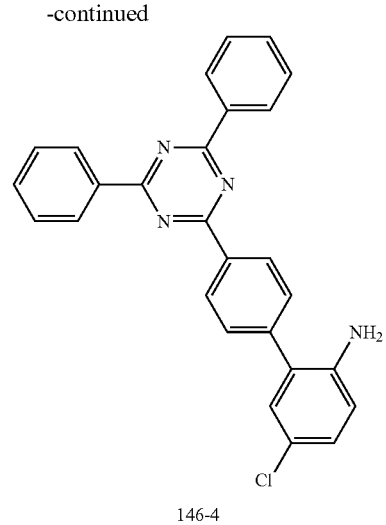

146-4

16 g of the synthesized intermediate 146-5, 120 mL of a mixed solution of tetrahydrofuran/distilled water in a ratio of 3/1 (V/V), 0.03 equivalent of tetrakis triphenyl palladium, 3 equivalents of potassium carbonate, and 1.1 equivalent of 2-bromo-4-chloro aniline were put in a 250 mL round-bottomed flask and then, heated and refluxed for 19 hours. When the reaction was complete, the reaction solution was cooled down and layer-separated to obtain an organic layer. Then, anhydrous magnesium sulfate and activated carbon were added to the organic layer, and the mixture was stirred and filtered through silica gel. The filtered solution was concentrated, and the concentrated residue was silica gel column-purified with a mixed solution of normal hexane and ethyl acetate to obtain 13 g of an intermediate 146-4.

d) Synthesis of Intermediate 146-3

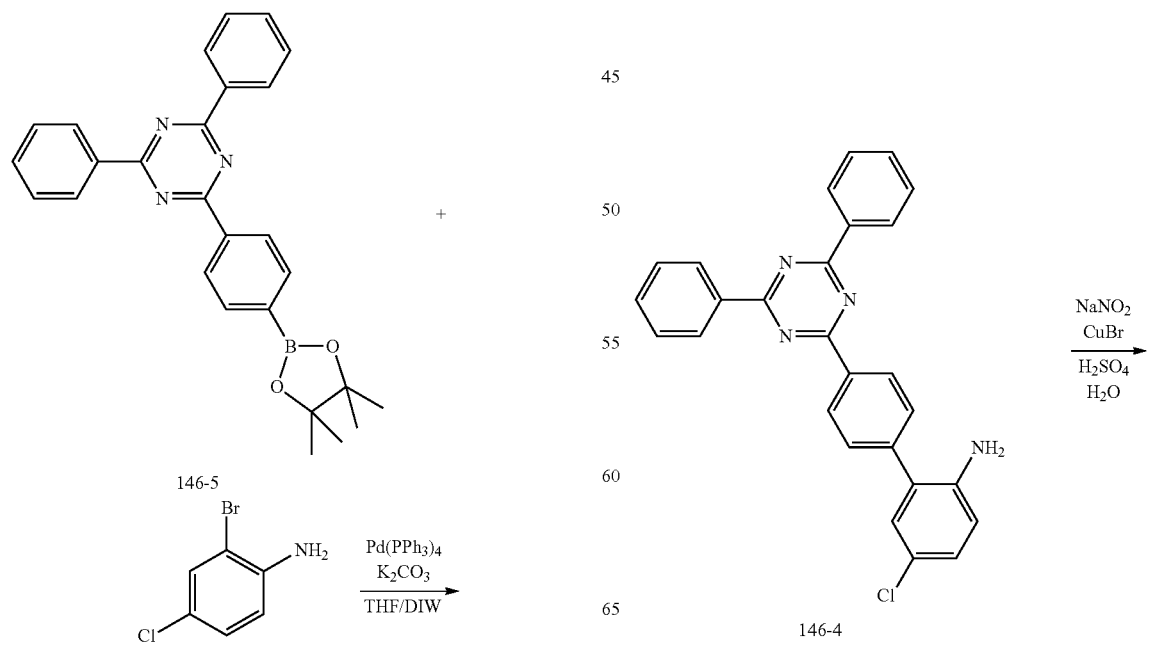

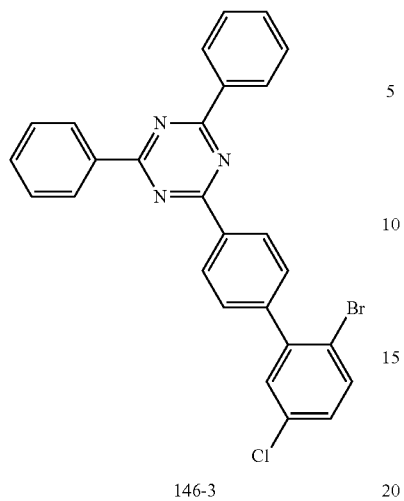

146-3

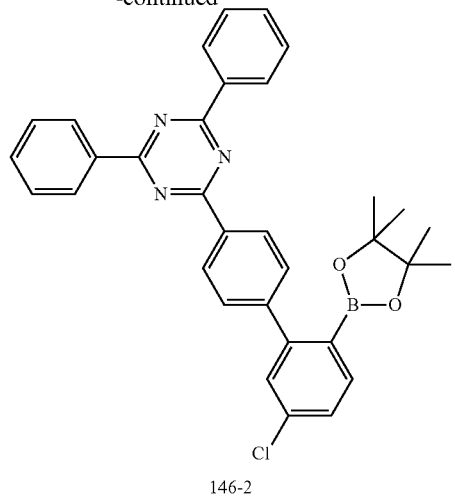

146-2

13 g of the synthesized intermediate 146-4 was suspended in 150 mL of water. The reaction solution was stirred, and 2 equivalents of strong sulfuric acid were added thereto in a dropwise fashion. Then, 1.1 equivalent of sodium nitrite was dissolved in 15 mL of distilled water, and the solution was slowly added to the reaction solution in a dropwise fashion in an ice water bath. After the addition in a dropwise fashion, the mixture is stirred for 2 hours. The stirred solution was put in a 500 mL reactor, 2 equivalents of copper bromide was added thereto, and the mixture was heated and refluxed for 1 hour. The reaction solution was cooled down and extracted with 100 mL of chloride methylene, an organic layer therefrom was dried with anhydrous magnesium sulfate, and the filtered solution was concentrated. The concentrated residue was silica gel column-purified with a mixed solution of normal hexane and chloride methylene to obtain 11 g of an intermediate 146-3.

e) Synthesis of Intermediate 146-2

12 g of the synthesized intermediate 146-3 was put in a 250 mL round-bottomed flask, 100 mL of anhydrous tetrahydrofuran and 1.2 equivalent of triisopropyloxy boron were added thereto, and the mixture was cooled down in a dry ice acetone bath under a nitrogen atmosphere. Then, a 2.5 normal butyllithium solution was added thereto in a dropwise fashion for 20 minutes. After the addition in a dropwise fashion, the mixture was stirred for one hour and slowly heated up to room temperature. The resultant was stirred at room temperature for 2 hours, and a 2 normal hydrochloric acid solution was added to the reaction solution in a dropwise fashion for 2 hours. The reaction solution was layer-separated to obtain an organic layer. The organic layer was dried with anhydrous magnesium sulfate and then, filtered and concentrated. The concentrated residue was used for the following reaction with no additional purification.

f) Synthesis of Intermediate 146-1

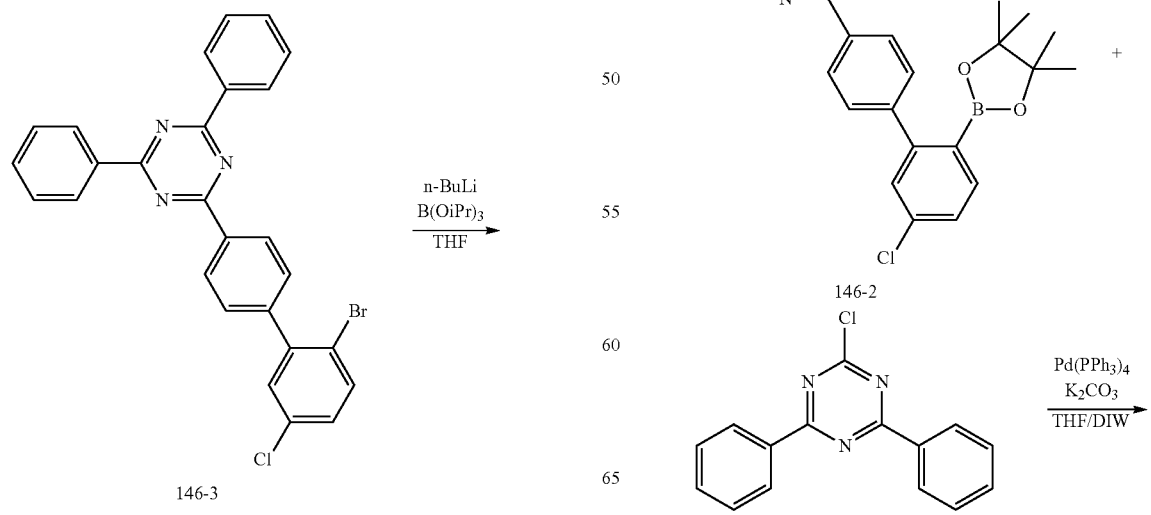

146-2

225
-continued

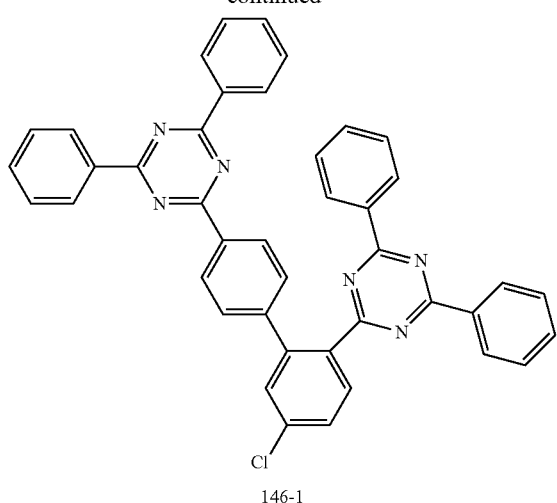
146-1

8 g of an intermediate 146-1 was obtained according to the same method as Synthesis Example AD-2 by using the synthesized intermediate 146-2 instead of 4-chlorophenylboronic acid.

g) Synthesis of Compound 146

226
-continued

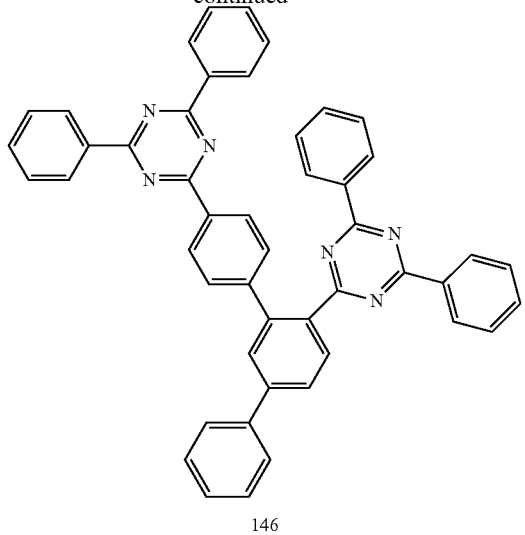
146

8 g of the synthesized intermediate 146-1 was dissolved in 120 mL of 1,4-dioxane in a 250 mL round-bottomed flask. Then, 1.2 equivalent of phenyl boronic acid, 0.03 equivalent of bis(dibenzylideneacetone)palladium, 0.12 equivalent of SPhos, and 3 equivalents of cesium carbonate were added to the reaction solution, and the mixture was heated and refluxed for 20 hours. The reaction solution was cooled down and then, added to 200 mL of ethyl acetate and 100 mL of distilled water to separate a layer. The organic layer was separated, treated with anhydrous magnesium sulfate and activated carbon, filtered, and concentrated. The concentrated residue was silica gel column-purified with a mixed solution of normal hexane and chloride methylene to obtain 5 g of a compound 146.

LC/MS calculated for: C48H32N6 Exact Mass: 692.27 found for: 693.37 [M+H].

(Synthesis of Second Compound)

Synthesis Example 10: Synthesis of Compound B-10

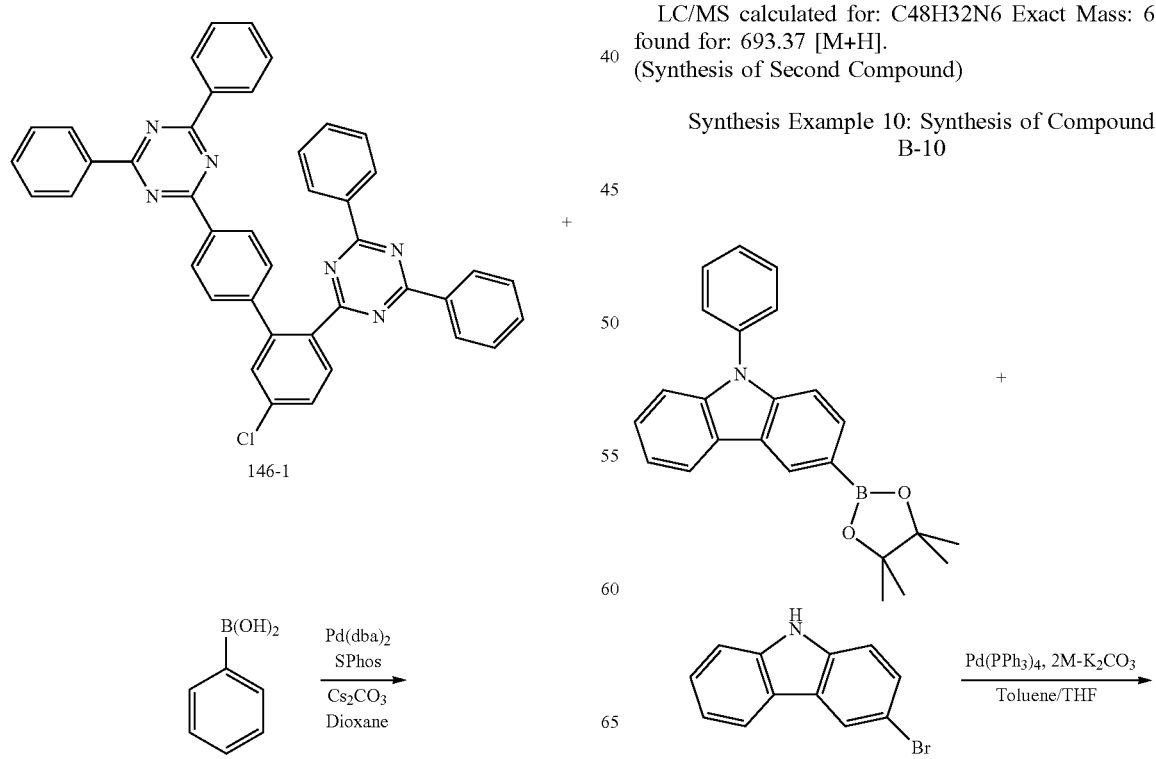

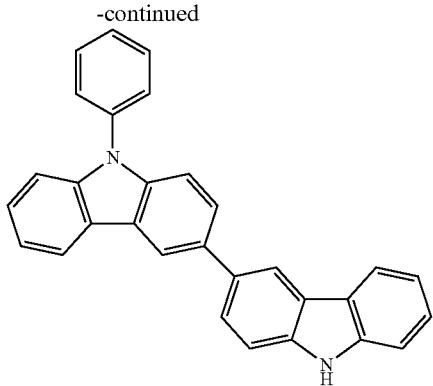

(J)

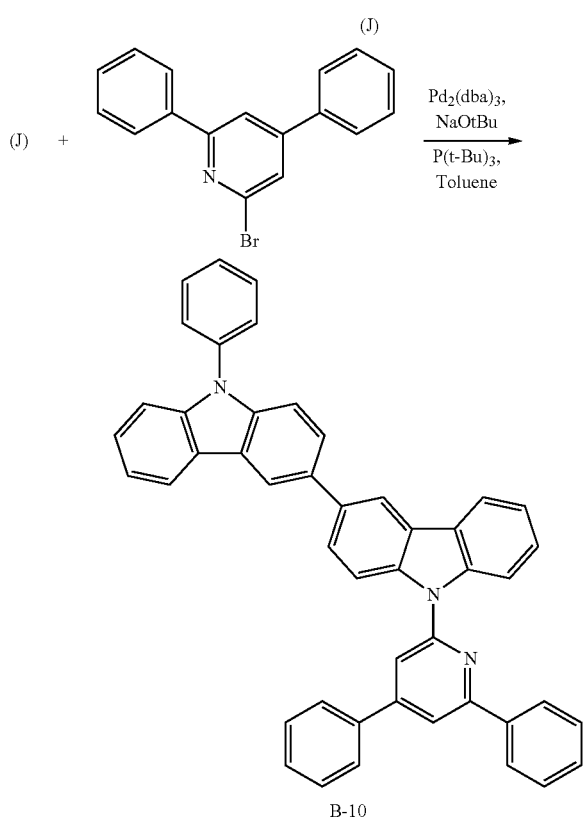

B-10

First Step: Synthesis of Compound J

The compound of 9-phenyl-3-(4,4,5,5-tetramethyl-1,3,2-dioxaborolan-2-yl)-9H-carbazole (26.96 g, 81.4 mmol) was dissolved in 0.2 L of toluene/THF in a nitrogen environment, 3-bromo-9H-carbazole (23.96 g, 97.36 mmol) and tetrakis(triphenylphosphine)palladium (0.90 g, 0.8 mmol) were added thereto, and the mixture was stirred. Then, potassium carbonate saturated in water (28 g, 203.49 mmol) was added thereto, and the obtained mixture was heated and refluxed at 120° C. for 12 hours. When the reaction was complete, water was added to the reaction solution, dichloromethane (DCM) was used for extraction, and an extract was treated with anhydrous MgSO4 to remove moisture, filtered, and concentrated under a reduced pressure. This obtained residue was separated and purified through flash column chromatography to obtain the compound J (22.6 g, 68%).

HRMS (70 eV, EI+): m/z calcd for C30H20N2: 408.16, found: 408.

Elemental Analysis: C, 88%; H, 5

Second Step: Synthesis of Compound B-10

The compound J (22.42 g, 54.88 mmol) was dissolved in 0.2 L of toluene in a nitrogen environment, 2-bromo-4,6-diphenylpyridine (20.43 g, 65.85 mmol), NaOtBu (7.92 g, 82.32 mmol), tris(dibenzylideneacetone)dipalladium (0) (1.65 g, 1.65 mmol), and tri-tert-butylphosphine (1.78 g, 4.39 mmol) were added thereto, and the mixture was heated and refluxed at 120° C. for 12 hours. When the reaction was complete, water was added to the reaction solution, dichloromethane (DCM) was used for extraction, and an extract was treated with anhydrous MgSO4 to remove moisture, filtered, and concentrated under a reduced pressure. This obtained residue was separated and purified through flash column chromatography to obtain the compound 6-10 (28.10 g, 80%).

HRMS (70 eV, EI+): m/z calcd for C47H31N3: 637.25, found: 637.

Elemental Analysis: C, 89%; H, 5%

Synthesis Example 11: Synthesis of Compound B-31

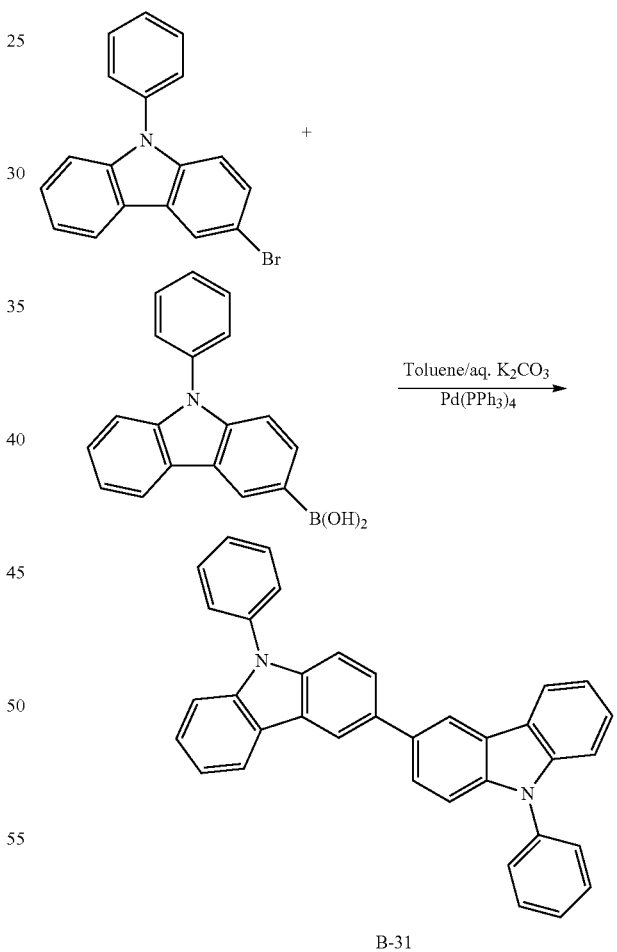

B-31

The compound phenylcarbazolyl bromide (9.97 g, 30.95 mmol) was dissolved in 0.2 L of toluene in a nitrogen environment, phenylcarbazolylboronic acid (9.78 g, 34.05 mmol) and tetrakis(triphenylphosphine)palladium (1.07 g, 0.93 mmol) were added thereto, and the mixture was stirred. Then, potassium carbonate saturated in water (12.83 g, 92.86 mmol) was added thereto, and the mixture was heated and refluxed at 120° C. for 12 hours. When the reaction was complete, water was added to the reaction, dichloromethane (DCM) was treated for an extraction, anhydrous MgSO₄ was used to remove moisture, and the resultant was filtered and concentrated under a reduced pressure. The obtained residue was separated and purified through flash column chromatography to obtain the compound B-31 (13.8 g, 92%).

HRMS (70 eV, EI+): m/z calcd for C36H24N2: 484.19, found: 484.

Elemental Analysis: C, 89%; H, 5%

Synthesis Example 12: Synthesis of Compound B-34

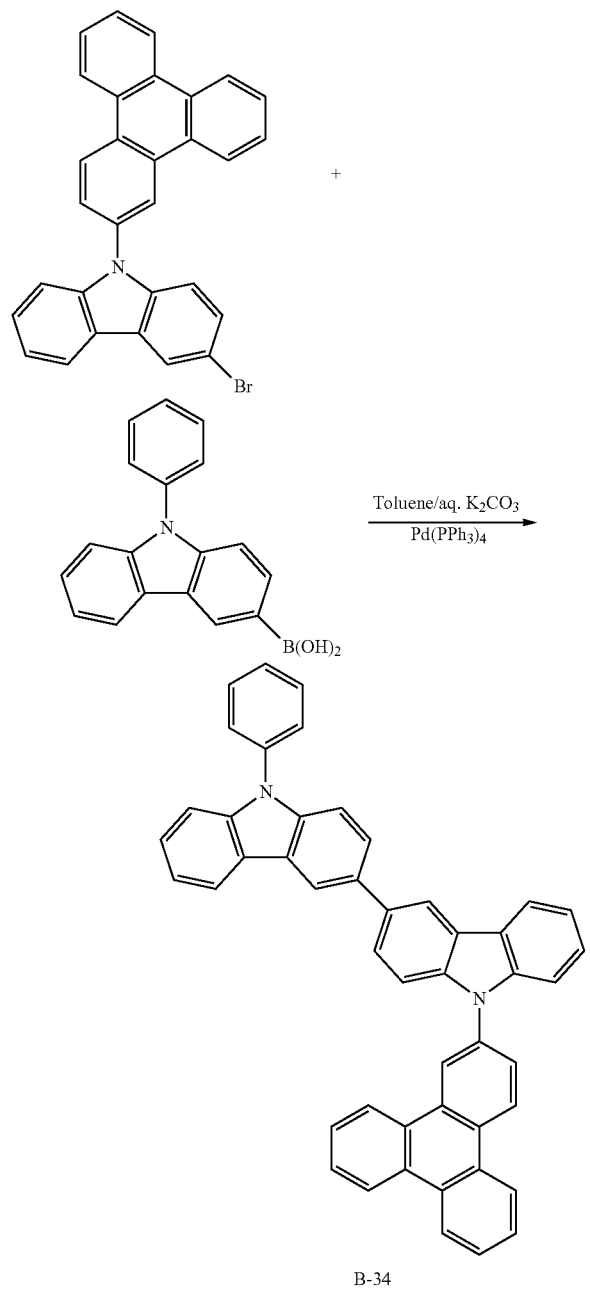

B-34

The compound triphenylcarbazolyl bromide (14.62 g, 30.95 mmol) was dissolved in 0.2 L of toluene in a nitrogen environment, phenylcarbazolylboronic acid (9.78 g, 34.05 mmol) and tetrakis(triphenylphosphine)palladium (1.07 g, 0.93 mmol) are added thereto, and the mixture was stirred. Then, potassium carbonate saturated in water (12.83 g, 92.86 mmol) was added thereto, and the mixture was heated and refluxed at 120° C. for 12 hours. When the reaction was complete, water was added to the reaction solution, dichloromethane (DCM) was used for an extraction, anhydrous MgSO4 was used to remove moisture, and the resultant was filtered and concentrated under a reduced pressure. The obtained residue was separated and purified through flash column chromatography to obtain the compound B-34 (16.7 g, 85%).

HRMS (70 eV, EI+): m/z calcd for C47H29N2: 621.23, found: 621.

Elemental Analysis: C, 91%; H, 5%

Synthesis Example 13: Synthesis of Compound B-43

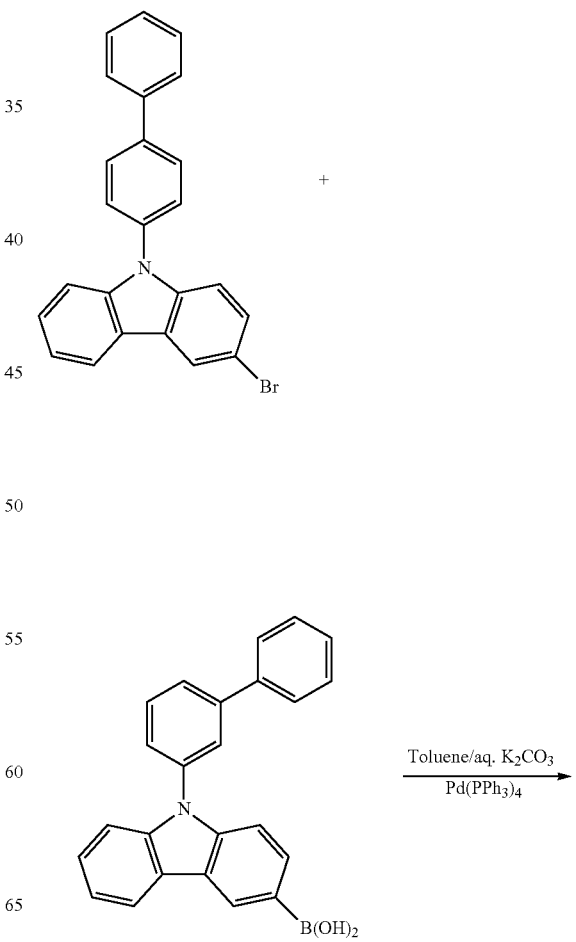

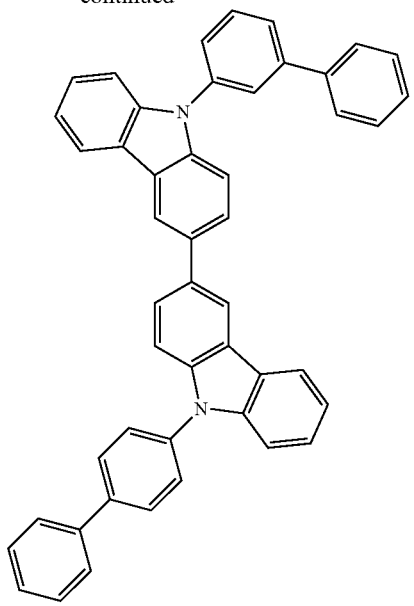

B-43

The compound of biphenylcarbazolyl bromide (12.33 g, 30.95 mmol) was dissolved in 0.2 L of toluene in a nitrogen environment, biphenylcarbazolylboronic acid (12.37 g, 34.05 mmol) and tetrakis(triphenylphosphine)palladium (1.07 g, 0.93 mmol) were added thereto, and the mixture was stirred. Then, potassium carbonate saturated in water (12.83 g, 92.86 mmol) was added thereto, and the mixture was heated and refluxed at 120° C. for 12 hours. When the reaction was complete, water was added to the reaction solution, dichloromethane (DCM) was used for an extraction, anhydrous MgSO4 was used to remove moisture, and the resultant was filtered and concentrated under a reduced pressure. The obtained residue was separated and purified through flash column chromatography to obtain a compound B-43 (18.7 g, 92%).

HRMS (70 eV, EI+): m/z calcd for C48H32N2: 636.26, found: 636.

Elemental Analysis: C, 91%; H, 5%

Synthesis Example 14: Synthesis of Compound B-114

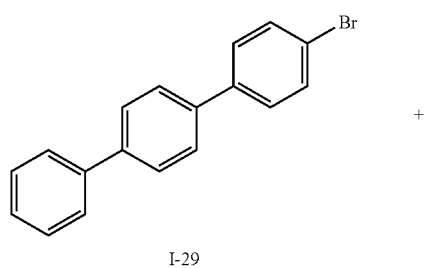

I-29

+

J

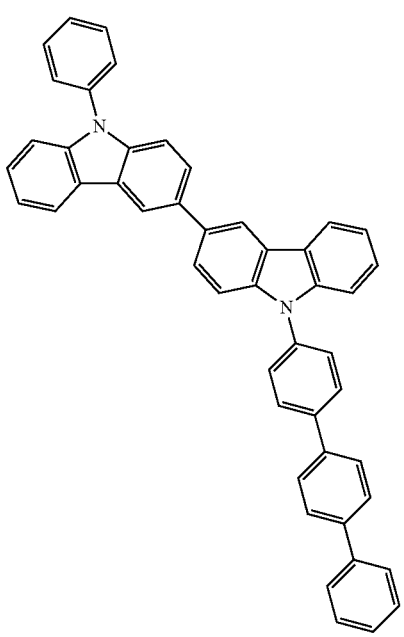

B-114

4-bromo-1,1':4',1''-terphenyl (15 g, 48.5 mmol) was dissolved in 0.2 L of toluene in a nitrogen environment, the compound J (20 g, 48.5 mmol), NaOtBu (6 g, 58.2 mmol), tris(dibenzylideneacetone)dipalladium (0) (0.439 g, 0.48 mmol), and tri-tert-butylphosphine (0.388 g, 1.92 mmol) were added thereto, and the mixture was heated and refluxed at 120° C. for 12 hours. When the reaction was complete, water was added to the reaction solution, dichloromethane (DCM) was used for an extraction, anhydrous MgSO4 was used to remove moisture, and the resultant was filtered and concentrated under a reduced pressure. This obtained residue was separated and purified through flash column chromatography to obtain the compound B-114 (25 g, 80%).

HRMS (70 eV, EI+): m/z calcd for C48H32N2: 636.2565, found: 636.

Elemental Analysis: C, 95%; H, 5%

Synthesis Example 15: Synthesis of Compound B-116
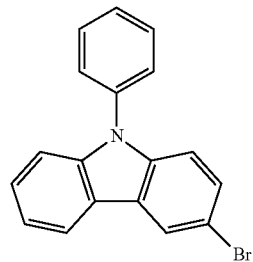
+
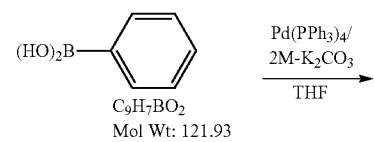
Pd(PPh₃)₄/
2M-K₂CO₃
——————→
THF
C₉H₇BO₂
Mol Wt: 121.93
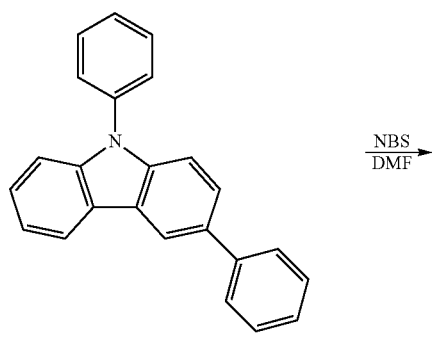
Intermediate a
NBS
———→
DMF
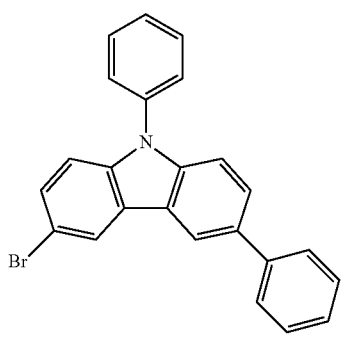
Intermediate b
-continued
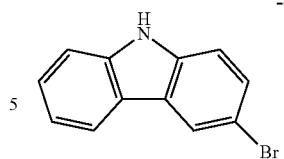
+
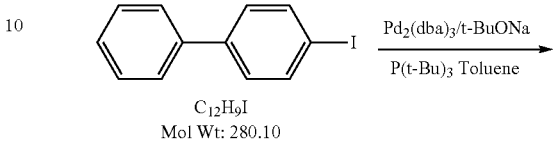
C₁₂H₉I
Mol Wt: 280.10
Pd₂(dba)₃/t-BuONa
————————→
P(t-Bu)₃ Toluene
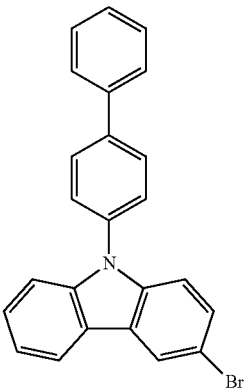
Intermediate c
Pd(dppf)Cl₂, K(OAc)
————————————→
Bi(pinacolato)diboron
Toluene
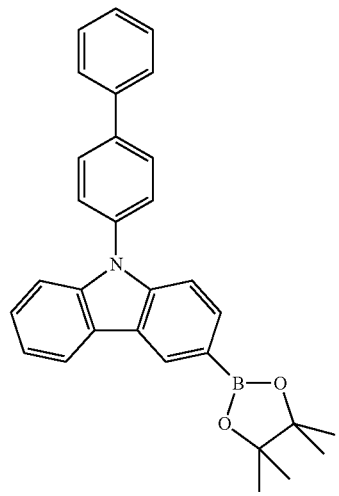
Intermediate d -continued

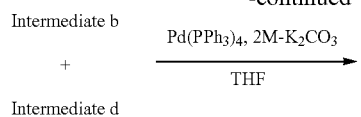
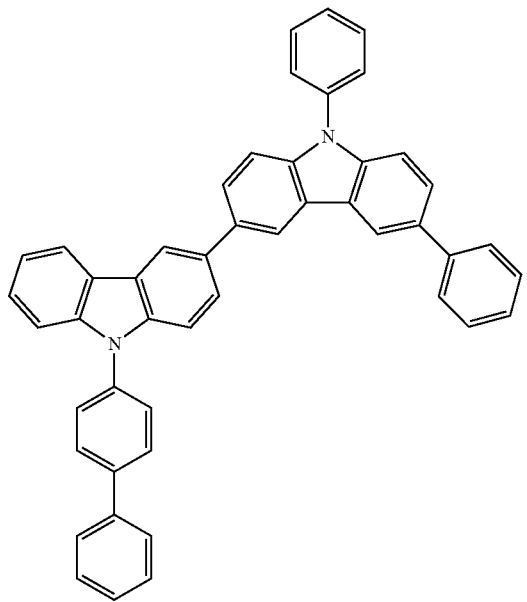

B-116

Synthesis Example 16: Synthesis of Compound B-118

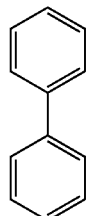

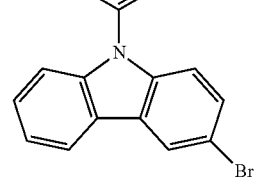

Intermediate c

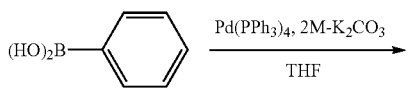

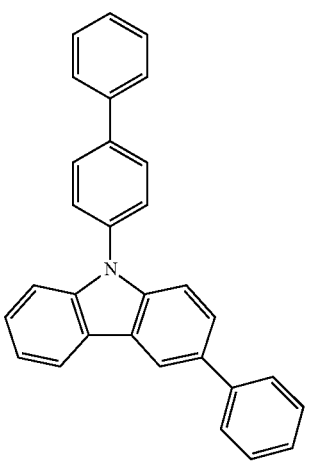

Intermediate e

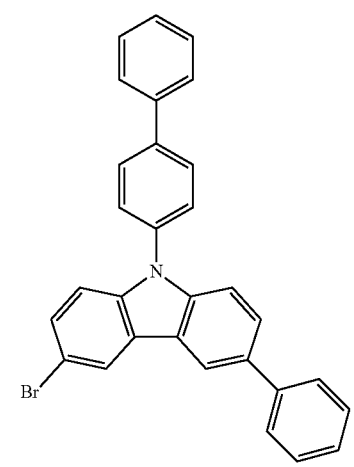

Intermediate f

First Step: Synthesis of Intermediate a

An intermediate a (32 g, 75%) was synthesized according to the same method as the method of synthesizing the compound B-31 by using 43.2 g (134.2 mmol) of 3-bromo-N-phenyl carbazole and 18 g (147.6 mmol) of phenylboronic acid.

Second Step: Synthesis of Intermediate b

An intermediate b (35 g, 82%) was synthesized by dissolving 34.4 g (107.6 mmol) of the compound 1 in 500 mL of dichloromethane, adding 19.2 g (107.6 mmol) of N-bromosuccinimide, and stirring the mixture at room temperature for 8 hours.

Third Step: Synthesis of Intermediate c

An intermediate c (15 g, 53%) was synthesized according to the same method as the method of synthesizing the compound B-114 by using 17.65 g (71.74 mmol) of 3-Bromocarbazole and 22 g (78.91 mmol) of 4-Iodobiphenyl.

Fourth Step: Synthesis of Intermediate d

An intermediate d (20 g, 89%) was synthesized according to the same method as the method of synthesizing the intermediate 1-5 by using 20.1 g (50.5 mmol) of the intermediate c and 19.2 g (75.8 mmol) of bis(pinacolato)diboron.

Fifth Step: Synthesis of Compound B-116

A compound B-116 (18 g, 84%) was synthesized according to the same method as the method of synthesizing the compound B-31 by using 13 g (33.1 mmol) of the intermediate b and 16.2 g (36.4 mmol) of the intermediated.

HRMS (70 eV, EI+): m/z calcd for $C_{48}H_{32}N_2$: 636.2565, found: 636.

Elemental Analysis: C, 90%; H, 5%

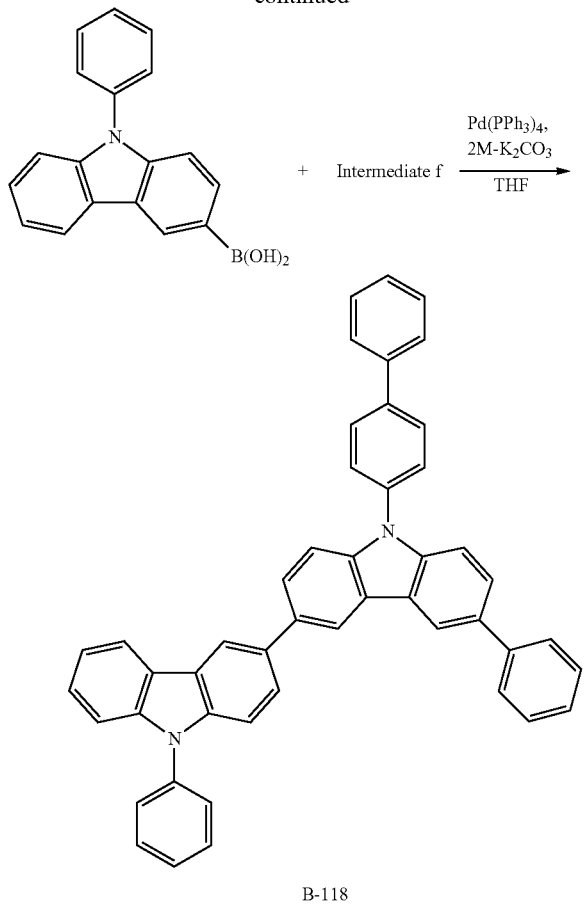

B-118

Synthesis Example 18: Synthesis of Compound B-156

The following intermediate h was synthesized through the first and second steps of Synthesis Example 15 by using 1,3-dibromo-N-phenyl carbazole instead of the 3-bromo-N-phenyl carbazole in the first step of Synthesis Example 15.

Subsequently, the compound B-156 was synthesized according to the same method as Synthesis Example 13 by using the intermediate h instead of biphenylcarbazolyl bromide of the starting material of Synthesis Example 13.

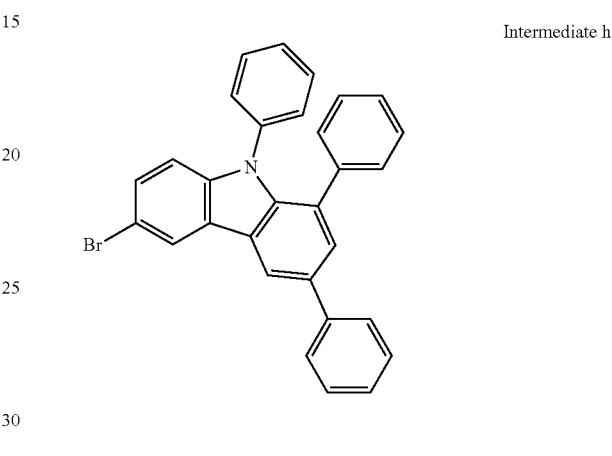

Intermediate h

Synthesis Example 19: Synthesis of Compound C-10

First Step: Synthesis of Intermediate e

An intermediate d (33 g, 77%) was synthesized according to the same method as Synthesis Example 11 by using 43.2 g (108.4 mmol) of the intermediate c and 14.5 g (119 mmol) of phenylboronic acid.

Second Step: Synthesis of Intermediate f

An intermediate f (29 g, 81%) was synthesized according to the same method as the method of synthesizing the intermediate b according to Synthesis Example 15 by using 29.8 g (75.28 mmol) of the intermediate e and 14 g (75.28 mmol) of N-bromosuccinimide.

Third Step: Synthesis of Compound B-118

A compound B-118 (17 g, 79%) was obtained according to the same method as the method of synthesizing the compound B-31 according to Synthesis Example 11 by using 9.7 g (33.65 mmol) of N-phenylcarbazole-3-yl-boronic acid and 16 g (33.65 mmol) of the intermediate f.

HRMS (70 eV, EI+): m/z calcd for C48H32N2: 636.2565, found: 636.

Elemental Analysis: C, 90%; H, 5%

Synthesis Example 17: Synthesis of Compound B-111

A compound B-111 was synthesized according to the same method as the first step of Synthesis Example 10 by using the intermediates c and d of Synthesis Example 15 as a starting material.

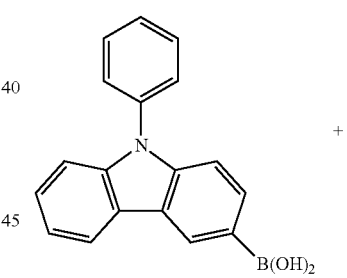

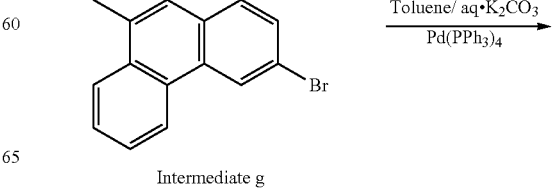

Intermediate g

-continued

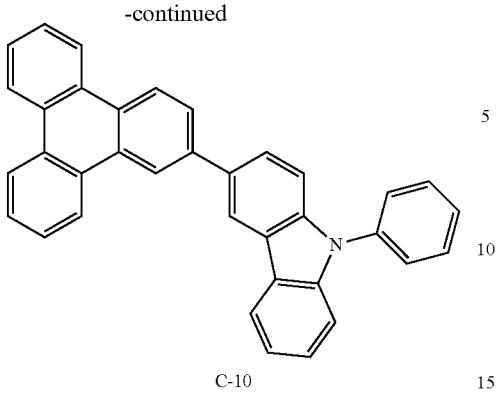

C-10

10 g (34.83 mmol) of phenylcarbazolyl boronic acid, 11.77 g (38.31 mmol) of the intermediate g, 14.44 g (104.49 mmol) of potassium carbonate, and 0.80 g (0.7 mmol) of tetrakis-(triphenylphosphine)palladium (0) were suspended in 140 ml of toluene, and 50 ml of distilled water and then, refluxed and stirred for 12 hours. Subsequently, the resultant was extracted with dichloromethane and distilled water, and an organic layer therefrom was silica gel-filtered. After removing an organic solution and silica gel-columning the residue with hexane:dichloromethane=7:3 (v/v), a solid produced therefrom was recrystallized with dichloromethane and n-hexane to obtain a compound C-10 14.4 g (a yield: 88%).

HRMS (70 eV, EI+): m/z calcd for C36H23N: 469.18, found: 469.

Elemental Analysis: C, 92%; H, 5%

Manufacture of Organic Light Emitting Diode

Example 1

A glass substrate coated with ITO (indium tin oxide) as a 1500 Å-thick thin film was ultrasonic wave-washed with distilled water. After washing with the distilled water, the glass substrate was ultrasonic wave-washed with a solvent such as isopropyl alcohol, acetone, methanol, and the like and dried and then, moved to a plasma cleaner, cleaned by using oxygen plasma for 10 minutes, and moved to a vacuum depositor. This obtained ITO transparent electrode was used as an anode, a 700 Å-thick hole injection layer was formed on the ITO substrate by vacuum depositing the compound A, and a hole transport layer was formed on the injection layer by depositing the compound B to be 50 Å thick and the compound C to be 1020 Å thick. On the hole transport layer (HTL), a 400 Å-thick emission layer was formed by vacuum-depositing the compound 1 of Synthesis Example 1 and the compound B-10 of Synthesis Example 10 simultaneously as a host and 10 wt % of tris(2-phenylpyridine)iridium(III) [Ir(ppy)$_3$] as a dopant. Herein, the compound 1 and the compound B-10 were used in a weight ratio of 3:7, but their ratio in the following Examples was separately provided. Subsequently, on the emission layer, a 300 Å-thick electron transport layer was formed by simultaneously vacuum-depositing the compound D and Liq in a ratio of 1:1, and on the electron transport layer, Liq and Al were sequentially vacuum-deposited to be 15 Å thick and 1200 Å thick, manufacturing an organic light emitting diode.

The organic light emitting diode had a structure of 5-layered organic thin films specifically as follows.

ITO/compound A 700 Å/compound B 50 Å/compound C 1020 Å/EML[compound 1:B-10:Ir(ppy)$_3$=27 wt %:63 wt %:10 wt %] 400 Å/compound D:Liq 300 Å/Liq 15 Å/Al 1200 Å.

Compound A: N4,N4'-diphenyl-N4,N4'-bis(9-phenyl-9H-carbazol-3-yl)biphenyl-4,4'-diamine Compound B: 1,4,5,8,9,11-hexaazatriphenylene-hexacarbonitrile (HAT-CN), Compound C: N-(biphenyl-4-yl)-9,9-dimethyl-N-(4-(9-phenyl-9H-carbazol-3-yl)phenyl)-9H-fluoren-2-amine Compound D: 8-(4-(4,6-di(naphthalen-2-yl)-1,3,5-triazin-2-yl)phenyl)quinoline

Example 2

An organic light emitting diode was manufactured according to the same method as Example 1 by using the compound 1 and the compound B-111 in a weight ratio of 3:7.

Example 3

An organic light emitting diode was manufactured according to the same method as Example 1 by using the compound 2 and the compound B-43 in a weight ratio of 5:5.

Example 4

An organic light emitting diode was manufactured according to the same method as Example 1 by using the compound 126 and the compound B-43 in a weight ratio of 4:6.

Example 5

An organic light emitting diode was manufactured according to the same method as Example 1 by using the compound 113 and the compound B-43 in a weight ratio of 5:5.

Example 6

An organic light emitting diode was manufactured according to the same method as Example 1 by using the compound 16 and the compound B-43 in a weight ratio of 3:7.

Example 7

An organic light emitting diode was manufactured according to the same method as Example 1 by using the compound 16 and the compound B-111 in a weight ratio of 3:7.

Example 8

An organic light emitting diode was manufactured according to the same method as Example 1 by using the compound 16 and the compound B-118 in a weight ratio of 3:7.

Example 9

An organic light emitting diode was manufactured according to the same method as Example 1 by using the compound 16 and the compound B-116 in a weight ratio of 3:7.

Example 10

An organic light emitting diode was manufactured according to the same method as Example 1 by using the compound 4 and the compound B-43 in a weight ratio of 3:7.

Example 11

An organic light emitting diode was manufactured according to the same method as Example 1 by using the compound 4 and the compound B-156 in a weight ratio of 3:7.

Example 12

An organic light emitting diode was manufactured according to the same method as Example 1 by using the compound 16 and the compound C-10 in a weight ratio of 3:7.

Example AD-1

An organic light emitting diode was manufactured according to the same method as Example 1 by using the compound 119 and the compound B-43 in a weight ratio of 3:7.

Example AD-2

An organic light emitting diode was manufactured according to the same method as Example 1 by using the compound 146 and the compound B-43 in a weight ratio of 3:7.

COMPARATIVE EXAMPLE

An organic light emitting diode was manufactured according to the same method as Example 1 by using the compound 1 as a single host.

Comparative Examples 2 to 12

As described in Table 1, each organic light emitting diode according to Comparative Examples 2 to 12 was manufactured according to the same method as Example 1 by using the first host or the second host as a single host.

Comparative Example 13

An organic light emitting diode was manufactured according to the same method as Example 1 by using the Comparative Example compound I and the compound B-43 in a weight ratio of 5:5.

[Comparative Example Compound I]

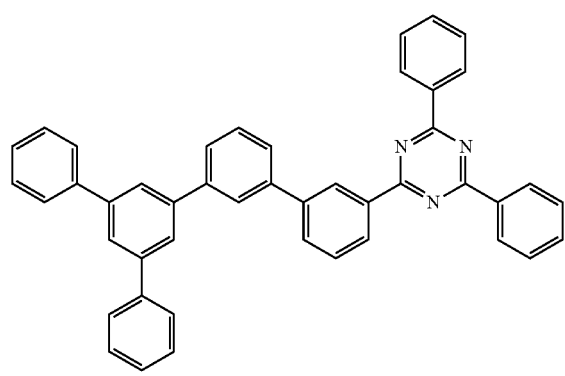 [SMILES: c1ccc(-c2cc(-c3ccccc3)cc(-c3cccc(-c4cccc(-c5nc(-c6ccccc6)nc(-c6ccccc6)n5)c4)c3)c2)cc1]

Comparative Example 14

An organic light emitting diode was manufactured according to the same method as Example 1 by using the compound 1 and mCP(1,3-bis(N-carbazolyl)benzene) in a weight ratio of 5:5 as a host.

Comparative Example 15

An organic light emitting diode was manufactured according to the same method as Example 1 by using the compound B-43 and Comparative Example compound II in a weight ratio of 5:5 as a host.

[Comparative Example Compound II]

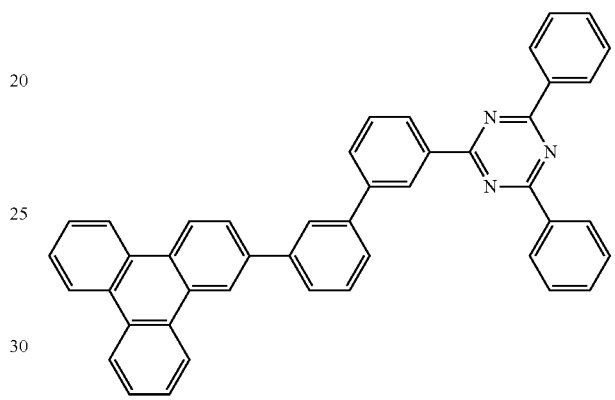

Evaluation 1: Luminous Efficiency and Life-Span Increase Effect

Luminous efficiency and life-span characteristics of the organic light emitting diodes according to Examples 1 to 12 and Comparative Examples 1 to 14 were evaluated. The measurements were specifically performed in the following methods, and the results are shown in Table 1.

(1) Measurement of Current Density Change Depending on Voltage Change

Current values flowing in the unit device of the manufactured organic light emitting diodes were measured for, while increasing the voltage from 0 V to 10 V using a current-voltage meter (Keithley 2400), and the measured current values were divided by an area to provide the results.

(2) Measurement of Luminance Change Depending on Voltage Change

Luminance of the manufactured organic light emitting diodes was measured for luminance, while increasing the voltage from 0 V to 10 V using a luminance meter (Minolta Cs-1000A).

(3) Measurement of Luminous Efficiency

Current efficiency (cd/A) at the same current density (10 mA/cm$^2$) was calculated by using the luminance, current density, and voltages (V) from the items (1) and (2).

(4) Measurement of Life-Span

T90 life-spans of the organic light emitting diodes according to Examples 1 to 12 and Comparative Examples 1 to 14 were measured as a time when their luminance decreased down to 90% relative to the initial luminance (cd/m$^2$) after emitting light with 5000 cd/m$^2$ as the initial luminance (cd/m$^2$) and measuring their luminance decrease depending on a time with a Polanonix life-span measurement system.

TABLE 1

| | First host | Second host | Ratio of First host + Second host | Color | Efficiency (Cd/A) | Life-span T90 |
|---|---|---|---|---|---|---|
| Example 1 | 1 | B-10 | 3:7 | green | 50.3 | 410 |
| Example 2 | 1 | B-111 | 3:7 | green | 50.7 | 186 |
| Example 3 | 2 | B-43 | 5:5 | green | 46.5 | 700 |
| Example 4 | 126 | B-43 | 4:6 | green | 40 | 210 |
| Example 5 | 113 | B-43 | 5:5 | green | 39.1 | 270 |
| Example 6 | 16 | B-43 | 3:7 | green | 45.3 | 480 |
| Example 7 | 16 | B-111 | 3:7 | green | 47.2 | 410 |
| Example 8 | 16 | B-118 | 3:7 | green | 50.3 | 120 |
| Example 9 | 16 | B-116 | 3:7 | green | 51.3 | 420 |
| Example 10 | 4 | B-43 | 3:7 | green | 48.7 | 470 |
| Example 11 | 4 | B-156 | 3:7 | green | 47 | 350 |
| Example 12 | 16 | C-10 | 3:7 | green | 51 | 320 |
| Example AD-1 | 119 | B-43 | 3:7 | green | 47.7 | 270 |
| Example AD-2 | 146 | B-43 | 3:7 | green | 45.4 | 120 |
| Comparative Example 1 | 1 | — | — | green | 35 | 71 |
| Comparative Example 2 | 2 | — | — | green | 35 | 80 |
| Comparative Example 3 | 4 | — | — | green | 37 | 75 |
| Comparative Example 4 | 16 | — | — | green | 40 | 77 |
| Comparative Example 5 | 113 | — | — | green | 20.6 | 32 |
| Comparative Example 6 | 126 | — | — | green | 33.6 | 10 |
| Comparative Example 7 | 140 | — | — | green | 20.5 | 30 |
| Comparative Example 8 | — | B-43 | — | green | 2.8 | 10 |
| Comparative Example 9 | — | B-111 | — | green | 3 | — |
| Comparative Example 10 | — | B-116 | — | green | 2.9 | 5 |
| Comparative Example 11 | — | B-118 | — | green | 5.1 | 3 |
| Comparative Example 12 | — | B-156 | — | green | 5.2 | 3 |
| Comparative Example 13 | Comparative Example compound I | B-43 | 5:5 | green | 46 | 80 |
| Comparative Example 14 | 1 | mCP | 5:5 | green | 40 | 75 |

Referring to Table 1, a host combination of the first and second hosts of the present invention superbly increased luminous efficiency and a life-span compared with a single first or second host. The organic light emitting diodes according to present invention showed at least 1.5 times or greater and at most 6 times or greater improved life-span compared with the organic light emitting diodes according to Comparative Examples.

Evaluation 2: Driving Voltage Decrease Effect (5) Measurement of Driving Voltage Driving voltage of each organic light emitting diode was measured at 15 mA/cm² by using a current-voltage meter (Keithley 2400), and the results are provided in Table 2.

TABLE 2

| | First host | Second host | Ratio of first host + second host | Color | Vd |
|---|---|---|---|---|---|
| Example 3 | 2 | B-43 | 5:5 | green | 3.95 |
| Exampe 5 | 113 | B-43 | 5:5 | green | 3.90 |
| Comparative Example 13 | Comparative Example compound I | B-43 | 5:5 | green | 4.26 |
| Comparative Example 14 | 1 | mCP | 5:5 | green | 4.80 |
| Comparative Example 15 | Comparative Example compound II | B-43 | 5:5 | green | 4.74 |

Referring to Table 2, the host combination of the present invention showed remarkably excellent effect in terms of a driving voltage compared with a host combination with a known host such as a Comparative Example compound I, a Comparative Example compound II, mCP, or the like.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

The invention claimed is:

1. A composition for an organic optoelectronic device, the composition comprising:

at least one first compound and at least one second compound mixed together, the at least one first compound being represented by Chemical Formula 1 and the at least one second compound being represented by Chemical Formula 2,

[Chemical Formula 1]

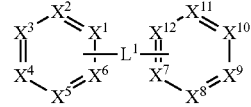

wherein, in Chemical Formula 1, $X^1$ to $X^{12}$ are independently N, C, or $CR^a$, at least one of $X^1$ to $X^6$ is N, at least one of $X^7$ to $X^{12}$ is N, $R^a$ is independently hydrogen, deuterium, a substituted or unsubstituted C1 to C30 alkyl group, a substituted or unsubstituted C1 to C30 alkenyl group, a substituted or unsubstituted C1 to C30 alkynyl group, a substituted or unsubstituted C6 to C30 aryl group, a substituted or unsubstituted C6 to C30 aryloxy group, a substituted or unsubstituted C6 to C30 arylthio group, a substituted or unsubstituted C2 to C30 heteroaryl group, a hydroxy group, a thiol group, or a combination thereof, $R^a$ is independently present or adjacent $R^a$s are linked to each other to provide a ring, and $L^1$ is a C1 to C40 silyl group, a C1 to C30 alkyl group, a C3 to C30 cycloalkyl group, a C2 to C30 heterocycloalkyl group, or a C6 to C30 arylene group substituted or unsubstituted with a C6 to C30 aryl group;

[Chemical Formula 2]

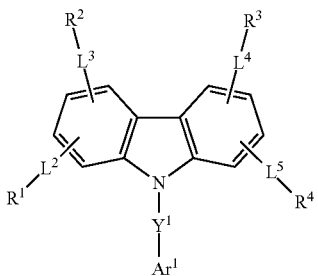

wherein, in Chemical Formula 2,
$L^2$ to $L^5$ and $Y^1$ are independently a single bond, or a substituted or unsubstituted C6 to C30 arylene group,
$Ar^1$ is a substituted or unsubstituted C6 to C30 aryl group, a substituted or unsubstituted C2 to C30 heterocyclic group, a substituted or unsubstituted C6 to C30 arylamine group, or a combination thereof,
$R^1$ to $R^4$ are independently hydrogen, deuterium, a substituted or unsubstituted C1 to C20 alkyl group, a substituted or unsubstituted C6 to C30 aryl group, a substituted or unsubstituted C2 to C30 heterocyclic group, a substituted or unsubstituted nitrile group, a substituted or unsubstituted isonitrile group, a hydroxy group, a thiol group, or a combination thereof,
$R^1$ to $R^4$ is independently present or adjacent groups are linked to each other to provide a ring,
at least one of $R^1$ to $R^4$ and $Ar^1$ is a substituted or unsubstituted triphenylene group, or a substituted or unsubstituted carbazolyl group,
one of $R^1$ and $R^2$ and one of $R^3$ and $R^4$ are not simultaneously a substituted or unsubstituted carbazolyl group, and
when one of $R^1$ to $R^4$ is a substituted carbazolyl group, the carbazolyl group is not substituted with a carbazolyl group,
wherein "substituted" of Chemical Formulae 1 and 2 refers to that at least one hydrogen is replaced by deuterium, a halogen, a hydroxy group, an amino group, a C1 to C30 amine group, a C6 to C30 arylamine group, a nitro group, a C1 to C40 silyl group, a C1 to C30 alkyl group, a C3 to C30 cycloalkyl group, a C2 to C30 heterocycloalkyl group, a C6 to C30 aryl group, a C2 to C30 heterocyclic group, a C1 to C20 alkoxy group, a C1 to C10 trifluoroalkyl group, or a cyano group.

2. The composition for an organic optoelectronic device of claim 1, wherein the Chemical Formula 1 is represented by one of Chemical Formula 1-I to Chemical Formula 1-III:

[Chemical Formula 1-I]

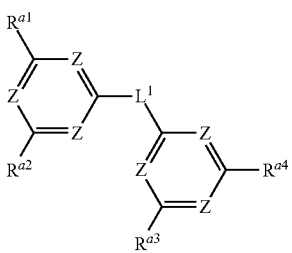

[Chemical Formula 1-II]

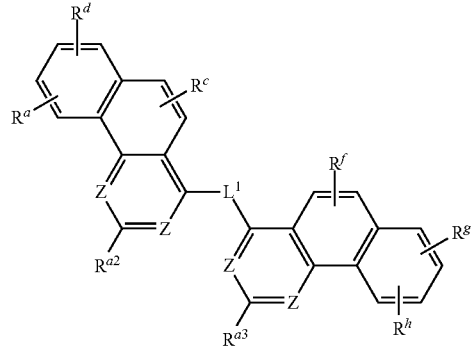

[Chemical Formula 1-III]

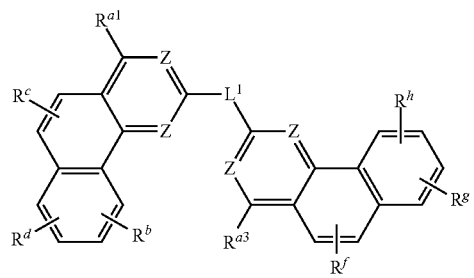

wherein, in Chemical Formulae 1-I to I-III,
Z is independently N, or $CR^a$,
at least one of Z is N,
$R^a$, $R^{a1}$ to $R^{a4}$, $R^c$, $R^d$, $R^e$, $R^f$, $R^g$, and $R^h$ are independently hydrogen, deuterium, a substituted or unsubstituted C1 to C30 alkyl group, a substituted or unsubstituted C6 to C30 aryl group, a substituted or unsubstituted C2 to C30 heteroaryl group, or a combination thereof, and
$L^1$ is a C1 to C40 silyl group, a C1 to C30 alkyl group, a C3 to C30 cycloalkyl group, a C2 to C30 heterocycloalkyl group, or a C6 to C30 arylene group substituted or unsubstituted with a C6 to C30 aryl group,
wherein, "substituted" is the same as defined in claim 1.

3. The composition for an organic optoelectronic device of claim 1, wherein the $L^1$ is:
a phenylene group that is unsubstituted or substituted with deuterium, a C1 to C40 silyl group, a C to C30 alkyl group, or a C6 to C30 aryl group;
a biphenylene group that is unsubstituted or substituted with deuterium, a C1 to C40 silyl group, a C1 to C30 alkyl group, or a C6 to C30 aryl group;
a terphenylene group that is unsubstituted or substituted with deuterium, a C to C40 silyl group, a C1 to C30 alkyl group, or a C6 to C30 aryl group; or
a quarterphenylene group that is unsubstituted or substituted with deuterium, a C1 to C40 silyl group, a C1 to C30 alkyl group, or a C6 to C30 aryl group.

4. The composition for an organic optoelectronic device of claim 1, wherein the $L^1$ is selected from substituted or unsubstituted linking groups of Group 2:
[Group 2]
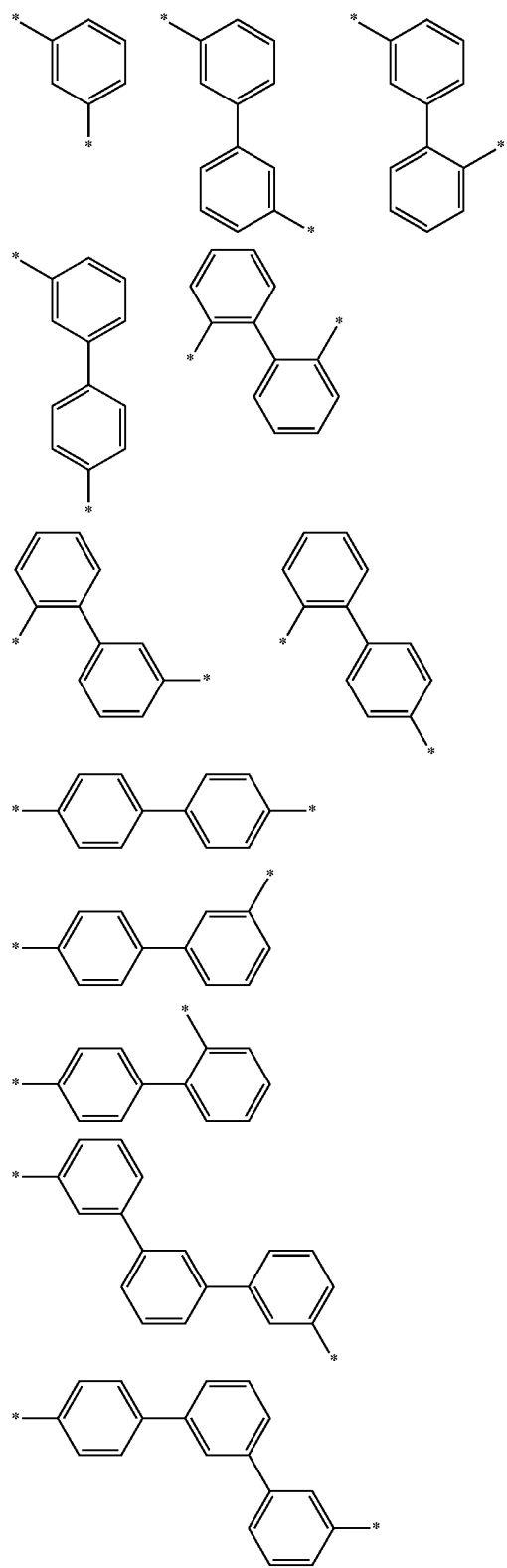
-continued
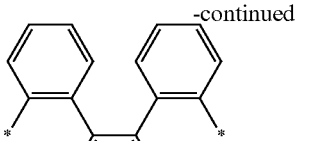
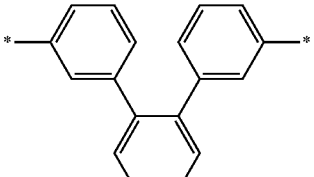
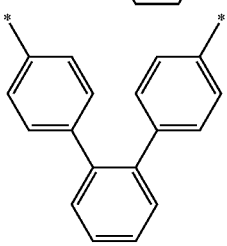
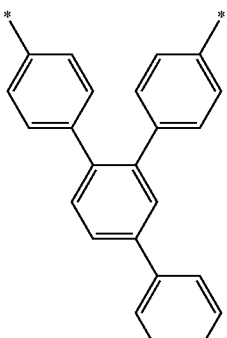
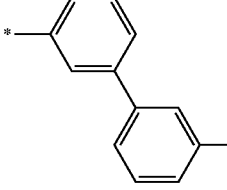
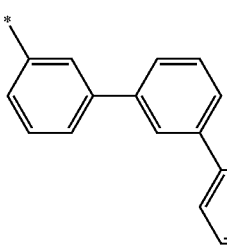

-continued

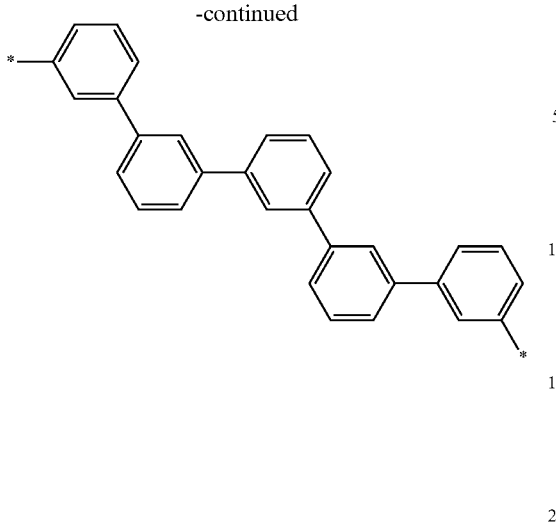

wherein, in Group 2, * is a linking point to an adjacent atom.

5. The composition for an organic optoelectronic device of claim 1, wherein $X^1$ to $X^{12}$ of Chemical Formula 1 are independently N, C, or $CR^a$, three of $X^1$ to $X^6$ are N, one to three of $X^7$ to $X^{12}$ are N, $R^a$ is independently, hydrogen, deuterium, a substituted or unsubstituted C1 to C30 alkyl group, a substituted or unsubstituted C6 to C30 aryl group, a substituted or unsubstituted C2 to C30 heteroaryl group, or a combination thereof, and $L^1$ is a C6 to C30 arylene group that is substituted or unsubstituted with deuterium, a C1 to C30 alkyl group, or a C6 to C30 aryl group, wherein "substituted" refers to that at least one hydrogen is replaced by deuterium, a halogen, a hydroxy group, a C1 to C40 silyl group, a C1 to C30 alkyl group, a C3 to C30 cycloalkyl group, a C2 to C30 heterocycloalkyl group, a C6 to C30 aryl group, or a C2 to C30 heterocyclic group.

6. The composition for an organic optoelectronic device of claim 5, wherein the $R^a$ is a substituted or unsubstituted C6 to C30 aryl group, wherein the C6 to C30 aryl group is substituted or unsubstituted phenyl group, a substituted or unsubstituted biphenyl group, a substituted or unsubstituted terphenyl group, a substituted or unsubstituted quarterphenyl group, a substituted or unsubstituted naphthyl group, a substituted or unsubstituted anthracenyl group, a substituted or unsubstituted fluorenyl group, a substituted or unsubstituted triphenylene group, or a substituted or unsubstituted phenanthrenyl group.

7. The composition for an organic optoelectronic device of claim 1, wherein the Chemical Formula 2 is represented by one of Chemical Formulae 2-I to 2-VI:

[Chemical Formula 2-I]

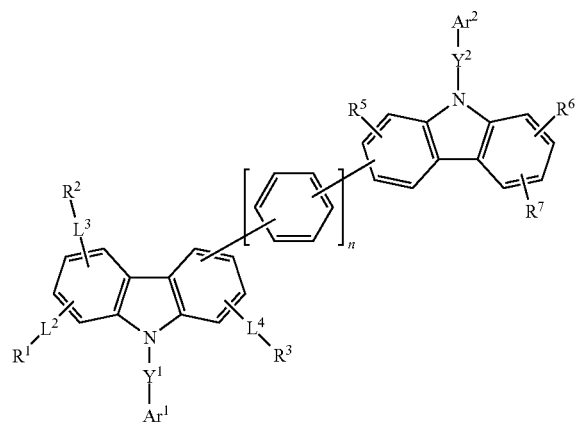

[Chemical Formula 2-II]

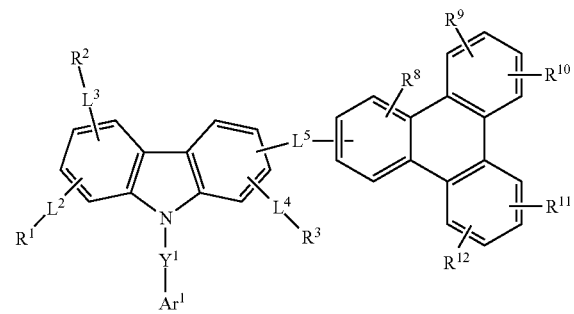

[Chemical Formula 2-III]

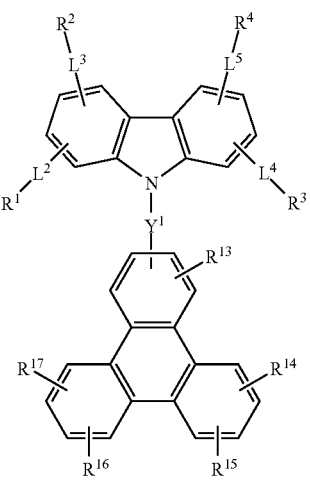

-continued

[Chemical Formula 2-IV]

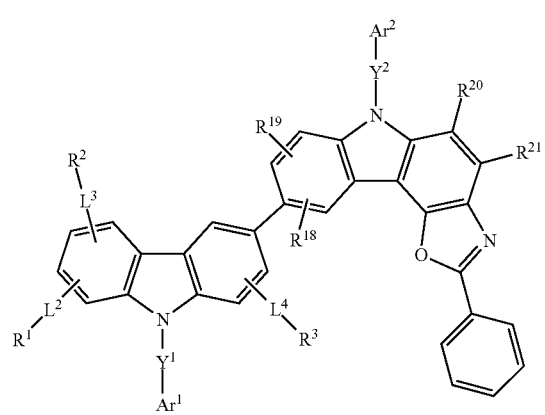

[Chemical Formula 2-V]

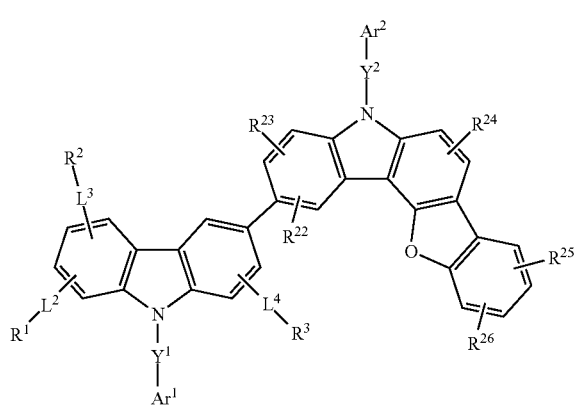

[Chemical Formula 2-VI]

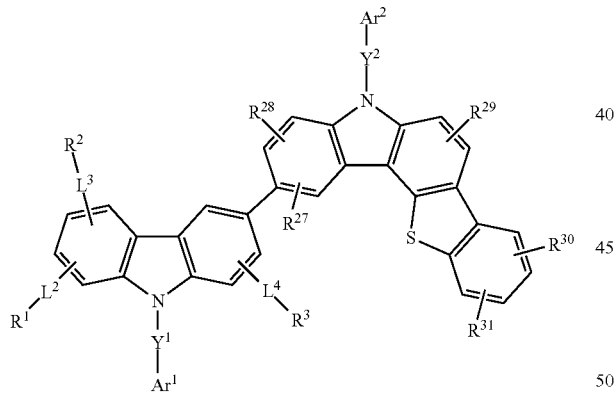

wherein, in Chemical Formulae 2-I to 2-VI,
$L^2$ to $L^5$, $Y^1$, and $Y^2$ are independently a single bond, or a substituted or unsubstituted C6 to C30 arylene group,
$Ar^1$ and $Ar^2$ are independently, a substituted or unsubstituted C6 to C30 aryl group, a substituted or unsubstituted C2 to C30 heterocyclic group, a substituted or unsubstituted C6 to C30 arylamine group, or a combination thereof,
$R^1$ to $R^4$ are independently hydrogen, deuterium, a substituted or unsubstituted C to C20 alkyl group, a substituted or unsubstituted C6 to C30 aryl group, a substituted or unsubstituted C2 to C30 heterocyclic group, a substituted or unsubstituted nitrile group, a substituted or unsubstituted isonitrile group, a hydroxy group, a thiol group, or a combination thereof, $R^1$ or $R^2$ of Chemical Formula 2-I is not a substituted or unsubstituted carbazolyl group,
$R^5$ to $R^{31}$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof,
provided that all the $R^5$ to $R^7$ are not a carbazolyl group, and
n is an integer of 0 to 5,
wherein, "substituted" is the same as defined in claim 1.

8. The composition for an organic optoelectronic device of claim 7, wherein $Ar^1$ and $Ar^2$ of Chemical Formulae 2-I to 2-VI are independently, a substituted or unsubstituted phenyl group, a substituted or unsubstituted biphenyl group, a substituted or unsubstituted terphenyl group, a substituted or unsubstituted naphthyl group, a substituted or unsubstituted triphenylenyl group, a substituted or unsubstituted fluorenyl group, a substituted or unsubstituted pyridinyl group, a substituted or unsubstituted quinolinyl group, a substituted or unsubstituted isoquinolinyl group, a substituted or unsubstituted dibenzofuranyl group, a substituted or unsubstituted dibenzothiophenyl group, or a combination thereof.

9. The composition for an organic optoelectronic device of claim 7, wherein $Ar^1$ and $Ar^2$ of Chemical Formula 2-I to 2-VI are selected from substituted or unsubstituted groups of Group 4:

[Group 4]

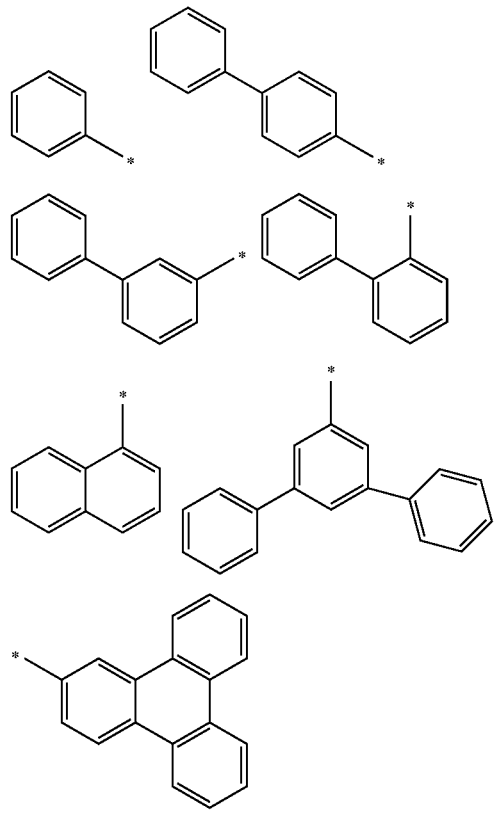

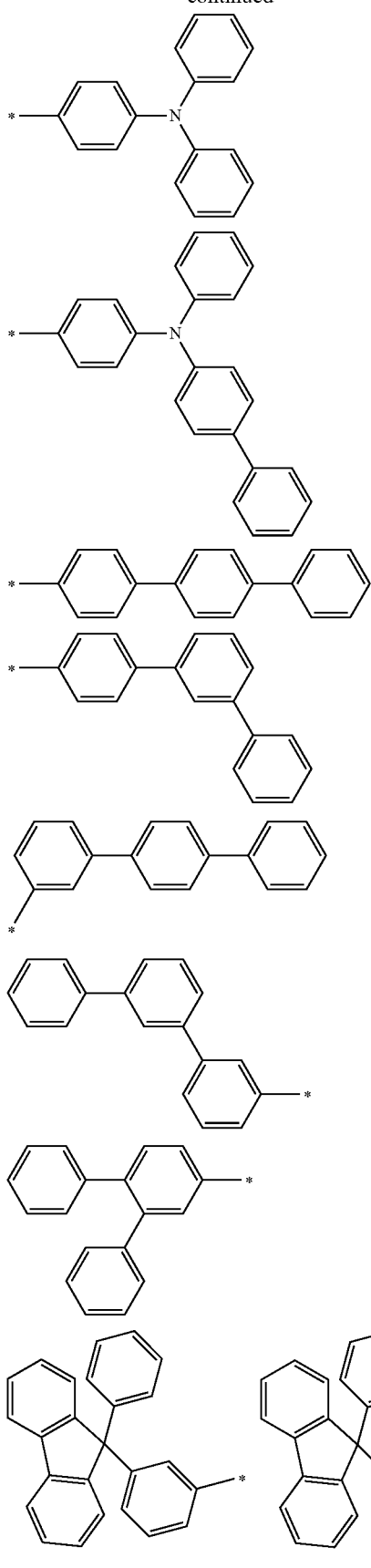
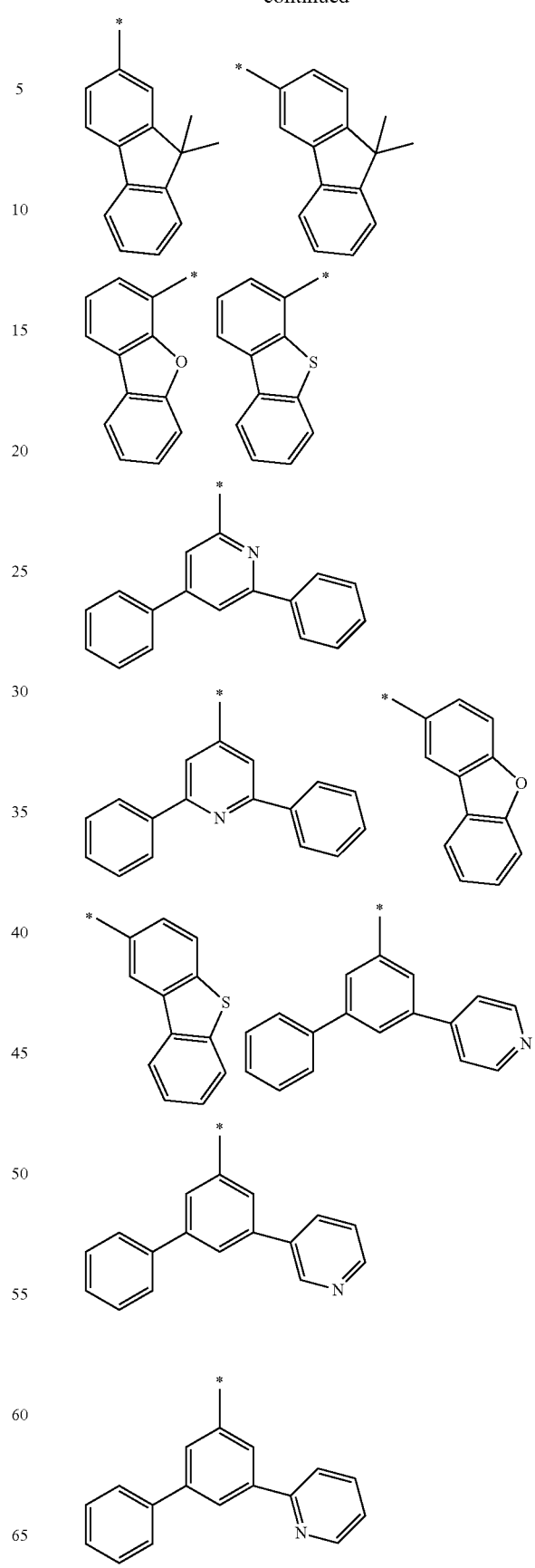

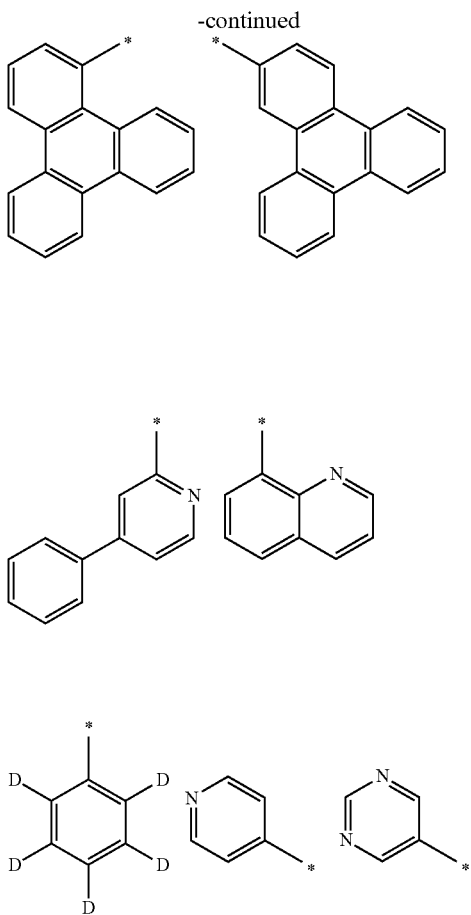

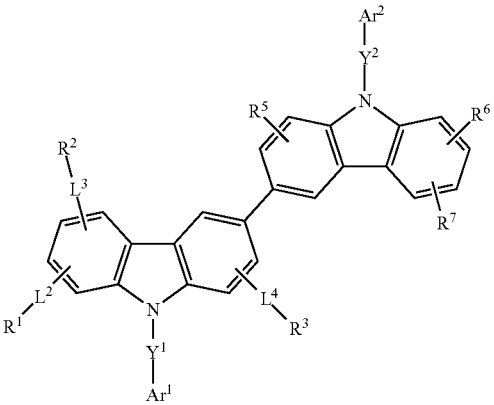

[Chemical Formula 1a]

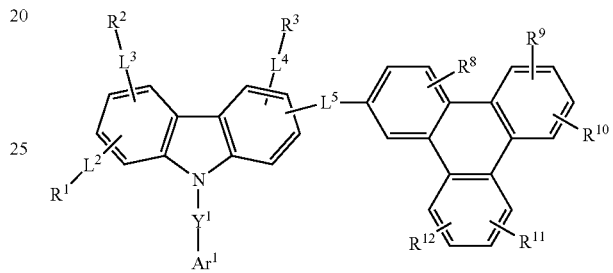

[Chemical Formula 2a-1]

wherein, in Group 4, * is a linking point to an adjacent atom.

10. The composition for an organic optoelectronic device of claim 1, wherein the first compound is represented by Chemical Formula 1-Ia, and the second compound is represented by Chemical Formula 1a or 2a-1

[Chemical Formula 1-Ia]

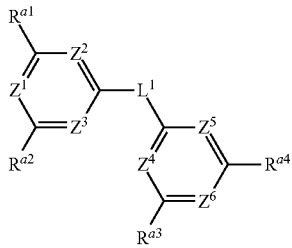

wherein, in Chemical Formula 1-I, $Z^1$ to $Z^6$ are independently N, or $CR^a$, at least two of $Z^1$ to $Z^3$ are N, at least two of $Z^4$ to $Z^6$ are N, $R^8$ and $R^{a1}$ to $R^{a4}$ are independently hydrogen, or a substituted or unsubstituted C6 to C30 aryl group, and $L^1$ is a C6 to C30 arylene group that is substituted or unsubstituted with deuterium, a C1 to C30 alkyl group, or a C6 to C30 aryl group;

wherein, in Chemical Formulae 1a and 2a-1, $L^2$ to $L^5$, $Y^1$, and $Y^2$ are independently a single bond, or a substituted or unsubstituted C6 to C30 arylene group, $Ar^1$ and $Ar^2$ are independently, a substituted or unsubstituted C6 to C30 aryl group, or a substituted or unsubstituted C2 to C30 heterocyclic group, $R^1$ to $R^3$ and $R^5$ to $R^{12}$ are independently, hydrogen, deuterium, or a substituted or unsubstituted C6 to C30 aryl group, $R^1$ or $R^2$ of Chemical Formula 1a is not a substituted or unsubstituted carbazolyl group, and all the $R^5$ to $R^7$ are not a carbazolyl group, wherein, "substituted" is the same as defined in claim 1.

11. The composition for an organic optoelectronic device of claim 1, which further comprises a phosphorescent dopant.

12. An organic optoelectronic device, comprising:
an anode and a cathode facing each other, and
one or more organic layers interposed between the anode and the cathode, wherein the composition for an organic optoelectronic device of claim 1 forms a same organic layer of the one or more organic layers, the at least one first compound and at least one second compound being simultaneously present as a mixture in the same organic layer.

13. The organic optoelectronic device of claim 12, wherein the same organic layer is an emission layer in which the at least one first compound and at least one second compound are present in the mixture.

14. The organic optoelectronic device of claim 12, wherein the organic optoelectronic device is selected from an organic light emitting diode, an organic photoelectric device, an organic solar cell, an organic transistor, an organic photo conductor drum, and an organic memory device.

15. A display device comprising the organic optoelectronic device of claim 12.

16. A composition for an organic optoelectronic device, the composition comprising:
   at least one first compound represented by Chemical Formula 1; and
   at least one second compound represented by one of Chemical Formulae 2-I to 2-VI,

[Chemical Formula 1]

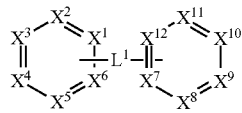

wherein, in Chemical Formula 1,
$X^1$ to $X^{12}$ are independently N, C, or $CR^a$,
at least one of $X^1$ to $X^6$ is N,
at least one of $X^7$ to $X^{12}$ is N,
$R^a$ is independently hydrogen, deuterium, a substituted or unsubstituted C1 to C30 alkyl group, a substituted or unsubstituted C1 to C30 alkenyl group, a substituted or unsubstituted C1 to C30 alkynyl group, a substituted or unsubstituted C6 to C30 aryl group, a substituted or unsubstituted C6 to C30 aryloxy group, a substituted or unsubstituted C6 to C30 arylthio group, a substituted or unsubstituted C2 to C30 heteroaryl group, a hydroxy group, a thiol group, or a combination thereof,
$R^a$ is independently present or adjacent $R^a$s are linked to each other to provide a ring, and
$L^1$ is a C1 to C40 silyl group, a C1 to C30 alkyl group, a C3 to C30 cycloalkyl group, a C2 to C30 heterocycloalkyl group, or a C6 to C30 arylene group substituted or unsubstituted with a C6 to C30 aryl group;

[Chemical Formula 2-I]

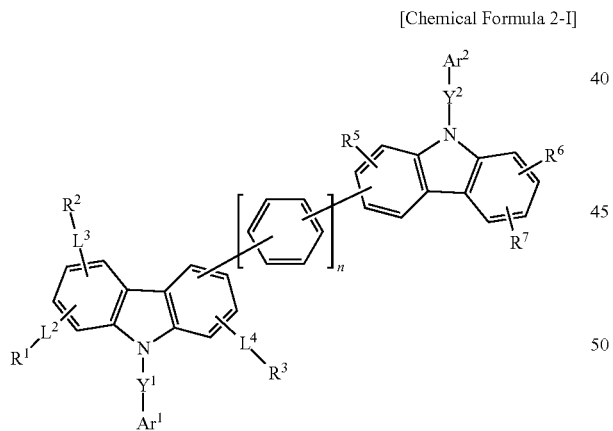

[Chemical Formula 2-II]

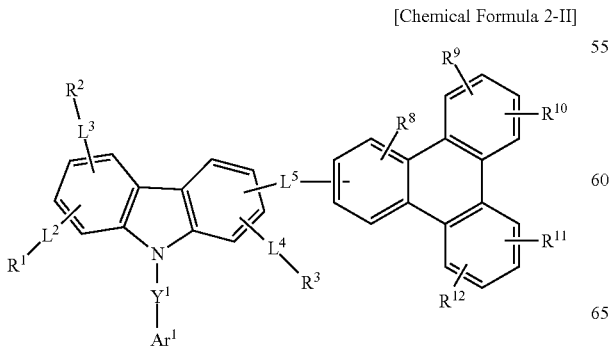

[Chemical Formula 2-III]

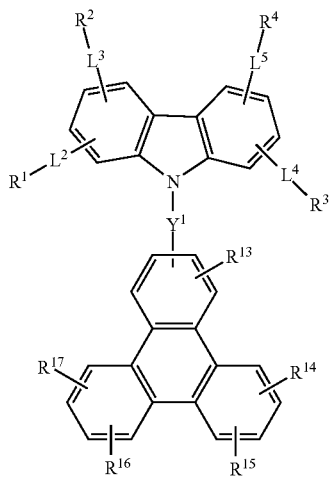

[Chemical Formula 2-IV]

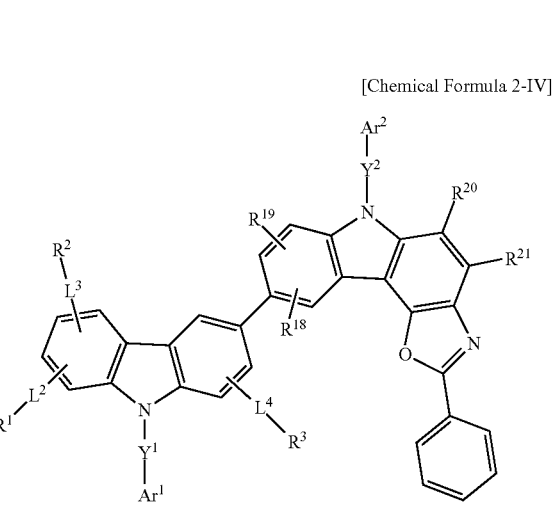

[Chemical Formula 2-V]

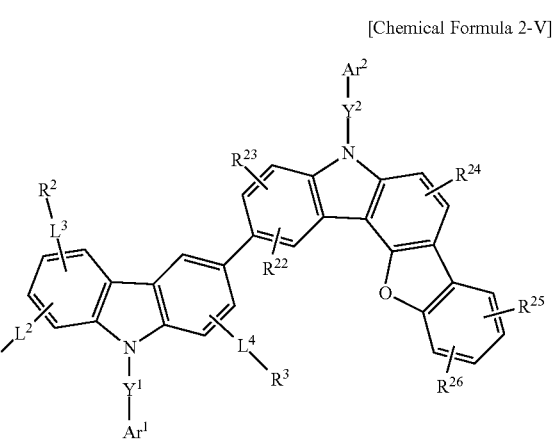

-continued

[Chemical Formula 2-VI]

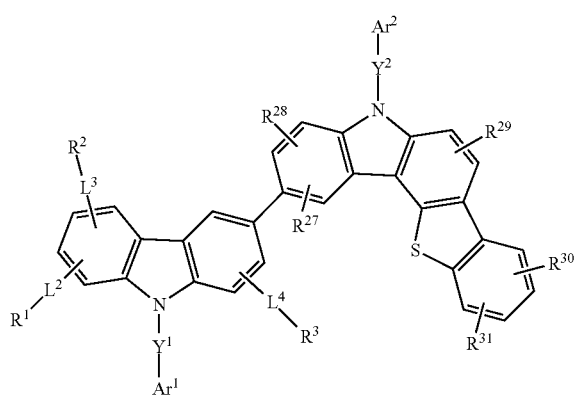

wherein, in Chemical Formulae 2-I to 2-VI, $L^2$ to $L^5$, $Y^1$, and $Y^2$ are independently a single bond, or a substituted or unsubstituted C6 to C30 arylene group, $Ar^1$ and $Ar^2$ are independently a substituted or unsubstituted C6 to C30 aryl group, a substituted or unsubstituted C2 to C30 heterocyclic group, a substituted or unsubstituted C6 to C30 arylamine group, or a combination thereof, $R^1$ to $R^4$ are independently hydrogen, deuterium, a substituted or unsubstituted C1 to C20 alkyl group, a substituted or unsubstituted C6 to C30 aryl group, a substituted or unsubstituted C2 to C30 heterocyclic group, a substituted or unsubstituted nitrile group, a substituted or unsubstituted isonitrile group, a hydroxy group, a thiol group, or a combination thereof, $R^1$ or $R^2$ of Chemical Formula 2-I is not a substituted or unsubstituted carbazolyl group, $R^5$ to $R^{31}$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof, provided that all the $R^5$ to $R^7$ are not a carbazolyl group, and n is an integer of 0 to 5, wherein "substituted" of Chemical Formulae 1 and Chemical Formulae 2-I to 2-VI refers to that at least one hydrogen is replaced by deuterium, a halogen, a hydroxy group, an amino group, a C1 to C30 amine group, a C6 to C30 arylamine group, a nitro group, a C1 to C40 silyl group, a C to C30 alkyl group, a C3 to C30 cycloalkyl group, a C2 to C30 heterocycloalkyl group, a C6 to C30 aryl group, a C2 to C30 heterocyclic group, a C1 to C20 alkoxy group, a C1 to C10 trifluoroalkyl group, or a cyano group.

* * * * *